United States Patent
Gunnarsson et al.

(10) Patent No.: US 12,428,461 B2
(45) Date of Patent: Sep. 30, 2025

(54) TREATING CANCER WITH A CONJUGATE COMPRISING AN IL-2 MOIETY

(71) Applicant: ASCENDIS PHARMA ONCOLOGY DIVISION A/S, Hellerup (DK)

(72) Inventors: Nina Gunnarsson, Hellerup (DK); Matiss Maleckis, Hellerup (DK); David B. Rosen, Palo Alto, CA (US)

(73) Assignee: ASCENDIS PHARMA ONCOLOGY DIVISION A/S, Hellerup (DK)

( * ) Notice: Subject to any disclaimer, the term of this patent is extended or adjusted under 35 U.S.C. 154(b) by 0 days.

(21) Appl. No.: 17/997,363

(22) PCT Filed: Jun. 2, 2021

(86) PCT No.: PCT/EP2021/064781
§ 371 (c)(1),
(2) Date: Oct. 27, 2022

(87) PCT Pub. No.: WO2021/245130
PCT Pub. Date: Dec. 9, 2021

(65) Prior Publication Data
US 2023/0174605 A1 Jun. 8, 2023

Related U.S. Application Data

(60) Provisional application No. 63/116,102, filed on Nov. 19, 2020.

(30) Foreign Application Priority Data

| Jun. 3, 2020 | (EP) | 20177974 |
| Oct. 16, 2020 | (EP) | 20202299 |
| Dec. 21, 2020 | (EP) | 20216052 |
| Mar. 3, 2021 | (EP) | 21160477 |
| Mar. 11, 2021 | (EP) | 21162030 |

(51) Int. Cl.
*C07K 14/55* (2006.01)
*A61K 47/54* (2017.01)
*A61K 47/60* (2017.01)
*A61P 35/00* (2006.01)

(52) U.S. Cl.
CPC ............ *C07K 14/55* (2013.01); *A61K 47/542* (2017.08); *A61K 47/60* (2017.08); *A61P 35/00* (2018.01)

(58) Field of Classification Search
CPC .... C07K 14/55; C07K 17/08; A61K 38/2013; A61K 47/542
See application file for complete search history.

(56) References Cited

U.S. PATENT DOCUMENTS

| 4,766,106 A | 8/1988 | Katre et al. |
| 4,902,502 A | 2/1990 | Nitecki et al. |
| 5,089,261 A | 2/1992 | Nitecki et al. |
| 5,206,344 A | 4/1993 | Katre et al. |
| 6,706,289 B2 | 3/2004 | Lewis et al. |
| 7,585,837 B2 | 9/2009 | Schechter et al. |
| 8,377,917 B2 | 2/2013 | Hersel et al. |
| 8,618,124 B2 | 12/2013 | Greenwald et al. |
| 8,754,190 B2 | 6/2014 | Ashley et al. |
| 8,946,405 B2 | 2/2015 | Ashley et al. |
| 9,266,938 B2 | 2/2016 | Ast |
| 9,272,048 B2 | 3/2016 | Rau et al. |
| 9,428,567 B2 | 8/2016 | Garcia et al. |
| 9,511,122 B2 | 12/2016 | Rasmussen et al. |
| 9,561,285 B2 | 2/2017 | Rau et al. |
| 10,799,563 B2 | 10/2020 | Kurpiers et al. |
| 10,835,578 B2 | 11/2020 | Rau et al. |
| 11,879,001 B2 | 1/2024 | Gunnarsson et al. |
| 2006/0269515 A1 | 11/2006 | Denis-Mize et al. |
| 2011/0091413 A1 | 4/2011 | Epstein et al. |
| 2012/0035101 A1 | 2/2012 | Fares et al. |
| 2017/0224777 A1 | 8/2017 | Wittrup et al. |
| 2021/0008168 A1 | 1/2021 | Knappe et al. |
| 2021/0024602 A1 | 1/2021 | Sprogøe et al. |
| 2023/0201355 A1 | 6/2023 | Gunnarsson et al. |
| 2023/0340055 A1 | 10/2023 | Okkels et al. |

FOREIGN PATENT DOCUMENTS

| AU | 2017359841 B2 | 8/2020 |
| CN | 111018961 A | 4/2020 |
| EP | 1 536 334 | 6/2005 |
| JP | 2007-530485 A | 11/2007 |
| JP | 2014-506793 A | 3/2014 |
| JP | 2017-535609 A | 11/2017 |
| WO | WO 99/60128 | 11/1999 |
| WO | WO 02/00243 | 1/2002 |
| WO | WO 02/089789 | 11/2002 |
| WO | WO 03/015697 | 2/2003 |
| WO | WO 2004/014424 A1 | 2/2004 |
| WO | WO 2005/027978 | 3/2005 |

(Continued)

OTHER PUBLICATIONS

U.S. Appl. No. 18/052,495, filed Nov. 3, 2022, Gunnarsson et al.
U.S. Appl. No. 18/043,319, filed Feb. 27, 2023, Okkels et al.
Anonymous, Supplemental data to Charych et al,, "NKTR-214 an Engineered Cytokine with Biased IL2 Receptor Binding, Increased Tumor Exposure, and Marked Efficacy in Mouse Tumor Models" Jan. 1, 2016, retrieved from URL: http://clincancerres.aacrjournals.org/content/suppl/2016/01/29/22.3.680.DC1.
Beresov, B.F. Korovkin Bilogical chemistry, M., "Medicine", 1998, p. 34 third paragraph, p. 59 last paragraph), English translation.

(Continued)

*Primary Examiner* — Gyan Chandra
(74) *Attorney, Agent, or Firm* — Alston & Bird LLP

(57) ABSTRACT

The present invention relates to an IL-2 protein sequence of the formula Ala-SEQ A-Cys*-SEQ B (I), wherein SEQ A has at least 94% sequence identity to SEQ ID NO:1; SEQ B has at least 94% sequence identity to SEQ ID NO:2; Ala is an alanine residue; and Cys* is a cysteine residue; to conjugates thereof and their uses in the treatment of cancer.

26 Claims, No Drawings
Specification includes a Sequence Listing.

(56) References Cited

FOREIGN PATENT DOCUMENTS

| | | |
|---|---|---|
| WO | WO 2005/086751 A2 | 9/2005 |
| WO | WO 2005/086798 A2 | 9/2005 |
| WO | WO 2005/099768 A2 | 10/2005 |
| WO | WO 2006/069246 | 6/2006 |
| WO | WO 2008/034122 | 3/2008 |
| WO | WO 2008/155134 | 12/2008 |
| WO | WO 2009/009712 | 1/2009 |
| WO | WO 2009/095479 | 8/2009 |
| WO | WO 2009/133137 A2 | 11/2009 |
| WO | WO 2009/143412 | 11/2009 |
| WO | WO 2010/085495 A1 | 7/2010 |
| WO | WO 2010/091122 | 8/2010 |
| WO | WO 2011/08611 | 2/2011 |
| WO | WO 2011/08612 | 2/2011 |
| WO | WO 2011/08613 | 2/2011 |
| WO | WO 2011/012715 | 2/2011 |
| WO | WO 2011/063770 A2 | 6/2011 |
| WO | WO 2011/073234 A1 | 6/2011 |
| WO | WO 2011/082368 | 7/2011 |
| WO | WO 2011/144756 | 11/2011 |
| WO | WO 2012/002047 | 5/2012 |
| WO | WO 2012/065086 | 5/2012 |
| WO | WO 2012/107417 A1 | 8/2012 |
| WO | WO 2013/024048 | 2/2013 |
| WO | WO 2013/036857 | 3/2013 |
| WO | WO 2014/028748 A1 | 2/2014 |
| WO | WO 2014/056923 | 4/2014 |
| WO | WO 2014/056926 | 4/2014 |
| WO | WO 2014/060512 | 4/2014 |
| WO | WO 2014/100014 A1 | 6/2014 |
| WO | WO 2015/042707 A1 | 4/2015 |
| WO | WO 2015/125159 A1 | 8/2015 |
| WO | WO 2016/020373 | 2/2016 |
| WO | WO 2016/025385 A1 | 2/2016 |
| WO | WO 2016/079114 | 5/2016 |
| WO | WO 2017/148883 A1 | 9/2017 |
| WO | WO 2018/060311 A1 | 4/2018 |
| WO | WO 2018/091003 A1 | 5/2018 |
| WO | WO 2018/175788 | 9/2018 |
| WO | WO 2019/028419 A1 | 2/2019 |
| WO | WO 2019/091384 A1 | 5/2019 |
| WO | WO 2019/131964 A1 | 7/2019 |
| WO | WO 2019/185705 A1 | 10/2019 |
| WO | WO 2020/020783 A1 | 1/2020 |
| WO | WO 2020/057646 A1 | 3/2020 |
| WO | WO 2020/0242884 A1 | 12/2020 |
| WO | WO 2020/254607 A1 | 12/2020 |
| WO | WO 2021/245130 A1 | 12/2021 |
| WO | WO 2022/043493 A1 | 3/2022 |

OTHER PUBLICATIONS

Bowie, et al., "Deciphering the Message in Protein Sequences: Tolerance to Amino Acid Substitutions," Science, 1306-1310, vol. 247, (1990).

Charych, et al., "NKTR-214 an Engineered Cytokine with Biased IL2 Receptor Binding, Increased Tumor Exposure, and Marked Efficacy in Mouse Tumor Models," Clinical Cancer Research, 680-690, vol. 22(3), (Feb. 1, 2016).

Database Geneseq, "Human mature IL-2 protein mutant R38C.", Geneseq Aug. 22, 2019 (Aug. 22, 2019), retrieved from EBI accession No. GSP:BGM81672 Database accession No. BGM81672 XP002800682.

Dyson, May p. "Chemistry of synthetic drugs" translated from English—M.: Mir, 1964, p. 12-19), English Translation.

Goodson, et al., "Site-Directed Pegylation of Recombinant Interleukin-2 at its Glycosylation Site," Biotechnology. The International Monthly for Industrial Biology, Nature Publishing Group, 343-346, vol. 8(4), (Apr. 1990).

Harris, et al., "A bispecific antibody agonist of the IL-2 heterodimeric receptor preferentially promotes in vivo expansion of CD8 and NK cells," Scientific Reports, 11:10592, (May 2021).

Jones, et al., "Polymeric Dibromomaleimides as Extremely Efficient Disulfide Bridging Bioconjugation and Pegylation Agents," J.Am. Chem. Soc., 1847-1852, vol. 134(3), (2012).

Levin, et al., "Exploiting a Natural Conformational Switch to Engineer an Interleukin-2 Superldnem," Nature Oct. 26, 2012, 529-533, vol. 484(7395).

Popular medical encyclopedia, chief editor V. I. Pokrovskij, fourth edition, "Knigočej", 1997, p. 317 (drugs), English Translation.

Sato, et al., "Further Studies on the Site-Specific Protein Modification by Microbial Transglutaminase," Bioconjugate Chem., 701-710, vol. 12(5), (2001).

Tystsikov, et al., Identification and Characterization of Two Alternative Splice Variants of Human Interleukin-2*, The Journal of Biological Chemistry, Sep. 20, 1996, 23055-23060, vol. 271(38).

Vazquez-Lombardi, et al., "Molecular Engineering of Therapeutic Cytokines," Antibodies, 426-451, vol. 2(3), (Jul. 7, 2013).

PCT Application No. PCT/EP2021/064781, PCT Written Opinion of the International Searching Authority mailed Aug. 5, 2021.

U.S. Appl. No. 17/042,610, Non-Final Office Action mailed Mar. 16, 2023.

U.S. Appl. No. 17/042,610, Requirement for Restriction/Election mailed Nov. 1, 2022.

WIPO Application No. PCT/EP2019/057709, PCT International Preliminary Report on Patentability mailed Sep. 29, 2020.

WIPO Application No. PCT/EP2019/057709, PCT International Search Report mailed Aug. 16, 2019.

WIPO Application No. PCT/EP2021/064781, PCT International Preliminary Report on Patentability mailed Dec. 6, 2022.

Grabenhorst et al., "Biosynthesis and secretion of human interleukin 2 glycoprotein variants from baculovirus-infected Sf21 Cells," European Journal of Biochemistry, vol. 215, No. 1, pp. 189-197, (Jul. 1993).

Carmenate et al., "Human IL-2 mutein with higher antitumor efficacy than wild type IL-2," The Journal of Immunology, vol. 190, No. 12, pp. 630-6238, (Jun. 2013).

WIPO Application No. PCT/EP2021/073735, PCT International Search Report mailed Dec. 21, 2021.

WIPO Application No. PCT/EP2021/073735, PCT International Preliminary Report on Patentability mailed Feb. 28, 2023.

Charych et al., "Modeling the receptor pharmacology, pharmacokinetics, and pharmacodynamics of NKTR-214, a kinetically-controlled interleukin-2 (IL2) receptor agonist for cancer immunotherapy," PLoS One 12(7):e0179431, (Jul. 2017).

Zhang et al., "Protein-drug conjugate programmed by pH-reversible linker for tumor hypoxia relief and enhanced cancer combination therapy," International Journal of Pharmaceutics, 582, 119321, (Apr. 2020).

U.S. Appl. No. 17/042,610, Non-Final Office Action mailed Feb. 2, 2024.

U.S. Appl. No. 18/052,495, Corrected Notice of Allowance mailed Oct. 13, 2023.

U.S. Appl. No. 18/052,495, Final Office Action mailed Jul. 27, 2023.

U.S. Appl. No. 18/052,495, Notice of Allowance mailed Sep. 27, 2023.

U.S. Appl. No. 18/052,495, Non-Final Office Action mailed Jun. 7, 2023.

U.S. Appl. No. 17/042,610, Final Office Action mailed Jun. 3, 2025.

SEQUENCE LISTING

<160> NUMBER OF SEQ ID NOS: 48

<210> SEQ ID NO 1
<211> LENGTH: 36
<212> TYPE: PRT
<213> ORGANISM: Artificial Sequence
<220> FEATURE:
<223> OTHER INFORMATION: SEQ A

<400> SEQUENCE: 1

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr
        35

<210> SEQ ID NO 2
<211> LENGTH: 95
<212> TYPE: PRT
<213> ORGANISM: Artificial Sequence
<220> FEATURE:
<223> OTHER INFORMATION: SEQ B

<400> SEQUENCE: 2

Met Leu Thr Phe Lys Phe Tyr Met Pro Lys Lys Ala Thr Glu Leu Lys
1               5                   10                  15

His Leu Gln Cys Leu Glu Glu Glu Leu Lys Pro Leu Glu Glu Val Leu
            20                  25                  30

Asn Leu Ala Gln Ser Lys Asn Phe His Leu Arg Pro Arg Asp Leu Ile
            35                  40                  45

Ser Asn Ile Asn Val Ile Val Leu Glu Leu Lys Gly Ser Glu Thr Thr
        50                  55                  60

Phe Met Cys Glu Tyr Ala Asp Glu Thr Ala Thr Ile Val Glu Phe Leu
65                  70                  75                  80

Asn Arg Trp Ile Thr Phe Cys Gln Ser Ile Ile Ser Thr Leu Thr
                85                  90                  95

<210> SEQ ID NO 3
<211> LENGTH: 36
<212> TYPE: PRT
<213> ORGANISM: Artificial Sequence
<220> FEATURE:
<223> OTHER INFORMATION: SEQ A with K34A mutation

<400> SEQUENCE: 3

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Ala Leu Thr
        35

<210> SEQ ID NO 4
<211> LENGTH: 36
<212> TYPE: PRT
<213> ORGANISM: Artificial Sequence
<220> FEATURE:
<223> OTHER INFORMATION: SEQ A with K34C mutation

<400> SEQUENCE: 4

Pro Thr Ser Ser Ser Thr Lys Lys Thr Gln Leu Gln Leu Glu His Leu

```
1               5                   10                  15
Leu Leu Asp Leu Gln Met Ile Leu Asn Gly Ile Asn Asn Tyr Lys Asn
            20                  25                  30

Pro Cys Leu Thr
        35

<210> SEQ ID NO 5
<211> LENGTH: 36
<212> TYPE: PRT
<213> ORGANISM: Artificial Sequence
<220> FEATURE:
<223> OTHER INFORMATION: SEQ A with K34G mutation

<400> SEQUENCE: 5

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Gly Leu Thr
        35

<210> SEQ ID NO 6
<211> LENGTH: 36
<212> TYPE: PRT
<213> ORGANISM: Artificial Sequence
<220> FEATURE:
<223> OTHER INFORMATION: SEQ A with K34S mutation

<400> SEQUENCE: 6

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Ser Leu Thr
        35

<210> SEQ ID NO 7
<211> LENGTH: 36
<212> TYPE: PRT
<213> ORGANISM: Artificial Sequence
<220> FEATURE:
<223> OTHER INFORMATION: SEQ A with K34T mutation

<400> SEQUENCE: 7

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Thr Leu Thr
        35

<210> SEQ ID NO 8
<211> LENGTH: 36
<212> TYPE: PRT
<213> ORGANISM: Artificial Sequence
<220> FEATURE:
<223> OTHER INFORMATION: SEQ A with K34Q mutation

<400> SEQUENCE: 8

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
```

```
                20                  25                  30

Pro Gln Leu Thr
        35

<210> SEQ ID NO 9
<211> LENGTH: 36
<212> TYPE: PRT
<213> ORGANISM: Artificial Sequence
<220> FEATURE:
<223> OTHER INFORMATION: SEQ A with K34E mutation

<400> SEQUENCE: 9

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Glu Leu Thr
        35

<210> SEQ ID NO 10
<211> LENGTH: 36
<212> TYPE: PRT
<213> ORGANISM: Artificial Sequence
<220> FEATURE:
<223> OTHER INFORMATION: SEQ A with K34N mutation

<400> SEQUENCE: 10

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Asn Leu Thr
        35

<210> SEQ ID NO 11
<211> LENGTH: 36
<212> TYPE: PRT
<213> ORGANISM: Artificial Sequence
<220> FEATURE:
<223> OTHER INFORMATION: SEQ A with K34D mutation

<400> SEQUENCE: 11

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Asp Leu Thr
        35

<210> SEQ ID NO 12
<211> LENGTH: 95
<212> TYPE: PRT
<213> ORGANISM: Artificial Sequence
<220> FEATURE:
<223> OTHER INFORMATION: SEQ B with C87S mutation

<400> SEQUENCE: 12

Met Leu Thr Phe Lys Phe Tyr Met Pro Lys Lys Ala Thr Glu Leu Lys
1               5                   10                  15

His Leu Gln Cys Leu Glu Glu Glu Leu Lys Pro Leu Glu Glu Val Leu
            20                  25                  30

Asn Leu Ala Gln Ser Lys Asn Phe His Leu Arg Pro Arg Asp Leu Ile
```

```
                35                  40                  45
Ser Asn Ile Asn Val Ile Val Leu Glu Leu Lys Gly Ser Glu Thr Thr
 50                  55                  60

Phe Met Cys Glu Tyr Ala Asp Glu Thr Ala Thr Ile Val Glu Phe Leu
 65                  70                  75                  80

Asn Arg Trp Ile Thr Phe Ser Gln Ser Ile Ile Ser Thr Leu Thr
                 85                  90                  95

<210> SEQ ID NO 13
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:1
      and SEQ B = SEQ ID NO:2

<400> SEQUENCE: 13

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Cys Met Leu Thr Phe Lys Phe Tyr Met Pro Lys
                35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
                130

<210> SEQ ID NO 14
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:1
      and SEQ B = SEQ ID NO:12

<400> SEQUENCE: 14

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Cys Met Leu Thr Phe Lys Phe Tyr Met Pro Lys
                35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
```

```
                100             105             110
Thr Ile Val Glu Phe Leu Asn Arg Trp Ile Thr Phe Ser Gln Ser Ile
            115             120             125

Ile Ser Thr Leu Thr
        130

<210> SEQ ID NO 15
<211> LENGTH: 132
<212> TYPE: PRT
<213> ORGANISM: Artificial Sequence
<220> FEATURE:
<223> OTHER INFORMATION: aldesleukin

<400> SEQUENCE: 15

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 16
<211> LENGTH: 402
<212> TYPE: DNA
<213> ORGANISM: Artificial Sequence
<220> FEATURE:
<223> OTHER INFORMATION: DNA sequence encoding for IL-2 of SEQ ID NO:18

<400> SEQUENCE: 16
cccacttctt cgtcaaccaa aaagacacaa cttcaattgg agcacttatt gctggacttg      60
cagatgatat tgaatggaat taataactac aaaaatccta agcttacttg tatgctgact     120
ttcaaatttt atatgccaaa aaaggcaact gagctaaagc atctgcaatg tttagaagag     180
gaactaaaac cattggaaga ggtattgaat ctcgctcaat ctaaaaactt tcatcttcgt     240
cctagagatt tgatttccaa catcaatgtt atcgtgctgg aattgaaggg tagcgaaaca     300
actttcatgt gcgaatacgc cgatgagaca gctactatcg tcgagttctt aaacagatgg     360
attacatttt cccagagtat tatctcaacg ttgacctaat ga                        402

<210> SEQ ID NO 17
<211> LENGTH: 405
<212> TYPE: DNA
<213> ORGANISM: Artificial Sequence
<220> FEATURE:
<223> OTHER INFORMATION: DNA encoding IL-2 of SEQ ID NO:14

<400> SEQUENCE: 17
```

```
gcacctacat cttcttcaac taaaaagact caattacagt tggagcatct cttgcttgat    60
ttgcaaatga ttctgaatgg tatcaacaac tataaaaatc caaagctaac ctgtatgttg   120
acgtttaagt tttacatgcc aaaaaagca  acagagctta agcacttgca atgtttggaa   180
gaggaactga aaccccttga agaggttttg aatctggctc agtccaaaaa cttccattta   240
agacctcgtg acctaatttc caacatcaat gtaatcgtct tggaattgaa gggatcagag   300
acaactttca tgtgcgaata cgctgatgag actgccacaa tagtggaatt tctgaataga   360
tggattacct tctcgcaaag cattatcagt actttaactt aatga                   405

<210> SEQ ID NO 18
<211> LENGTH: 132
<212> TYPE: PRT
<213> ORGANISM: Artificial Sequence
<220> FEATURE:
<223> OTHER INFORMATION: IL-2 sequence of SEQ ID NO:1 + cysteine + SEQ
      ID NO:12

<400> SEQUENCE: 18

Pro Thr Ser Ser Ser Thr Lys Lys Thr Gln Leu Gln Leu Glu His Leu
 1               5                   10                  15

Leu Leu Asp Leu Gln Met Ile Leu Asn Gly Ile Asn Asn Tyr Lys Asn
            20                  25                  30

Pro Lys Leu Thr Cys Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 19
<211> LENGTH: 4844
<212> TYPE: DNA
<213> ORGANISM: Artificial Sequence
<220> FEATURE:
<223> OTHER INFORMATION: Vector pCSP1007

<400> SEQUENCE: 19
gggccccaaa catttgctcc ccctagtctc cagggaaatg taaaatatac tgctaataga    60
aaacagtaag acgctcagtt gtcaggataa ttacgttcga ctgtagtaaa acaggaatct   120
gtattgttag aaagaacgag agttttttac ggcgccgcca tattgggccg tgtgaaaaca   180
gcttgaaacc ccactacttt caaaggttct gttgctatac acgaaccatg tttaaccaac   240
ctcgcttttg acttgactga agtcatcggt taacaatcaa gtaccctagt ctgtctgaat   300
gctcctttcc atattcagta ggtgtttctt gcacttttgc atgcactgcg aagaattag    360 ccaatagcgc gtttcatatg cgcttttacc ccctcttttg tcaagcgcaa aatgcctgta   420
agatttggtg ggggtgtgag ccgttagctg aagtacaaca ggctaattcc ctgaaaaaac   480
tgcagctcag ggattcccac tatttggtat tctgatatgt ttttcctgat atgcatcaaa   540
```

```
actctaatct aaaacctgaa tctccgctat tttttttttt tttgatgacc ccgttttcgt    600
gacaaattaa tttccaacgg ggtcttgtcc ggataagaga attttgtttg attatccgtt    660
cggataaatg gacgcctgct ccatattttt ccggttatta ccccacctgg aagtgcccag    720
aattttccgg ggattacgga taatacggtg gtctggatta attaatacga gatctcaggg    780
attcccacta tttggtattc tgatatgttt ttcctgatat gcatcaaaac tctaatctaa    840
aacctgaatc tccgctattt tttttttttt tgatgacccc gttttcgtga caaattaatt    900
tccaacgggg tcttgtccgg ataagagaat tttgtttgat tatccgttcg gataaatgga    960
cgcctgctcc atattttttcc ggttattacc ccacctggaa gtgcccagaa ttttccgggg   1020
attacggata atacggtggt ctggattaat taatacgcca agtcttacat tttgttgcag   1080
tctcgtgcga gtatgtgcaa taataaacaa gatgagccaa tttattggat tagttgcagc   1140
ttgaccccgc catagctagg catagccaag tgctatgggt gttagatgat gcacttggat   1200
gcagtgagtt ttggagtata aaagatcctt aaaattccac ccttcctgca ggccatgaga   1260
tttccttcaa ttttttactgc tgttttattc gcagcatcct ccgcattagc tgctccagtc   1320
aacactacaa cagaagatga aacggcacaa attccggctg aagctgtcat cggttactca   1380
gatttagaag gggatttcga tgttgctgtt ttgccatttt ccaacagcac aaataacggg   1440
ttattgttta aaatactac tattgccagc attgctgcta aagaagaagg ggtatctctc    1500
gagaaaagac ccacttcttc gtcaaccaaa aagacacaac ttcaattgga gcacttattg   1560
ctggacttgc agatgatatt gaatggaatt aataactaca aaaatcctaa gcttacttgt   1620
atgctgactt tcaaatttta tatgccaaaa aaggcaactg agctaaagca tctgcaatgt   1680
ttagaagagg aactaaaacc attggaagag gtattgaatc tcgctcaatc taaaaacttt   1740
catcttcgtc ctagagattt gatttccaac atcaatgtta tcgtgctgga attgaagggt   1800
agcgaaacaa ctttcatgtg cgaatacgcc gatgagacag ctactatcgt cgagttctta   1860
aacagatgga ttacattttc ccagagtatt atctcaacgt tgacctaata gcggccgcct   1920
cggccggatc cacgtccgac ggcggcccac gggtccgagg cctcggagat ccgtcccccct  1980 tttcctttgt cgatatcatg taattagtta tgtcacgctt acattcacgc cctccccccca  2040 catccgctct aaccgaaaag gaaggagtta gacaacctga agtctaggtc cctatttatt   2100 ttttatagt tatgttagta ttaagaacgt tatttatatt tcaaattttt ctttttttc     2160 tgtacagacg cgtgtacgca tgtaacatta tactgaaaac cttgcttgag aaggttttgg   2220
gacgctcgaa ggctttaatt tgcaagctac cggtggtacc acacaccata gcttcaaaat   2280
gtttctactc cttttttact cttccagatt ttctcggact ccgcgcatcg ccgtaccact   2340
tcaaaacacc caagcacagc atactaaatt tcccctcttt cttcctctag ggtgtcgtta   2400
attacccgta ctaaaggttt ggaaaagaaa aagagaccg cctcgtttct ttttcttcgt    2460 cgaaaaggc aataaaaatt tttatcacgt ttctttttct tgaaaatttt ttttttgat     2520 tttttctct ttcgatgacc tcccattgat atttaagtta ataaacggtc ttcaatttct    2580
caagtttcag tttcattttt cttgttctat tacaacttttt tttacttctt gctcattaga   2640
aagaaagcat agcaatctaa tctaagggcg tgttgacaa ttaatcatcg gcatagtata    2700
tcggcatagt ataatacgac aaggtgagga actaaaccat ggccaagttg accagtgccg   2760
ttccggtgct caccgcgcgc gacgtcgccg gagcggtcga gttctggacc gaccggctcg   2820
ggttctcccg ggacttcgtg gaggacgact tcgccggtgt ggtccgggac gacgtgaccc   2880
```

| | |
|---|---:|
| tgttcatcag cgcggtccag gaccaggtgg tgccggacaa cacoctggcc tgggtgtggg | 2940 |
| tgcgcggcct ggacgagctg tacgccgagt ggtcggaggt cgtgtccacg aacttccggg | 3000 |
| acgcctccgg gccggccatg accgagatcg gcgagcagcc gtggggggcgg gagttcgccc | 3060 |
| tgcgcgaccc ggccggcaac tgcgtgcact tcgtggccga ggagcaggac tgatcagtac | 3120 |
| ttactgacaa taaaaagatt cttgttttca agaacttgtc atttgtatag ttttttttata | 3180 |
| ttgtagttgt tctattttaa tcaaatgtta gcgtgattta tatttttttt cgcctcgaca | 3240 |
| tcatctgccc agatgcgaag ttaagtgcgc agaaagtaat atcatgcgtc aatcgtatgt | 3300 |
| gaatgctggt cgctatactg gtaccgagct ctgagcaaaa ggccagcaaa gggccaggaa | 3360 |
| ccgtaaaaag gccgcgttgc tggcgttttt ccataggctc cgcccccctg acgagcatca | 3420 |
| caaaaatcga cgctcaagtc agaggtggcg aaacccgaca ggactataaa gataccaggc | 3480 |
| gtttccccct ggaagctccc tcgtgcgctc tcctgttccg accctgccgc ttaccggata | 3540 |
| cctgtccgcc tttctccctt cgggaagcgt ggcgctttct catagctcac gctgtaggta | 3600 |
| tctcagttcg gtgtaggtcg ttcgctccaa gctgggctgt gtgcacgaac cccccgttca | 3660 |
| gcccgaccgc tgcgccttat ccggtaacta tcgtcttgag tccaacccgg taagacacga | 3720 |
| cttatcgcca ctggcagcag ccactggtaa caggattagc agagcgaggt atgtaggcgg | 3780 |
| tgctacagag ttcttgaagt ggtggcctaa ctacggctac actagaagaa cagtatttgg | 3840 |
| tatctgcgct ctgctgaagc cagttacctt cggaaaaaga gttggtagct cttgatccgg | 3900 |
| cagacaaacc accgctggta gcggtggttt ttttgtttgc aagcagcaga ttacgcgcag | 3960 |
| aaaaaaagga tctcaagaag atcctttgat cttttctacg ggagctctta attaagcggc | 4020 |
| cgcagcaacg ttgtcactga agttggcatc agtatctaca aaccctacat acctcttgaa | 4080 |
| ggtccagaag gtaagcattt gcccgctcca ttcctacccg acatatccac tctacatttt | 4140 |
| atagttcaag gcaccgaaaa agttcgaaac aagaagtttg ttcctgataa caaggatttc | 4200 |
| tttattggtg ggacttcatt tactgtctcc aagaaggaca tttctgctgt cataaccgag | 4260 |
| atagtctcac agttcgagtc tactgatgac caaaagtcag agaaatttac catgaaatct | 4320 |
| cctcctccgg ttgctttagt tgggcataat ctgataggag acctcaagac actgaagaat | 4380 |
| gcgggtatca ccattcccat acttccaatc ataggatccg gcgcgccgat actcgagaat | 4440 |
| tatggcttaa tcaagtgaat acatcaaagt caaacttaaa atacattctt cgcaggcttg | 4500 |
| gcttgccaca tagttttctt cacaatgctg caaatgacgc ttattatacc cttttggcat | 4560 |
| cgttgaagct tgcacaaacg aacgtcccac ttaatcttct gtactctgaa gaggagtggg | 4620 |
| aaataccaag aaaaacatca aactcgaatg attttcccga accoctacca caagatattc | 4680 |
| atcagctgcg agataggctg atcaggagca agctcgtacg agaagaaaca aaatgacaaa | 4740 |
| aaaaatccta tactatatag gttacaaata aaaaagtatc aaaaatgaag cctgcatctc | 4800 |
| tcaggcaaat ggcattctga catcctctgc ggccgcttaa ttaa | 4844 |

<210> SEQ ID NO 20
<211> LENGTH: 4847
<212> TYPE: DNA
<213> ORGANISM: Artificial Sequence
<220> FEATURE:
<223> OTHER INFORMATION: Vector pCKP1036

<400> SEQUENCE: 20

| | |
|---|---:|
| gggcccaaa catttgctcc ccctagtctc cagggaaatg taaatatac tgctaataga | 60 |
| aaacagtaag acgctcagtt gtcaggataa ttacgttcga ctgtagtaaa acaggaatct | 120 |

-continued

```
gtattgttag aaagaacgag agttttttac ggcgccgcca tattgggccg tgtgaaaaca   180
gcttgaaacc ccactacttt caaaggttct gttgctatac acgaaccatg tttaaccaac   240
ctcgcttttg acttgactga agtcatcggt taacaatcaa gtaccctagt ctgtctgaat   300
gctcctttcc atattcagta ggtgtttctt gcacttttgc atgcactgcg gaagaattag   360
ccaatagcgc gtttcatatg cgcttttacc ccctcttttg tcaagcgcaa aatgcctgta   420
agatttggtg ggggtgtgag ccgttagctg aagtacaaca ggctaattcc ctgaaaaaac   480
tgcagctcag ggattcccac tatttggtat tctgatatgt ttttcctgat atgcatcaaa   540
actctaatct aaaacctgaa tctccgctat tttttttttt tttgatgacc ccgttttcgt   600
gacaaattaa tttccaacgg ggtcttgtcc ggataagaga attttgtttg attatccgtt   660
cggataaatg gacgcctgct ccatattttt ccggttatta ccccacctgg aagtgcccag   720
aattttccgg ggattacgga taatacggtg gtctggatta attaatacga gatctcaggg   780
attcccacta tttggtattc tgatatgttt ttcctgatat gcatcaaaac tctaatctaa   840
aacctgaatc tccgctattt ttttttttttt tgatgacccc gttttcgtga caaattaatt   900
tccaacgggg tcttgtccgg ataagagaat tttgtttgat tatccgttcg gataaatgga   960
cgcctgctcc atatttttcc ggttattacc ccacctggaa gtgcccagaa ttttccgggg  1020
attacggata atacggtggt ctggattaat taatacgcca gtcttacat tttgttgcag  1080 tctcgtgcga gtatgtgcaa taataaacaa gatgagccaa tttattggat tagttgcagc  1140
ttgaccccgc atagctagg catagccaag tgctatgggt gttagatgat gcacttggat  1200
gcagtgagtt ttggagtata aagatccttt aaaattccac ccttcctgca ggccatgaga  1260
tttccttcaa ttttttactgc tgttttattc gcagcatcct ccgcattagc tgctccagtc  1320
aacactacaa cagaagatga aacggcacaa attccggctg aagctgtcat cggttactca  1380
gatttagaag gggatttcga tgttgctgtt ttgccatttt ccaacagcac aaataacggg  1440
ttattgttta taaatactac tattgccagc attgctgcta aagaagaagg ggtatctctc  1500
gagaaaagag cacctacatc ttcttcaact aaaaagactc aattacagtt ggagcatctc  1560
ttgcttgatt tgcaaatgat tctgaatggt atcaacaact ataaaaatcc aaagctaacc  1620
tgtatgttga cgtttaagtt ttacatgcca aaaaaagcaa cagagcttaa gcacttgcaa  1680
tgtttggaag aggaactgaa accccttgaa gaggttttga atctggctca gtccaaaaac  1740
ttccatttaa gacctcgtga cctaattttcc aacatcaatg taatcgtctt ggaattgaag  1800
ggatcagaga caacttttcat gtgcgaatac gctgatgaga ctgccacaat agtggaattt  1860
ctgaatagat ggattacctt ctcgcaaagc attatcagta ctttaactta atagcggccg  1920
cctcggccgg atccacgtcc gacggcggcc cacgggtccg aggcctcgga gatccgtccc  1980
ccttttcctt tgtcgatatc atgtaattag ttatgtcacg cttacattca cgccctcccc  2040
ccacatccgc tctaaccgaa aaggaaggag ttagacaacc tgaagtctag gtccctattt  2100
atttttttat agttatgtta gtattaagaa cgttatttat atttcaaatt tttctttttt  2160
ttctgtacag acgcgtgtac gcatgtaaca ttatactgaa aaccttgctt gagaaggttt  2220
tgggacgctc gaaggcttta atttgcaagc taccggtggt accacacacc atagcttcaa  2280
aatgtttcta ctcctttttt actcttccag attttctcgg actccgcgca tcgccgtacc  2340
acttcaaaac acccaagcac agcatactaa atttcccctc tttcttcctc tagggtgtcg  2400
ttaattaccc gtactaaagg tttggaaaag aaaaaagaga ccgcctcgtt tctttttctt  2460
```

```
cgtcgaaaaa ggcaataaaa attttatca cgtttctttt tcttgaaaat ttttttttt      2520
gatttttttc tctttcgatg acctcccatt gatatttaag ttaataaacg gtcttcaatt      2580
tctcaagttt cagtttcatt tttcttgttc tattacaact tttttactt cttgctcatt      2640
agaaagaaag catagcaatc taatctaagg gcggtgttga caattaatca tcggcatagt      2700
atatcggcat agtataatac gacaaggtga ggaactaaac catggccaag ttgaccagtg      2760
ccgttccggt gctcaccgcg cgcgacgtcg ccggagcggt cgagttctgg accgaccggc      2820
tcgggttctc ccgggacttc gtggaggacg acttcgccgg tgtggtccgg gacgacgtga      2880
ccctgttcat cagcgcggtc caggaccagg tggtgccgga caacaccctg gcctgggtgt      2940
gggtgcgcgg cctggacgag ctgtacgccg agtggtcgga ggtcgtgtcc acgaacttcc      3000
gggacgcctc cgggccggcc atgaccgaga tcggcgagca gccgtggggg cgggagttcg      3060
ccctgcgcga cccggccggc aactgcgtgc acttcgtggc cgaggagcag gactgatcag      3120
tacttactga caataaaaag attcttgttt tcaagaactt gtcatttgta tagttttttt      3180
atattgtagt tgttctattt taatcaaatg ttagcgtgat ttatatttt tttcgcctcg      3240
acatcatctg cccagatgcg aagttaagtg cgcagaaagt aatatcatgc gtcaatcgta      3300
tgtgaatgct ggtcgctata ctggtaccga gctctgagca aaaggccagc aaagggccag      3360
gaaccgtaaa aaggccgcgt tgctggcgtt tttccatagg ctccgccccc ctgacgagca      3420
tcacaaaaat cgacgctcaa gtcagaggtg gcgaaacccg acaggactat aaagatacca      3480
ggcgtttccc cctggaagct ccctcgtgcg ctctcctgtt ccgaccctgc cgcttaccgg      3540
atacctgtcc gcctttctcc cttcgggaag cgtggcgctt tctcatagct cacgctgtag      3600
gtatctcagt tcggtgtagg tcgttcgctc caagctgggc tgtgtgcacg aaccccccgt      3660
tcagcccgac cgctgcgcct tatccggtaa ctatcgtctt gagtccaacc cggtaagaca      3720
cgacttatcg ccactggcag cagccactgg taacaggatt agcagagcga ggtatgtagg      3780
cggtgctaca gagttcttga agtggtggcc taactacggc tacactagaa gaacagtatt      3840
tggtatctgc gctctgctga agccagttac cttcggaaaa agagttggta gctcttgatc      3900
cggcagacaa accaccgctg gtagcggtgg ttttttgtt tgcaagcagc agattacgcg      3960
cagaaaaaaa ggatctcaag aagatccttt gatcttttct acgggagctc ttaattaagc      4020
ggccgcagca acgttgtcac tgaagttggc atcagtatct acaaacccta catcctctt      4080
gaaggtccag aaggtaagca tttgcccgct ccattcctac ccgacatatc cactctacat      4140
tttatagttc aaggcaccga aaagttcga acaagaagtt ttgttcctga taacaaggat      4200
ttctttattg gtgggacttc atttactgtc tccaagaagg acatttctgc tgtcataacc      4260
gagatagtct cacagttcga gtctactgat gaccaaaagt cagagaaatt taccatgaaa      4320
tctcctcctc cggttgcttt agttgggcat aatctgatag gagacctcaa gacactgaag      4380
aatgcgggta tcaccattcc catacttcca atcataggat ccggcgcgcc gatactcgag      4440
aattatggct taatcaagtg aatacatcaa agtcaaactt aaaatacatt cttcgcaggc      4500
ttggcttgcc acatagtttt cttcacaatg ctgcaaatga cgcttattat acccttttgg      4560
catcgttgaa gcttgcacaa acgaacgtcc cacttaatct tctgtactct gaagaggagt      4620
gggaaatacc aagaaaaaca tcaaactcga atgatttcc cgaacccta ccacaagata      4680
ttcatcagct gcgagatagg ctgatcagga gcaagctcgt acgagaagaa acaaaatgac      4740
aaaaaaaatc ctatactata taggttacaa ataaaaagt atcaaaaatg aagcctgcat      4800
ctctcaggca aatggcattc tgacatcctc tgcggccgct taattaa      4847
```

```
<210> SEQ ID NO 21
<211> LENGTH: 132
<212> TYPE: PRT
<213> ORGANISM: Artificial Sequence
<220> FEATURE:
<223> OTHER INFORMATION: IL-2 mutein

<400> SEQUENCE: 21

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Cys Met Leu Thr Phe Lys Phe Tyr Met Pro Lys Lys
            35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 22
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:3
      and SEQ B = SEQ ID NO:2

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Ala Leu Thr Cys Met Leu Thr Phe Lys Phe Tyr Met Pro Lys
            35                  40                  45

Lys Ala Thr Glu Leu Lys His Leu Gln Cys Leu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 23
<211> LENGTH: 133
```

<212> TYPE: PRT
<213> ORGANISM: Artificial Sequence
<220> FEATURE:
<223> OTHER INFORMATION: IL-2 of formula (I) with SEQ A = SEQ ID NO:3
      and SEQ B = SEQ ID NO:12

<400> SEQUENCE: 23

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Ala Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 24
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:4
      and SEQ B = SEQ ID NO:2

<400> SEQUENCE: 24

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Cys Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 25
<211> LENGTH: 133
<212> TYPE: PRT
<213> ORGANISM: Artificial Sequence
<220> FEATURE:

```
<223> OTHER INFORMATION: IL-2 of formula (I) with SEQ A = SEQ ID NO:4
      and SEQ B = SEQ ID NO:12

<400> SEQUENCE: 25

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Cys Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 26
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:5
      and SEQ B = SEQ ID NO:2

<400> SEQUENCE: 26

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Gly Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 27
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:5
      and SEQ B = SEQ ID NO:12
```

<400> SEQUENCE: 27

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Gly Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 28
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:6
      and SEQ B = SEQ ID NO:2

<400> SEQUENCE: 28

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Ser Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 29
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:6
      and SEQ B = SEQ ID NO:12

<400> SEQUENCE: 29

Ala Pro Thr Ser Ser Ser Thr Lys Lys Thr Gln Leu Gln Leu Glu His

```
                1               5                   10                  15
Leu Leu Leu Asp Leu Gln Met Ile Leu Asn Gly Ile Asn Asn Tyr Lys
            20                  25                  30

Asn Pro Ser Leu Thr Cys Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 30
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:7
      and SEQ B = SEQ ID NO:2

<400> SEQUENCE: 30

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Thr Leu Thr Cys Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
            130

<210> SEQ ID NO 31
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:7
      and SEQ B = SEQ ID NO:12

<400> SEQUENCE: 31

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
```

```
                20                  25                  30

Asn Pro Thr Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 32
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:8
      and SEQ B = SEQ ID NO:2

<400> SEQUENCE: 32

Ala Pro Thr Ser Ser Ser Thr Lys Lys Thr Gln Leu Gln Leu Glu His
 1                   5                  10                  15

Leu Leu Leu Asp Leu Gln Met Ile Leu Asn Gly Ile Asn Asn Tyr Lys
                20                  25                  30

Asn Pro Gln Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 33
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:8
      and SEQ B = SEQ ID NO:12

<400> SEQUENCE: 33

Ala Pro Thr Ser Ser Ser Thr Lys Lys Thr Gln Leu Gln Leu Glu His
 1                   5                  10                  15

Leu Leu Leu Asp Leu Gln Met Ile Leu Asn Gly Ile Asn Asn Tyr Lys
                20                  25                  30

Asn Pro Gln Leu Thr Cys Met Leu Thr Phe Lys Phe Tyr Met Pro Lys
```

```
                35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
                130

<210> SEQ ID NO 34
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:9
      and SEQ B = SEQ ID NO:2

<400> SEQUENCE: 34

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Glu Leu Thr Cys Met Leu Thr Phe Lys Phe Tyr Met Pro Lys
                 35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
                130

<210> SEQ ID NO 35
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:9
      and SEQ B = SEQ ID NO:12

<400> SEQUENCE: 35

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Glu Leu Thr Cys Met Leu Thr Phe Lys Phe Tyr Met Pro Lys
                 35                  40                  45

Lys Ala Thr Glu Leu Lys His Leu Gln Cys Leu Glu Glu Glu Leu Lys
```

```
                 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 36
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:10
      and SEQ B = SEQ ID NO:2

<400> SEQUENCE: 36

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Asn Leu Thr Cys Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 37
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:10
      and SEQ B = SEQ ID NO:12

<400> SEQUENCE: 37

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Asn Leu Thr Cys Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
```

```
                65                  70                  75                  80
Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 38
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:11
      and SEQ B = SEQ ID NO:2

<400> SEQUENCE: 38

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Asp Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 39
<211> LENGTH: 133
<212> TYPE: PRT
<213> ORGANISM: Artificial Sequence
<220> FEATURE:
<223> OTHER INFORMATION: IL-2 of formula (I) with SEQ A = SEQ ID NO:11
      and SEQ B = SEQ ID NO:12

<400> SEQUENCE: 39

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Asp Leu Thr Cys Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
```

```
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
    130

<210> SEQ ID NO 40
<211> LENGTH: 402
<212> TYPE: DNA
<213> ORGANISM: Artificial Sequence
<220> FEATURE:
<223> OTHER INFORMATION: DNA sequence encoding SEQ ID NO:14 in E.Coli

<400> SEQUENCE: 40
gcacctactt caagttctac aaagaaaaca cagctacaac tggagcattt acttctggat     60
ttacagatga ttttgaatgg aattaataat tacaagaatc ccaaactcac ctgtatgctc    120
acatttaagt tttacatgcc caagaaggcc acagaactga acatcttca gtgtctagaa     180 gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct tttctcaaag catcatctca acactgactt aa                      402

<210> SEQ ID NO 41
<211> LENGTH: 402
<212> TYPE: DNA
<213> ORGANISM: Artificial Sequence
<220> FEATURE:
<223> OTHER INFORMATION: DNA sequence encoding SEQ ID NO:35 in E.Coli

<400> SEQUENCE: 41
gcacctactt caagttctac aaagaaaaca cagctacaac tggagcattt acttctggat     60
ttacagatga ttttgaatgg aattaataat tacaagaatc ccgaactcac ctgtatgctc    120
acatttaagt tttacatgcc caagaaggcc acagaactga acatcttca gtgtctagaa     180 gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct tttctcaaag catcatctca acactgactt aa                      402

<210> SEQ ID NO 42
<211> LENGTH: 402
<212> TYPE: DNA
<213> ORGANISM: Artificial Sequence
<220> FEATURE:
<223> OTHER INFORMATION: DNA sequence encoding SEQ ID NO:39 in E.Coli

<400> SEQUENCE: 42
gcacctactt caagttctac aaagaaaaca cagctacaac tggagcattt acttctggat     60
ttacagatga ttttgaatgg aattaataat tacaagaatc ccgacctcac ctgtatgctc    120
acatttaagt tttacatgcc caagaaggcc acagaactga acatcttca gtgtctagaa     180 gaagaactca aacctctgga ggaagtgcta aatttagctc aaagcaaaaa ctttcactta    240
agacccaggg acttaatcag caatatcaac gtaatagttc tggaactaaa gggatctgaa    300
```

```
acaacattca tgtgtgaata tgctgatgag acagcaacca ttgtagaatt tctgaacaga    360
tggattacct tttctcaaag catcatctca acactgactt aa                       402
```

<210> SEQ ID NO 43
<211> LENGTH: 402
<212> TYPE: DNA
<213> ORGANISM: Artificial Sequence
<220> FEATURE:
<223> OTHER INFORMATION: DNA sequence encoding SEQ ID NO:33 in E.Coli

<400> SEQUENCE: 43

```
gcacctactt caagttctac aaagaaaaca cagctacaac tggagcattt acttctggat    60
ttacagatga ttttgaatgg aattaataat tacaagaatc cccaactcac ctgtatgctc    120
acatttaagt tttacatgcc caagaaggcc acagaactga acatcttca gtgtctagaa     180 gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct tttctcaaag catcatctca acactgactt aa                       402
```

<210> SEQ ID NO 44
<211> LENGTH: 401
<212> TYPE: DNA
<213> ORGANISM: Artificial Sequence
<220> FEATURE:
<223> OTHER INFORMATION: DNA sequence encoding SEQ ID NO:29 in E.Coli

<400> SEQUENCE: 44

```
gcacctactt caagttctac aaagaaaaca cagctacaac tggagcattt acttctggat    60
ttacagatga ttttgaatgg aattaataat tacaagaatc ccagcctcac ctgtatgctc    120
acatttaagt tttacatgcc caagaaggcc acagaactga acatcttca gtgtctagaa     180 gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct tttctcaaag catcatctca acactgactt a                        401
```

<210> SEQ ID NO 45
<211> LENGTH: 134
<212> TYPE: PRT
<213> ORGANISM: Artificial Sequence
<220> FEATURE:
<223> OTHER INFORMATION: IL-2 variant

<400> SEQUENCE: 45

```
Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95
```

```
Leu Lys Gly Ser Glu Thr Thr Phe Met Cys Glu Tyr Ala Asp Glu Thr
            100                 105                 110
Ala Thr Ile Val Glu Phe Leu Asn Arg Trp Ile Thr Phe Ala Gln Ser
        115                 120                 125
Ile Ile Ser Thr Leu Thr
        130
```

<210> SEQ ID NO 46
<211> LENGTH: 139
<212> TYPE: PRT
<213> ORGANISM: Artificial Sequence
<220> FEATURE:
<223> OTHER INFORMATION: IL-2 variant with His-tag

<400> SEQUENCE: 46

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr His His His His His His
    130                 135
```

<210> SEQ ID NO 47
<211> LENGTH: 19
<212> TYPE: PRT
<213> ORGANISM: Artificial Sequence
<220> FEATURE:
<223> OTHER INFORMATION: Signal peptide S1

<400> SEQUENCE: 47

```
Met Glu Phe Gly Leu Ser Trp Leu Phe Leu Val Ala Ile Leu Lys Gly
1               5                   10                  15
Val Gln Cys
```

<210> SEQ ID NO 48
<211> LENGTH: 16
<212> TYPE: PRT
<213> ORGANISM: Artificial Sequence
<220> FEATURE:
<223> OTHER INFORMATION: Signal peptide S2

<400> SEQUENCE: 48

```
Met Pro Leu Leu Leu Leu Leu Pro Leu Leu Trp Ala Gly Ala Leu Ala
1               5                   10                  15
```

TREATING CANCER WITH A CONJUGATE COMPRISING AN IL-2 MOIETY

CROSS-REFERENCE TO RELATED APPLICATIONS

This application is a national stage entry of International Application No. PCT/EP2021/064781 filed Jun. 2, 2021, which claims the benefit of EP Application Serial No. 20177974.1 filed Jun. 3, 2020, EP Application Serial No. 20202299.2 filed Oct. 16, 2020, EP Application Serial No. 20216052.9 filed Dec. 21, 2020, EP Application Serial No. 21160477.2 filed Mar. 3, 2021, and EP Application Serial No. 21162030.7 filed Mar. 11, 2021, and U.S. Application No. 63/116,102 filed Nov. 19, 2020.

REFERENCE TO SEQUENCE LISTING

This application includes an electronic sequence listing in a file named 587191SEQLST, created on Oct. 26, 2022, and containing 57,258 bytes, which is hereby incorporated by reference.

The present invention relates to an IL-2 protein sequence of the formula Ala-SEQ A-Cys*-SEQ B (I), wherein SEQ A has at least 94% sequence identity to SEQ ID NO:1; SEQ B has at least 94% sequence identity to SEQ ID NO:2; Ala is an alanine residue; and Cys* is a cysteine residue; to conjugates thereof and their uses in the treatment of cell-proliferation disorders.

In healthy humans, the immune system can often discriminate between healthy cells and cancerous cells. Upon identifying a given cell as cancerous, the immune system typically eliminates it. However, when the immune system is compromised from e.g. acute or chronic defects or is overwhelmed, cancers can develop resulting from a compromised immune system's inability to differentiate, and then eliminate, cancer cells. In a patient suffering from cancer, administration of an immunomodulatory protein to the patient may help activate that patient's immune system so that the immune system's ability to eliminate cancer cells is enhanced. In a patient suffering from a viral infection, administration of an immunomodulatory protein to the patient may help activate that patient's immune system so that the immune system's ability to eliminate the viral infection is enhanced. Similarly, even in a healthy patient the immune response to a vaccine can be enhanced by the addition of such immunomodulatory proteins.

One such immunomodulatory protein used in the treatment of patients suffering from certain cancers is interleukin-2 (IL-2). IL-2 plays a central role in the generation, differentiation, survival and homeostasis of immune effector cells. IL-2 is synthesized by activated CD4+ helper T cells, and through differential receptor interaction IL-2 can modulate the immune response towards immunity or tolerance.

IL-2 acts by binding to IL-2 receptors (IL-2R). Association of the α-(CD25), β-(CD122) and common γ-(γc, CD132) subunits results in the trimeric high-affinity IL-2R. The dimeric intermediate affinity IL-2Rβγ consists of the β- and γ-subunits and binds IL-2 with 50-fold lower affinity. CD25 is not required for IL-2 signaling but confers the high affinity binding of the trimeric receptor, whereas the β- and γ-subunits mediate signal transduction. IL-2Rβγ is expressed on NK cells, monocytes, macrophages, γδ T cells and resting CD4+ and CD8+ T cells, while IL-2Rαβγ is transiently induced on activated T and NK cells, and is constitutively expressed on T regulatory cells as well as type 2 innate lymphocyte cells (ILC2s), eosinophils and endothelial cells. The ability of IL-2 to expand and activate innate and adaptive effector cells is the basis of its antitumor activity.

In patients, IL-2 can stimulate antitumor efficacy, characterized by increases in cytotoxic lymphocytes, including effector T and NK cells, when given at high-doses (i.e., 600 000-720 000 IU/kg body weight three times daily for up to 14 doses per cycle in humans). Presumably during this therapy all T cells are stimulated by IL-2 after high-doses are administered and when the therapy cycle ends as well as at the later timepoints after any individual dose and IL-2 levels drop at some point IL-2 will become limiting and T regulatory (Treg) cells expressing IL-2Rαβγ will outcompete effector T cells expressing IL-2Rβγ for the remaining wild type IL-2.

However, IL-2's antitumor immunity is dose limited by severe cardiovascular, pulmonary, hepatic, gastrointestinal, neurologic and hematological side effects, such that it is only given to patients at specialized centers. Many of these adverse events are characterized by a vascular leak syndrome (VLS) also known as capillary leak syndrome. There are several proposed mechanisms for causing VLS many of which involve interaction between wild type IL-2 and IL-2Rαβγ expressing cells such as ILC2s, eosinophils, and endothelial cells.

Effector CD4+ T cells, CD8+ T cells, γδ T cells, in particular Vγ9Vδ2 T cells, and NK cells, which significantly enhance anti-tumor immune responses, preferentially express the IL-2Rβγ form of the IL-2R. Thus, administration of compounds that bind to and are agonists for IL-2Rβγ can be expected to enhance the immune response against tumors (by, e.g., increasing the proliferation and activity of effect of CD4+ T cells, CD8+ T cells, γδ T cells, in particular Vγ9Vδ2 T cells, and NK cells).

Thus, administration of IL-2Rβγ-selective agonists (having reduced or no binding to IL-2Rα or enhanced binding to IL-2Rβγ) would be beneficial to patients suffering from certain cancers as doing so is expected to reduce systemic vascular leak side effects such as pulmonary edema, providing an improved therapeutic window.

One way of synthesizing such biased IL-2, i.e. an IL-2 protein that preferentially binds to IL-2Rβγ, is mutating a certain amino acid involved in binding to IL-2Rα, for example by replacing it with a cysteine. Such cysteine may optionally be used to conjugate certain moieties to it, which may enhance the non-IL-2Rα binding bias even further.

However, manufacturing proteins, such as IL-2, with an additional cysteine may be problematic, because such proteins may have a tendency to aggregate and it may be difficult or impossible to ensure proper renaturation of such protein with sufficient quality and in sufficient amounts.

It is therefore an object of the present invention to at least partially overcome the above-mentioned disadvantage.

This object is achieved with an IL-2 protein sequence of formula (I)

$$\text{(I)} \qquad \text{Ala-SEQ A-Cys*-SEQ B,}$$

wherein
SEQ A has at least 94% sequence identity to SEQ ID NO:1;
SEQ B has at least 94% sequence identity to SEQ ID NO:2;
Ala is an alanine residue; and
Cys* is a cysteine residue.

It was surprisingly found that the addition of an N-terminal alanine residue significantly improved yields when such IL-2 protein is expressed as a soluble protein in, for example, a mammalian expression system or a yeast expression system, compared to the corresponding IL-2 sequence without such N-terminal alanine. The cysteine marked with the asterisk may be a free cysteine, i.e. one where the thiol is not part of a disulfide bond, or it may be coupled to a thiol-comprising compound, such as to a cysteine, via a disulfide bridge.

Such IL-2 of formula (I) may be a biased IL-2.

Within the present invention the terms are used having the meaning as follows.

In general, the term "interleukin-2" or "IL-2" refers to all IL-2 proteins, preferably from mammalian species, more preferably from primate species and most preferably from human, as well as their variants, analogs, orthologs, homologs, and derivatives and fragments thereof, that are characterized by playing a central role in lymphocyte generation, survival and homeostasis, and also encompasses naturally occurring variants of IL-2, e.g. splice variants or allelic variants.

In the context of this invention the terms "interleukin-2" and "IL-2" refer to the protein having the sequence of formula (I).

As used herein, the term "biased IL-2" refers to a modified IL-2, in which the ratio of the $K_D$ of said biased IL-2 to IL-2Rα to the $K_D$ of said biased IL-2 to IL-2Rβ is larger than the ratio of the $K_D$ of aldesleukin of SEQ ID NO:15 to IL-2Rα to the $K_D$ of aldesleukin to IL-2Rβ. This is described by the following formula:

$$\frac{Ratio_{biased\,IL-2}}{Ratio_{aldesleukin}} > 1$$

wherein $$Ratio_{biased\,IL-2} = \frac{K_D\ biased\ IL-2\ to\ IL-2R\alpha}{K_D\ biased\ IL-2\ to\ IL-2\beta}$$

$$Ratio_{aldesleukin} = \frac{K_D\ aldesleukin\ to\ IL-2R\alpha}{K_D\ aldesleukin\ to\ IL-2\beta}$$

with

"$K_D$ biased IL-2 to IL-2Rα" being the $K_D$ of biased IL-2 to IL-2Rα,

"$K_D$ biased IL-2 to IL-2Rβ" being the $K_D$ of biased IL-2 to IL-2Rβ,

"$K_D$ aldesleukin to IL-2Rα" being the $K_D$ of aldesleukin to IL-2Rα, and

"$K_D$ aldesleukin to IL-2Rβ" being the $K_D$ of aldesleukin to IL-2Rβ.

Aldesleukin (SEQ ID NO:15) has the following sequence:

PTSSSTKKTQLQLEHLLLDLQMILNGINNYKNPKLTRMLTFKFYMPKKAT

ELKHLQCLEEELKPLEEVLNLAQSKNFHLRPRDLISNINVIVLELKGSET

TFMCEYADETATIVEFLNRWITFSQSIISTLT

Binding affinity/kinetics needed to determine the $K_D$ of biased IL-2 to IL-2Rα, the $K_D$ of biased IL-2 to IL-2Rβ, the $K_D$ of aldesleukin to IL-2Rα and the $K_D$ of aldesleukin to IL-2Rβ may be assessed using surface plasmon resonance (SPR), measured on a Biacore instrument (GE Healthcare) as follows: A human Fc capture surface on a CM5 (or alternatively C1 or CM4) chip is prepared by covalent coating with anti-human Fc antibody or alternatively a protein A chip is used. Next, IL-2Rβ-Fc or IL2-Rα-Fc is immobilized on the chip. To measure the affinity/kinetic constants, serial dilutions of the analytes are made starting at for example between 1 nM and 2 µM or at 30 nM and 500 nM for IL-2 compounds. Analytes are each exposed to the receptor-modified chip for a suitable amount of time, such as for 1 to 30 minutes, which may for example be 2 minutes or may be 3 minutes and are then washed away for a suitable amount of time, such as 2 to 60 minutes, which may for example be 10 minutes. The resulting binding curves from the dilution series are fit to a 1:1 kinetic model to correlate observed response units (R) to the association and dissociation rate constants, $k_a$ and $k_d$:

$$R = \frac{k_a C R_{max}}{k_a C + k_d} \times \left(1 - e^{-(k_a C + k_d)t}\right)$$

wherein t is time;

C is the concentration of the analyte; and $R_{max}$ is the maximum binding capacity of the surface.

If determined via a kinetic 1:1 model the ratio of the dissociation and association rates provides the equilibrium dissociation constant $K_D$.

Alternatively, the resulting binding curves from the dilution series are fit to a 1:1 steady state interaction model which calculates $K_D$ for a 1:1 interaction from a plot of steady-state binding levels ($R_{eq}$) against analyte concentration (C):

$$R_{eq} = \frac{C \times R_{max}}{K_D + C}$$

wherein $R_{eq}$ is the steady-state binding level;

C is the concentration of the analyte; and $R_{max}$ is the maximum binding capacity of the surface.

It is understood that not every calculation method may be possible for every biased IL-2 molecule. If, for example, the reactions are too fast, it may not be possible to use a 1:1 kinetic model and a 1:1 steady state interaction model may be used. If, for example, no equilibrium is obtained, it may not be possible to use a 1:1 interaction model and a 1:1 kinetic model may be used.

As used herein, the term "affinity" refers to the strength of the sum of non-covalent interactions between a single binding site of a molecule (such as a receptor) and its binding partner (such as a ligand). Unless indicated otherwise, as used herein, "affinity" refers to intrinsic binding affinity which reflects a 1:1 interaction between members of a binding pair (such as between a receptor and a ligand). The affinity of a molecule X for its partner Y can generally be represented by the equilibrium dissociation constant ($K_D$), which is the ratio of dissociation and association rate constants ($k_d$ and $k_a$, respectively) measured in a state of equilibrium. Thus, equivalent affinities may comprise different rate constants, as long as the ratio of the rate constants remains the same. Affinity can be measured by well-established methods known in the art, including those described herein.

As used herein, the terms "α-subunit of the IL-2 receptor" and "IL-2Rα" refer to human CD25.

As used herein, the terms "β-subunit of the IL-2 receptor" and "IL-2Rβ" refer to human CD122.

As used herein, the terms "γ-subunit of the IL-2 receptor" and "IL-2Rγ" refer to human CD132.

As used herein the term "pattern recognition receptor agonist" ("PRRA") refers to a molecule that binds to and activates one or more immune cell-associated receptor that recognizes pathogen-associated molecular patterns (PAMPs) or damage-associated molecular patterns (DAMPs), leading to immune cell activation and/or pathogen- or damage-induced inflammatory responses. Pattern recognition receptors are typically expressed by cells of the innate immune system such as monocytes, macrophages, dendritic cells (DCs), neutrophils, and epithelial cells, as well as cells of the adaptive immune system.

As used herein the terms "cytotoxic agent" and "chemotherapeutic agent" are used synonymously and refer to compounds that are toxic to cells, which prevent cellular replication or growth, leading to cellular destruction/death. Examples of cytotoxic agents include chemotherapeutic agents and toxins, such as small molecule toxins or enzymatically active toxins of bacterial, fungal, plant or animal origin, including synthetic analogues and derivatives thereof.

As used herein the terms "immune checkpoint inhibitor" and "immune checkpoint antagonist" are used synonymously and refer to compounds that interfere with the function of, or inhibit binding of ligands that induce signaling through, cell-membrane expressed receptors that inhibit inflammatory immune cell function upon receptor activation. Such compounds may for example be biologics, such as antibodies, antibody fragments, affibodies, affilins, affimers, affitins, alphamabs, alphabodies, anticalins, avimers, DARPins, Fynomers®, Kunitz domain peptides, monobodies, nanoCLAMPs, cyclic peptides, peptides, Heavy Chain only antibodies, VHH antibodies or Nanobodies®, single chain variable Fragments (scFvs), natural or modified ligands or binding partners for these receptors or small molecule inhibitors.

As used herein the term "immune activating agonist" refers to compounds that directly or indirectly activate cell-membrane expressed checkpoint receptors.

As used herein the term "immune activating receptor agonist" refers to compounds that stimulate immune cell function upon activating or costimulatory receptor activation. Examples of such stimulatory receptors include CD3 subunits CD3γ, CD3δ, CD3ε and CD3ζ ((CD247), T cell receptor (TCR) subunits TCRα, TCRβ, TCRγ, and TCRδ, B cell receptor (BCR) chains or signaling units CD79a or CD79b, CD2, CD4, CD8, CD16, CD32a, CD64, CD27, CD28, CD134 (OX40), CD137 (41BB), CD244 (2B4), CD278 (ICOS), CD357 (GITR), CRACC(CS1), LFA-1, NKG2D, NKG2C, NKp30, NKp46, NKp44, NKp80, NTB-A, activating short form KIR (KIR2DS1, KIR2DS2, KIR2DS3, KIR2DS4, KIR2DS5, KIR3DS1), CD40, SIRP-β, Dectin-1, Dectin-2, TREM1, TREM2, ILT1, ILT6, ILT7, ILT8, LIR-6, MDL1, and other immune receptors which utilize an immunotyrosine receptor based activation motif (ITAM) or induce signaling through the PI3K, JAK/STAT, MyD88, IRF, NFKB or JNK/AP1 pathways. Many multi-specific drugs are types of immune activating receptor agonists.

As used herein the terms "multi-specific" and "multi-specific drugs" refer to compounds that simultaneously bind to two or more different antigens and can mediate antagonistic, agonistic, or specific antigen binding activity in a target-dependent manner. In this context, the term "simultaneously" does not refer to a temporal or spatial dependency but means that a single multi-specific drug is capable of binding two or more antigens, either at the same or a different location, at the same or a different time point.

As used herein the term "antibody-drug conjugate" (ADC) refers to compounds typically consisting of an antibody linked to a biologically active cytotoxic payload, radiotherapy, or other drug designed to deliver cytotoxic agents to the tumor environment. ADCs are particularly effective for reducing tumor burden without significant systemic toxicity and may act to improve the effectiveness of the immune response induced by checkpoint inhibitor antibodies.

As used herein the term "antibody-adjuvant conjugate" (AAC) refers to compounds consisting of an antibody linked to a biologically active adjuvant, either directly or through a linker.

As used herein, the term "adjuvant" refers to a substance which enhances the body's immune response to an antigen.

As used herein the term "boltbody" refers to an antibody-adjuvant conjugate comprising (a) an antibody moiety comprising (i) an antigen binding domain and (ii) an Fc domain, (b) an adjuvant moiety, and (c) a linker comprising an ethylene glycol group or a glycine residue, wherein each adjuvant moiety is covalently bonded to the antibody moiety via the linker, which linker can be cleavable or non-cleavable.

As used herein the term "radionuclides" refers to radioactive isotopes that emit ionizing radiation leading to cellular destruction/death. Radionuclides conjugated to tumor targeting carriers are referred to as "targeted radionuclide therapeutics".

As used herein the term "DNA damage repair inhibitor" refers to a drug that targets DNA damage repair elements, such as for example CHK1, CHK2, ATM, ATR and PARP. Certain cancers are more susceptive to targeting these pathways due to existing mutations or pathway alterations, such as BRCA1 mutated patients or homologous recombination pathway deficient patients to PARP inhibitors due to the concept of synthetic lethality.

As used herein the term "tumor metabolism inhibitor" refers to a compound that interferes with the function of one or more enzymes expressed in the tumor environment that produce metabolic intermediates that may inhibit immune cell function.

As used herein the term "protein kinase inhibitor" refers to compounds that inhibit the activity of one or more protein kinases. Protein kinases are enzymes that phosphorylate proteins, which in turn can modulate protein function. It is understood that a protein kinase inhibitor may target more than one kinase and any classification for protein kinase inhibitors used herein refers to the main or most characterized target.

As used herein the term "chemokine receptor and chemoattractant receptor agonist" refers to compounds that activate chemokine or chemoattractant receptors, a subset of G-protein coupled receptors or G-protein coupled-like receptors that are expressed on a wide variety of cells and are primarily involved in controlling cell motility (chemotaxis or chemokinesis). These receptors may also participate in non-cell migratory processes, such as angiogenesis, cell maturation or inflammation.

As used herein the term "cytokine receptor agonist" refers to soluble proteins which control immune cell activation and proliferation. Cytokines include for example interferons, interleukins, lymphokines, and tumor necrosis factor.

As used herein the term "death receptor agonist" refers to a molecule which is capable of inducing pro-apoptotic signaling through one or more of the death receptors, such as DR4 (TRAIL-R1) or DR5 (TRAIL-R2). The death receptor agonist may be selected from the group consisting of antibodies, death ligands, cytokines, death receptor agonist expressing vectors, peptides, small molecule agonists, cells (such as for example stem cells) expressing the death receptor agonist, and drugs inducing the expression of death ligands.

As used herein the term "antigen-presenting cell" or "APC" refers to a cell, such as a macrophage, a B cell, or a dendritic cell, that presents processed antigenic peptides via MHC class II molecules to the T cell receptor on CD4 T cells. APCs can be identified by a person skilled in the art by using phenotypic techniques such as flow cytometry. Phenotypic markers used to identify APCs vary by species and by tissue but may include myeloid or dendritic cell surface markers (e.g. CD11b, CD11c, CD14, CD16, CD33, CD34, CD68, CD206, MHC-II, CD163, Ly6C, Ly6G, GR-1, F4/80) or B cell surface markers (e.g. CD19, CD20, B220).

As used herein the term "MHCII" refers to a class of major histocompatibility complex (MHC) molecules normally found only on antigen-presenting cells such as myeloid cells, dendritic cells, and B cells. MHCII presents processed antigenic peptides to the T cell receptor on CD4 T cells. MHCII expression can be measured by a person skilled in the art using protein expression profiling techniques such as flow cytometry. Changes in MHCII expression can be determined by analyzing changes in the median fluorescence intensity signal of MHCII, or the percentage of cells positive for MHCII, in a specific cell subset of interest.

As used herein the term "T cells" refers to a type of immune cell that plays a central role in the adaptive immune response. T cells are distinguished from other immune cells by the presence of either an $\alpha\beta$ or $\gamma\delta$ T cell receptor (TCR) on their cell surface. T cells also express CD3—a protein complex critical for TCR signaling. $\alpha\beta$ T cells can be divided into either CD4, CD8, or CD4/CD8 double negative subsets. Due to the high surface density of CD4 and CD8 on $CD4^+$ and $CD8^+$ T cells, CD4 and CD8 alone can often be used to identify $CD4^+$ and $CD8^+$ T cells respectively. $\gamma\delta$ T cells are equipped with a TCR consisting of a $\gamma$ chain and $\delta$ chain, which, like the $\alpha\beta$ TCR, is central for recognition of antigens and cellular activation. This TCR is also used to distinguish between the different subsets of $\gamma\delta$ T cells, being V$\delta$1 and V$\delta$2. V$\delta$1 T cells are the minority (<5%) and a heterogeneous population of $\gamma\delta$ T cells with both anti- and pro-inflammatory functions. V$\delta$2 T cells are a single relatively homogenous T cell population of V$\gamma$9V$\delta$2 (V$\delta$2) T cells that make up ~95% of $\gamma\delta$ T cells in circulation. Due to the unique properties of their TCR and additional innate immune receptors, V$\delta$2 T cells are endowed with potent anti-tumor properties that can be harnessed for immunotherapy. Following activation via TCR recognition of cognate antigen presented by MHC molecules, T cells can mature and divide to generate effector or memory T cells. Memory T cells are a subset of T cells that have previously encountered and responded to their cognate antigen. Such T cells can recognize pathogenic antigens, such as antigens derived from bacteria or viruses, as well as cancer-associated antigens. T cells can be identified by a person skilled in the art by using phenotypic techniques such as flow cytometry. Phenotypic markers used to identify T cells are generally conserved in mammals and include CD3, TCR$\alpha$, TCR$\beta$, TCR$\delta$, CD4, and CD8. Phenotypic markers used to identify memory T cells can vary by species and by tissue, but may include cell surface markers such as CD45RO, LY6C, CD44, and CD95.

As used herein the term "epitope spreading" refers to the diversification of epitope specificity from an initial focused, dominant epitope-specific immune response, to subdominant and/or cryptic epitopes on the same protein (intramolecular spreading) or other proteins (intermolecular spreading).

As used herein the term "index tumor" refers to the most extensive tumor area, i.e. to the largest nodule, in a surgical specimen.

As used herein, the term "reversible", "reversibly", "degradable" or "degradably" with regard to the attachment of a first moiety to a second moiety means that the linkage that connects said first and second moiety is cleavable under physiological conditions, which are aqueous buffer at pH 7.4, 37° C., with a half-life ranging from one hour to three months, such as from one hour o two months, from three hours to one month, from 12 hours to three weeks or from 24 hours to two weeks. Cleavage may be enzymatically or non-enzymatically and is in certain embodiments non-enzymatically. Accordingly, the term "stable" or "permanent" with regard to the attachment of a first moiety to a second moiety means that the linkage that connects said first and second moiety is cleavable with a half-life of more than three months under physiological conditions.

As used herein, the term "modifying moiety" in certain embodiments refers to a substituent or a polymeric moiety.

As used herein, the term "disulfide bridging" refers to the insertion of a moiety between the two sulfur atoms of a disulfide bridge. This is achieved by using a reagent that has said moiety between two thiol-reactive functional groups and reacting each thiol-reactive functional group with one of the sulfur atoms of the disulfide bridge, such that the moiety is inserted between said sulfur atoms after foregone reduction of the disulfide bond. If more than one disulfide bridge is present in a peptide or protein, the disulfide bridge may either be inserted between the sulfur atoms of one disulfide bridge or may be inserted between the sulfur atoms from different disulfide bridges. Such disulfide bridge may be naturally occurring in a peptide or protein or may have been artificially introduced, for example by replacing existing amino acid moieties with or by adding cysteine moieties to a peptide or protein.

As used herein, the term "reagent" means a chemical compound, which comprises at least one functional group for reaction with the functional group of another chemical compound or drug. It is understood that a drug comprising a functional group (such as a primary or secondary amine or hydroxyl functional group) is also a reagent.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "-" indicates attachment to another moiety. Accordingly, a drug moiety is released from a reversible linkage as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N($R^1$)—" can be attached to two moieties or interrupting a moiety either as "—C(O)N($R^1$)—" or as "—N($R^1$)C(O)—". Similarly, a moiety

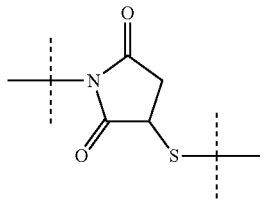

can be attached to two moieties or can interrupt a moiety either as

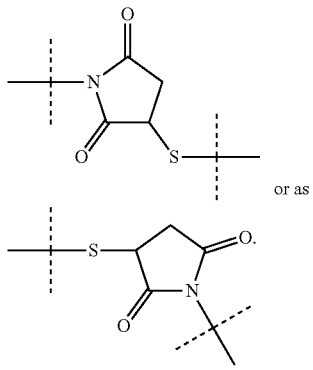

or as

The term "substituted" as used herein means that one or more —H atom(s) of a molecule or moiety are replaced by a different atom or a group of atoms, which are referred to as "substituent".

As used herein, the term "substituent" refers in certain embodiments to a moiety selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$_0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$_0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

—R$^{x1}$, —R$^{x1a}$, —R$^{x1b}$ are independently of each other selected from the group consisting of —H, -T$_0$, C$_{1-50}$ alkyl, C$_{2-50}$ alkenyl, and C$_{2-50}$ alkynyl; wherein -T$_0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$), —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$ which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each —R$^{x3}$, —R$^{x3a}$, —R$^{x4}$, R$^{x4a}$, —R$^{x4b}$ is independently selected from the group consisting of —H and C$_{1-6}$ alkyl; wherein C$_{1-6}$ alkyl is optionally substituted with one or more halogen, which are the same or different.

In certain embodiments a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

As used herein, the term "fatty acid" refers to a saturated or unsaturated monocarboxylic acid having an aliphatic tail, which may include from 4 to 28 carbon atoms. The fatty acid may be saturated or unsaturated, linear or branched. The term "fatty acid variant" refers to a modified fatty acid in which certain carbon atoms may be replaced by other atoms or groups of atoms and which may be substituted.

The term "peptide" as used herein refers to a chain of at least 2 and up to and including 50 amino acid monomer moieties linked by peptide (amide) linkages. The term "peptide" also includes peptidomimetics, such as D-peptides, peptoids or beta-peptides, and covers such peptidomimetic chains with up to and including 50 monomer moieties.

As used herein, the term "protein" refers to a chain of more than 50 amino acid monomer moieties, which may also be referred to as "amino acid residues", linked by peptide linkages, in which in certain embodiments no more than 12000 amino acid monomers are linked by peptide linkages, such as no more than 10000 amino acid monomer moieties, no more than 8000 amino acid monomer moieties, no more than 5000 amino acid monomer moieties or no more than 2000 amino acid monomer moieties.

As used herein the term "about" in combination with a numerical value is used to indicate a range ranging from and including the numerical value plus and minus no more than 25% of said numerical value, in certain embodiments plus and minus no more than 20% of said numerical value and in certain embodiments plus and minus no more than 10% of said numerical value.

For example, the phrase "about 200" is used to mean a range ranging from and including 200+/−25%, i.e. ranging from and including 150 to 250; in certain embodiments 200+/−20%, i.e. ranging from and including 160 to 240; and in certain embodiments from and including 200+/−10%, i.e. ranging from and including 180 to 220. It is understood that a percentage given as "about 50%" does not mean "50%+/−25%", i.e. ranging from and including 25 to 75%, but "about 50%" means ranging from and including 37.5 to 62.5%, i.e. plus and minus 25% of the numerical value which is 50.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical group(s) and/or moiety/moieties, such as, for example, one or more functional group(s). Likewise, it is understood that also a peptide or protein is a polymer, even though the side chains of individual amino acid residues may be different. In certain embodiments a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it in certain embodiments has a molecular weight of at most 1000 kDa, such as at most 750 kDa, such as at most 500 kDa, such as at most 300 kDa, such as at most 200 kDa, such as at most 100 kDa. It is understood that for insoluble polymers, such as hydrogels, no meaningful molecular weight ranges can be provided.

As used herein, the term "polymeric" means a reagent or a moiety comprising one or more polymer(s) or polymer moiety/moieties. A polymeric reagent or moiety may optionally also comprise one or more other moiety/moieties, which are in certain embodiments selected from the group consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

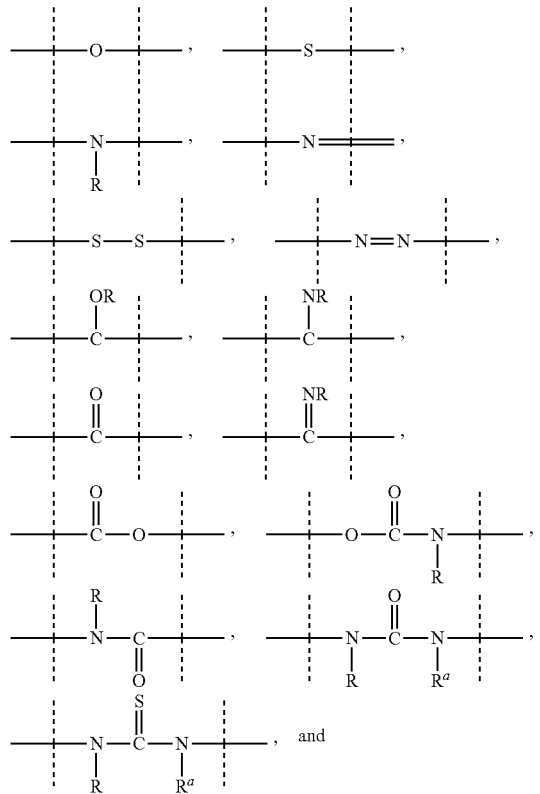

-continued

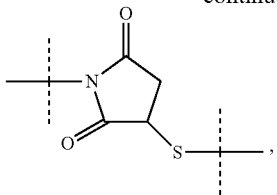

wherein dashed lines indicate attachment to the remainder of the moiety or reagent, and —R and —$R^a$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x+/−25%, preferably x+/−20% and more preferably x+/−10%.

As used herein, the term "number average molecular weight" means the ordinary arithmetic mean of the molecular weights of the individual polymers.

As used herein, the term "PEG-based" in relation to a moiety or reagent means that said moiety or reagent comprises PEG. In certain embodiments a PEG-based moiety or reagent comprises at least 10% (w/w) PEG, such as at least 20% (w/w) PEG, such as at least 30% (w/w) PEG, such as at least 40% (w/w) PEG, such as at least 50% (w/w), such as at least 60 (w/w) PEG, such as at least 70% (w/w) PEG, such as at least 80% (w/w) PEG, such as at least 90% (w/w) PEG, such as at least 95%. The remaining weight percentage of the PEG-based moiety or reagent are other moieties that in certain embodiments are selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

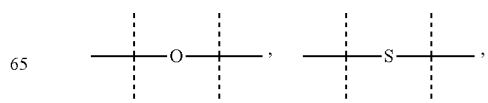

-continued

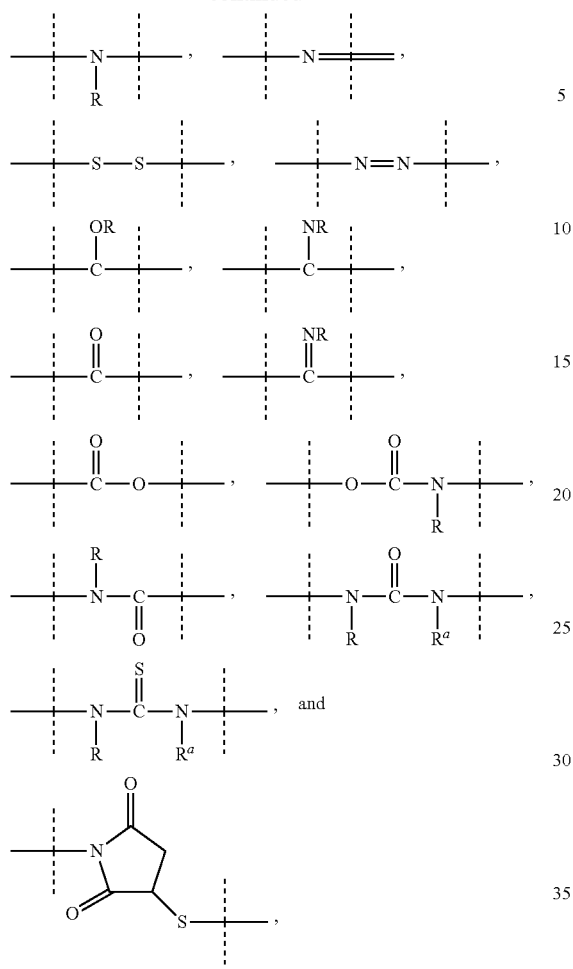

wherein
dashed lines indicate attachment to the remainder of the moiety or reagent, and
—R and —$R^a$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl.

The term "hyaluronic acid-based" is used accordingly.

As used herein, the term "PEG-based comprising at least X % PEG" in relation to a moiety or reagent means that said moiety or reagent comprises at least X % (w/w) ethylene glycol units (—$CH_2CH_2O$—), wherein the ethylene glycol units may be arranged blockwise, alternating or may be randomly distributed within the moiety or reagent and in certain embodiments all ethylene glycol units of said moiety or reagent are present in one block; the remaining weight percentage of the PEG-based moiety or reagent are other moieties that in certain embodiments are selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

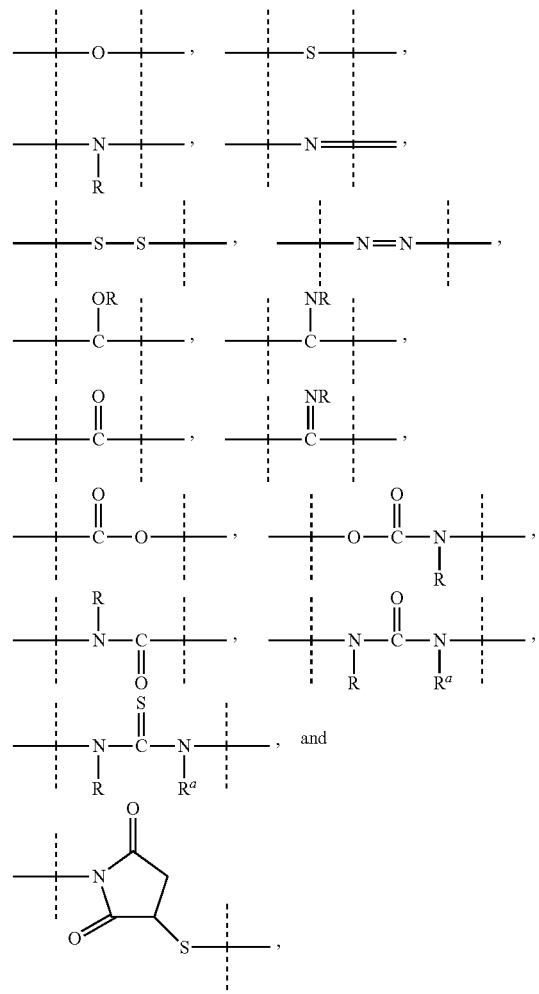

wherein
dashed lines indicate attachment to the remainder of the moiety or reagent, and
—R and —$R^a$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl.

The term "hyaluronic acid-based comprising at least X % hyaluronic acid" is used accordingly.

As used herein, the term "hydrogel" means a hydrophilic or amphiphilic polymeric network composed of homopolymers or copolymers, which is insoluble due to the presence of hydrophobic interactions, hydrogen bonds, ionic interactions and/or covalent chemical crosslinks. In certain embodiments a hydrogel is insoluble due to the presence of covalent chemical crosslinks. In general, the crosslinks provide the network structure and physical integrity.

The term "interrupted" means that a moiety is inserted between two carbon atoms or—if the insertion is at one of the moiety's ends—between a carbon or heteroatom and a hydrogen atom.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the $C_{2-6}$ alkenyl group, then an example for such $C_{2-6}$ alkenyl is —CH=CH—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means a straight-chain or branched hydrocarbon moiety comprising at least one carbon-carbon triple bond having 2 to 6 carbon atoms. If present at the end of a molecule, examples are —C≡CH, —CH$_2$—C≡CH, —CH$_2$—CH$_2$—C≡CH and CH$_2$—C≡C—CH$_3$. When two moieties of a molecule are linked by the alkynyl group, then an example is —C≡C—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkynyl or $C_{2-50}$ alkynyl may optionally be interrupted by one or more moieties which are preferably selected from the group consisting of

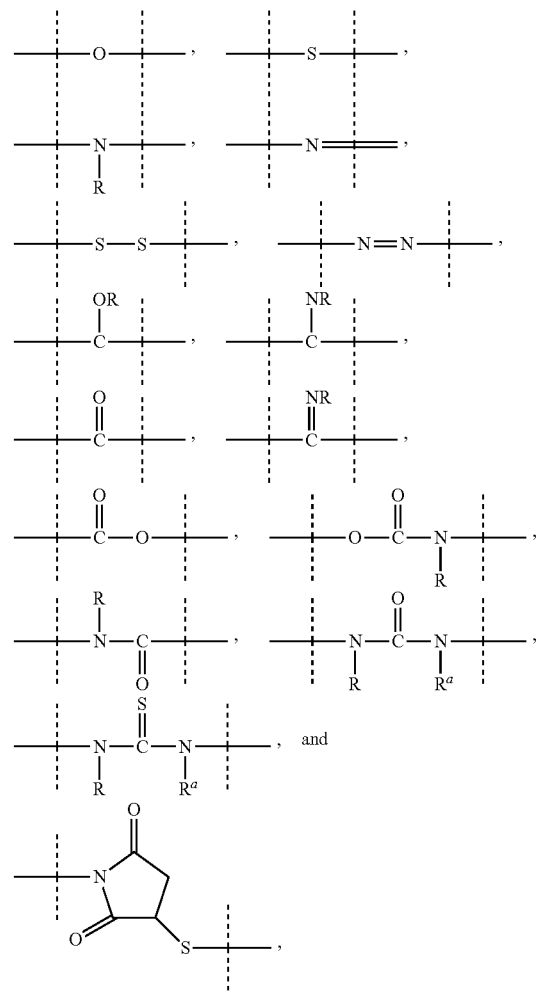

wherein
dashed lines indicate attachment to the remainder of the moiety or reagent; and
—R and —R$^a$ are independently of each other selected from the group consisting of —H, and methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably an 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

It is understood that the phrase "the pair $R^x/R^y$ is joined together with the atom to which they are attached to form a $C_{3-10}$ cycloalkyl or a 3- to 10-membered heterocyclyl" in relation with a moiety of the structure

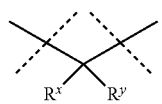

means that $R^x$ and $R^y$ form the following structure:

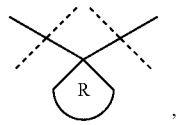

wherein R is $C_{3-10}$ cycloalkyl or 3- to 10-membered heterocyclyl.

It is also understood that the phrase "the pair $R^x/R^y$ is joint together with the atoms to which they are attached to form a ring A" in relation with a moiety of the structure

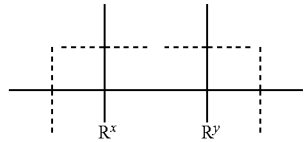

means that $R^x$ and $R^y$ form the following structure:

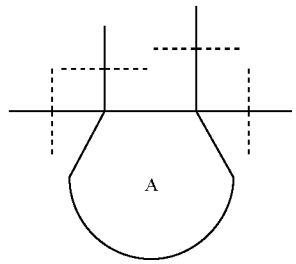

As used herein, "halogen" means fluoro, chloro, bromo or iodo. It is generally preferred that halogen is fluoro or chloro.

As used herein, the term "functional group" means a group of atoms which can react with other groups of atoms. Exemplary functional groups are, for example, carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxyl (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, sulfonamides, sulfuric acid, vinyl sulfone, vinyl ketone, diazoalkane, oxirane, and aziridine.

In case the IL-2 proteins or conjugates of the present invention comprise one or more acidic or basic groups, the invention also comprises their corresponding pharmaceutically or toxicologically acceptable salts, in particular their pharmaceutically utilizable salts. Thus, the IL-2 proteins or conjugates of the present invention comprising acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. IL-2 proteins or conjugates of the present invention comprising one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the IL-2 proteins or conjugates of the present invention simultaneously comprise acidic and basic groups, the invention also includes, in addition to the salt forms mentioned, inner salts or betaines (zwitterions). The respective salts can be obtained by customary methods, which are known to the person skilled in the art like, for example by contacting these prodrugs with an organic or inorganic acid or base in a solvent or dispersant, or by anion exchange or cation exchange with other salts. The present invention also includes all salts of the IL-2 proteins or conjugates of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means a substance that does not cause harm when administered to a patient and preferably means approved by a regulatory agency, such as the EMA (Europe) and/or the FDA (US) and/or any other national regulatory agency for use in animals, such as for use in humans.

As used herein, the term "excipient" refers to a diluent, adjuvant, or vehicle with which the therapeutic, such as a drug or prodrug, is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or biologically active moiety, together with a suitable amount of excipient so as to provide the form for proper administration to the patient. The formulation should suit the mode of administration.

In general, the term "comprise" or "comprising" also encompasses "consist of" or "consisting of".

SEQ A of formula (I) has at least 94% sequence identity to SEQ ID NO:1. SEQ ID NO:1 has the following sequence:

PTSSSTKKTQLQLEHLLLDLQMILNGINNYKNPKLT

SEQ B of formula (I) has at least 94% sequence identity to SEQ ID NO:2. SEQ ID NO:2 has the following sequence:

MLTFKFYMPKKATELKHLQCLEEELKPLEEVLNLAQSKNFHLRPRDLISN

INVIVLELKGSETTFMCEYADETATIVEFLNRWITFCQSIISTLT

Unless stated otherwise all amino acid positions given herein are based on SEQ ID NO:1 or SEQ ID NO:2, respectively.

In certain embodiments SEQ A comprises two amino acid changes compared to SEQ ID NO:1. In certain embodiments the sequence SEQ A comprises one amino acid change compared to SEQ ID NO:1. Such amino acid change may be an amino acid deletion, amino acid addition or the exchange of one amino acid for another amino acid, i.e. a mutation. Such mutation may also be the exchange of a proteinogenic amino acid for a non-proteinogenic amino acid or for the D-stereoisomers of a proteinogenic amino acid.

In certain embodiments SEQ A has the sequence of SEQ ID NO:1 comprising one amino acid change at position K34. In certain embodiments such amino acid change is the exchange of one amino acid, in this case lysine, for another amino acid, which in certain embodiments is selected from the group consisting of alanine, cysteine, glycine, serine, threonine, glutamine, glutamic acid, asparagine and aspartic acid. In certain embodiments said amino acid change at position K34 is selected from the group consisting of K34A (SEQ ID NO:3), K34C (SEQ ID NO:4), K34G (SEQ ID NO:5), K34S (SEQ ID NO:6), K34T (SEQ ID NO:7), K34Q (SEQ ID NO:8), K34E (SEQ ID NO:9), K34N (SEQ ID NO:10) and K34D (SEQ ID NO:11). Accordingly, in certain embodiments SEQ A has the sequence of SEQ ID NO: 3: PTSSSTKKTQLQLEHLLLDLQMILNGINNYKNPALT. In certain embodiments SEQ A has the sequence of SEQ ID NO:4: PTSSSTKKTQLQLEHLLLDLQMILNGINNYKNPCLT. In certain embodiments SEQ A has the sequence of SEQ ID NO:5: PTSSSTKKTQLQLEHLLLDLQMILNGINNYKNPGLT. In certain embodiments SEQ A has the sequence of SEQ ID NO:6: PTSSSTKKTQLQLEHLLLDLQMILNGINNYKNPSLT. In certain embodiments SEQ A has the sequence of SEQ ID NO:7: PTSSSTKKTQLQLEHLLLDLQMILNGINNYKNPTLT. In certain embodiments SEQ A has the sequence of SEQ ID NO:8: PTSSSTKKTQLQLEHLLLDLQMILNGINNYKNPQLT. In certain embodiments SEQ A has the sequence of SEQ ID NO:9: PTSSSTKKTQLQLEHLLLDLQMILNGINNYKNPELT. In certain embodiments SEQ A has the sequence of SEQ ID NO:10: PTSSSTKKTQLQLEHLLLDLQMILNGINNYKNPNLT. In certain embodiments SEQ A has the sequence of SEQ ID NO:11: PTSSSTKKTQLQLEHLLLDLQMILNGINNYKNPDLT. In certain embodiments SEQ A has the sequence of SEQ ID NO:1.

It was surprisingly found that introducing an amino acid change at position K34 of SEQ A improved solubility and refolding of the IL-2 protein of formula (I).

In certain embodiments SEQ B comprises 1 to 5 amino acid changes compared to SEQ ID NO:2. In certain embodiments SEQ B comprises 1 to 4 amino acid changes compared to SEQ ID NO:2. In certain embodiments SEQ B comprises five amino acid changes compared to SEQ ID NO:2. In certain embodiments SEQ B comprises four amino acid changes compared to SEQ ID NO:2. In certain embodiments SEQ B comprises three amino acid changes compared to SEQ ID NO:2. In certain embodiments SEQ B comprises two amino acid changes compared to SEQ ID NO:2. In certain embodiments SEQ B comprises one amino acid change compared to SEQ ID NO:2. In certain embodiments SEQ B comprises no amino acid change compared to SEQ ID NO:2. Such amino acid change may be an amino acid deletion, amino acid addition or the exchange of one amino acid for another amino acid, i.e. a mutation. Such mutation may also be the exchange of a proteinogenic amino acid for a non-proteinogenic amino acid or for the D-stereoisomers of proteinogenic amino acids.

In certain embodiments said 1 to 4 amino acid changes replace an amino acid with an amino acid selected from the group consisting of alanine, cysteine, glycine, serine, threonine, glutamine, glutamic acid and asparagine. In certain embodiments said 1 to 4 amino acid changes replace an amino acid with an alanine. In certain embodiments said 1 to 4 amino acid changes replace an amino acid with a cysteine. In certain embodiments said 1 to 4 amino acid changes replace an amino acid with a glycine. In certain embodiments said 1 to 4 amino acid changes replace an amino acid with a serine. In certain embodiments said 1 to 4 amino acid changes replace an amino acid with a threonine. In certain embodiments said 1 to 4 amino acid changes replace an amino acid with a glutamine. In certain embodiments said 1 to 4 amino acid changes replace an amino acid with a glutamic acid. In certain embodiments said 1 to 4 amino acid changes replace an amino acid with an asparagine.

In certain embodiments said 1 to 4 amino acid changes are selected from amino acids changes occurring at a position selected from the group consisting of M1, T3, F4, K5, F6, Y7, E24, E30, L34 and C87 of SEQ ID NO:2. In certain embodiments one of said 1 to 4 amino acid changes occurs at position M1 of SEQ ID NO:2. In certain embodiments one of said 1 to 4 amino acid changes occurs at position T3 of SEQ ID NO:2. In certain embodiments one of said 1 to 4 amino acid changes occurs at position F4 of SEQ ID NO:2. In certain embodiments one of said 1 to 4 amino acid changes occurs at position K5 of SEQ ID NO:2. In certain embodiments one of said 1 to 4 amino acid changes occurs at position F6 of SEQ ID NO:2. In certain embodiments one of said 1 to 4 amino acid changes occurs at position Y7 of SEQ ID NO:2. In certain embodiments one of said 1 to 4 amino acid changes occurs at position E24 of SEQ ID NO:2. In certain embodiments one of said 1 to 4 amino acid changes occurs at position E30 of SEQ ID NO:2. In certain embodiments one of said 1 to 4 amino acid changes occurs at position L34 of SEQ ID NO:2. In certain embodiments one of said 1 to 4 amino acid changes occurs at position C87 of SEQ ID NO:2.

In certain embodiments said 1 to 4 amino acid changes are selected from the group consisting of M1A, M1C, M1G, M1S, M1T, M1Q, M1E, M1N, T3A, T3C, T3G, T3S, T3Q, T3E, T3N, F4A, F4C, F4G, F4S, F4T, F4Q, F4E, F4N, K5A, K5C, K5G, K5S, K5T, K5Q, K5E, K5N, F6A, F6C, F6G, F6S, F6T, F6Q, F6E, F6N, Y7A, Y7C, Y7G, Y7S, Y7T, Y7Q, Y7E, Y7N, E24A, E24C, E24G, E24S, E24T, E24Q, E24N, E30A, E30C, E30G, E30S, E30T, E30Q, E24N, L34A, L34C, L34G, L34S, L34T, L34Q, L34E, L34N, C87A, C87G, C87S, C87T, C87Q, C87E and C87N, based on the sequence of SEQ ID NO:2. It is understood that a term "M1A" means that the methionine at position 1 is replaced by an alanine and that the other terms are used accordingly. In certain embodiments SEQ B comprises the M1A mutation. In certain embodiments SEQ B comprises the M1C mutation. In certain embodiments SEQ B comprises the M1G mutation. In certain embodiments SEQ B comprises the M1S mutation. In certain embodiments SEQ B comprises the M1T mutation. In certain embodiments SEQ B comprises the M1Q mutation. In certain embodiments SEQ B comprises the M1E mutation. In certain embodiments SEQ B comprises the MIN mutation. In certain embodiments SEQ B comprises the T3A mutation. In certain embodiments SEQ B comprises the T3C mutation. In certain embodiments SEQ B comprises the T3G mutation. In certain embodiments SEQ B comprises the T3S mutation. In certain embodiments SEQ B comprises the T3Q mutation. In certain embodiments SEQ B comprises the T3E mutation. In certain embodiments SEQ B comprises the T3N mutation. In certain embodiments SEQ B comprises the F4A mutation. In certain embodiments SEQ B comprises the F4C mutation. In certain embodiments SEQ B comprises the F4G mutation. In certain embodiments SEQ B comprises the F4S mutation. In certain embodiments SEQ B comprises the F4T mutation. In certain embodiments SEQ B comprises the F4Q mutation. In certain embodiments SEQ B comprises the F4E mutation. In certain embodiments SEQ B comprises the F4N mutation. In certain embodiments SEQ B comprises the K5A mutation. In certain embodiments SEQ B comprises the K5C mutation. In certain embodiments SEQ B comprises the K5G mutation. In certain embodiments SEQ B comprises the K5S mutation. In certain embodiments SEQ B comprises the K5T mutation. In certain embodiments SEQ B comprises the K5Q mutation. In certain embodiments SEQ B comprises the K5E mutation. In certain embodiments SEQ B comprises the K5N mutation. In certain embodiments SEQ B comprises the F6A mutation. In certain embodiments SEQ B comprises the F6C mutation. In certain embodiments SEQ B comprises the F6G mutation. In certain embodiments SEQ B comprises the F5S mutation. In certain embodiments SEQ B comprises the F6T mutation. In certain embodiments SEQ B comprises the F6Q mutation. In certain embodiments SEQ B comprises the F6E mutation. In certain embodiments SEQ B comprises the F6N mutation. In certain embodiments SEQ B comprises the Y7A mutation. In certain embodiments SEQ B comprises the Y7C mutation. In certain embodiments SEQ B comprises the Y7G mutation. In certain embodiments SEQ B comprises the Y7S mutation. In certain embodiments SEQ B comprises the Y7T mutation. In certain embodiments SEQ B comprises the Y7Q mutation. In certain embodiments SEQ B comprises the Y7E mutation. In certain embodiments SEQ B comprises the Y7N mutation. In certain embodiments SEQ B comprises the E24A mutation. In certain embodiments SEQ B comprises the E24C mutation. In certain embodiments SEQ B comprises the E24G mutation. In certain embodiments SEQ B comprises the E24S mutation. In certain embodiments SEQ B comprises the E24T mutation. In certain embodiments SEQ B comprises the E24Q mutation. In certain embodiments SEQ B comprises the E24N mutation. In certain embodiments SEQ B comprises the E30A mutation. In certain embodiments SEQ B comprises the E30C mutation. In certain embodiments SEQ B comprises the E30G mutation. In certain embodiments SEQ B comprises the E30S mutation. In certain embodiments SEQ B comprises the E30T mutation. In certain embodiments SEQ B comprises the E30Q mutation. In certain embodiments SEQ B comprises the E30N mutation. In certain embodiments SEQ B comprises the L34A mutation. In certain embodiments SEQ B comprises the L34C mutation. In certain embodiments SEQ B comprises the L34G mutation. In certain embodiments SEQ B comprises the L34S mutation. In certain embodiments SEQ B comprises the L34T mutation. In certain embodiments SEQ B comprises the L34Q mutation. In certain embodiments SEQ B comprises the L34E mutation. In certain embodiments SEQ B comprises the L34N mutation. In certain embodiments SEQ B comprises the C87A mutation. In certain embodiments SEQ B comprises the C87G mutation. In certain embodiments SEQ B comprises the C87S mutation. In certain embodiments SEQ B comprises the C87T mutation. In certain embodiments SEQ B comprises the C87Q mutation. In certain embodiments SEQ B comprises the C87E mutation. In certain embodiments SEQ B comprises the C87N mutation.

In certain embodiments SEQ B has the sequence of SEQ ID NO:2. In certain embodiments SEQ B has the sequence of SEQ ID NO:12.

In certain embodiments SEQ B has the sequence of SEQ ID NO:12:

MLTFKFYMPKKATELKHLQCLEEELKPLEEVLNLAQSKNFHLRPRDLISN

INVIVLELKGSETTFMCEYADETATIVEFLNRWITFSQSIISTLT

In certain embodiments SEQ A has the sequence of SEQ ID NO:1 and SEQ B has the sequence of SEQ ID NO:2. Accordingly, the IL-2 protein of formula (I) has the sequence of SEQ ID NO:13:

APTSSSTKKTQLQLEHLLLDLQMILNGINNYKNPKLTCMLTFKFYMPKKA

TELKHLQCLEEELKPLEEVLNLAQSKNFHLRPRDLISNINVIVLELKGSE

TTFMCEYADETATIVEFLNRWITFCQSIISTLT

In certain embodiments SEQ A has the sequence of SEQ ID NO:1 and SEQ B has the sequence of SEQ ID NO:12. Accordingly, the IL-2 protein of formula (I) has the sequence of SEQ ID NO:14:

APTSSSTKKTQLQLEHLLLDLQMILNGINNYKNPKLTCMLTFKFYMPKKA

TELKHLQCLEEELKPLEEVLNLAQSKNFHLRPRDLISNINVIVLELKGSE

TTFMCEYADETATIVEFLNRWITFSQSIISTLT

In certain embodiments SEQ A has the sequence of SEQ ID NO:3 and SEQ B has the sequence of SEQ ID NO:2. Accordingly, the IL-2 protein of formula (I) has the sequence of SEQ ID NO:22:

APTSSSTKKTQLQLEHLLLDLQMILNGINNYKNPALTCMLTFKFYMPKKA

TELKHLQCLEEELKPLEEVLNLAQSKNFHLRPRDLISNINVIVLELKGSE

TTFMCEYADETATIVEFLNRWITFCQSIISTLT

In certain embodiments SEQ A has the sequence of SEQ ID NO:3 and SEQ B has the sequence of SEQ ID NO:12. Accordingly, the IL-2 protein of formula (I) has the sequence of SEQ ID NO:23:

APTSSSTKKTQLQLEHLLLDLQMILNGINNYKNPALTCMLTFKFYMPKKA

TELKHLQCLEEELKPLEEVLNLAQSKNFHLRPRDLISNINVIVLELKGSE

TTFMCEYADETATIVEFLNRWITFSQSIISTLT

In certain embodiments SEQ A has the sequence of SEQ ID NO:4 and SEQ B has the sequence of SEQ ID NO:2. Accordingly, the IL-2 protein of formula (I) has the sequence of SEQ ID NO:24:

APTSSSTKKTQLQLEHLLLDLQMILNGINNYKNPCLTCMLTFKFYMPKKA

TELKHLQCLEEELKPLEEVLNLAQSKNFHLRPRDLISNINVIVLELKGSE

TTFMCEYADETATIVEFLNRWITFCQSIISTLT

In certain embodiments SEQ A has the sequence of SEQ ID NO:4 and SEQ B has the sequence of SEQ ID NO:12. Accordingly, the IL-2 protein of formula (I) has the sequence of SEQ ID NO:25:

APTSSSTKKTQLQLEHLLLDLQMILNGINNYKNPC

LTCMLTFKFYMPKKATELKHLQCLEEELKPLEEVL

NLAQSKNFHLRPRDLISNINVIVLELKGSETTFMC

EYADETATIVEFLNRWITFSQSIISTLT

In certain embodiments SEQ A has the sequence of SEQ ID NO:5 and SEQ B has the sequence of SEQ ID NO:2. Accordingly, the IL-2 protein of formula (I) has the sequence of SEQ ID NO:26:

APTSSSTKKTQLQLEHLLLDLQMILNGINNYKNPG

LTCMLTFKFYMPKKATELKHLQCLEEELKPLEEVL

NLAQSKNFHLRPRDLISNINVIVLELKGSETTFMC

EYADETATIVEFLNRWITFCQSIISTLT

In certain embodiments SEQ A has the sequence of SEQ ID NO:5 and SEQ B has the sequence of SEQ ID NO:12. Accordingly, the IL-2 protein of formula (I) has the sequence of SEQ ID NO:27:

APTSSSTKKTQLQLEHLLLDLQMILNGINNYKNPG

LTCMLTFKFYMPKKATELKHLQCLEEELKPLEEVL

NLAQSKNFHLRPRDLISNINVIVLELKGSETTFMC

EYADETATIVEFLNRWITFSQSIISTLT

In certain embodiments SEQ A has the sequence of SEQ ID NO:6 and SEQ B has the sequence of SEQ ID NO:2. Accordingly, the IL-2 protein of formula (I) has the sequence of SEQ ID NO:28:

APTSSSTKKTQLQLEHLLLDLQMILNGINNYKNPS

LTCMLTFKFYMPKKATELKHLQCLEEELKPLEEVL

NLAQSKNFHLRPRDLISNINVIVLELKGSETTFMC

EYADETATIVEFLNRWITFCQSIISTLT

In certain embodiments SEQ A has the sequence of SEQ ID NO:6 and SEQ B has the sequence of SEQ ID NO:12. Accordingly, the IL-2 protein of formula (I) has the sequence of SEQ ID NO:29:

APTSSSTKKTQLQLEHLLLDLQMILNGINNYKNPS

LTCMLTFKFYMPKKATELKHLQCLEEELKPLEEVL

NLAQSKNFHLRPRDLISNINVIVLELKGSETTFMC

EYADETATIVEFLNRWITFSQSIISTLT

In certain embodiments SEQ A has the sequence of SEQ ID NO:7 and SEQ B has the sequence of SEQ ID NO:2. Accordingly, the IL-2 protein of formula (I) has the sequence of SEQ ID NO:30:

APTSSSTKKTQLQLEHLLLDLQMILNGINNYKNPT

LTCMLTFKFYMPKKATELKHLQCLEEELKPLEEVL

NLAQSKNFHLRPRDLISNINVIVLELKGSETTFMC

EYADETATIVEFLNRWITFCQSIISTLT

In certain embodiments SEQ A has the sequence of SEQ ID NO:7 and SEQ B has the sequence of SEQ ID NO:12. Accordingly, the IL-2 protein of formula (I) has the sequence of SEQ ID NO:31:

APTSSSTKKTQLQLEHLLLDLQMILNGINNYKNPT

LTCMLTFKFYMPKKATELKHLQCLEEELKPLEEVL

NLAQSKNFHLRPRDLISNINVIVLELKGSETTFMC

EYADETATIVEFLNRWITFSQSIISTLT

In certain embodiments SEQ A has the sequence of SEQ ID NO:8 and SEQ B has the sequence of SEQ ID NO:2. Accordingly, the IL-2 protein of formula (I) has the sequence of SEQ ID NO:32:

APTSSSTKKTQLQLEHLLLDLQMILNGINNYKNPQ

LTCMLTFKFYMPKKATELKHLQCLEEELKPLEEVL

NLAQSKNFHLRPRDLISNINVIVLELKGSETTFMC

EYADETATIVEFLNRWITFCQSIISTLT

In certain embodiments SEQ A has the sequence of SEQ ID NO:8 and SEQ B has the sequence of SEQ ID NO:12. Accordingly, the IL-2 protein of formula (I) has the sequence of SEQ ID NO:33:

APTSSSTKKTQLQLEHLLLDLQMILNGINNYKNPQ

LTCMLTFKFYMPKKATELKHLQCLEEELKPLEEVL

NLAQSKNFHLRPRDLISNINVIVLELKGSETTFMC

EYADETATIVEFLNRWITFSQSIISTLT

In certain embodiments SEQ A has the sequence of SEQ ID NO:9 and SEQ B has the sequence of SEQ ID NO:2. Accordingly, the IL-2 protein of formula (I) has the sequence of SEQ ID NO:34:

APTSSSTKKTQLQLEHLLLDLQMILNGINNYKNPE

LTCMLTFKFYMPKKATELKHLQCLEEELKPLEEVL

NLAQSKNFHLRPRDLISNINVIVLELKGSETTFMC

EYADETATIVEFLNRWITFCQSIISTLT

In certain embodiments SEQ A has the sequence of SEQ ID NO:9 and SEQ B has the sequence of SEQ ID NO:12. Accordingly, the IL-2 protein of formula (I) has the sequence of SEQ ID NO:35:

APTSSSTKKTQLQLEHLLLDLQMILNGINNYKNPE

LTCMLTFKFYMPKKATELKHLQCLEEELKPLEEVL

NLAQSKNFHLRPRDLISNINVIVLELKGSETTFMC

EYADETATIVEFLNRWITFSQSIISTLT

In certain embodiments SEQ A has the sequence of SEQ ID NO:10 and SEQ B has the sequence of SEQ ID NO:2. Accordingly, the IL-2 protein of formula (I) has the sequence of SEQ ID NO:36:

```
APTSSSTKKTQLQLEHLLLDLQMILNGINNYKNPN

LTCMLTFKFYMPKKATELKHLQCLEEELKPLEEVL

NLAQSKNFHLRPRDLISNINVIVLELKGSETTFMC

EYADETATIVEFLNRWITFCQSIISTLT
```

In certain embodiments SEQ A has the sequence of SEQ ID NO:10 and SEQ B has the sequence of SEQ ID NO:12. Accordingly, the IL-2 protein of formula (I) has the sequence of SEQ ID NO:37:

```
APTSSSTKKTQLQLEHLLLDLQMILNGINNYKNPN

LTCMLTFKFYMPKKATELKHLQCLEEELKPLEEVL

NLAQSKNFHLRPRDLISNINVIVLELKGSETTFMC

EYADETATIVEFLNRWITFSQSIISTLT
```

In certain embodiments SEQ A has the sequence of SEQ ID NO:11 and SEQ B has the sequence of SEQ ID NO:2. Accordingly, the IL-2 protein of formula (I) has the sequence of SEQ ID NO:38:

```
APTSSSTKKTQLQLEHLLLDLQMILNGINNYKNPD

LTCMLTFKFYMPKKATELKHLQCLEEELKPLEEVL

NLAQSKNFHLRPRDLISNINVIVLELKGSETTFMC

EYADETATIVEFLNRWITFCQSIISTLT
```

In certain embodiments SEQ A has the sequence of SEQ ID NO:11 and SEQ B has the sequence of SEQ ID NO:12. Accordingly, the IL-2 protein of formula (I) has the sequence of SEQ ID NO:39:

```
APTSSSTKKTQLQLEHLLLDLQMILNGINNYKNPD

LTCMLTFKFYMPKKATELKHLQCLEEELKPLEEVL

NLAQSKNFHLRPRDLISNINVIVLELKGSETTFMC

EYADETATIVEFLNRWITFSQSIISTLT
```

In another aspect the present invention relates to an oligonucleotide sequence encoding the IL-2 protein of formula (I). Such oligonucleotide sequence may be selected from the group consisting of DNA, RNA and cDNA sequences. In certain embodiments the oligonucleotide sequence is a DNA sequence. In certain embodiments the oligonucleotide sequence is an RNA sequence. In certain embodiments the oligonucleotide sequence is a cDNA sequence. In certain embodiments the oligonucleotide encoding the IL-2 protein of formula (I) is for expression in a prokaryotic system, in a eukaryotic system or in a cell-free system. In certain embodiments the oligonucleotide sequence encoding the IL-2 protein of formula (I) is for expression in a prokaryotic system. In certain embodiments the oligonucleotide sequence encoding the IL-2 protein of formula (I) is for expression in a eukaryotic system. In certain embodiments the oligonucleotide sequence encoding the IL-2 protein of formula (I) is for expression in a cell-free system.

In certain embodiments the oligonucleotide sequence encoding the IL-2 protein of formula (I) is for expression in a prokaryotic system, such as a bacterial system selected from the group consisting of *Escherichia coli; Bacillus* sp., such *Bacillus subtilis; Corynebacterium* sp., such as *Corynebacterium glutamicum*; and *Pseudomonas fluorescens*. In certain embodiments such oligonucleotide is a DNA sequence in the form of a plasmid.

In certain embodiments the oligonucleotide sequence encoding the IL-2 protein of formula (I) is for expression in a eukaryotic system, such as a eukaryotic system selected from the group consisting of yeasts, such as *Saccharomyces cerevisiae* or *Pichia pastoris*; filamentous fungi, such as *Aspergillus, Trichoderma* or *Myceliophthora thermophila*; baculovirus-infected cells, such baculovirus-infected insect cells, such as Sf9, Sf21, Hi-5 strains, or baculovirus-infected mammalian cells, such as HeLa, human embryotic kidney cells HEK 293 or Chinese hamster ovary cells (CHO); mammalian systems, such as mouse myeloma lymphoblastoid (such as NS0 cells), mouse fibroblasts (such as NIH3T3 cells), CHO cells, and fully human cells, such as HEK 293 cells, human embryonic retinal cells (such as Crucell's Per.C6) and human amniocyte cells (such as Glycotope and CEVEC); and non-lytic insect cell expression systems, such as Sf9, Sf21, Hi-5, Schneider 2 cells or Schneider 3 cells. In certain embodiments the oligonucleotide sequence encoding IL-2 protein of formula (I) is for expression in a mammalian system. In certain embodiments the oligonucleotide sequence encoding an IL-2 protein of formula (I) has the sequence of SEQ ID NO:17. In certain embodiments such oligonucleotide is a DNA sequence in the form of a plasmid. In certain embodiments plasmid has the sequence of SEQ ID NO:20.

In another aspect the present invention relates to a method for the expression of a recombinant IL-2 protein of formula (I), said method comprising: a) culturing host cells expressing one or more genes encoding the IL-2 protein of formula (I); and b) separating said recombinant IL-2 protein of interest from the host cell culture.

In certain embodiments the host cells are prokaryotic cells, such as bacterial cells. In certain embodiments the host cells are selected from the group consisting of *Escherichia coli; Bacillus* sp., such *Bacillus subtilis; Corynebacterium* sp., such as *Corynebacterium glutamicum*; and *Pseudomonas fluorescens*. In certain embodiments the host cells are *Escherichia coli*. In certain embodiments the host cells are a *Bacillus* sp. In certain embodiments the host cells are a *Corynebacterium* sp. In certain embodiments the host cells are *Pseudomonas fluorescens*.

In certain embodiments the host cells are eukaryotic cells. In certain embodiments the host cells are selected from the group consisting of yeasts, such as *Saccharomyces cerevisiae* or *Pichia pastoris*; filamentous fungi, such as *Aspergillus, Trichoderma* or *Myceliophthora thermophila*; baculovirus-infected cells, such baculovirus-infected insect cells, such as Sf9, Sf21, Hi-5 strains, or baculovirus-infected mammalian cells, such as HeLa, human embryotic kidney cells HEK 293 or Chinese hamster ovary cells (CHO); mammalian systems, such as mouse myeloma lymphoblastoid (such as NS0 cells), mouse fibroblasts (such as NIH3T3 cells), CHO cells, and fully human cells, such as HEK 293 cells, human embryonic retinal cells (such as Crucell's Per.C6) and human amniocyte cells (such as Glycotope and CEVEC); and non-lytic insect cell expression systems, such as Sf9, Sf21, Hi-5, Schneider 2 cells or Schneider 3 cells. In certain embodiments the host cells are yeast cells. In certain embodiments the host cells are *Saccharomyces cerevisiae* cells. In certain embodiments the host cells are *Pichia pastoris* cells. In certain embodiments the host cells are cells of a filamentous fungus. In certain embodiments the host cells are cells of an *Aspergillus* species. In certain embodiments the host cells are cells of a *Trichoderma* species. In certain embodiments the host cells are *Myceliophthora thermophila* cells. In certain embodiments the host cells are baculovirus-infected cells, such as a baculovirus-infected insect cells or baculovirus-infected mammalian cells. In certain embodiments the host cells are baculovirus-infected Sf9 cells. In certain embodiments the host cells are baculovirus-infected Sf21 cells. In certain embodiments the host cells are cells of a baculovirus-infected Hi-5 strain. In certain embodiments the host cells are baculovirus-infected HeLa cells. In certain embodiments the host cells are baculovirus-infected human kidney cells. In certain embodiments the host cells are baculovirus-infected Sf9 cells. In certain embodiments the host cells are baculovirus-infected CHO cells. In certain embodiments the host cells are mammalian cells. In certain embodiments the host cells are mouse myeloma lymphoblastoid cells. In certain embodiments the host cells are mouse fibroblast cells. In certain embodiments the host cells are CHO cells. In certain embodiments the host cells are HEK 293 cells. In certain embodiments the host cells are human embryotic retinal cells. In certain embodiments the host cells are human amniocyte cells. In certain embodiments the host cells are mouse fibroblast cells. In certain embodiments the host cells are non-lytic insect cell expression systems. In certain embodiments the host cells are Sf9 cells. In certain embodiments the host cells are Sf21 cells. In certain embodiments the host cells are Hi-5 cells. In certain embodiments the host cells are Schneider 2 cells. In certain embodiments the host cells are Schneider 3 cells.

It is understood that based on the host cells used the IL-2 protein of formula (I) may comprise post-translational modifications, such as glycosylation, in particular O-linked and N-linked glycosylation. Even though not explicitly mentioned, it is understood that the IL-2 protein of formula (I) may comprise such post-translational modifications and that such modified IL-2 proteins are also covered by the present invention. One example for such post-translational modification is the O-linked glycosylation of the threonine at position 2 of SEQ ID NO:1 when the IL-2 protein of formula (I) is expressed CHO cells. The O-linked glycan may for example be N1 (NeuAc(a2-3)Gal(b1-3)GalNAc-ol) or N2 (NeuAc(a2-3)Gal(b1-3)(NeuAc(a2-6))GalNAc-ol), wherein NeuAc is N-acetylneuraminic acid (Sialic acid), Gal is galactose and GalNac-ol is Acetylgalactosaminitol. The IL-2 protein of formula (I) may in certain embodiments comprise at least one O-linked N1 glycan, at least one O-linked N2 glycan, a combination of at least one O-linked N1 and at least one O-linked N2 glycan or may be non-glycosylated. In certain embodiments the IL-2 protein of formula (I) comprises at least one, such as one, O-linked N1 glycan. In certain embodiments the IL-2 protein of formula (I) comprises at least one, such as one, O-linked N2 glycan. In certain embodiments the IL-2 protein of formula (I) comprises a combination of at least one, such as one, O-linked N1 glycan and at least one, such as one, O-linked N2 glycan. In certain embodiments the IL-2 protein of formula (I) is non-glycosylated. The ratio of N1 to N2 glycans may for example be 1:1.

In certain embodiments the IL-2 protein of formula (I) is expressed in eukaryotic cells, such as CHO cells, and at least 80% of N-terminal ends that correspond to amino acids 1 to 8 are O-glycosylated. In certain embodiments the IL-2 protein of formula (I) is expressed in eukaryotic cells, such as CHO cells, and at least 90% of N-terminal ends that correspond to amino acids 1 to 8 are O-glycosylated.

It was surprisingly found that the use of a eukaryotic expression system such as CHO cells resulted in improved solubility and secretion of the IL-2 protein of formula (I). It was found that expression in CHO cells resulted in efficient O-glycosylation of the N-terminal end (amino acids 1 to 8) of the IL-2 protein of formula (I). Such O-glycosylation may have a positive effect on solubility and secretion by preventing protein aggregation and ensuring proper secretion.

In certain embodiments the IL-2 protein of formula (I) is expressed in a predominantly insoluble form, such as for example in inclusion bodies. In certain embodiments the IL-2 protein of formula (I) is expressed as a soluble protein. Expressing the IL-2 protein of formula (I) as a soluble protein has the advantage that no renaturing step is necessary. Such soluble protein may remain within the cell or it may be excreted into the cultivation media or, in the case of Gram-negative bacteria, into the periplasmatic space.

The presence of a free, unpaired cysteine in the protein sequence poses challenges for recombinant production, whether choosing an inclusion-body based strategy or a soluble secretion strategy.

Accordingly, in certain embodiments the IL-2 protein of formula (I) is produced in inclusion-bodies. Such method of expression further involves the step of solubilizing the insoluble protein and the step of in vitro refolding. To achieve correct disulfide bridge formation during the refolding, it is normally beneficial to start from a solubilized unfolded protein without any existing disulfide bridges. Accordingly, in certain embodiments the method further involves addition of a reducing agent during solubilization.

A typical challenge during refolding of a protein containing a free cysteine is to achieve correct disulfide bridge formation between the intended pair(s) of cysteine while maintaining the free unpaired cysteine in a free, reduced form.

In certain embodiments the IL-2 protein of formula (I) is produced by secretion of a soluble IL-2 protein. When expressing a protein containing a free, unpaired cysteine in a soluble, secreted form, the resulting secreted correctly folded monomeric protein often carries an additional thiol-comprising compound, such as cysteine, coupled to its free unpaired cysteine via a disulfide bridge, also termed "cysteine capping". Thus, one step in the method of synthesizing the IL-2 protein of formula (I) in soluble form via secretion is an optional capping of the free cysteine. Capping by cysteine may take place extracellularly after secretion of the protein of interest, with the thiol-comprising compound, such as cysteine, cystine or glutathione, originating from the cultivation medium as substrate for disulfide-bridging. Alternatively, it may take place intracellularly, in which case the thiol-comprising compound, such as cysteine, used for capping originates from the metabolism of the cells, such as from the amino acid metabolism.

As a side product, free cysteines in the protein of interest may react to form disulfide bridges between molecules, resulting in formation of dimers of the protein of interest. The amount of correctly folded monomer capped by a thiol-comprising compound, such as cysteine, may be increased by optimizing the cell culture conditions, e.g. by varying the concentration of cystine, the oxidized dimeric form of cysteine, in the medium. It is also possible to obtain capping of the free cysteine with glutathione rather than cysteine, by modifying the concentration of glutathione in the medium. Accordingly, in certain embodiments the IL-2 protein of formula (I) is capped with cysteine. In certain embodiments the IL-2 protein of formula (I) is capped with glutathione.

Disulfide-linked high-molecular weight aggregates and multimers are often generated when expressing a protein containing a free cysteine. Furthermore, incorrect disulfide-bond formation between unintended pairs of cysteine (inter- and intra-molecular), i.e. "scrambling" of disulfide bonds, may occur. Scrambling of disulfide bridges and formation of aggregates and multimers during secretion may be reduced by, e.g., optimizing the sequence of the leader or signal sequence used to direct secretion or choosing a completely different leader sequence, by increasing expression of folding chaperones and protein disulfide isomerase enzymes, by expressing folding chaperones and protein disulfide isomerase enzymes from other organisms, by expressing synthetic folding chaperones and protein disulfide isomerases, by altering the temperature, by adding short-chain fatty acid supplements to the cultivation medium, or by adding anti-oxidants to the medium.

The challenges described above for secretion of proteins containing a free cysteine often results in a low yield of correctly folded, cysteine-capped monomeric protein secreted into the medium.

One way to increase the yield of a secreted protein of interest is to improve the mechanism of cleaving off the signal or leader sequence directing the protein for secretion. Correct processing of the signal or leader sequence is a crucial step in the secretion pathway, as it liberates the N-terminus of the mature secreted protein and is usually required to achieve efficient secretion. Incomplete cleavage of the signal or leader sequence typically leads to intracellular accumulation of protein, although in some cases, incompletely processed product may be secreted as well.

In most expression systems, secretion is guided by a secretion signal peptide which is fused to the N-terminus of the protein to be secreted, and which is cleaved off by specific processing enzymes of the host cell, prior to or in conjunction with secretion. Accordingly, the IL-2 protein of formula (I) is in certain embodiments expressed with a secretion signal peptide, which is cleaved off by specific processing enzymes of the host cell, prior to or in conjunction with the secretion.

In mammalian expression systems, the signal peptide is in certain embodiments the signal peptide of any naturally secreted protein. In certain embodiments the signal peptide for mammalian expression systems is in certain embodiments thus the signal peptide of a naturally secreted protein. In certain embodiments the signal peptide for mammalian expression systems is a non-natural synthetic signal sequenced designed in silico or experimentally found to efficiently guide secretion.

In *E. coli*, the signal sequence guiding the protein to periplasmic secretion can be the signal peptide of any bacterial naturally secreted to the periplasm. In certain embodiments the signal peptide for expression of the IL-2 protein of formula (I) in *E. coli* is selected from the group consisting of phoA, dsbA, glII, mal, OmpA, OmpC, OmpT, pelB, torA, torT, EOX, STII, SfmC, lamB, MglB, MmAp, and tolB. In certain embodiments the signal peptide is a non-natural sequence designed in silico, or experimentally found to guide secretion efficiently.

In yeast expression systems, such as *S. cerevisiae* and *Pichia pastoris*, the leader sequence guiding expression may comprise a signal sequence and a propeptide, whereof the signal sequence guides the protein to be secreted to the ER and is cleaved off in conjunction with transport into the ER, and the propeptide is cleaved off in the Golgi apparatus by the Kex2 enzyme prior to secretion into the growth medium. The leader sequence may be the leader sequence of a naturally secreted enzyme or pheromone. In certain embodiments the leader sequence of the IL-2 protein of formula (I) for expression in a yeast expression system is thus selected from the group consisting of the *S. cerevisiae* mating factor Alpha leader sequence, the SUC2 leader sequence and the VOA1 leader sequence. In certain embodiments the leader sequence is from a secreted protein from another yeast or filamentous fungus, or it may be a non-natural leader sequence designed in silico, or it may be a leader sequence experimentally found to efficiently guide folding and secretion. The leader sequence may also have been experimentally identified form a large library of leader sequences, e.g. comprising many combinations of random amino acid substitutions.

Correct cleavage of the signal or leader sequence by the endogenous processing enzymes of the host cell is dependent on the sequence of amino acids immediately following the cleavage site, which constitute the N-terminus of the mature processed and secreted recombinant protein. In addition to the specific N-terminal amino acid sequence of the protein of interest, the accessibility of the N-terminus in the folded protein of interest may influence how efficiently the signal sequence or leader is processed. For example, a buried N-terminus may be inaccessible to the processing protease and will therefore be problematic for a secretion strategy.

Using prediction models built on available experimental data, the probability of cleavage of a certain amino acid sequence by the signal peptidase complex can be calculated. Such tools are available online, allowing a person skilled in the art to predict the likelihood of correct processing of the signal peptide in eukarya and bacteria. In yeast expression systems, the leader sequence typically comprises both a signal sequence, cleaved by the signal peptidase complex in the ER, and a propeptide, cleaved by a Kex2 furin protease in the Golgi. The recognition site for Kex2, KR, is well conserved among Kex2 substrates across yeast species. It is known that negatively charged amino acids are overrepresented in the P1', P2' and P4' positions of Kex2 substrates. However, potential cleavage by Kex2 typically needs to be experimentally examined on a case-to-case basis.

It is well known to a person of ordinary skills in the art that correct processing of the signal or leader sequence is one of several features required for efficient secretion of correctly folded and soluble protein. Examples of important features are adequate rates of transcription and translation, co- or post translational translocation into the ER, folding and formation of correct disulfide bridges in the ER, and vesicular transport out of the cell. Experimental verification of any computer-aided prediction of secretion efficiency is therefore of essence.

It is known that intracellular accumulation of incorrectly folded or aggregated protein may negatively affect the physiology of the host cell, potentially inducing stress responses and causing decreased growth rate and cell fitness. Therefore, avoiding intracellular accumulation by improving processing of the signal or leader sequence, may result in increased growth rates, cell densities and cell mass productivity, positively contributing to the overall productivity of the protein of interest. In addition, a more fit cell line is more likely to be performing robustly across scales and cultivation conditions and better cope with process disturbances. Furthermore, it is generally recognized by persons skilled in the art that cell lines with normal growth rates and cell fitness have lower risk of instability than cell lines with reduced growth rates and cell fitness resulting from effects of transgene expression, such as intracellular accumulation of product. For a cell line with reduced growth rate conferred by transgene expression, the occurrence of an event that reduces transgene expression (e.g. a gene silencing event, mutation, or looping out of transgenes through direct-repeat recombination) results in a competitive growth advantage. Cells with reduced expression will rapidly outcompete other cells in the population still expressing the transgene at high levels, resulting in an instable expression phenotype.

In certain embodiments the host cells expressing one or more genes encoding the IL-2 protein of formula (I) may comprise the one or more genes encoding for the IL-2 protein of formula (I) within their genome.

In another aspect the present invention relates to a conjugate comprising one or more of the IL-2 proteins of formula (I).

In certain embodiments said conjugate comprises a moiety $M_{mod}$ conjugated to the cysteine marked with the asterisk in the IL-2 protein of formula (I). Optionally, additional moieties $M_{mod}$ may be conjugated to the IL-2 protein of formula (I) at other positions, which additional moieties $M_{mod}$ may be the same or different. Attachment of such additional moiety $M_{mod}$ may be at the N-terminus, C-terminus, at an amino acid side chain or at an internal site of the IL-2 protein. In certain embodiments attachment of such additional moiety $M_{mod}$ is at the N-terminus of the IL-2 protein of formula (I). In certain embodiments attachment of such additional moiety $M_{mod}$ is at the C-terminus of the IL-2 protein of formula (I). In certain embodiments attachment of such additional moiety $M_{mod}$ is at an internal site of the IL-2 moiety, such as at an amino acid side chain of the IL-2 protein of formula (I). If more than one additional moiety $M_{mod}$ is attached to the IL-2 protein of formula (I), attachment may occur at any combination of attachment sites selected from the group consisting of the N-terminus, C-terminus and an internal site. Embodiments for $M_{mod}$ are as described elsewhere herein. Optionally, one or more moieties -$L^1$-$L^2$-Z may be conjugated to a moiety $M_{mod}$, wherein -$L^1$-, -$L^2$- and Z are as defined elsewhere herein. In certain embodiments one or more moiety -$L^1$-$L^2$-Z is conjugated to the moiety $M_{mod}$ which is conjugated to the cysteine marked with the asterisk in formula (I).

Specific embodiments for $M_{mod}$ are as described elsewhere herein.

In certain embodiments the conjugate is an IL-2 conjugate or a pharmaceutically acceptable salt thereof of formula (Ia) or (Ib)

(Ia)

(Ib)

wherein
-D comprises the IL-2 protein of formula (I);
-$L^1$- is a linker moiety covalently and reversibly attached to -D;
-$L^2$- is a chemical bond or is a spacer moiety;
—Z is a polymeric moiety or a substituted fatty acid moiety;

x is an integer selected from the group consisting of 1, 2, 3, 4, 5, 6, 7, 8, 9, 10, 11, 12, 13, 14, 15 or 16; and y is an integer selected from the group consisting of 2, 3, 4 and 5.

In certain embodiments the conjugates of formula (Ia) and (Ib) release a biased IL-2 moiety or biased IL-2 protein of formula (I), wherein the ratio of $Ratio_{biased\ IL}$-2 to $Ratio_{aldeskeukin}$ is larger than 1, preferably larger than 2, preferably larger then 3, preferably larger than 4 and even more preferably larger than 5. In certain embodiments the ratio of $Ratio_{biased\ IL}$-2 to $Ratio_{aldeskeukin}$ is larger than 10, larger than 20, larger than 50, larger than 70, larger than 100 or larger than 150.

In certain embodiments -D of formula (Ia) or (Ib) comprises a modifying moiety $M_{mod}$ conjugated to the thiol of the cysteine residue marked with the asterisk in the IL-2 protein of formula (I). In certain embodiments such moiety $M_{mod}$ is stably conjugated to the thiol of the cysteine residue marked with the asterisk in the IL-2 protein of formula (I). Optionally, -D may comprise one or more further moieties $M_{mod}$ stably conjugated to -D, which may be the same or different moieties $M_{mod}$. Optionally, one or more further moiety -$L^1$-$L^2$-Z is conjugated to $M_{mod}$.

In one embodiment $M_{mod}$ is a substituent. Preferably, such substituent has a molecular weight ranging from 15 Da to 1 kDa.

Such moiety $M_{mod}$ may in one embodiment be introduced in the form of a disulfide bridging, such as a disulfide bridge formed between the thiol groups of two cysteine residues, of which one is the cysteine marked with the asterisk in formula (I). The other cysteine residue of the disulfide bridging may be a naturally occurring cysteine residue. In certain embodiments such other cysteine does not naturally occur but was added to or inserted into the IL-2 protein of formula (I) or replaced a naturally occurring amino acid residue of the IL-2 protein of formula (I). Ways of obtaining such disulfide bridging are disclosed in Jones et al. (J. Am. Chem. Soc., 2012, 134 (3), pp 1847-1852), WO2011/018611, WO2011/018612 and WO2011/018613.

In another embodiment $M_{mod}$ is a polymeric moiety. Such polymeric moiety may comprise a linear, branched or multi-arm polymer. In one embodiment the polymer is a linear polymer. In another embodiment the polymer is a branched polymer. Such branched polymer in certain embodiments has one, two, three, four or five branching points. From each branching point two, three or four polymer arms may extend. In another embodiment the polymer is a multi-arm polymer. Such multi-arm polymer may have 3, 4, 5, 6, 7 or 8 polymeric arms.

If $M_{mod}$ is a polymeric moiety, such polymeric moiety in certain embodiments has a molecular weight ranging from 0.5 kDa to 1000 kDa, such as from 1 kDa to 1000 kDa, such as from 2 kDa to 500 kDa, from 3 kDa to 200 kDa, from 5 kDa to 120 kDa or from 7 to 40 kDa. In one embodiment such polymer has a molecular weight of about 0.5 kDa. In one embodiment such polymer has a molecular weight of about 1 kDa. In one embodiment such polymer has a molecular weight of about 2 kDa. In one embodiment such polymer has a molecular weight of about 3 kDa. In one embodiment such polymer has a molecular weight of about 4 kDa. In one embodiment such polymer has a molecular weight of about 5 kDa. In one embodiment such polymer has a molecular weight of about 7.5 kDa. In another embodiment such polymeric moiety has a molecular weight of about 10 kDa. In another embodiment such polymeric moiety has a molecular weight of about 15 kDa. In another embodiment such polymeric moiety has a molecular weight of about 20 kDa. In another embodiment such polymeric moiety has a molecular weight of about 30 kDa. In another embodiment such polymeric moiety has a molecular weight of about 40 kDa. In another embodiment such polymeric moiety has a molecular weight of about 50 kDa. In another embodiment such polymeric moiety has a molecular weight of about 70 kDa. In another embodiment such polymeric moiety has a molecular weight of about 80 kDa. In another embodiment such polymeric moiety has a molecular weight of about 90 kDa. In another embodiment such polymeric moiety has a molecular weight of about 100 kDa. In one embodiment such polymer has a molecular weight of 0.5 kDa. In one embodiment such polymer has a molecular weight of 1 kDa. In one embodiment such polymer has a molecular weight of 2 kDa. In one embodiment such polymer has a molecular weight of 3 kDa. In one embodiment such polymer has a molecular weight of 4 kDa. In one embodiment such polymer has a molecular weight of 5 kDa. In one embodiment such polymer has a molecular weight of 7.5 kDa. In another embodiment such polymeric moiety has a molecular weight of 10 kDa. In another embodiment such polymeric moiety has a molecular weight of 15 kDa. In another embodiment such polymeric moiety has a molecular weight of 20 kDa. In another embodiment such polymeric moiety has a molecular weight of 30 kDa. In another embodiment such polymeric moiety has a molecular weight of 40 kDa. In another embodiment such polymeric moiety has a molecular weight of 50 kDa. In another embodiment such polymeric moiety has a molecular weight of 70 kDa. In another embodiment such polymeric moiety has a molecular weight of 80 kDa. In another embodiment such polymeric moiety has a molecular weight of 90 kDa. In another embodiment such polymeric moiety has a molecular weight of 100 kDa.

If $M_{mod}$ is a polymeric moiety, such polymeric moiety in certain embodiments comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, alginate, mannans, pectins, rhamnogalacturonans, starches, hydroxyalkyl starches, hydroxyethyl starches and other carbohydrate-based polymers, xylans, and copolymers thereof.

In one embodiment $M_{mod}$ is a PEG-based polymer.

In another embodiment $M_{mod}$ is a hyaluronic acid-based polymer.

In another embodiment $M_{mod}$ comprises a peptide or protein moiety, which may be chemically conjugated to the IL-2 protein of formula (I). In certain embodiments this peptide or protein moiety $M_{mod}$ is not a fragment of IL-2 or an IL-2-moiety.

$M_{mod}$ in the form of a peptide or protein moiety may be a synthetic or natural protein moiety or a portion or variant thereof. Exemplary peptides and proteins include albumin; antibody domains, such as Fc domains or antigen binding domains of immunoglobulins; CTP, and CD25; each either in their naturally occurring form or as a variant or fragment thereof.

Attachment of $M_{mod}$ to the IL-2 protein of formula (I) may be via a stable linkage. In certain embodiments the linkage between the IL-2 protein of formula (I) and a moiety $M_{mod}$ is via an amide. In certain embodiments the linkage between the IL-2 protein of formula (I) and a moiety $M_{mod}$ is via a moiety

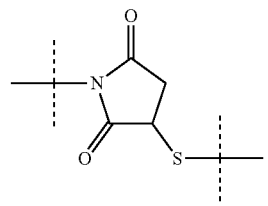

The conjugate of the present invention may comprise a moiety $M_{mod}$ conjugated to the cysteine marked with the asterisk in the IL-2 protein of formula (I) and may optionally comprise one or more additional moieties $M_{mod}$ conjugated to the IL-2 protein of formula (I).

Attachment of such one or more additional moieties $M_{mod}$ may be at a proteinogenic or non-proteinogenic amino acid residue of the IL-2 protein. In certain embodiments attachment of such one or more additional moieties $M_{mod}$ occurs at a proteinogenic amino acid. Such proteinogenic amino acid residue is in certain embodiments selected from the group consisting of cysteine, methionine, histidine, lysine, tryptophan, serine, threonine, tyrosine, aspartic acid, glutamic acid, glutamine and arginine. In certain embodiments attachment of such one or more additional moieties $M_{mod}$ occurs to a non-proteinogenic amino acid. In this case it is understood that such non-proteinogenic amino acid residue is artificially introduced into the IL-2 protein of formula (I). Such non-proteinogenic amino acid residue may be any non-proteinogenic amino acid residue having a functional group available for conjugating $M_{mod}$ to the IL-2 protein of formula (I). In certain embodiments such non-proteinogenic amino acid comprises a functional group in its side chain selected from the group consisting of carbonyl; carbonyl derivatives, such as carbonyl-like, marked carbonyl and protected carbonyl groups; azide; oxime; and hydroxylamine.

In certain embodiments such non-proteinogenic amino acid is a non-proteinogenic amino acid as described in WO2006/069246A2, which non-proteinogenic amino acids are incorporated by reference herewith. In certain embodiments the non-proteinogenic amino acid has a structure as described in formula (I) in [00265] to [00283], of formula (XXX) in [00284], of formula (XXX-A) in [00285], of formula (XXX-B) in [00286], of formula (XXXI) in [00287], of formula (XXXI-A) in [00288], of formula (XXXI-B) in [00289], of formula (XXXII) in [00290], of formula (XXXII-A) in [00291], of formula (XXXII-B) in [00292], of formula (XXXX) in [00293], of formula (XXXXI) in [00294], of formula (XXXXII) in erroneously labelled paragraph [0100], i.e. the paragraph between [00294] and [00295], of formula (XXXXIII) in [00295] and [00296], of formula (XIV) in [00302] to [00305], of formula (XV) in [00306] and [00307], of formula (XI) in [00310] to [00312], of formula (XII) in [00313], of formula (XII) in [00314] and [00315], of formula (XIV) in [00316], of formula (XVI) in [00317], of formula (XVI) in [00318] and [00319], of formula (XVIII) in [00320] and [00321], or of formula (XXIX) in [00530] of WO2006/069246A2, which non-proteinogenic amino acids are incorporated by reference herewith.

In certain embodiments attachment of such one or more additional moieties $M_{mod}$ occurs at a lysine residue of the IL-2 moiety of formula (I). In certain embodiments attachment of such one or more additional moieties $M_{mod}$ occurs at a threonine residue of the IL-2 moiety of formula (I). In certain embodiments attachment of such one or more additional moieties $M_{mod}$ occurs at a serine residue of the IL-2 moiety of formula (I). In certain embodiments attachment of such one or more additional moieties $M_{mod}$ occurs at a tyrosine residue of the IL-2 moiety of formula (I). In certain embodiments attachment of such one or more additional moieties $M_{mod}$ occurs at a histidine residue of the IL-2 moiety of formula (I). In certain embodiments attachment of such one or more additional moieties $M_{mod}$ occurs at a tryptophan residue of the IL-2 moiety of formula (I). In certain embodiments attachment of such one or more additional moieties $M_{mod}$ occurs at an aspartic acid residue of the IL-2 moiety of formula (I). In certain embodiments attachment of such one or more additional moieties $M_{mod}$ occurs at a glutamic acid residue of the IL-2 moiety of formula (I). In certain embodiments attachment of such one or more additional moieties $M_{mod}$ occurs at an arginine residue of the IL-2 moiety of formula (I). In certain embodiments attachment of such one or more additional moieties $M_{mod}$ occurs at a cysteine residue of the IL-2 moiety of formula (I) other than the one marked with the asterisk. In certain embodiments attachment of such one or more additional moieties $M_{mod}$ occurs at a methionine residue of the IL-2 moiety of formula (I). In certain embodiments attachment of such one or more additional moieties $M_{mod}$ occurs at a glutamine residue of the IL-2 moiety of formula (I).

It is understood that in certain embodiments the conjugate of the present invention may have such one or more additional moieties $M_{mod}$ attached to more than one type of amino acid residue, such as to an additional cysteine and to a lysine.

In certain embodiments attachment of at least one of such one or more additional moieties $M_{mod}$ occurs at an amino acid position of the IL-2 protein of formula (I) known to be involved in binding to IL-2Rα. Thus, in certain embodiments, attachment of at least one of such one or more additional moieties $M_{mod}$ results in a reduced affinity of the IL-2 protein of formula (I) to IL-2Rαβ compared to aldesleukin, i.e. results in a biased IL-2 moiety. In certain embodiments attachment of at least one of such one or more additional moieties $M_{mod}$ occurs at a position selected from the group consisting of K34 of SEQ ID NO:1, M1 of SEQ ID NO:2, T3 of SEQ ID NO:2, F4 of SEQ ID NO:2, K5 of SEQ ID NO:2, F6 of SEQ ID NO:2, Y7 of SEQ ID NO:2, E24 of SEQ ID NO:2, E30 of SEQ ID NO:2, L34 of SEQ ID NO:2, M1 of SEQ ID NO:12, T3 of SEQ ID NO:12, F4 of SEQ ID NO:12, K5 of SEQ ID NO:12, F6 of SEQ ID NO:12, Y7 of SEQ ID NO:12, E24 of SEQ ID NO:12, E30 of SEQ ID NO:12 and L34 of SEQ ID NO:12 In certain embodiments attachment of at least one of such one or more additional moieties $M_{mod}$ occurs at a position selected from the group consisting of F4 of SEQ ID NO:2, Y7 of SEQ ID NO:2, E24 of SEQ ID NO:2, E30 of SEQ ID NO:2 and L34 of SEQ ID NO:2. In certain embodiments attachment of at least one of such one or more additional moieties $M_{mod}$ occurs at a position selected from the group consisting of F4 of SEQ ID NO:12, Y7 of SEQ ID NO:12, E24 of SEQ ID NO:12, E30 of SEQ ID NO:12 and L34 of SEQ ID NO:12. In certain embodiments attachment of at least one of such one or more additional moieties $M_{mod}$ occurs at K34 of SEQ ID NO:1. In certain embodiments attachment of at least one of such one or more additional moieties $M_{mod}$ occurs at M1 of SEQ ID NO:2. In certain embodiments attachment of at least one of such one or more additional moieties $M_{mod}$ occurs at T3 of SEQ ID NO:2. In certain embodiments attachment of at least one of such one or more additional moieties $M_{mod}$ occurs at F4 of SEQ ID NO:2. In certain embodiments attachment of at least one of such one or more additional moieties $M_{mod}$ occurs at a K5 of SEQ ID NO:2. In certain embodiments attachment of at least one of such one or more additional moieties $M_{mod}$ occurs at F6 of SEQ ID NO:2. In certain embodiments attachment of at least one of such one or more additional moieties $M_{mod}$ occurs at Y7 of SEQ ID NO:2. In certain embodiments attachment of at least one of such one or more additional moieties $M_{mod}$ occurs at E24 of SEQ ID NO:2. In certain embodiments attachment of at least one of such one or more additional moieties $M_{mod}$ occurs at E30 of SEQ ID NO:2. In certain embodiments attachment of at least one of such one or more additional moieties $M_{mod}$ occurs at L34 of SEQ ID NO:2. In certain embodiments attachment of at least one of such one or more additional moieties $M_{mod}$ occurs at M1 of SEQ ID NO:12. In certain embodiments attachment of at least one of such one or more additional moieties $M_{mod}$ occurs at T3 of SEQ ID NO:12. In certain embodiments attachment of at least one of such one or more additional moieties $M_{mod}$ occurs at F4 of SEQ ID NO:12. In certain embodiments attachment of at least one of such one or more additional moieties $M_{mod}$ occurs at a K5 of SEQ ID NO:12. In certain embodiments attachment of at least one of such one or more additional moieties $M_{mod}$ occurs at F6 of SEQ ID NO:12. In certain embodiments attachment of at least one of such one or more additional moieties $M_{mod}$ occurs at Y7 of SEQ ID NO:12. In certain embodiments attachment of at least one of such one or more additional moieties $M_{mod}$ occurs at E24 of SEQ ID NO:12. In certain embodiments attachment of at least one of such one or more additional moieties $M_{mod}$ occurs at E30 of SEQ ID NO:12. In certain embodiments attachment of at least one of such one or more additional moieties $M_{mod}$ occurs at L34 of SEQ ID NO:12.

In certain embodiments $M_{mod}$ is of formula (A-1)

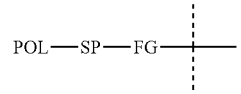

(A-1)

wherein

—FG— is a linkage;

—SP— is a spacer moiety; and

-POL is a polymer.

In certain embodiments —FG— of formula (A-1) is of formula (FG-1a)

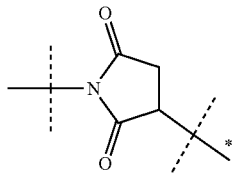

(FG-1a)

wherein
the dashed line marked with the asterisk indicates attachment to the sulfur of the cysteine marked with the asterisk in formula (I) and the unmarked dashed line indicates attachment —SP—.

In certain embodiments —FG— of formula (A-1) is of formula (FG-1b)

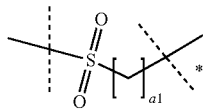

(FG-1b)

wherein
the dashed line marked with the asterisk indicates attachment to the sulfur of the cysteine marked with the asterisk in formula (I);
the unmarked dashed line indicates attachment to —SP—; and
a1 is selected from the group consisting of 1, 2, 3, 4, 5, 6, 7, 8, 9, 10, 11, 12, 13, 14, 15, 16, 17, 18. 19 and 20.

In certain embodiments a1 of formula (FG-1b) is an integer ranging from 1 to 8. In certain embodiments a1 of formula (FG-1b) an integer ranging from 1 to 6. In certain embodiments a1 of formula (FG-1b) is an integer ranging from 1 to 4. In certain embodiments a1 of formula (FG-1b) is 1. In certain embodiments a1 of formula (FG-1b) is 2. In certain embodiments a1 of formula (FG-1b) is 3. In certain embodiments a1 of formula (FG-1b) is 4. In certain embodiments a1 of formula (FG-1b) is 5. In certain embodiments a1 of formula (FG-1b) is 6.

In certain embodiments —FG— of formula (A-1) is of formula (FG-1c)

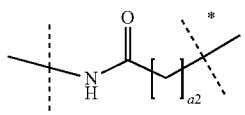

(FG-1c)

wherein
the dashed line marked with the asterisk indicates attachment to the sulfur of the cysteine marked with the asterisk in formula (I);
the unmarked dashed line indicates attachment to —SP—; and
a2 is an integer selected from the group consisting of 1, 2, 3, 4, 5, 6, 7, 8, 9, 10, 11, 12, 13, 14, 15, 16, 17, 18. 19 and 20.

In certain embodiments a2 of formula (FG-1c) is an integer ranging from 1 to 8. In certain embodiments a2 of formula (FG-1c) is an integer ranging from 1 to 6. In certain embodiments a2 of formula (FG-1c) is an integer ranging from 1 to 4. In certain embodiments a2 of formula (FG-1c) is 1. In certain embodiments a2 of formula (FG-1c) is 2. In certain embodiments a2 of formula (FG-1c) is 3. In certain embodiments a2 of formula (FG-1c) is 4. In certain embodiments a2 of formula (FG-1c) is 5. In certain embodiments a2 of formula (FG-1c) is 6.

In certain embodiments $M_{mod}$ is conjugated to the cysteine residue marked with the asterisk in formula (I) via the reaction of the thiol of said cysteine with a maleimide functional group resulting in a linkage according to structure FG-1a. The resulting thiosuccinimide ring may undergo a retro-Michael reaction which may cause the release of $M_{mod}$. This reaction may be minimized or avoided by subjecting a compound comprising such thiosuccinimide or derivative thereof, such as a bromated thiosuccinimide, to conditions that result in hydrolysis, which results in opening of the five-membered ring. The resulting linear thioether is significantly more stable, which decreases the risk of release of $M_{mod}$. While the hydrolysis of the thiosuccinimide occurs slowly at acidic pH, it is significantly faster at neutral or basic pH and elevated temperature. It was found that incubation at elevated pH and elevated temperature for several hours results in linkages as shown in formula (FG-1d) and (FG-1e), thereby resulting in a stable linkage of $M_{mod}$ to the cysteine residue marked with the asterisk in formula (I).

In certain embodiments conjugates comprising a moiety $M_{mod}$ are incubated at elevated pH, such a pH 9, and elevated temperature, such as 25° C., for several hours, such as at least 10 hours or at least 12 hours.

Accordingly, in certain embodiments —FG— of formula (A-1) is of formula (FG-1d)

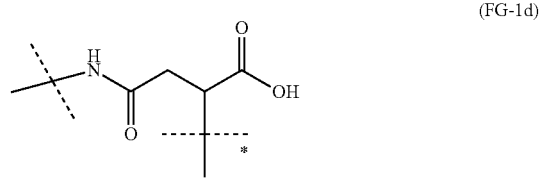

(FG-1d)

wherein the dashed line marked with the asterisk indicates attachment to the sulfur of the cysteine marked with the asterisk in formula (I) and the unmarked dashed line indicates attachment —SP—.

Accordingly, in certain embodiments —FG— of formula (A-1) is of formula (FG-1e)

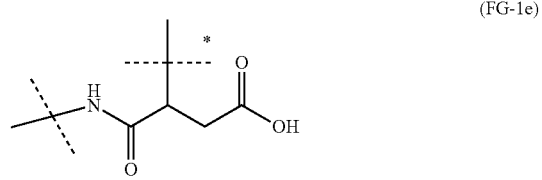

(FG-1e)

wherein the dashed line marked with the asterisk indicates attachment to the sulfur of the cysteine marked with the asterisk in formula (I) and the unmarked dashed line indicates attachment —SP—.

In certain embodiments —SP— of formula (A-1) is selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $R^9$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{10}$)—, —S(O)$_2$N($R^{10}$)—, —S(O)N($R^{10}$)—, —S(O)$_2$—, —S(O)—, —N($R^{10}$)S(O)$_2$N($R^{10a}$)—, —S—, —N($R^{10}$)—, —OC(O$R^{10}$)($R^{10a}$)—, —N($R^{10}$)C(O)N($R^{10a}$)—, and —OC(O)N($R^{10}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^9$, which are the same or different;

each —$R^9$ is independently selected from the group consisting of halogen, —CN, oxo (=O), —COO$R^{11}$, —O$R^{11}$, —C(O)$R^{11}$, —C(O)N($R^{11}R^{11a}$), —S(O)$_2$N($R^{11}R^{11a}$), —S(O)N($R^{11}R^{11a}$), —S(O)$_2R^{11}$, —S(O)$R^{11}$, —N($R^{11}$)S(O)$_2$N($R^{11a}R^{11b}$), —S$R^{11}$, —N($R^{11}R^{11a}$), —NO$_2$, —OC(O)$R^{11}$, —N($R^{11}$)C(O)$R^{11a}$, —N($R^{11}$)S(O)$_2R^{11a}$, —N($R^{11}$)S(O)$R^{11a}$, —N($R^{11}$)C(O)O$R^{11a}$, —N($R^{11}$)C(O)N($R^{11a}R^{11b}$), —OC(O)N($R^{11}R^{11a}$), and $C_{1-6}$ alkyl; wherein $C_{1-6}$ alkyl is optionally substituted with one or more halogen, which are the same or different; and each —$R^{10}$, —$R^{10a}$, —$R^{11}$, —$R^{11a}$ and —$R^{11b}$ is independently selected from the group consisting of —H, and $C_{1-6}$ alkyl, wherein $C_{1-6}$ alkyl is optionally substituted with one or more halogen, which are the same or different.

In certain embodiments —SP— of formula (A-1) is $C_{1-20}$ alkyl, which $C_{1-20}$ alkyl is optionally substituted with one or more —$R^9$, and which $C_{1-20}$ alkyl is optionally interrupted by one or more groups selected from the group consisting of —O—, —C(O)N($R^{10}$)—, —S(O)$_2$—, —S(O)—, —S—, —N($R^{10}$)—, —OC(O$R^{10}$)($R^{10a}$)—, —N($R^{10}$)C(O)N($R^{10a}$)—, and —OC(O)N($R^{10}$)—; wherein each —$R^9$ is selected from the group consisting of $C_{1-6}$ alkyl; and each —$R^{10}$ and —$R^{10a}$ is independently selected from the group consisting of —H and $C_{1-6}$ alkyl.

In certain embodiments —SP— of formula (A-1) is $C_{1-10}$ alkyl, which $C_{1-10}$ alkyl is optionally substituted with one or more —$R^9$, and which $C_{1-10}$ alkyl is optionally interrupted by one or more groups selected from the group consisting of —O—, —C(O)N($R^{10}$)—, —S(O)$_2$—, —S(O)—, —S—, —N($R^{10}$)—, —OC(O$R^{10}$)($R^{10a}$)—, —N($R^{10}$)C(O)N($R^{10a}$)—, and —OC(O)N($R^{10}$)—; wherein each —$R^9$ is selected from the group consisting of $C_{1-6}$ alkyl; and each —$R^{10}$ and —$R^{10a}$ is independently selected from the group consisting of —H and $C_{1-6}$ alkyl.

In certain embodiments -POL of formula (A-1) is a PEG-based polymer. In certain embodiments -POL is of formula (A-1i)

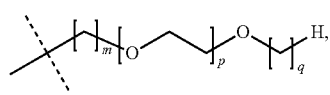

(A-1i)

wherein
the dashed line indicates attachment to —SP—;
m is 0 or 1;
p is an integer ranging from 12 to 22700; and
q is selected from the group consisting of 1, 2, 3, 4, 5, and 6.

In certain embodiments m of formula (A-1i) is 0. In certain embodiments m of formula (A-1i) is 1.

In certain embodiments p of formula (A-1i) is an integer ranging from 23 to 227000, such as from 45 to 11300, or from 69 to 4540, or from 114 to 2700. In certain embodiments p of formula (A-1i) is about 12. In certain embodiments p of formula (A-1i) is about 23. In certain embodiments p of formula (A-1i) is about 46. In certain embodiments p of formula (A-1i) is about 68. In certain embodiments p of formula (A-1i) is about 90. In certain embodiments p of formula (A-1i) is about 112. In certain embodiments p of formula (A-1i) is about 170. In certain embodiments p of formula (A-1i) is about 227. In certain embodiments p of formula (A-1i) is about 340. In certain embodiments p of formula (A-1i) is about 450. In certain embodiments p of formula (A-1i) is about 680. In certain embodiments p of formula (A-1i) is about 900. In certain embodiments p of formula (A-1i) is about 1130. In certain embodiments p of formula (A-1i) is about 1350. In certain embodiments p of formula (A-1i) is about 1590. In certain embodiments p of formula (A-1i) is about 1800. In certain embodiments p of formula (A-1i) is about 2045. In certain embodiments p of formula (A-1i) is about 2275.

In certain embodiments q of formula (A-1i) is 1. In certain embodiments q of formula (A-1i) is 2. In certain embodiments q of formula (A-1i) is 3. In certain embodiments q of formula (A-1i) is 4. In certain embodiments q of formula (A-1i) is 5. In certain embodiments q of formula (A-1i) is 6.

In certain embodiments -POL of formula (A-1) is of formula (A-1ii)

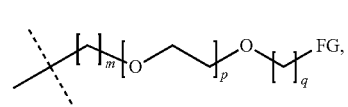

(A-1ii)

wherein
the dashed line indicates attachment to —SP—;
FG is a functional group;
m is 0 or 1;
p is an integer ranging from 12 to 22700; and
q is selected from the group consisting of 1, 2, 3, 4, 5, and 6.

If the moiety $M_{mod}$ of formula (A-1) is to be conjugated to further moieties, such as to one or more moieties -$L^1$-$L^2$-Z, it is advantageous if a moiety -POL ends with a functional group. It is understood the if -POL is of formula (A-1ii), such compound is a reagent and that after conjugation of such one or more moieties, such as one or more moieties -$L^1$-$L^2$-Z, to the functional group of said reagent, FG is no longer present, but has formed a linkage with a suitable functional group present in the reagent form of the one or more further moieties.

It is also understood that also other attachment sites for moieties to be conjugated to $M_{mod}$, such as moieties -$L^1$-$L^2$-Z, may be possible.

In certain embodiments m of formula (A-1ii) is 0. In certain embodiments m of formula (A-1ii) is 1.

In certain embodiments p of formula (A-1ii) is an integer ranging from 23 to 227000, such as from 45 to 11300, or from 69 to 4540, or from 114 to 2700. In certain embodiments p of formula (A-1ii) is about 12. In certain embodiments p of formula (A-1ii) is about 23. In certain embodiments p of formula (A-1ii) is about 46. In certain embodiments p of formula (A-1ii) is about 68. In certain embodiments p of formula (A-1ii) is about 90. In certain embodiments p of formula (A-1ii) is about 112. In certain embodiments p of formula (A-1ii) is about 170. In certain embodiments p of formula (A-1ii) is about 227. In certain embodiments p of formula (A-1ii) is about 340. In certain embodiments p of formula (A-1ii) is about 450. In certain embodiments p of formula (A-1ii) is about 680. In certain embodiments p of formula (A-1ii) is about 900. In certain embodiments p of formula (A-1ii) is about 1130. In certain embodiments p of formula (A-1ii) is about 1350. In certain embodiments p of formula (A-1ii) is about 1590. In certain embodiments p of formula (A-1ii) is about 1800. In certain embodiments p of formula (A-1ii) is about 2045. In certain embodiments p of formula (A-1ii) is about 2275.

In certain embodiments q of formula (A-1ii) is 1. In certain embodiments q of formula (A-1ii) is 2. In certain embodiments q of formula (A-1ii) is 3. In certain embodiments q of formula (A-1ii) is 4. In certain embodiments q of formula (A-1ii) is 5. In certain embodiments q of formula (A-1ii) is 6.

If a further moiety, such as a moiety $-L^1-L^2-Z$, is conjugated to $M_{mod}$ via a moiety -POL of formula (A-1), the moiety -POL may be of formula (A-1iii), (A-1iv), (A-1v) or (A-1vi)

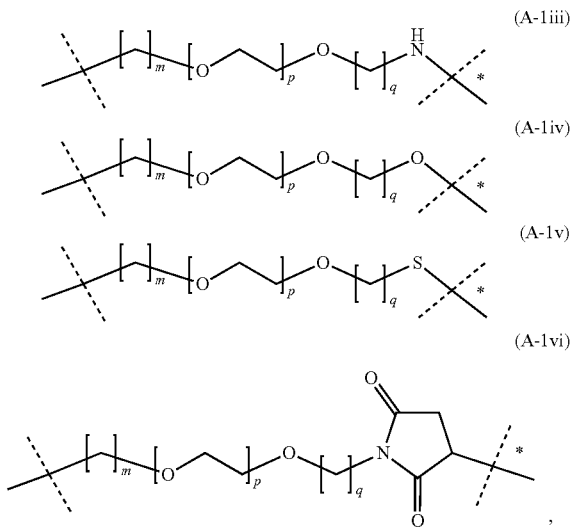

(A-1iii)
(A-1iv)
(A-1v)
(A-1vi)

wherein
the dashed line marked with the asterisk indicates attachment to the further moiety, such as to a moiety $-L^1-L^2-Z$;
the unmarked dashed line indicates attachment to —SP—; and
m, p and q are used as defined in formula (A-1i).

In certain embodiments a further moiety, such as a moiety $-L^1-L^2-Z$, is conjugated to $M_{mod}$ via a moiety -POL of formula (A-1), resulting in a moiety of -POL of formula (A-1iii). In certain embodiments a further moiety, such as a moiety $-L^1-L^2-Z$, is conjugated to $M_{mod}$ via a moiety -POL of formula (A-1), resulting in a moiety of -POL of formula (A-1iv). In certain embodiments a further moiety, such as a moiety $-L^1-L^2-Z$, is conjugated to $M_{mod}$ via a moiety -POL of formula (A-1), resulting in a moiety of -POL of formula (A-1v). In certain embodiments a further moiety, such as a moiety $-L^1-L^2-Z$, is conjugated to $M_{mod}$ via a moiety -POL of formula (A-1), resulting in a moiety of -POL of formula (A-1vi).

In certain embodiments -POL of formula (A-1) is a hyaluronic acid-based polymer.

In certain embodiments $M_{mod}$ is of formula (A-1a)

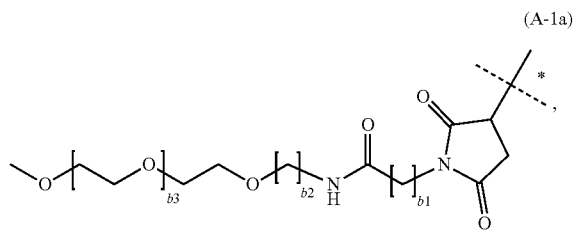

(A-1a)

wherein
the dashed line marked with the asterisk indicates attachment to the sulfur of the cysteine marked with the asterisk in formula (I);
b1 is an integer selected from the group consisting of 1, 2, 3, 4, 5, 6, 7, 8, 9, 10, 11, 12, 13, 14, 15, 16, 17, 18. 19 and 20;
b2 is an integer selected from the group consisting of 1, 2, 3, 4, 5, 6, 7, 8, 9, 10, 11, 12, 13, 14, 15, 16, 17, 18. 19 and 20; and b3 is an integer ranging from 12 to 22700.

In certain embodiments b1 of formula (A-1a) is an integer ranging from 1 to 8. In certain embodiments b1 of formula (A-1a) is an integer ranging from 1 to 6. In certain embodiments b1 of formula (A-1a) is an integer ranging from 1 to 4. In certain embodiments b1 of formula (A-1a) is 1. In certain embodiments b1 of formula (A-1a) is 2. In certain embodiments b1 of formula (A-1a) is 3. In certain embodiments b1 of formula (A-1a) is 4. In certain embodiments b1 of formula (A-1a) is 5. In certain embodiments b1 of formula (A-1a) is 6.

In certain embodiments b2 of formula (A-1a) is an integer ranging from 1 to 8. In certain embodiments b2 of formula (A-1a) is an integer ranging from 1 to 6. In certain embodiments b2 of formula (A-1a) is an integer ranging from 1 to 4. In certain embodiments b2 of formula (A-1a) is 1. In certain embodiments b2 of formula (A-1a) is 2. In certain embodiments b2 of formula (A-1a) is 3. In certain embodiments b2 of formula (A-1a) is 4. In certain embodiments b2 of formula (A-1a) is 5. In certain embodiments b2 of formula (A-1a) is 6.

In certain embodiments b3 of formula (A-1a) is an integer ranging from 23 to 227000, such as from 45 to 11300, or from 69 to 4540, or from 114 to 2700. In certain embodiments b3 of formula (A-1a) is about 12. In certain embodiments b3 of formula (A-1a) is about 23. In certain embodiments b3 of formula (A-1a) is about 46. In certain embodiments b3 of formula (A-1a) is about 68. In certain embodiments b3 of formula (A-1a) is about 90. In certain embodiments b3 of formula (A-1a) is about 112. In certain embodiments b3 of formula (A-1a) is about 170. In certain embodiments b3 of formula (A-1a) is about 227. In certain embodiments b3 of formula (A-1a) is about 340. In certain embodiments b3 of formula (A-1a) is about 450. In certain embodiments b3 of formula (A-1a) is about 680. In certain embodiments b3 of formula (A-1a) is about 900. In certain embodiments b3 of formula (A-1a) is about 1130. In certain embodiments b3 of formula (A-1a) is about 1350. In certain embodiments b3 of formula (A-1a) is about 1590. In certain embodiments b3 of formula (A-1a) is about 1800. In certain embodiments b3 of formula (A-1a) is about 2045. In certain embodiments b3 of formula (A-1a) is about 2275.

In certain embodiments b1 of formula (A-1a) is 2, b2 of formula (A-1a) is 3 and b3 of formula (A-1a) is about 12. In certain embodiments b1 of formula (A-1a) is 2, b2 of formula (A-1a) is 3 and b3 of formula (A-1a) is about 23. In certain embodiments b1 of formula (A-1a) is 2, b2 of formula (A-1a) is 3 and b3 of formula (A-1a) is about 46. In certain embodiments b1 of formula (A-1a) is 2, b2 of formula (A-1a) is 3 and b3 of formula (A-1a) is about 68. In certain embodiments b1 of formula (A-1a) is 2, b2 of formula (A-1a) is 3 and b3 of formula (A-1a) is about 90. In certain embodiments b1 of formula (A-1a) is 2, b2 of formula (A-1a) is 3 and b3 of formula (A-1a) is about 112. In certain embodiments b1 of formula (A-1a) is 2, b2 of formula (A-1a) is 3 and b3 of formula (A-1a) is about 170. In certain embodiments b1 of formula (A-1a) is 2, b2 of formula (A-1a) is 3 and b3 of formula (A-1a) is about 227. In certain embodiments b1 of formula (A-1a) is 2, b2 of formula (A-1a) is 3 and b3 of formula (A-1a) is about 340. In certain embodiments b1 of formula (A-1a) is 2, b2 of formula (A-1a) is 3 and b3 of formula (A-1a) is about 450.

In certain embodiments b1 of formula (A-1a) is 2, b2 of formula (A-1a) is 2 and b3 of formula (A-1a) is about 12. In certain embodiments b1 of formula (A-1a) is 2, b2 of formula (A-1a) is 2 and b3 of formula (A-1a) is about 23. In certain embodiments b1 of formula (A-1a) is 2, b2 of formula (A-1a) is 2 and b3 of formula (A-1a) is about 46. In certain embodiments b1 of formula (A-1a) is 2, b2 of formula (A-1a) is 2 and b3 of formula (A-1a) is about 68. In certain embodiments b1 of formula (A-1a) is 2, b2 of formula (A-1a) is 2 and b3 of formula (A-1a) is about 90. In certain embodiments b1 of formula (A-1a) is 2, b2 of formula (A-1a) is 2 and b3 of formula (A-1a) is about 112. In certain embodiments b1 of formula (A-1a) is 2, b2 of formula (A-1a) is 2 and b3 of formula (A-1a) is about 170. In certain embodiments b1 of formula (A-1a) is 2, b2 of formula (A-1a) is 2 and b3 of formula (A-1a) is about 227. In certain embodiments b1 of formula (A-1a) is 2, b2 of formula (A-1a) is 2 and b3 of formula (A-1a) is about 340. In certain embodiments b1 of formula (A-1a) is 2, b2 of formula (A-1a) is 2 and b3 of formula (A-1a) is about 450.

In certain embodiments $M_{mod}$ is of formula (A-1b)

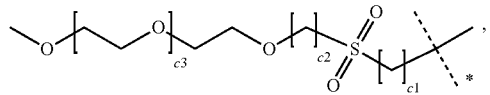 (A-1b)

wherein
the dashed line marked with the asterisk indicates attachment to the sulfur of the cysteine marked with the asterisk in formula (I);
c1 is an integer selected from the group consisting of 1, 2, 3, 4, 5, 6, 7, 8, 9, 10, 11, 12, 13, 14, 15, 16, 17, 18, 19 and 20;
c2 is an integer selected from the group consisting of 1, 2, 3, 4, 5, 6, 7, 8, 9, 10, 11, 12, 13, 14, 15, 16, 17, 18, 19 and 20; and
c3 is an integer ranging from 12 to 22700.

In certain embodiments c1 of formula (A-1b) is an integer ranging from 1 to 8. In certain embodiments c1 of formula (A-1b) is an integer ranging from 1 to 6. In certain embodiments c1 of formula (A-1b) is an integer ranging from 1 to 4. In certain embodiments c1 of formula (A-1b) is 1. In certain embodiments c1 of formula (A-1b) is 2. In certain embodiments c1 of formula (A-1b) is 3. In certain embodiments c1 of formula (A-1b) is 4. In certain embodiments c1 of formula (A-1b) is 5. In certain embodiments c1 of formula (A-1b) is 6.

In certain embodiments c2 of formula (A-1b) is an integer ranging from 1 to 8. In certain embodiments c2 of formula (A-1b) is an integer ranging from 1 to 6. In certain embodiments c2 of formula (A-1b) is an integer ranging from 1 to 4. In certain embodiments c2 of formula (A-1b) is 1. In certain embodiments c2 of formula (A-1b) is 2. In certain embodiments c2 of formula (A-1b) is 3. In certain embodiments c2 of formula (A-1b) is 4. In certain embodiments c2 of formula (A-1b) is 5. In certain embodiments c2 of formula (A-1b) is 6.

In certain embodiments c3 of formula (A-1b) is an integer ranging from 23 to 227000, such as from 45 to 11300, or from 69 to 4540, or from 114 to 2700. In certain embodiments c3 of formula (A-1b) is about 12. In certain embodiments c3 of formula (A-1b) is about 23. In certain embodiments c3 of formula (A-1b) is about 46. In certain embodiments c3 of formula (A-1b) is about 68. In certain embodiments c3 of formula (A-1b) is about 90. In certain embodiments c3 of formula (A-1b) is about 112. In certain embodiments c3 of formula (A-1b) is about 170. In certain embodiments c3 of formula (A-1b) is about 227. In certain embodiments c3 of formula (A-1b) is about 340. In certain embodiments c3 of formula (A-1b) is about 450. In certain embodiments c3 of formula (A-1b) is about 680. In certain embodiments c3 of formula (A-1b) is about 900. In certain embodiments c3 of formula (A-1b) is about 1130. In certain embodiments c3 of formula (A-1b) is about 1350. In certain embodiments c3 of formula (A-1b) is about 1590. In certain embodiments c3 of formula (A-1b) is about 1800. In certain embodiments c3 of formula (A-1b) is about 2045. In certain embodiments c3 of formula (A-1b) is about 2275.

In certain embodiments c1 of formula (A-1b) is 2, c2 of formula (A-1b) is 3 and c3 of formula (A-1b) is about 12. In certain embodiments c1 of formula (A-1b) is 2, c2 of formula (A-1b) is 3 and c3 of formula (A-1b) is about 23. In certain embodiments c1 of formula (A-1b) is 2, c2 of formula (A-1b) is 3 and c3 of formula (A-1b) is about 46. In certain embodiments c1 of formula (A-1b) is 2, c2 of formula (A-1b) is 3 and c3 of formula (A-1b) is about 68. In certain embodiments c1 of formula (A-1b) is 2, c2 of formula (A-1b) is 3 and c3 of formula (A-1b) is about 90. In certain embodiments c1 of formula (A-1b) is 2, c2 of formula (A-1b) is 3 and c3 of formula (A-1b) is about 112. In certain embodiments c1 of formula (A-1b) is 2, c2 of formula (A-1b) is 3 and c3 of formula (A-1b) is about 170. In certain embodiments c1 of formula (A-1b) is 2, c2 of formula (A-1b) is 3 and c3 of formula (A-1b) is about 227. In certain embodiments c1 of formula (A-1b) is 2, c2 of formula (A-1b) is 3 and c3 of formula (A-1b) is about 340. In certain embodiments c1 of formula (A-1b) is 2, c2 of formula (A-1b) is 3 and c3 of formula (A-1b) is about 450.

In certain embodiments b1 of formula (A-1b) is 2, b2 of formula (A-1b) is 2 and b3 of formula (A-1b) is about 12. In certain embodiments b1 of formula (A-1b) is 2, b2 of formula (A-1b) is 2 and b3 of formula (A-1b) is about 23. In certain embodiments b1 of formula (A-1b) is 2, b2 of formula (A-1b) is 2 and b3 of formula (A-1b) is about 46.

In certain embodiments b1 of formula (A-1b) is 2, b2 of formula (A-1b) is 2 and b3 of formula (A-1b) is about 68. In certain embodiments b1 of formula (A-1b) is 2, b2 of formula (A-1b) is 2 and b3 of formula (A-1b) is about 90. In certain embodiments b1 of formula (A-1b) is 2, b2 of formula (A-1b) is 2 and b3 of formula (A-1b) is about 112. In certain embodiments b1 of formula (A-1b) is 2, b2 of formula (A-1b) is 2 and b3 of formula (A-1b) is about 170. In certain embodiments b1 of formula (A-1b) is 2, b2 of formula (A-1b) is 2 and b3 of formula (A-1b) is about 227. In certain embodiments b1 of formula (A-1b) is 2, b2 of formula (A-1b) is 2 and b3 of formula (A-1b) is about 340. In certain embodiments b1 of formula (A-1b) is 2, b2 of formula (A-1b) is 2 and b3 of formula (A-1b) is about 450.

In certain embodiments $M_{mod}$ is of formula (A-1c)

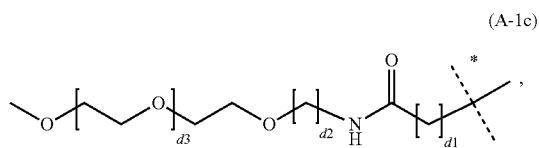

(A-1c)

wherein
the dashed line marked with the asterisk indicates attachment to the sulfur of the cysteine marked with the asterisk in formula (I);
d1 is an integer selected from the group consisting of 1, 2, 3, 4, 5, 6, 7, 8, 9, 10, 11, 12, 13, 14, 15, 16, 17, 18, 19 and 20;
d2 is an integer selected from the group consisting of 1, 2, 3, 4, 5, 6, 7, 8, 9, 10, 11, 12, 13, 14, 15, 16, 17, 18, 19 and 20; and
d3 is an integer ranging from 12 to 22700.

In certain embodiments d1 of formula (A-1c) is an integer ranging from 1 to 8. In certain embodiments d1 of formula (A-1c) is an integer ranging from 1 to 6. In certain embodiments d1 of formula (A-1c) is an integer ranging from 1 to 4. In certain embodiments d1 of formula (A-1c) is 1. In certain embodiments d1 of formula (A-1c) is 2. In certain embodiments d1 of formula (A-1c) is 3. In certain embodiments d1 of formula (A-1c) is 4. In certain embodiments d1 of formula (A-1c) is 5. In certain embodiments d1 of formula (A-1c) is 6.

In certain embodiments d2 of formula (A-1c) is an integer ranging from 1 to 8. In certain embodiments d2 of formula (A-1c) is an integer ranging from 1 to 6. In certain embodiments d2 of formula (A-1c) is an integer ranging from 1 to 4. In certain embodiments d2 of formula (A-1c) is 1. In certain embodiments d2 of formula (A-1c) is 2. In certain embodiments d2 of formula (A-1c) is 3. In certain embodiments d2 of formula (A-1c) is 4. In certain embodiments d2 of formula (A-1c) is 5. In certain embodiments d2 of formula (A-1c) is 6.

In certain embodiments d3 of formula (A-1c) is an integer ranging from 23 to 227000, such as from 45 to 11300, or from 69 to 4540, from 114 to 2700 or from 160 to 900. In certain embodiments d3 of formula (A-1c) is about 12. In certain embodiments d3 of formula (A-1c) is about 23. In certain embodiments d3 of formula (A-1c) is about 46. In certain embodiments d3 of formula (A-1c) is about 68. In certain embodiments d3 of formula (A-1c) is about 90. In certain embodiments d3 of formula (A-1c) is about 112. In certain embodiments d3 of formula (A-1c) is about 170. In certain embodiments d3 of formula (A-1c) is about 227. In certain embodiments d3 of formula (A-1c) is about 340. In certain embodiments d3 of formula (A-1c) is about 450. In certain embodiments d3 of formula (A-1c) is about 680. In certain embodiments d3 of formula (A-1c) is about 900. In certain embodiments d3 of formula (A-1c) is about 1130. In certain embodiments d3 of formula (A-1c) is about 1350. In certain embodiments d3 of formula (A-1c) is about 1590. In certain embodiments d3 of formula (A-1c) is about 1800. In certain embodiments d3 of formula (A-1c) is about 2045. In certain embodiments d3 of formula (A-1c) is about 2275.

In certain embodiments d1 of formula (A-1c) is 2, d2 of formula (A-1c) is 3 and d3 of formula (A-1cd) is about 12. In certain embodiments d1 of formula (A-1c) is 2, d2 of formula (A-1c) is 3 and d3 of formula (A-1c) is about 23. In certain embodiments d1 of formula (A-1c) is 2, d2 of formula (A-1c) is 3 and d3 of formula (A-1c) is about 46. In certain embodiments d1 of formula (A-1c) is 2, d2 of formula (A-1c) is 3 and d3 of formula (A-1c) is about 68. In certain embodiments d1 of formula (A-1c) is 2, d2 of formula (A-1c) is 3 and d3 of formula (A-1c) is about 90. In certain embodiments d1 of formula (A-1c) is 2, d2 of formula (A-1c) is 3 and d3 of formula (A-1c) is about 112. In certain embodiments d1 of formula (A-1c) is 2, d2 of formula (A-1c) is 3 and d3 of formula (A-1c) is about 170. In certain embodiments d1 of formula (A-1c) is 2, d2 of formula (A-1c) is 3 and d3 of formula (A-1c) is about 227. In certain embodiments d1 of formula (A-1c) is 2, d2 of formula (A-1c) is 3 and d3 of formula (A-1c) is about 340. In certain embodiments d1 of formula (A-1c) is 2, d2 of formula (A-1c) is 3 and d3 of formula (A-1c) is about 450.

In certain embodiments b1 of formula (A-1c) is 2, b2 of formula (A-1c) is 2 and b3 of formula (A-1c) is about 12. In certain embodiments b1 of formula (A-1c) is 2, b2 of formula (A-1c) is 2 and b3 of formula (A-1c) is about 23. In certain embodiments b1 of formula (A-1c) is 2, b2 of formula (A-1c) is 2 and b3 of formula (A-1c) is about 46. In certain embodiments b1 of formula (A-1c) is 2, b2 of formula (A-1c) is 2 and b3 of formula (A-1c) is about 68. In certain embodiments b1 of formula (A-1c) is 2, b2 of formula (A-1c) is 2 and b3 of formula (A-1c) is about 90. In certain embodiments b1 of formula (A-1c) is 2, b2 of formula (A-1c) is 2 and b3 of formula (A-1c) is about 112. In certain embodiments b1 of formula (A-1c) is 2, b2 of formula (A-1c) is 2 and b3 of formula (A-1c) is about 170. In certain embodiments b1 of formula (A-1c) is 2, b2 of formula (A-1c) is 2 and b3 of formula (A-1c) is about 227. In certain embodiments b1 of formula (A-1c) is 2, b2 of formula (A-1c) is 2 and b3 of formula (A-1c) is about 340. In certain embodiments b1 of formula (A-1c) is 2, b2 of formula (A-1c) is 2 and b3 of formula (A-1c) is about 450.

In certain embodiments $M_{mod}$ is of formula (A-1d)

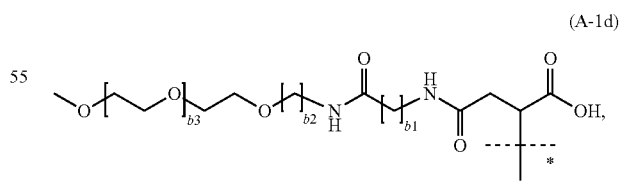

(A-1d)

wherein
the dashed line marked with the asterisk indicates attachment to the sulfur of the cysteine marked with the asterisk in formula (I);
b1 is an integer selected from the group consisting of 1, 2, 3, 4, 5, 6, 7, 8, 9, 10, 11, 12, 13, 14, 15, 16, 17, 18, 19 and 20;

b2 is an integer selected from the group consisting of 1, 2, 3, 4, 5, 6, 7, 8, 9, 10, 11, 12, 13, 14, 15, 16, 17, 18, 19 and 20; and b3 is an integer ranging from 12 to 22700.

In certain embodiments b1 of formula (A-1d) is an integer ranging from 1 to 8. In certain embodiments b1 of formula (A-1d) is an integer ranging from 1 to 6. In certain embodiments b1 of formula (A-1d) is an integer ranging from 1 to 4. In certain embodiments b1 of formula (A-1d) is 1. In certain embodiments b1 of formula (A-1d) is 2. In certain embodiments b1 of formula (A-1d) is 3. In certain embodiments b1 of formula (A-1d) is 4. In certain embodiments b1 of formula (A-1d) is 5. In certain embodiments b1 of formula (A-1d) is 6.

In certain embodiments b2 of formula (A-1d) is an integer ranging from 1 to 8. In certain embodiments b2 of formula (A-1d) is an integer ranging from 1 to 6. In certain embodiments b2 of formula (A-1d) is an integer ranging from 1 to 4. In certain embodiments b2 of formula (A-1d) is 1. In certain embodiments b2 of formula (A-1d) is 2. In certain embodiments b2 of formula (A-1d) is 3. In certain embodiments b2 of formula (A-1d) is 4. In certain embodiments b2 of formula (A-1d) is 5. In certain embodiments b2 of formula (A-1d) is 6.

In certain embodiments b3 of formula (A-1d) is an integer ranging from 23 to 227000, such as from 45 to 11300, or from 69 to 4540, or from 114 to 2700. In certain embodiments b3 of formula (A-1d) is about 12. In certain embodiments b3 of formula (A-1d) is about 23. In certain embodiments b3 of formula (A-1d) is about 46. In certain embodiments b3 of formula (A-1d) is about 68. In certain embodiments b3 of formula (A-1d) is about 90. In certain embodiments b3 of formula (A-1d) is about 112. In certain embodiments b3 of formula (A-1d) is about 170.

In certain embodiments b3 of formula (A-1d) is about 227. In certain embodiments b3 of formula (A-1d) is about 340. In certain embodiments b3 of formula (A-1d) is about 450. In certain embodiments b3 of formula (A-1d) is about 680. In certain embodiments b3 of formula (A-1d) is about 900. In certain embodiments b3 of formula (A-1d) is about 1130. In certain embodiments b3 of formula (A-1d) is about 1350. In certain embodiments b3 of formula (A-1d) is about 1590. In certain embodiments b3 of formula (A-1d) is about 1800. In certain embodiments b3 of formula (A-1d) is about 2045. In certain embodiments b3 of formula (A-1d) is about 2275.

In certain embodiments b1 of formula (A-1d) is 2, b2 of formula (A-1d) is 3 and b3 of formula (A-1d) is about 12. In certain embodiments b1 of formula (A-1d) is 2, b2 of formula (A-1d) is 3 and b3 of formula (A-1d) is about 23. In certain embodiments b1 of formula (A-1d) is 2, b2 of formula (A-1d) is 3 and b3 of formula (A-1d) is about 46. In certain embodiments b1 of formula (A-1d) is 2, b2 of formula (A-1d) is 3 and b3 of formula (A-1d) is about 68. In certain embodiments b1 of formula (A-1d) is 2, b2 of formula (A-1d) is 3 and b3 of formula (A-1d) is about 90. In certain embodiments b1 of formula (A-1d) is 2, b2 of formula (A-1d) is 3 and b3 of formula (A-1d) is about 112. In certain embodiments b1 of formula (A-1d) is 2, b2 of formula (A-1d) is 3 and b3 of formula (A-1d) is about 170. In certain embodiments b1 of formula (A-1d) is 2, b2 of formula (A-1d) is 3 and b3 of formula (A-1d) is about 227. In certain embodiments b1 of formula (A-1d) is 2, b2 of formula (A-1d) is 3 and b3 of formula (A-1d) is about 340. In certain embodiments b1 of formula (A-1d) is 2, b2 of formula (A-1d) is 3 and b3 of formula (A-1d) is about 450.

In certain embodiments b1 of formula (A-1d) is 2, b2 of formula (A-1d) is 2 and b3 of formula (A-1d) is about 12. In certain embodiments b1 of formula (A-1d) is 2, b2 of formula (A-1d) is 2 and b3 of formula (A-1d) is about 23. In certain embodiments b1 of formula (A-1d) is 2, b2 of formula (A-1d) is 2 and b3 of formula (A-1d) is about 46. In certain embodiments b1 of formula (A-1d) is 2, b2 of formula (A-1d) is 2 and b3 of formula (A-1d) is about 68. In certain embodiments b1 of formula (A-1d) is 2, b2 of formula (A-1d) is 2 and b3 of formula (A-1d) is about 90. In certain embodiments b1 of formula (A-1d) is 2, b2 of formula (A-1d) is 2 and b3 of formula (A-1d) is about 112. In certain embodiments b1 of formula (A-1d) is 2, b2 of formula (A-1d) is 2 and b3 of formula (A-1d) is about 170. In certain embodiments b1 of formula (A-1d) is 2, b2 of formula (A-1d) is 2 and b3 of formula (A-1d) is about 227. In certain embodiments b1 of formula (A-1d) is 2, b2 of formula (A-1d) is 2 and b3 of formula (A-1d) is about 340. In certain embodiments b1 of formula (A-1d) is 2, b2 of formula (A-1d) is 2 and b3 of formula (A-1d) is about 450.

In certain embodiments $M_{mod}$ is of formula (A-1e)

$$\text{(A-1e)}$$

wherein the dashed line marked with the asterisk indicates attachment to the sulfur of the cysteine marked with the asterisk in formula (I);

b1 is an integer selected from the group consisting of 1, 2, 3, 4, 5, 6, 7, 8, 9, 10, 11, 12, 13, 14, 15, 16, 17, 18, 19 and 20;

b2 is an integer selected from the group consisting of 1, 2, 3, 4, 5, 6, 7, 8, 9, 10, 11, 12, 13, 14, 15, 16, 17, 18, 19 and 20; and b3 is an integer ranging from 12 to 22700.

In certain embodiments b1 of formula (A-1e) is an integer ranging from 1 to 8. In certain embodiments b1 of formula (A-1e) is an integer ranging from 1 to 6. In certain embodiments b1 of formula (A-1e) is an integer ranging from 1 to 4. In certain embodiments b1 of formula (A-1e) is 1. In certain embodiments b1 of formula (A-1e) is 2. In certain embodiments b1 of formula (A-1e) is 3. In certain embodiments b1 of formula (A-1e) is 4. In certain embodiments b1 of formula (A-1e) is 5. In certain embodiments b1 of formula (A-1e) is 6.

In certain embodiments b2 of formula (A-1e) is an integer ranging from 1 to 8. In certain embodiments b2 of formula (A-1e) is an integer ranging from 1 to 6. In certain embodiments b2 of formula (A-1e) is an integer ranging from 1 to 4. In certain embodiments b2 of formula (A-1e) is 1. In certain embodiments b2 of formula (A-1e) is 2. In certain embodiments b2 of formula (A-1e) is 3. In certain embodiments b2 of formula (A-1e) is 4. In certain embodiments b2 of formula (A-1e) is 5. In certain embodiments b2 of formula (A-1e) is 6.

In certain embodiments b3 of formula (A-1e) is an integer ranging from 23 to 227000, such as from 45 to 11300, or from 69 to 4540, or from 114 to 2700. In certain embodiments b3 of formula (A-1e) is about 12. In certain embodiments b3 of formula (A-1e) is about 23. In certain embodiments b3 of formula (A-1e) is about 46. In certain embodiments b3 of formula (A-1e) is about 68. In certain embodiments b3 of formula (A-1e) is about 90. In certain embodiments b3 of formula (A-1e) is about 112. In certain embodiments b3 of formula (A-1e) is about 170. In certain embodiments b3 of formula (A-1e) is about 227. In certain embodiments b3 of formula (A-1e) is about 340. In certain embodiments b3 of formula (A-1e) is about 450. In certain embodiments b3 of formula (A-1e) is about 680. In certain embodiments b3 of formula (A-1e) is about 900. In certain embodiments b3 of formula (A-1e) is about 1130. In certain embodiments b3 of formula (A-1e) is about 1350. In certain embodiments b3 of formula (A-1e) is about 1590. In certain embodiments b3 of formula (A-1e) is about 1800. In certain embodiments b3 of formula (A-1e) is about 2045. In certain embodiments b3 of formula (A-1e) is about 2275.

In certain embodiments b1 of formula (A-1e) is 2, b2 of formula (A-1e) is 3 and b3 of formula (A-1e) is about 12. In certain embodiments b1 of formula (A-1e) is 2, b2 of formula (A-1e) is 3 and b3 of formula (A-1e) is about 23. In certain embodiments b1 of formula (A-1e) is 2, b2 of formula (A-1e) is 3 and b3 of formula (A-1e) is about 46. In certain embodiments b1 of formula (A-1e) is 2, b2 of formula (A-1e) is 3 and b3 of formula (A-1e) is about 68. In certain embodiments b1 of formula (A-1e) is 2, b2 of formula (A-1e) is 3 and b3 of formula (A-1e) is about 90. In certain embodiments b1 of formula (A-1e) is 2, b2 of formula (A-1e) is 3 and b3 of formula (A-1e) is about 112. In certain embodiments b1 of formula (A-1e) is 2, b2 of formula (A-1e) is 3 and b3 of formula (A-1e) is about 170. In certain embodiments b1 of formula (A-1e) is 2, b2 of formula (A-1e) is 3 and b3 of formula (A-1e) is about 227. In certain embodiments b1 of formula (A-1e) is 2, b2 of formula (A-1e) is 3 and b3 of formula (A-1e) is about 340. In certain embodiments b1 of formula (A-1e) is 2, b2 of formula (A-1e) is 3 and b3 of formula (A-1e) is about 450.

In certain embodiments b1 of formula (A-1e) is 2, b2 of formula (A-1e) is 2 and b3 of formula (A-1e) is about 12. In certain embodiments b1 of formula (A-1e) is 2, b2 of formula (A-1e) is 2 and b3 of formula (A-1e) is about 23. In certain embodiments b1 of formula (A-1e) is 2, b2 of formula (A-1e) is 2 and b3 of formula (A-1e) is about 46. In certain embodiments b1 of formula (A-1e) is 2, b2 of formula (A-1e) is 2 and b3 of formula (A-1e) is about 68. In certain embodiments b1 of formula (A-1e) is 2, b2 of formula (A-1e) is 2 and b3 of formula (A-1e) is about 90. In certain embodiments b1 of formula (A-1e) is 2, b2 of formula (A-1e) is 2 and b3 of formula (A-1e) is about 112. In certain embodiments b1 of formula (A-1e) is 2, b2 of formula (A-1e) is 2 and b3 of formula (A-1e) is about 170. In certain embodiments b1 of formula (A-1e) is 2, b2 of formula (A-1e) is 2 and b3 of formula (A-1e) is about 227. In certain embodiments b1 of formula (A-1e) is 2, b2 of formula (A-1e) is 2 and b3 of formula (A-1e) is about 340. In certain embodiments b1 of formula (A-1e) is 2, b2 of formula (A-1e) is 2 and b3 of formula (A-1e) is about 450.

In a plurality of IL-2 conjugates, the moiety $M_{mod}$ is present as a mixture comprising the moieties formula (A-1d) and (A-1e). This means that a certain percentage of IL-2 conjugates is conjugated to a moiety $M_{mod}$ of formula (A-1d) and a certain percentage is conjugated to a moiety $M_{mod}$ of formula (A-1e). Optionally, a certain percentage of IL-2 conjugates is conjugated to a moiety $M_{mod}$ of formula (A-1a). It is understood that in such IL-2 conjugates hydrolysis of the thiosuccinimide ring did not occur. Such a plurality of IL-2 conjugates may be present for example in a pharmaceutical composition comprising such IL-2 conjugates.

In a plurality of IL-2 conjugates the moiety $M_{mod}$ is in certain embodiments present as a mixture, wherein at least 70% of the moieties $M_{mod}$ are of formula (A-1d) and (A-1e). In a plurality of IL-2 conjugates the moiety $M_{mod}$ is in certain embodiments present as a mixture, wherein at least 80% of the moieties $M_{mod}$ are of formula (A-1d) and (A-1e). In a plurality of IL-2 conjugates the moiety $M_{mod}$ is in certain embodiments present as a mixture, wherein at least 90% of the moieties $M_{mod}$ are of formula (A-1d) and (A-1e).

In a plurality of IL-2 conjugates the moiety $M_{mod}$ is present as a mixture comprising the moieties of formula (A1-a), (A-1d) and (A-1e). In a plurality of IL-2 conjugates the moiety $M_{mod}$ is present as a mixture comprising the moieties of formula (A1-a), (A-1d) and (A-1e), wherein at least 70% of $M_{mod}$ are of formula (A-1d) and (A-1e). In a plurality of IL-2 conjugates the moiety $M_{mod}$ is present as a mixture comprising the moieties of formula (A1-a), (A-1d) and (A-1e), wherein at least 80% of $M_{mod}$ are of formula (A-1d) and (A-1e). In a plurality of IL-2 conjugates the moiety $M_{mod}$ is present as a mixture comprising the moieties of formula (A1-a), (A-1d) and (A-1e), wherein at least 90% of $M_{mod}$ are of formula (A-1d) and (A-1e).

The IL-2 conjugate of formula (Ia) or (Ib) comprises at least one covalently and reversibly attached polymeric moiety and/or substituted fatty acid moiety —Z.

The addition of such at least one covalently and reversibly attached polymeric moiety and/or substituted fatty acid moiety results in an extension of the circulation half-life of the IL-2 moiety of formula (I) beyond the extension provided by an optionally present moiety $M_{mod}$, while its reversible attachment ensures sufficient pharmaceutical activity.

In one embodiment the IL-2 conjugate is of formula (Ia) and comprises one moiety —Z, which is either a substituted fatty acid or a polymeric moiety. In one embodiment —Z is a substituted fatty acid. In another embodiment —Z is a polymeric moiety.

In another embodiment the IL-2 conjugate is of formula (Ib) and comprises two moieties —Z, which may be the same or different. In one embodiment both moieties —Z are a substituted fatty acid, which may be the same or different. In another embodiment both moieties —Z are a polymeric moiety, which may be the same or different. In another embodiment one moiety —Z is a substituted fatty acid and the other moiety —Z is a polymeric moiety.

In another embodiment the IL-2 conjugate of is of formula (Ib) and comprises three moieties —Z, which may be the same or different. In one embodiment all three moieties —Z are a substituted fatty acid, which may be the same or different. In another embodiment all three moieties —Z are a polymeric moiety, which may be the same or different. In another embodiment one or two moieties —Z are a substituted fatty acid and the remaining moiety/moieties —Z is/are a polymeric moiety.

In another embodiment the IL-2 conjugate is of formula (Ib) and comprises four moieties —Z, which may be the same or different. In one embodiment all four moieties —Z are a substituted fatty acid, which may be the same or different. In another embodiment all four moieties —Z are a polymeric moiety, which may be the same or different. In another embodiment one, two or three moieties —Z are a substituted fatty acid and the remaining moiety/moieties —Z is/are a polymeric moiety.

If —Z of formula (Ia) or (Ib) is a substituted fatty acid moiety it is preferably a substituted fatty acid moiety disclosed in WO 2005/027978 A2 and WO 2014/060512 A1, which are herewith incorporated by reference.

If —Z of formula (Ia) or (Ib) is a polymeric moiety, such polymeric moiety has in certain embodiments a molecular weight ranging from 1 kDa to 1000 kDa, such as from 2 kDa to 500 kDa, from 3 kDa to 200 kDa, from 5 kDa to 120 kDa, from 10 kDa to 100 kDa or from 15 kDa to 80 kDa. In one embodiment —Z is a polymeric moiety having a molecular weight of about 2 kDa. In another embodiment —Z is a polymeric moiety having a molecular weight of about 5 kDa. In another embodiment —Z is a polymeric moiety having a molecular weight of about 10 kDa. In another embodiment —Z is a polymeric moiety having a molecular weight of about 15 kDa. In another embodiment —Z is a polymeric moiety having a molecular weight of about 20 kDa. In another embodiment —Z is a polymeric moiety having a molecular weight of about 30 kDa. In another embodiment —Z is a polymeric moiety having a molecular weight of about 40 kDa. In another embodiment —Z is a polymeric moiety having a molecular weight of about 50 kDa. In another embodiment —Z is a polymeric moiety having a molecular weight of about 60 kDa. In another embodiment —Z is a polymeric moiety having a molecular weight of about 70 kDa. In another embodiment —Z is a polymeric moiety having a molecular weight of about 80 kDa. In another embodiment —Z is a polymeric moiety having a molecular weight of about 90 kDa. In another embodiment —Z is a polymeric moiety having a molecular weight of about 100 kDa. In one embodiment —Z is a polymeric moiety having a molecular weight of 2 kDa. In another embodiment —Z is a polymeric moiety having a molecular weight of 5 kDa. In another embodiment —Z is a polymeric moiety having a molecular weight of 10 kDa. In another embodiment —Z is a polymeric moiety having a molecular weight of 15 kDa. In another embodiment —Z is a polymeric moiety having a molecular weight of 20 kDa. In another embodiment —Z is a polymeric moiety having a molecular weight of 30 kDa. In another embodiment —Z is a polymeric moiety having a molecular weight of 40 kDa. In another embodiment —Z is a polymeric moiety having a molecular weight of 50 kDa. In another embodiment —Z is a polymeric moiety having a molecular weight of 60 kDa. In another embodiment —Z is a polymeric moiety having a molecular weight of 70 kDa. In another embodiment —Z is a polymeric moiety having a molecular weight of 80 kDa. In another embodiment —Z is a polymeric moiety having a molecular weight of 90 kDa. In another embodiment —Z is a polymeric moiety having a molecular weight of 100 kDa.

In certain embodiments —Z of formula (Ia) or (Ib) is a polymeric moiety comprising a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextranes, dextrins, gelatins, hyaluronic acids and derivatives, functionalized hyaluronic acids, alginate, mannans, pectins, rhamnogalacturonans, starches, hydroxyalkyl starches, hydroxyethyl starches and other carbohydrate-based polymers, xylans, and copolymers thereof.

In one embodiment —Z of formula (Ia) or (Ib) is a peptide or protein moiety. Preferably, such peptide or protein moiety is not an IL-2-moiety or fragment thereof. Such peptide or protein moiety —Z may be chemically conjugated to -D via -$L^1$-$L^2$- or may be translationally fused to -D via a reversible linker moiety -$L^1$-, in which case -$L^1$- is a peptide or protein moiety and -$L^2$- is preferably a chemical bond. In one embodiment such peptide or protein moiety —Z is chemically conjugated to -D via -$L^1$-$L^2$-. In another embodiment such peptide or protein moiety —Z is translationally fused to -D via a reversible linker moiety -$L^1$-, in which case -$L^1$- is a peptide or protein moiety and -$L^2$- is preferably a chemical bond. It is understood that such peptide or protein reversible linker moiety -$L^1$- may be enzymatically or non-enzymatically degradable. To facilitate enzymatic degradation -$L^1$- may comprise a protease recognition site.

If —Z of formula (Ia) or (Ib) is a peptide or protein moiety it is in certain embodiments selected from the group consisting of moieties comprising the carboxyl-terminal peptide of the chorionic gonadotropin as described in US 2012/0035101 A1, which are herewith incorporated by reference; albumin moieties; random coil protein moieties and Fc fusion protein moieties.

In certain embodiments —Z of formula (Ia) or (Ib) comprises a random coil peptide or protein moiety.

In certain embodiments such random coil peptide or protein moiety comprises at least 25 amino acid residues and at most 2000 amino acids, such as 30 amino to 1500 amino acid residues or 50 to 500 amino acid residues.

In certain embodiments —Z of formula (Ia) or (Ib) comprises a random coil protein moiety of which at least 80%, such as at least 85%, at least 90%, at least 95%, at least 98% or at least 99%, of the total number of amino acids forming said random coil protein moiety are selected from alanine and proline. In certain embodiments at least 10%, but less than 75%, such as less than 65%, of the total number of amino acid residues of such random coil protein moiety are proline residues. In certain embodiments such random coil protein moiety is as described in WO 2011/144756 A1, which is hereby incorporated by reference in its entirety. In certain embodiments —Z comprises at least one moiety selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:51 and SEQ ID NO:61 as disclosed in WO2011/144756. A moiety comprising such random coil protein comprising alanine and proline is referred to herein as "PA" or "PA moiety".

Accordingly, in one embodiment —Z of formula (Ia) or (Ib) comprises a PA moiety.

In certain embodiments —Z of formula (Ia) or (Ib) comprises a random coil protein moiety of which at least 80%, such as at least 85%, at least 90%, at least 95%, at least 98% or at least 99% of the total number of amino acids forming said random coil protein moiety are selected from alanine, serine and proline. In certain embodiments at least 4%, but less than 40% of the total number of amino acid residues of such random coil protein moiety are proline residues. In certain embodiments such random coil protein moiety is as described in WO 2008/155134 A1, which is hereby incorporated by reference. In certain embodiments —Z comprises at least one moiety selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:40, SEQ ID NO:42, SEQ ID NO:44, SEQ ID NO:46, SEQ ID NO:50, SEQ ID NO:52, SEQ ID NO:54 and SEQ ID NO:56 as disclosed in WO 2008/155134 A1. A moiety comprising such random coil protein moiety comprising alanine, serine and proline is referred to herein as "PAS" or "PAS moiety".

Accordingly, in one embodiment —Z of formula (Ia) or (Ib) comprises a PAS moiety.

In certain embodiments —Z of formula (Ia) or (Ib) comprises a random coil protein moiety of which at least 80%, such as at least 85%, at least 90%, at least 95%, at least 98% or at least 99% of the total number of amino acids forming said random coil protein moiety are selected from alanine, glycine, serine, threonine, glutamate and proline. In certain embodiments such random coil protein moiety is as described in WO 2010/091122 A1, which is hereby incorporated by reference. In certain embodiments —Z comprises at least one moiety selected from the group consisting of SEQ ID NO:182, SEQ ID NO:183, SEQ ID NO:184; SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:1715, SEQ ID NO:1716, SEQ ID NO:1718, SEQ ID NO:1719, SEQ ID NO:1720, SEQ ID NO:1721 and SEQ ID NO:1722 as disclosed in WO2010/091122A1. A moiety comprising such random coil protein moiety comprising alanine, glycine, serine, threonine, glutamate and proline is referred to herein as "XTEN" or "XTEN moiety".

Accordingly, in certain embodiments —Z of formula (Ia) or (Ib) comprises an XTEN moiety.

In certain embodiments —Z of formula (Ia) or (Ib) is a hyaluronic acid-based polymer.

In certain embodiments —Z of formula (Ia) or (Ib) is a PEG-based moiety, such as a linear, branched or multi-arm PEG-based moiety. In certain embodiments —Z is a branched PEG-based moiety, such as a branched PEG-based moiety having one, two, three, four, five or six branching points. In certain embodiments —Z is a branched PEG-based moiety having one, two or three branching points. In certain embodiments —Z is a branched PEG-based moiety having one branching point. In certain embodiments —Z is a branched PEG-based moiety having two branching points. In certain embodiments —Z is a branched PEG-based moiety having three branching points.

Each branching point may be independently selected from the group consisting of —N<, —CH< and >C<.

In certain embodiments —Z of formula (Ia) or (Ib) comprises a moiety of formula (A)

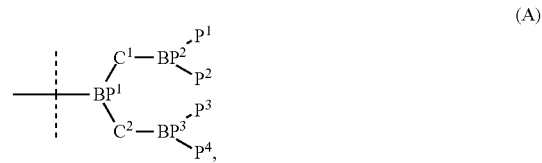

wherein
—BP$^1$<, —BP$^2$<, —BP$^3$< are independently of each other selected from the group consisting of —N< and —C(R$^8$<;
—R$^8$ is selected from the group consisting of —H, C$_{1-6}$ alkyl, C$_{2-6}$ alkenyl and C$_{2-6}$ alkynyl;
P$^1$, —P$^2$, —P$^3$, —P$^4$ are independently of each other a PEG-based chain comprising at least 40% PEG and having a molecular weight ranging from 3 to 40 kDa;
—C$^1$—, —C$^2$— are independently of each other selected from the group consisting of C$_{1-50}$ alkyl, C$_{2-50}$ alkenyl, and C$_{2-50}$ alkynyl; wherein C$_{1-50}$ alkyl, C$_{2-50}$ alkenyl, and C$_{2-50}$ alkynyl are optionally substituted with one or more —R$^9$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{10}$)—, —S(O)$_2$N(R$^{10}$)—, —S(O)N(R$^{10}$)—, —S(O)$_2$—, —S(O)—, —N(R$^{10}$)S(O)$_2$N(R$^{10a}$)—, —S—, —N(R$^{10}$)—, —OC(OR$^{10}$)(R$^{10a}$)—, —N(R$^{10}$)C(O)N(R$^{10a}$)—, and —OC(O)N(R$^{10}$)—;
each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^9$, which are the same or different;
each —R$^9$ is independently selected from the group consisting of halogen, —CN, oxo (=O), —COOR$^{11}$, —OR$^{11}$, —C(O)R$^{11}$, —C(O)N(R$^{11}$R$^{11a}$), —S(O)$_2$N(R$^{11}$R$^{11a}$), —S(O)N(R$^{11}$R$^{11a}$), —S(O)$_2$R$^{11}$, —S(O)R$^{11}$, —N(R$^{11}$)S(O)$_2$N(R$^{11a}$R$^{11b}$), —SR$^{11}$, —N(R$^{11}$R$^{11a}$), —NO$_2$, —OC(O)R$^{11}$, —N(R$^{11}$)C(O)R$^{11a}$, —N(R$^{11}$)S(O)$_2$R$^{11a}$, —N(R$^{11}$)S(O)R$^{11a}$, —N(R$^{11}$)C(O)OR$^{11a}$, —N(R$^{11}$)C(O)N(R$^{11a}$R$^{11b}$), —OC(O)N(R$^{11}$R$^{11a}$), and C$_{1-6}$ alkyl; wherein C$_{1-6}$ alkyl is optionally substituted with one or more halogen, which are the same or different; and
each —R$^{10}$, —R$^{10a}$, —R$^{11}$, —R$^{11a}$ and —R$^{11b}$ is independently selected from the group consisting of —H, and C$_{1-6}$ alkyl, wherein C$_{1-6}$ alkyl is optionally substituted with one or more halogen, which are the same or different.

In certain embodiments —$P^1$, —$P^2$, —$P^3$, —$P^4$ of formula (A) are independently of each other a PEG-based chain comprising at least 50% PEG and having a molecular weight ranging from 3 to 40 kDa. In certain embodiments —$P^1$, —$P^2$, —$P^3$, —$P^4$ are independently of each other a PEG-based chain comprising at least 60% PEG and having a molecular weight ranging from 3 to 40 kDa. In certain embodiments —$P^1$, —$P^2$, —$P^3$, —$P^4$ are independently of each other a PEG-based chain comprising at least 70% PEG and having a molecular weight ranging from 3 to 40 kDa. In certain embodiments —$P^1$, —$P^2$, —$P^3$, —$P^4$ are independently of each other a PEG-based chain comprising at least 80% PEG and having a molecular weight ranging from 3 to 40 kDa.

In certain embodiments the molecular weight of a moiety —$P^1$, —$P^2$, —$P^3$ and —$P^4$ of formula (A) ranges independently of each other from 5 to 30 kDa, such as from 5 to 25 kDa or from 8 to 20 kDa. In certain embodiments the molecular weight of a moiety —$P^1$, —$P^2$, —$P^3$ and —$P^4$ may be about 5 kDa. In certain embodiments the molecular weight of a moiety —$P^1$, —$P^2$, —$P^3$ and —$P^4$ may be about 7 kDa. In certain embodiments the molecular weight of a moiety —$P^1$, —$P^2$, —$P^3$ and —$P^4$ may be about 10 kDa. In certain embodiments the molecular weight of a moiety —$P^1$, —$P^2$, —$P^3$ and —$P^4$ may be about 12 kDa. In certain embodiments the molecular weight of a moiety —$P^1$, —$P^2$, —$P^3$ and —$P^4$ may be about 15 kDa. In certain embodiments the molecular weight of a moiety —$P^1$, —$P^2$, —$P^3$ and —$P^4$ may be about 20 kDa. In certain embodiments the molecular weight of a moiety —$P^1$, —$P^2$, —$P^3$ and —$P^4$ may be about 25 kDa. In certain embodiments the molecular weight of a moiety —$P^1$, —$P^2$, —$P^3$ and —$P^4$ may be about 30 kDa. In certain embodiments the molecular weight of a moiety —$P^1$, —$P^2$, —$P^3$ and —$P^4$ may be 7 kDa. In certain embodiments the molecular weight of a moiety —$P^1$, —$P^2$, —$P^3$ and —$P^4$ may be 10 kDa. In certain embodiments the molecular weight of a moiety —$P^1$, —$P^2$, —$P^3$ and —$P^4$ may be 12 kDa. In certain embodiments the molecular weight of a moiety —$P^1$, —$P^2$, —$P^3$ and —$P^4$ may be 15 kDa. In certain embodiments the molecular weight of a moiety —$P^1$, —$P^2$, —$P^3$ and —$P^4$ may be 20 kDa. In certain embodiments the molecular weight of a moiety —$P^1$, —$P^2$, —$P^3$ and —$P^4$ may be 25 kDa. In certain embodiments the molecular weight of a moiety —$P^1$, —$P^2$, —$P^3$ and —$P^4$ may be 30 kDa.

In certain embodiments —$P^1$, —$P^2$, —$P^3$ and —$P^4$ of formula (A) have the same structure.

In certain embodiments $BP^1$ of formula (A) is —N<.

In certain embodiments $BP^2$ and $BP^2$ of formula (A) have the same structure. In certain embodiments $BP^2$ and $BP^2$ of formula (A) are both —CH<.

In certain embodiments —$C^1$— and —$C^2$— of formula (A) have the same structure. In certain embodiments —$C^1$— and —$C^2$— of formula (A) are $C_{1-50}$ alkyl interrupted by one or more of the groups selected from the group consisting of —O—, —C(O)N($R^{10}$)— and 3- to 10 membered heterocyclyl; wherein the 3- to 10 membered heterocyclyl is substituted with at least one oxo (=O).

In certain embodiments —$C^1$— and —$C^2$— of formula (A) are of formula (A-a)

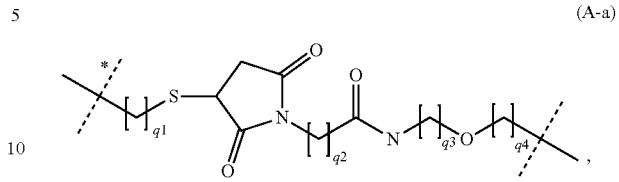

(A-a)

wherein
the dashed line marked with the asterisk indicates attachment to $BP^1$;
the unmarked dashed line indicates attachment to $BP^2$ or $BP^3$, respectively;
q1 is selected from the group consisting of 1, 2, 3, 4, 5, 6, 7 and 8;
q2 is selected from the group consisting of 1, 2, 3, 4, and 5;
q3 is selected from the group consisting of 1, 2, 3, 4, 5, 6, 7 and 8; and
q4 is selected from the group consisting of 1, 2 and 3.

In certain embodiments q1 of formula (A-a) is selected from the group consisting of 4, 5, 6, 7, and 8. In certain embodiments q1 of formula (A-a) is selected from the group consisting of 5, 6 and 7. In certain embodiments q1 of formula (A-a) is 1. In certain embodiments q1 of formula (A-a) is 2. In certain embodiments q1 of formula (A-a) is 3. In certain embodiments q1 of formula (A-a) is 4. In certain embodiments q1 of formula (A-a) is 5. In certain embodiments q1 of formula (A-a) is 6. In certain embodiments q1 of formula (A-a) is 7. In certain embodiments q1 of formula (A-a) is 8.

In certain embodiments q2 of formula (A-a) is selected from the group consisting of 1, 2 and 3. In certain embodiments q2 of formula (A-a) is 1. In certain embodiments q2 of formula (A-a) is 2. In certain embodiments q2 of formula (A-a) is 3. In certain embodiments q2 of formula (A-a) is 4. In certain embodiments q2 of formula (A-a) is 5.

In certain embodiments q3 of formula (A-a) is selected from the group consisting of 2, 3, 4, and 5. In certain embodiments q3 of formula (A-a) is selected from the group consisting of 2, 3 and 4. In certain embodiments q3 of formula (A-a) is 1. In certain embodiments q3 of formula (A-a) is 2. In certain embodiments q3 of formula (A-a) is 3. In certain embodiments q3 of formula (A-a) is 4. In certain embodiments q3 of formula (A-a) is 5. In certain embodiments q3 of formula (A-a) is 6. In certain embodiments q3 of formula (A-a) is 7. In certain embodiments q3 of formula (A-a) is 8.

In certain embodiments q4 of formula (A-a) is 1. In certain embodiments q4 of formula (A-a) is 2. In certain embodiments q4 of formula (A-a) is 3.

In certain embodiments —$P^1$, —$P^2$, —$P^3$ and —$P^4$ of formula (A) are independently of each other of formula (A-b)

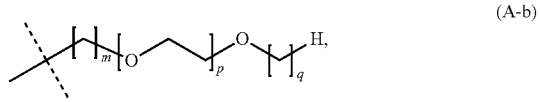

(A-b)

wherein
the dashed line indicates attachment to the remainder of —Z;
m is 0 or 1;

p is an integer ranging from 70 to 900; and
q is selected from the group consisting of 1, 2, 3, 4, 5, and 6.

In certain embodiments m of formula (A-b) is 0. In certain embodiments m of formula (A-b) is 1.

In certain embodiments p of formula (A-b) is an integer ranging from 115 to 680. In certain embodiments p of formula (A-b) is an integer ranging from 115 to 560. In certain embodiments p of formula (A-b) is an integer ranging from 185 to 450. In certain embodiments p of formula (A-b) is about 115. In certain embodiments p of formula (A-b) is about 160. In certain embodiments p of formula (A-b) is about 225. In certain embodiments p of formula (A-b) is about 270. In certain embodiments p of formula (A-b) is about 340. In certain embodiments p of formula (A-b) is about 450. In certain embodiments p of formula (A-b) is about 560.

In certain embodiments q of formula (A-b) is 1. In certain embodiments q of formula (A-b) is 2. In certain embodiments q of formula (A-b) is 3. In certain embodiments q of formula (A-b) is 4. In certain embodiments q of formula (A-b) is 5. In certain embodiments q of formula (A-b) is 6.

In certain embodiments —Z of formula (Ia) or (Ib) comprises a moiety of formula (A-c):

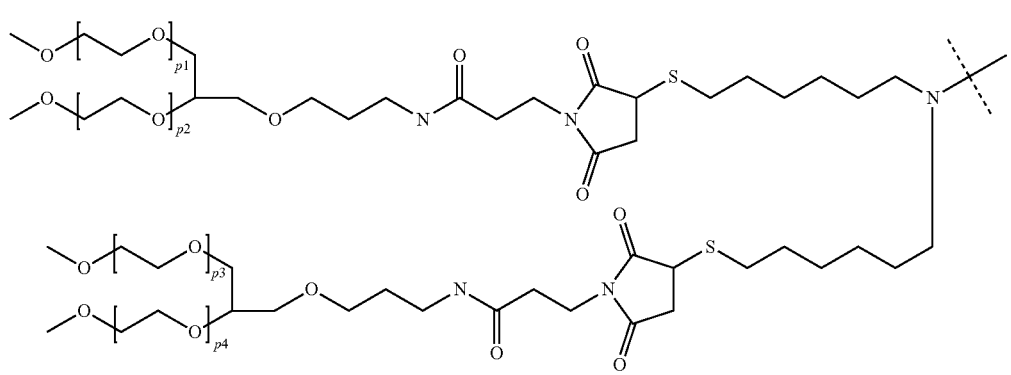

wherein
p1, p2, p3, p4 are independently of each other an integer ranging from 70 to 900.

In certain embodiments p1 of formula (A-c) is an integer ranging from 115 to 680. In certain embodiments p1 of formula (A-c) is an integer ranging from 115 to 560. In certain embodiments p1 of formula (A-c) is an integer ranging from 185 to 450. In certain embodiments p1 of formula (A-c) is an integer ranging from 220 to 240. In certain embodiments p1 of formula (A-c) is about 115. In certain embodiments p1 of formula (A-c) is about 160. In certain embodiments p1 of formula (A-c) is about 225. In certain embodiments p1 of formula (A-c) is about 270. In certain embodiments p1 of formula (A-c) is about 340. In certain embodiments p1 of formula (A-c) is about 450. In certain embodiments p1 of formula (A-c) is about 560.

In certain embodiments p2 of formula (A-c) is an integer ranging from 115 to 680. In certain embodiments p2 of formula (A-c) is an integer ranging from 115 to 560. In certain embodiments p2 of formula (A-c) is an integer ranging from 185 to 450. In certain embodiments p2 of formula (A-c) is an integer ranging from 220 to 240. In certain embodiments p2 of formula (A-c) is about 115. In certain embodiments p2 of formula (A-c) is about 160. In certain embodiments p2 of formula (A-c) is about 225. In certain embodiments p2 of formula (A-c) is about 270. In certain embodiments p2 of formula (A-c) is about 340. In certain embodiments p2 of formula (A-c) is about 450. In certain embodiments p2 of formula (A-c) is about 560.

In certain embodiments p3 of formula (A-c) is an integer ranging from 115 to 680. In certain embodiments p3 of formula (A-c) is an integer ranging from 115 to 560. In certain embodiments p3 of formula (A-c) is an integer ranging from 185 to 450. In certain embodiments p3 of formula (A-c) is an integer ranging from 220 to 240. In certain embodiments p3 of formula (A-c) is about 115. In certain embodiments p3 of formula (A-c) is about 160. In certain embodiments p3 of formula (A-c) is about 225. In certain embodiments p3 of formula (A-c) is about 270. In certain embodiments p3 of formula (A-c) is about 340. In certain embodiments p3 of formula (A-c) is about 450. In certain embodiments p3 of formula (A-c) is about 560.

In certain embodiments p4 of formula (A-c) is an integer ranging from 115 to 680. In certain embodiments p4 of formula (A-c) is an integer ranging from 115 to 560. In certain embodiments p4 of formula (A-c) is an integer ranging from 185 to 450. In certain embodiments p4 of formula (A-c) is an integer ranging from 220 to 240. In certain embodiments p4 of formula (A-c) is about 115. In certain embodiments p4 of formula (A-c) is about 160. In certain embodiments p4 of formula (A-c) is about 225. In certain embodiments p4 of formula (A-c) is about 270. In certain embodiments p4 of formula (A-c) is about 340. In certain embodiments p4 of formula (A-c) is about 450. In certain embodiments p4 of formula (A-c) is about 560.

In certain embodiments p1, p2, p3 of formula (A-c) and p4 are identical. In certain embodiments p1, p2, p3 and p4 range from 220 to 240.

In one embodiment —Z of formula (Ia) or (Ib) is a moiety as disclosed in WO 2012/02047 A1, which is herewith incorporated by reference.

In another embodiment —Z of formula (Ia) or (Ib) is a moiety as disclosed in WO 2013/024048 A1, which is herewith incorporated by reference.

In certain embodiments the conjugate comprising one or more of the IL-2 proteins of formula (I) or a pharmaceutically acceptable salt thereof comprises a plurality of moieties -D, which are said IL-2 proteins of formula (I), conjugated via at least one moiety -$L^1$-$L^2$- to at least one moiety Z', wherein a moiety -$L^1$- is conjugated to -D via a reversible linkage and wherein a moiety -$L^2$- is conjugated to Z', wherein -$L^1$- and -$L^2$- are used as defined for formula (Ia) and (Ib) and wherein Z' is a water-insoluble hydrogel.

In certain embodiments such hydrogel Z' comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(alkylene glycols), such as poly(ethylene glycols) and poly(propylene glycol), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In certain embodiments Z' is a poly(alkylene glycol)-based or hyaluronic acid-based hydrogel.

In certain embodiments Z' is a poly(propylene glycol)-based hydrogel.

In certain embodiments Z' is a PEG-based hydrogel.

In certain embodiments Z' is a PEG-based hydrogel as disclosed in WO2011/012715A1 or WO2014/056926A1, which are herewith incorporated by reference.

In certain embodiments Z' is a hyaluronic acid-based hydrogel.

In certain embodiments Z' is a hyaluronic acid-based hydrogel as disclosed in WO2018/175788A1, which is herewith incorporated by reference.

In certain embodiments Z' is a hydrogel as disclosed in WO2013/036847 A1. In particular, in certain embodiments Z' is a hydrogel produced by a method comprising the step of reacting at least a first reactive polymer with a cleavable crosslinker compound, wherein said cleavable crosslinker compound comprises a first functional group —$Y^1$ that reacts with the first reactive polymer and further comprises a moiety that is cleaved by elimination under physiological conditions wherein said moiety comprises a second functional group —$Y^2$ that reacts with a second reactive polymer. In certain embodiments the cleavable crosslinker compound is of formula (PL-1)

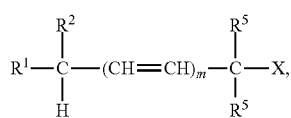

(PL-1)

wherein
m is 0 or 1;
—X comprises a functional group capable of connecting to a reactive polymer that is amenable to elimination under physiological conditions and said second functional group —$Y^2$
at least one of —$R^1$, —$R^2$ and —$R^5$ comprises said first functional group —$Y^1$ capable of connecting to a polymer;
one and only one of —$R^1$ and —$R^2$ is selected from the group consisting of —H, alkyl, arylalkyl, and heteroarylalkyl;
optionally, —$R^1$ and —$R^2$ may be joined to form a 3- to 8-membered ring;
at least one or both of —$R^1$ and —$R^2$ is independently selected from the group consisting of —CN, —$NO_2$, aryl, heteroaryl, alkenyl, alkynyl, —$COR^3$, —$SOR^3$, —$SO_2R^3$ and —$SR^4$;
—$R^3$ is selected from the group consisting of —H, alkyl, aryl, arylalkyl, heteroaryl, heteroarylalkyl, —$OR^9$ and —$NR^9_2$;
—$R^4$ is selected from the group consisting of alkyl, aryl, arylalkyl, heteroaryl and heteroarylalkyl;
each —$R^5$ is independently selected from the group consisting of —H, alkyl, alkenylalkyl, alkynylalkyl, $(OCH_2CH_2)_pO$-alkyl with p being an integer ranging from 1 to 1000, aryl, arylalkyl, heteroaryl and heteroarylalkyl;
each —$R^9$ is independently selected from the group consisting of —H and alkyl or both —$R^9$ together with the nitrogen to which they are attached form a heterocyclic ring; and wherein the moiety of formula (PL-1) is optionally further substituted.

The following paragraphs describe such hydrogel in more detail.

In certain embodiments —X of formula (PL-1) is selected from the group consisting of succinimidyl carbonate, sulfosuccinimidyl carbonate halides, thioethers, esters, nitrophenyl carbonate, chloroformate, fluoroformate, optionally substituted phenols and formula (PL-2)

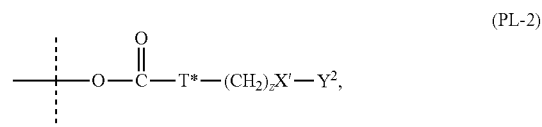

(PL-2)

wherein
the dashed line indicates attachment to the remainder of formula (PL-1);
-T*- is selected from the group consisting of —O—, —S— and —$NR^6$—;
z is an integer selected from the group consisting of 1, 2, 3, 4, 5 and 6;
—X'— is absent or is selected from the group consisting of —$OR^7$— and —$SR^7$—;
—$Y^2$ is a functional group capable of connecting with a reactive polymer;
—$R^6$ is selected from the group consisting of —H, alkyl, aryl, heteroaryl, arylalkyl, and heteroarylalkyl; and
—$R^7$ is selected from the group consisting of alkylene, phenylene and $(OCH_2CH_2)_p$, with p being an integer ranging from 1 to 1000.

In certain embodiments —X of formula (PL-1) comprises an activated carbonate such as succinimidyl carbonate, sulfosuccinimidyl carbonate, or nitrophenyl carbonate. In certain embodiments —X of formula (PL-1) comprises a carbonyl halide such as O(C=O)Cl or O(C=O)F. In certain embodiments —X of formula (PL-1) has the formula (PL-2). In certain embodiments —X of formula (PL-1) is —OR$^7$ or —SR$^7$, wherein —R$^7$ is optionally substituted alkylene, optionally substituted phenylene or (OCH$_2$CH$_2$)$_p$, wherein p is 1 to 1000.

In certain embodiments p of formula (PL-2) is an integer ranging from 1 to 100. In certain embodiments p of formula (PL-2) is an integer ranging from 1 to 10.

In certain embodiments —Y$^1$ of formula (PL-1) and —Y$^2$ of formula (PL-2) independently comprise —N$_3$, —NH$_2$, —NH—CO$_2$$^t$Bu, —SH, —S$^t$Bu, maleimide, —CO$_2$H, —CO$_2$$^t$Bu, 1,3-diene, cyclopentadiene, furan, alkyne, cyclooctyne, acrylate or acrylamide, wherein —$^t$Bu is tert-butyl, and wherein when one of —Y$^1$ or —Y$^2$ comprises —N$_3$ the other does not comprise alkyne or cyclooctyne; when one of —Y$^1$ or —Y$^2$ comprises —SH the other does not comprise maleimide, acrylate or acrylamide; when one of —Y$^1$ or —Y$^2$ comprises —NH$_2$ the other does not comprise —CO$_2$H; when one of —Y$^1$ or —Y$^2$ comprises 1,3-diene or cyclopentadiene the other does not comprise furan.

In certain embodiments the cleavable crosslinker compound is of formula (PL-3)

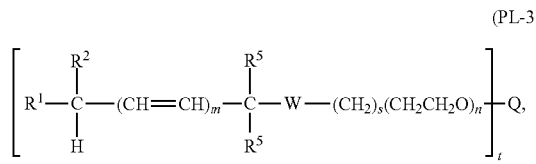

(PL-3)

wherein m is 0 or 1;

n is an integer selected from 1 to 1000;

s is 0, 1 or 2;

t is selected from the group consisting of 2, 4, 8, 16 and 32;

—W— is selected from the group consisting of —O(C=O)O—, —O(C=O)NH—, —O(C=O)S—, —O(C=O)NR$^6$CH$_2$O— and —O(C=O)NR$^6$S—;

-Q is a core group having a valency=t; which connects the multiple arms of the cleavable crosslinking compound, wherein t is an integer selected from 2, 4, 8, 16 and 32, and wherein —R$^1$, —R$^2$ and —R$^5$ are defined as in formula (PL-1).

In certain embodiments t of formula (PL-3) is 2. In certain embodiments t of formula (PL-3) is 4. In certain embodiments t of formula (PL-3) is 8. In certain embodiments t of formula (PL-3) is 16. In certain embodiments t of formula (PL-3) is 32.

In certain embodiments -Q of formula (PL-3) has a structure selected from the group consisting of

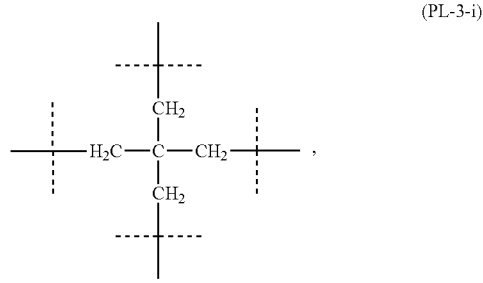

(PL-3-i)

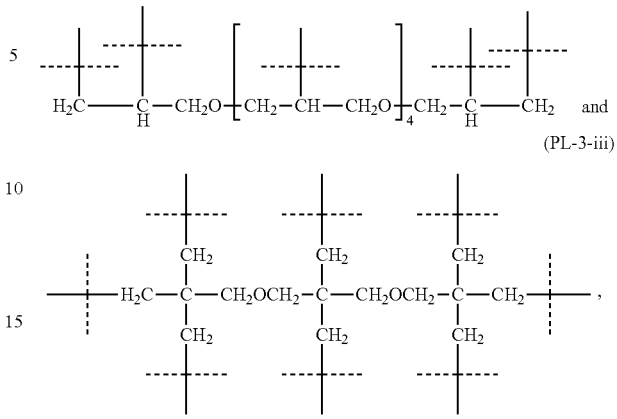

wherein the dashed lines indicate attachment to the remainder of the cleavable crosslinker compound.

In certain embodiments -Q of formula (PL-3) has the structure of (PL-3-i). In certain embodiments -Q of formula (PL-3) has the structure of (PL-3-ii). In certain embodiments -Q of formula (PL-3) has the structure of (PL-3-iii).

In certain embodiments the cleavable crosslinker compound is of formula (PL-3), wherein m is 0, n is approximately 100, s is 0, t is 4, —W— is —O(C=O)NH—, -Q has the structure of (PL-3i), —R$^2$ is —H, one —R$^5$ is —H and the other —R$^5$ is —(CH$_2$)$_5$N$_3$, and —R$^1$ is (4-chlorophenyl)SO$_2$, phenyl substituted with —SO$_2$, morpholino-SO$_2$, or —CN.

In certain embodiments —Y$^1$ of formula (PL-3) comprises —N$_3$, —NH$_2$, —NH—CO$_2$$^t$Bu, —SH, —S$^t$Bu, maleimide, —CO$_2$H, —CO$_2$$^t$Bu, 1,3-diene, cyclopentadiene, furan, alkyne, cyclooctyne, acrylate or acrylamide, wherein -$^t$Bu is tert-butyl.

In certain embodiments each —Y$^1$ of formula (PL-1) or (PL-3) and —Y$^2$ of formula (PL-2) independently comprises —N$_3$, —NH$_2$, —NH—CO$_2$$^t$Bu, —SH, —S$^t$Bu, maleimide, —CO$_2$H, —CO$_2$$^t$Bu, 1,3-diene, cyclopentadiene, furan, alkyne, cyclooctyne, acrylate or acrylamide.

In certain embodiments one of —Y$^1$ and —Y$^2$ is azide and the other is a reactive functional group selected from the group consisting of acetylene, cyclooctyne, and maleimide. In certain embodiments one of —Y$^1$ and —Y$^2$ is thiol and the other is a reactive functional group selected from the group consisting of maleimide, acrylate, acrylamide, vinylsulfone, vinylsulfonamide, and halocarbonyl. In certain embodiments one of —Y$^1$ and —Y$^2$ is amine and the other is a selective reactive functional group selected from carboxylic acid and activated carboxylic acid. In certain embodiments one of —Y$^1$ and —Y$^2$ is maleimide and the other is a selective reactive functional group selected from the group consisting of 1,3-diene, cyclopentadiene, and furan.

In certain embodiments the first and any second polymer is selected from the group consisting of homopolymeric or copolymeric polyethylene glycols, polypropylene glycols, poly(N-vinylpyrrolidone), polymethacrylates, polyphosphazenes, polylactides, polyacrylamides, polyglycolates, polyethylene imines, agaroses, dextrans, gelatins, collagens, polylysines, chitosans, alginates, hyaluronans, pectins and carrageenans that either comprise suitable reactive functionalities or is of formula [Y$^3$—(CH$_2$)$_s$(CH$_2$CH$_2$O)$_n$]$_t$Q, wherein —Y$^3$ is a reactive functional group, s is 0, 1 or 2, n is an integer selected from the group ranging from 10 to 1000, -Q is a core group having valency t, and t is an integer selected from the group consisting of 2, 4, 8, 16 and 32.

In certain embodiments the first polymer comprises a multi-arm polymer. In certain embodiments the first polymer comprises at least three arms. In certain embodiments the first polymer comprises at least four arms. In certain embodiments the first polymer comprises at least five arms. In certain embodiments the first polymer comprises at least six arms. In certain embodiments the first polymer comprises at least seven arms. In certain embodiments the first polymer comprises at least eight arms.

In certain embodiments the second polymer comprises a multi-arm polymer. In certain embodiments the second polymer comprises at least three arms. In certain embodiments the second polymer comprises at least four arms. In certain embodiments the second polymer comprises at least five arms. In certain embodiments the second polymer comprises at least six arms. In certain embodiments the second polymer comprises at least seven arms. In certain embodiments the second polymer comprises at least eight arms.

In certain embodiments the first polymer comprises a 2-arm polyethylene glycol polymer. In certain embodiments the first polymer comprises a 4-arm polyethylene glycol polymer. In certain embodiments the first polymer comprises an 8-arm polyethylene glycol polymer. In certain embodiments the first polymer comprises a 16-arm polyethylene glycol polymer. In certain embodiments the first polymer comprises a 32-arm polyethylene glycol polymer.

In certain embodiments the second polymer comprises a 2-arm polyethylene glycol polymer. In certain embodiments the second polymer comprises a 4-arm polyethylene glycol polymer. In certain embodiments the second polymer comprises an 8-arm polyethylene glycol polymer. In certain embodiments the second polymer comprises a 16-arm polyethylene glycol polymer. In certain embodiments the second polymer comprises a 32-arm polyethylene glycol polymer.

In certain embodiments the first and a second reactive polymer are reacted with said cleavable crosslinker compound, either sequentially or simultaneously.

In certain embodiments the first and second functional groups are the same.

Only in the context of formulas (PL-1), (PL-2) and (PL-3) the terms used have the following meaning:

The term "a moiety capable of being cleaved by elimination under physiological conditions" refers to a structure comprising a group H—C—(CH=CH)$_m$—C—X' wherein m is 0 or 1 and X' is a leaving group, wherein an elimination reaction as described above to remove the elements of HX' can occur at a rate such that the half-life of the reaction is between 1 and 10,000 hours under physiological conditions of pH and temperature. Preferably, the half-life of the reaction is between 1 and 5,000 hours, and more preferably between 1 and 1,000 hours, under physiological conditions of pH and temperature. By physiological conditions of pH and temperature is meant a pH of between 7 and 8 and a temperature between 30 and 40 degrees centigrade The term "reactive polymer and reactive oligomer" refers to a polymer or oligomer comprising functional groups that are reactive towards other functional groups, most preferably under mild conditions compatible with the stability requirements of peptides, proteins, and other biomolecules. Suitable functional groups found in reactive polymers include maleimides, thiols or protected thiols, alcohols, acrylates, acrylamides, amines or protected amines, carboxylic acids or protected carboxylic acids, azides, alkynes including cycloalkynes, 1,3-dienes including cyclopentadienes and furans, alpha-halocarbonyls, and N-hydroxysuccinimidyl, N-hydroxysulfosuccinimidyl, or nitrophenyl esters or carbonates.

The term "functional group capable of connecting to a reactive polymer" refers to a functional group that reacts to a corresponding functional group of a reactive polymer to form a covalent bond to the polymer. Suitable functional groups capable of connecting to a reactive polymer include maleimides, thiols or protected thiols, acrylates, acrylamides, amines or protected amines, carboxylic acids or protected carboxylic acids, azides, alkynes including cycloalkynes, 1,3-dienes including cyclopentadienes and furans, alpha-halocarbonyls, and N-hydroxysuccinimidyl, N-hydroxysulfosuccinimidyl, or nitrophenyl esters or carbonates.

The term "substituted" refers to an alkyl, alkenyl, alkynyl, aryl, or heteroaryl group comprising one or more substituent groups in place of one or more hydrogen atoms. Substituent groups may generally be selected from halogen including —F, —Cl, —Br, and —I; lower alkyl including linear, branched, and cyclic; lower haloalkyl including fluoroalkyl, chloroalkyl, bromoalkyl, and iodoalkyl; —OH; lower alkoxy including linear, branched, and cyclic; —SH; lower alkylthio including linear, branched, and cyclic; amino, alkylamino, dialkylamino, silyl including alkylsilyl, alkoxysilyl, and arylsilyl; nitro; cyano; carbonyl; carboxylic acid, carboxylic ester, carboxylic amide; aminocarbonyl; aminoacyl; carbamate; urea; thiocarbamate; thiourea; ketone; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

The properties of —R$^1$ and —R$^2$ may be modulated by the optional addition of electron-donating or electron-withdrawing substituents. By the term "electron-donating group" is meant a substituent resulting in a decrease in the acidity of the R$^1$R$^2$CH; electron-donating groups are typically associated with negative Hammett σ or Taft σ* constants and are well-known in the art of physical organic chemistry. (Hammett constants refer to aryl/heteroaryl substituents, Taft constants refer to substituents on non-aromatic moieties.) Examples of suitable electron-donating substituents include lower alkyl, lower alkoxy, lower alkylthio, amino, alkylamino, dialkylamino, and silyl.

The term "electron-withdrawing group" refers to a substituent resulting in an increase in the acidity of the R$^1$R$^2$CH group; electron-withdrawing groups are typically associated with positive Hammett σ or Taft σ* constants and are well-known in the art of physical organic chemistry. Examples of suitable electron-withdrawing substituents include halogen, difluoromethyl, trifluoromethyl, nitro, cyano, C(=O)—R$^x$, wherein —R$^x$ is H, lower alkyl, lower alkoxy, or amino, or S(O)$_m$R$^Y$, wherein m is 1 or 2 and —R$^Y$ is lower alkyl, aryl, or heteroaryl.

As is well-known in the art, the electronic influence of a substituent group may depend upon the position of the substituent. For example, an alkoxy substituent on the ortho- or para-position of an aryl ring is electron-donating, and is characterized by a negative Hammett σ constant, while an alkoxy substituent on the meta-position of an aryl ring is electron-withdrawing and is characterized by a positive Hammett σ constant.

The terms "alkyl", "alkenyl", and "alkynyl" include linear, branched or cyclic hydrocarbon groups of 1 to 8 carbons or 1 to 6 carbons or 1 to 4 carbons wherein alkyl is a saturated hydrocarbon, alkenyl includes one or more carbon-carbon double bonds and alkynyl includes one or more carbon-carbon triple bonds. Unless otherwise specified these contain 1 to 6 carbons.

The term "aryl" includes aromatic hydrocarbon groups of 6 to 18 carbons, preferably 6 to 10 carbons, including groups such as phenyl, naphthyl, and anthracenyl. "Heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

The term "halogen" includes fluoro, chloro, bromo and iodo.

The term "maleimido" is a group of the formula

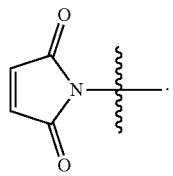 [SMILES: *N1C(=O)C=CC1=O]

In certain embodiments Z' is a hydrogel as disclosed in WO2020/206358 A1. In particular, in certain embodiments Z' is a hydrogel produced by a method comprising the steps of (a) providing a first prepolymer comprising a multi-arm polymer —$P^2$, wherein said first prepolymer is of formula (PL-4)

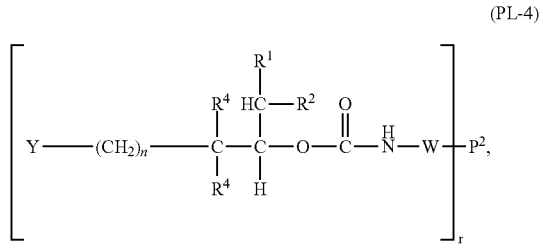

(PL-4)

wherein n is an integer selected from 0, 1, 2, 3, 4, 5 and 6;

r is an integer higher than 2;

—Y is a reactive functional group for connecting said first prepolymer to a second prepolymer;

—$R^1$ and —$R^2$ are independently an electron-withdrawing group, alkyl, or —H, and wherein at least one of —$R^1$ and —$R^2$ is an electron-withdrawing group;

each —$R^4$ is independently $C_1$-$C_3$ alkyl or the two —$R^4$ form together with the carbon atom to which they are attached a 3- to 6-membered ring;

—W— is absent or is

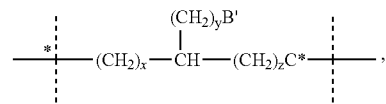

wherein the dashed line marked with the asterisk indicates the attachment to —NH— and the unmarked dashed line indicates the attachment to —$P^2$;

each of x, y, and z is independently an integer selected from 0, 1, 2, 3, 4, 5 and 6;

—B' is —$NH_2$, —$ONH_2$, ketone, aldehyde, —SH, —OH, —$CO_2H$, carboxamide group, or a group comprising a cyclooctyne or bicyclononyne; and —C* is carboxamide, thioether, thiosuccinimidyl, triazole, or oxime;

(b) providing the second prepolymer comprising a multi-arm polymer —$P^1$ wherein each arm is terminated by a reactive functional group —Y" that reacts with —Y of step (a);

(c) mixing the two prepolymers of steps (a) and (b) under conditions wherein —Y and —Y" react to form a linkage —Y*—; and optionally (d) isolating the resulting hydrogel.

Accordingly, —Z' is a hydrogel obtainable from the method described above. In certain embodiments the hydrogel produced by the preceding method is degradable.

In certain embodiments —Y and —Y" react under step (c) to form an insoluble hydrogel matrix comprising crosslinks of formula (PL-4'):

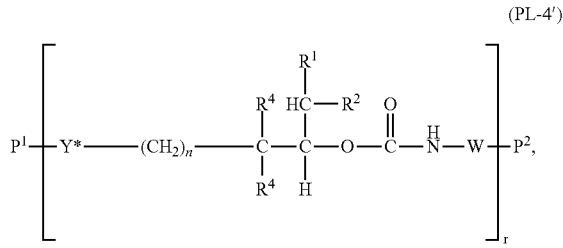

(PL-4')

wherein n, r, —$P^1$, —Y*—, —$R^4$, —$R^1$, —$R^2$, —W— and —$P^2$ are as defined above.

In certain embodiments n of formula (PL-4) or (PL-4') is an integer selected from 1, 2, 3, 4, 5 and 6. In certain embodiments n of formula (PL-4) or (PL-4') is an integer selected from 1, 2 and 3. In certain embodiments n of formula (PL-4) or (PL-4') is an integer selected from 0, 1, 2 and 3. In certain embodiments n of formula (PL-4) or (PL-4') is 1. In certain embodiments n of formula (PL-4) is 2. In certain embodiments n of formula (PL-4) or (PL-4') is 3.

In certain embodiments the multi-arm —$P^2$ of formula (PL-4) or (PL-4') is an r-armed polymer, wherein r is an integer selected from 2, 3, 4, 5, 6, 7, 8, 9, 10, 11 and 12. In certain embodiments r of formula (PL-4) or (PL-4') is an integer selected from 2, 3, 4, 5, 6, 7 and 8. In certain embodiments r of formula (PL-4) or (PL-4') is an integer selected from 2, 4, 6 and 8. In certain embodiments r of formula (PL-4) or (PL-4') is 2. In certain embodiments r of formula (PL-4) or (PL-4') is 4. In certain embodiments r of formula (PL-4) or (PL-4') is 6. In certain embodiments r of formula (PL-4) or (PL-4') is 8.

In certain embodiments —$P^2$ of formula (PL-4) or (PL-4') has a molecular weight of at least 1 kDa. In certain embodiments —$P^2$ of formula (PL-4) or (PL-4') has a molecular weight of 1 to 100 kDa. In certain embodiments —$P^2$ of formula (PL-4) or (PL-4') has a molecular weight of 1 to 80 kDa. In certain embodiments —$P^2$ of formula (PL-4) or (PL-4') has a molecular weight of 1 to 60 kDa. In certain embodiments —$P^2$ of formula (PL-4) or (PL-4') has a molecular weight of 1 to 40 kDa. In certain embodiments —$P^2$ of formula (PL-4) or (PL-4') has a molecular weight of 1 to 20 kDa. In certain embodiments —$P^2$ of formula (PL-4) or (PL-4') has a molecular weight of 1 to 10 kDa. In certain embodiments —$P^2$ of formula (PL-4) or (PL-4') has a molecular weight of 1 to 5 kDa. In certain embodiments —$P^2$ of formula (PL-4) or (PL-4') has a molecular weight of about 20 kDa. In certain embodiments —$P^2$ of formula (PL-4) or (PL-4') has a molecular weight of about 40 kDa. In certain embodiments —$P^2$ of formula (PL-4) or (PL-4') has a molecular weight of about 60 kDa. In certain embodiments —$P^2$ of formula (PL-4) or (PL-4') has a molecular weight of about 80 kDa.

In certain embodiments the multi-arm polymer —$P^1$ of step (b) is an r-armed polymer, wherein r is an integer selected from 2, 3, 4, 5, 6, 7, 8, 9, 10, 11 and 12. In certain embodiments the multi-arm —$P^1$ of step (b) is an r-armed polymer, wherein r is an integer selected from 2, 3, 4, 5, 6, 7 and 8. In certain embodiments the multi-arm —$P^1$ of step (b) is an r-armed polymer, wherein r is an integer selected from 2, 4, 6 and 8. In certain embodiments the multi-arm —$P^1$ of step (b) is an r-armed polymer, wherein r is 2. In certain embodiments the multi-arm —$P^1$ of step (b) is an r-armed polymer, wherein r is 4. In certain embodiments the multi-arm —$P^1$ of step (b) is an r-armed polymer, wherein r is 6. In certain embodiments the multi-arm —$P^1$ of step (b) is an r-armed polymer, wherein r is 8.

In certain embodiments —$P^1$ of step (b) has a molecular weight of at least 1 kDa. In certain embodiments the multi-arm polymer —$P^1$ of step (b) has a molecular weight of 1 to 100 kDa. In certain embodiments the multi-arm polymer —$P^1$ of step (b) has a molecular weight of 1 to 80 kDa. In certain embodiments the multi-arm polymer —$P^1$ of step (b) has a molecular weight of 1 to 60 kDa. In certain embodiments the multi-arm polymer —$P^1$ of step (b) has a molecular weight of 1 to 40 kDa. In certain embodiments the multi-arm polymer —$P^1$ of step (b) has a molecular weight of 1 to 20 kDa. In certain embodiments the multi-arm polymer —$P^1$ of step (b) has a molecular weight of 1 to 10 kDa. In certain embodiments the multi-arm polymer —$P^1$ of step (b) has a molecular weight of 1 to 5 kDa. In certain embodiments the multi-arm polymer —$P^1$ of step (b) has a molecular weight of about 20 kDa. In certain embodiments the multi-arm polymer —$P^1$ of step (b) has a molecular weight of about 40 kDa. In certain embodiments the multi-arm polymer —$P^1$ of step (b) has a molecular weight of about 60 kDa. In certain embodiments the multi-arm polymer —$P^1$ of step (b) has a molecular weight of about 80 kDa.

In certain embodiments —$P^1$ of step (b) and —$P^2$ of formula (PL-4) or (PL-4') comprise poly(ethylene glycol) (PEG), poly(ethylene oxide) (PEO), poly(ethylene imine) (PEI), dextrans, hyaluronic acids, or co-polymers thereof. In certain embodiments —$P^1$ of step (b) and $P^2$ of formula (PL-4) or (PL-4') are PEG-based polymers. In certain embodiments —$P^1$ of step (b) and —$P^2$ of formula (PL-4) or (PL-4') are hyaluronic acid-based polymers.

In certain embodiments —$R^1$ and —$R^2$ of formula (PL-4) or (PL-4') are independently electron-withdrawing groups, alkyl, or —H, and wherein at least one of —$R^1$ and —$R^2$ is an electron-withdrawing group.

In certain embodiments the electron-withdrawing group of —$R^1$ and —$R^2$ of formula (PL-4) or (PL-4') is —CN, —$NO_2$, optionally substituted aryl, optionally substituted heteroaryl, optionally substituted alkenyl, optionally substituted alkynyl, —$COR^3$, —$SOR^3$, or —$SO_2R^3$, wherein —$R^3$ is —H, optionally substituted alkyl, optionally substituted aryl, optionally substituted arylalkyl, optionally substituted heteroaryl, optionally substituted heteroarylalkyl, —$OR^8$ or —$NR^8_2$, wherein each —$R^8$ is independently —H or optionally substituted alkyl, or both —$R^8$ groups are taken together with the nitrogen to which they are attached to form a heterocyclic ring; or —$SR^9$, wherein —$R^9$ is optionally substituted alkyl, optionally substituted aryl, optionally substituted arylalkyl, optionally substituted heteroaryl, or optionally substituted heteroarylalkyl.

In certain embodiments the electron-withdrawing group of —$R^1$ and —$R^2$ of formula (PL-4) or (PL-4') is —CN. In certain embodiments the electron-withdrawing group of —$R^1$ and —$R^2$ of formula (PL-4) or (PL-4') is —$NO_2$. In certain embodiments the electron-withdrawing group of —$R^1$ and —$R^2$ of formula (PL-4) or (PL-4') is optionally substituted aryl containing 6 to 10 carbons. In certain embodiments the electron-withdrawing group of —$R^1$ and —$R^2$ of formula (PL-4) or (PL-4') is optionally substituted phenyl, naphthyl, or anthracenyl. In certain embodiments the electron-withdrawing group of —$R^1$ and —$R^2$ of formula (PL-4) or (PL-4') is optionally substituted heteroaryl comprising 3 to 7 carbons and containing at least one N, O, or S atom. In certain embodiments the electron-withdrawing group of —$R^1$ and —$R^2$ of formula (PL-4) or (PL-4') is optionally substituted pyrrolyl, pyridyl, pyrimidinyl, imidazolyl, oxazolyl, isoxazolyl, thiazolyl, isothiazolyl, quinolyl, indolyl, or indenyl. In certain embodiments the electron-withdrawing group of —$R^1$ and —$R^2$ of formula (PL-4) or (PL-4') is optionally substituted alkenyl containing 2 to 20 carbon atoms. In certain embodiments the electron-withdrawing group of —$R^1$ and —$R^2$ of formula (PL-4) or (PL-4') is optionally substituted alkynyl containing 2 to 20 carbon atoms. In certain embodiments the electron-withdrawing group of —$R^1$ and —$R^2$ of formula (PL-4) or (PL-4') is —$COR^3$, —$SOR^3$, or —$SO_2R^3$, wherein —$R^3$ is —H, optionally substituted alkyl containing 1 to 20 carbon atoms, optionally substituted aryl, optionally substituted arylalkyl, optionally substituted heteroaryl, optionally substituted heteroarylalkyl, —$OR^8$ or —$NR^8_2$, wherein each —$R^8$ is independently —H or optionally substituted alkyl containing 1 to 20 carbon atoms, or both —$R^8$ groups are taken together with the nitrogen to which they are attached to form a heterocyclic ring. In certain embodiments the electron-withdrawing group of —$R^1$ and —$R^2$ of formula (PL-4) or (PL-4') is —$SR^9$, wherein —$R^9$ is optionally substituted alkyl containing 1 to 20 carbon atoms, optionally substituted aryl, optionally substituted arylalkyl, optionally substituted heteroaryl, or optionally substituted heteroarylalkyl. In certain embodiments at least one of —$R^1$ and —$R^2$ is —CN or —$SO_2R^3$.

In certain embodiments at least one of —$R^1$ and —$R^2$ of formula (PL-4) or (PL-4') is —CN, —$SOR^3$ or —$SO_2R^3$. In certain embodiments at least one of —$R^1$ and —$R^2$ of formula (PL-4) or (PL-4') is —CN or —$SO_2R^3$. In certain embodiments at least one of —$R^1$ and —$R^2$ of formula (PL-4) or (PL-4') is —CN or —$SO_2R^3$, wherein —$R^3$ is optionally substituted alkyl, optionally substituted aryl, or —$NR^8_2$. In certain embodiments at least one of —$R^1$ and —$R^2$ of formula (PL-4) or (PL-4') is —CN, —$SO_2N(CH_3)_2$, —$SO_2CH_3$, phenyl substituted with —$SO_2$, phenyl substituted with —$SO_2$ and —Cl, —$SO_2N(CH_2CH_2)_2O$, —$SO_2CH(CH_3)_2$, —$SO_2N(CH_3)(CH_2CH_3)$, or —$SO_2N(CH_2CH_2OCH_3)_2$.

In certain embodiments each —R⁴ of formula (PL-4) or (PL-4') is independently $C_1$-$C_3$ alkyl or taken together may form a 3- to 6-membered ring. In certain embodiments each —R⁴ of formula (PL-4) or (PL-4') is independently $C_1$-$C_3$ alkyl. In certain embodiments both —R⁴ of formula (PL-4) or (PL-4') are methyl.

In certain embodiments —Y and —Y" are independently selected from the group consisting of amine, aminooxy, ketone, aldehyde, maleimidyl, thiol, alcohol, azide, 1,2,4,6-tetrazinyl, trans-cyclooctenyl, bicyclononynyl, cyclooctynyl, and protected variants thereof.

In certain embodiments Y and Y" may react with each other such as in a selective way. For example, when —Y is amine, —Y" is carboxylic acid, active ester, or active carbonate to yield a residual connecting functional group —Y*— that is amide or carbamate. As another example, when —Y is azide, —Y" is alkynyl, bicyclononynyl, or cyclooctynyl to yield a residual connecting functional group —Y*— that is 1,2,3-triazole. As another example, when —Y is —NH₂O, —Y" is ketone or aldehyde to yield a residual connecting functional group —Y*— that is oxime. As another example, when —Y is —SH, —Y" is maleimide or halocarbonyl to yield a residual connecting functional group —Y*— that is thiosuccinimidyl or thioether. Similarly, these roles of —Y and —Y" can be reversed to yield —Y*— of opposing orientation.

In certain embodiments —Y*— comprises an amide, oxime, 1,2,3-triazole, thioether, thiosuccinimide, or ether. In certain embodiments —Y*— is -L²-.

These conjugation reactions may be performed under conditions known in the art, for example when —Y is azide and —Y" is cyclooctyne the conjugation occurs in any solvent wherein both components show adequate solubility, although it is known that aqueous solutions show more favorable reaction rates. When mixed in an appropriate solvent, typically an aqueous buffer at a pH of 2 to 7 when —Y and —Y" are azide/cyclooctyne, or at a pH of 6 to 9 when —Y and —Y" are an activated ester and an amine, the —Y and —Y" groups react to form an insoluble hydrogel matrix comprising crosslinks of formula (PL-4'). This process may be carried out in bulk phase, or under conditions of emulsification in a mixed organic/aqueous system so as to form microparticle suspensions such as microspheres that are suitable for injection.

In certain embodiments a conjugate comprising a hydrogel Z' is produced by a method comprising the steps of
(a) providing a first prepolymer of formula (PL-4)
(b) reacting the prepolymer of formula (PL-4) with a linker-drug of formula (PL-5)

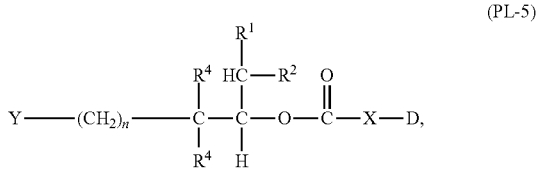

(PL-5)

wherein
n, —R¹, —R², —R⁴ and —Y are as defined in formula (PL-4);
D is a drug moiety;
—X— is absent when -D is a drug moiety connected through an amine, or —X— is —N(R⁶)CH₂— when -D is a drug moiety connected through a phenol, alcohol, thiol, thiophenol, imidazole, or non-basic amine; wherein —R⁶ is optionally substituted $C_1$-$C_6$ alkyl, optionally substituted aryl, or optionally substituted heteroaryl;
so that —Y of formula (PL-5) reacts with —B' of formula (PL-4);
(c) providing the second prepolymer comprising a multi-arm polymer —P¹ wherein each arm is terminated by a reactive functional group —Y" that reacts with —Y of step (a) and wherein embodiments for —P¹ are described above;
(d) mixing the two prepolymers of steps (a) and (b) under conditions wherein —Y and —Y" react to form a residual connecting functional group —Y*—; and optionally
(e) isolating the resulting hydrogel.

In certain embodiments a conjugate is obtained by a method comprising the step of reacting a hydrogel Z' with the linker-drug of formula (PL-5), wherein —B' on the hydrogel Z' reacts with —Y of formula (PL-5).

Only in the context of formulas (PL-4), (PL-4') and (PL-5) the terms used have the following meaning:

The term "alkyl" refers to linear, branched, or cyclic saturated hydrocarbon groups of 1 to 20, 1 to 12, 1 to 8, 1 to 6, or 1 to 4 carbon atoms. In certain embodiments an alkyl is linear or branched. Examples of linear or branched alkyl groups include methyl, ethyl, n-propyl, isopropyl, n-butyl, t-butyl, isobutyl, sec-butyl, n-pentyl, n-hexyl, n-heptyl, n-octyl, n-nonyl, and n-decyl. In certain embodiments an alkyl is cyclic. Examples of cyclic alkyl groups include cyclopropyl, cyclobutyl, cyclopentyl, cyclopentadienyl, and cyclohexyl.

The term "alkoxy" refers to alkyl groups bonded to oxygen, including methoxy, ethoxy, isopropoxy, cyclopropoxy, and cyclobutoxy.

The term "alkenyl" refers to non-aromatic unsaturated hydrocarbons with carbon-carbon double bonds and 2 to 20, 2 to 12, 2 to 8, 2 to 6, or 2 to 4 carbon atoms.

The term "alkynyl" refers to non-aromatic unsaturated hydrocarbons with carbon-carbon triple bonds and 2 to 20, 2 to 12, 2 to 8, 2 to 6, or 2 to 4 carbon atoms.

The term "aryl" refers to aromatic hydrocarbon groups of 6 to 18 carbons, preferably 6 to 10 carbons, including groups such as phenyl, naphthyl, and anthracenyl. The term "heteroaryl" refers to aromatic rings comprising 3 to 15 carbons comprising at least one N, O or S atom, preferably 3 to 7 carbons comprising at least one N, O or S atom, including groups such as pyrrolyl, pyridyl, pyrimidinyl, imidazolyl, oxazolyl, isoxazolyl, thiazolyl, isothiazolyl, quinolyl, indolyl, and indenyl.

In certain embodiments alkenyl, alkynyl, aryl or heteroaryl moieties may be coupled to the remainder of the molecule through an alkyl linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" or "halo" refers to bromo, fluoro, chloro and iodo.

The term "heterocyclic ring" or "heterocyclyl" refers to a 3- to 15-membered aromatic or non-aromatic ring comprising at least one N, O, or S atom. Examples include piperidinyl, piperazinyl, tetrahydropyranyl, pyrrolidine, and tetrahydrofuranyl, as well as the exemplary groups provided for the term "heteroaryl" above. In certain embodiments a heterocyclic ring or heterocyclyl is non-aromatic. In certain embodiments a heterocyclic ring or heterocyclyl is aromatic.

The term "optionally substituted" refers to a group may be unsubstituted or substituted by one or more (e.g., 1, 2, 3, 4 or 5) of the substituents which may be the same or different. Examples of substituents include alkyl, alkenyl, alkynyl, halogen, —CN, —OR$^{aa}$, —SR$^{aa}$, —NR$^{aa}$R$^{bb}$, —NO$_2$, —C≡NH(OR$^{aa}$), —C(O)R$^{aa}$, —OC(O)R$^{aa}$, —C(O)OR$^{aa}$, —C(O)NR$^{aa}$R$^{bb}$, —OC(O)NR$^{aa}$R$^{bb}$, —NR$^{aa}$C(O)R$^{bb}$, —NR$^{aa}$C(O)OR$^{bb}$, —S(O)R$^{aa}$, —S(O)$_2$R$^{aa}$, —NR$^{aa}$S(O)R$^{bb}$, —C(O)NR$^{aa}$S(O)R$^{bb}$, —NR$^{aa}$S(O)$_2$R$^{bb}$, —C(O)NR$^{aa}$S(O)$_2$R$^{bb}$, —S(O)NR$^{aa}$R$^{bb}$, —S(O)$_2$NR$^{aa}$R$^{bb}$, —P(O)(OR$^{aa}$)(OR$^{bb}$), heterocyclyl, heteroaryl, or aryl, wherein the alkyl, alkenyl, alkynyl, cycloalkyl, heterocyclyl, heteroaryl, and aryl are each independently optionally substituted by —R$^{cc}$, wherein —R$^{aa}$ and —R$^{bb}$ are each independently —H, alkyl, alkenyl, alkynyl, heterocyclyl, heteroaryl, or aryl, or —R$^{aa}$ and —R$^{bb}$ are taken together with the nitrogen atom to which they attach to form a heterocyclyl, which is optionally substituted by alkyl, alkenyl, alkynyl, halogen, hydroxyl, alkoxy, or —CN, and wherein: each —R$^{cc}$ is independently alkyl, alkenyl, alkynyl, halogen, heterocyclyl, heteroaryl, aryl, —CN, or —NO$_2$.

A moiety -L$^1$- may be attached to -D through the IL-2 moiety of formula (I), in particular through an amino acid residue of said IL-2 moiety, or through a modifying moiety M$_{mod}$ present in -D. In one embodiment -L$^1$- is attached to -D through the IL-2 moiety, in particular through an amino acid residue of the IL-2 moiety. In another embodiment -L$^1$- is attached to -D through a modifying moiety M$_{mod}$ present in -D. It is understood that one or more moieties -L$^1$- may be attached to a moiety M$_{mod}$. In certain embodiments an IL-2 conjugate may comprise a moiety -L$^1$- attached to one amino acid residue of the IL-2 moiety of formula (I) and may comprise a moiety -L$^1$- attached to a moiety M$_{mod}$.

In one embodiment all moieties -L$^1$- present in an IL-2 conjugate are attached to an amino acid residue of -D.

If -L$^1$- is attached to an amino acid residue of the IL-2 moiety, such amino acid residue may be a proteinogenic or non-proteinogenic amino acid residue of -D. In certain embodiments -L$^1$- is attached to a non-proteinogenic amino acid residue. In certain embodiments attachment of -L$^1$- is to a proteinogenic amino acid residue. If attachment occurs at a proteinogenic amino acid residue, said proteinogenic amino acid residue is in certain embodiments selected from the group consisting of cysteine, methionine, histidine, lysine, tryptophan, serine, threonine, tyrosine, aspartic acid, glutamic acid, glutamine and arginine. In certain embodiments such proteinogenic amino acid residue is selected from the group consisting of cysteine, histidine, lysine, tryptophan, serine, threonine, tyrosine, aspartic acid, glutamic acid and arginine.

In certain embodiments -L$^1$- is attached to a cysteine residue of -D. In certain embodiments -L$^1$- is attached to a histidine residue of -D. In certain embodiments -L$^1$- is attached to a lysine residue. In certain embodiments -L$^1$- is attached to a tryptophan residue. In certain embodiments -L$^1$- is attached to a serine residue. In certain embodiments -L$^1$- is attached to a threonine residue. In certain embodiments -L$^1$- is attached to a tyrosine residue. In certain embodiments -L$^1$- is attached to an aspartic acid residue. In certain embodiments -L$^1$- is attached to a glutamic acid residue. In certain embodiments -L$^1$- is attached to an arginine residue.

In certain embodiments at least one moiety -L$^1$- is attached to an amino acid residue of -D and one or more additional moieties -L$^1$- are attached to a modifying moiety present in -D.

The moiety -L$^1$- may be connected to -D through any type of linkage, provided that it is reversible. In certain embodiments -L$^1$- is connected to -D through a linkage selected from the group consisting of amide, ester, carbamate, acetal, aminal, imine, oxime, hydrazone, disulfide and acylguanidine. In certain embodiments -L$^1$- is connected to -D through a linkage selected from the group consisting of amide, ester, carbamate and acylguanidine. It is understood that these linkages may not be reversible per se, but that reversibility may be an effect of certain groups of atoms or moieties present in -L$^1$-.

In certain embodiments -L$^1$- is connected to -D through an ester linkage. In certain embodiments -L$^1$- is connected to -D through a carbamate linkage. In certain embodiments -L$^1$- is connected to -D through an acylguanidine. In certain embodiments -L$^1$- is connected to -D through an amide linkage.

In certain embodiments -L$^1$- is connected to -D via the nitrogen of an amine functional group of a side chain of a lysine residue or the N-terminus of -D. In certain embodiments -L$^1$- is connected to -D via the nitrogen of an amine functional group of a side chain of a lysine residue or the N-terminus of -D and the linkage formed between -D and -L$^1$- is a carbamate.

In certain embodiments -L$^1$- is connected to -D via the nitrogen of an amine functional group of a side chain of a lysine residue of -D. In certain embodiments -L$^1$- is connected to -D via the nitrogen of an amine functional group of a side chain of a lysine residue of -D and the linkage formed between -D and -L$^1$- is a carbamate.

In certain embodiments -L$^1$- is connected to -D via the nitrogen of an amine functional group of the N-terminus of -D. In certain embodiments -L$^1$- is connected to -D via the nitrogen of an amine functional group of the N-terminus of -D and the linkage formed between -D and -L$^1$- is a carbamate.

In certain embodiments -L$^1$- has a structure as disclosed in WO 2009/095479 A2. Accordingly, in certain embodiments the moiety -L$^1$- is of formula (II):

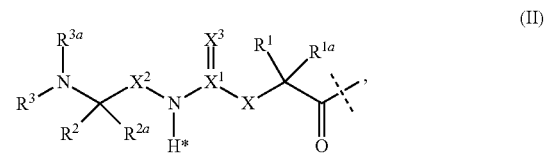

(II)

wherein the dashed line indicates attachment to a nitrogen of -D by forming an amide bond;
—X— is —C(R$^4$R$^{4a}$)—; —N(R$^4$)—; —O—; —C(R$^4$R$^{4a}$)—C(R$^5$R$^{5a}$)—; —C(R$^5$R$^{5a}$)—C(R$^4$R$^{4a}$)—; —C(R$^4$R$^{4a}$)—N(R$^6$)—; —N(R$^6$)—C(R$^4$R$^{4a}$)—; —C(R$^4$R$^{4a}$)—O—; —O—C(R$^4$R$^{4a}$)—; or —C(R$^7$R$^{7a}$)—;
X$^1$ is C; or S(O);
—X$^2$— is —C(R$^8$R$^{8a}$)—; or —C(R$^8$R$^{8a}$)—C(R$^9$R$^{9a}$)—;
=X$^3$ is =O; =S; or =N—CN;
—R$^1$, —R$^{1a}$, —R$^2$, —R$^{2a}$, —R$^4$, —R$^{4a}$, —R$^5$, —R$^{5a}$, —R$^6$, —R$^8$, —R$^{8a}$, —R$^9$, —R$^{9a}$ are independently selected from the group consisting of —H; and C$_{1-6}$ alkyl;
—R$^3$, —R$^{3a}$ are independently selected from the group consisting of —H; and C$_{1-6}$ alkyl, provided that in case one of —R$^3$, —R$^{3a}$ or both are other than —H they are connected to N to which they are attached through an SP³-hybridized carbon atom;

—R⁷ is —N(R¹⁰R¹⁰ᵃ); or —NR¹⁰—(C=O)—R¹¹;

—R⁷ᵃ, —R¹⁰, —R¹⁰ᵃ, —R¹¹ are independently of each other —H; or C₁₋₆ alkyl;

optionally, one or more of the pairs —R¹ᵃ/—R⁴ᵃ, —R¹ᵃ/—R⁵ᵃ, —R¹ᵃ/—R⁷ᵃ, —R⁴ᵃ/—R⁵ᵃ, —R⁸ᵃ/—R⁹ᵃ form a chemical bond;

optionally, one or more of the pairs —R¹/—R¹ᵃ, —R²/—R²ᵃ, —R⁴/—R⁴ᵃ, —R⁵/—R⁵ᵃ, —R⁸/—R⁸ᵃ, —R⁹/—R⁹ᵃ are joined together with the atom to which they are attached to form a C₃₋₁₀ cycloalkyl; or 3- to 10-membered heterocyclyl;

optionally, one or more of the pairs —R¹/—R⁴, —R¹/—R⁵, —R¹/—R⁶, —R¹/—R⁷ᵃ, —R⁴/—R⁵, —R⁴/—R⁶, —R⁸/—R⁹, —R²/—R³ are joined together with the atoms to which they are attached to form a ring A;

optionally, R³/R³ᵃ are joined together with the nitrogen atom to which they are attached to form a 3- to 10-membered heterocycle;

A is selected from the group consisting of phenyl; naphthyl; indenyl; indanyl; tetralinyl; C₃₋₁₀ cycloalkyl; 3- to 10-membered heterocyclyl; and 8- to 11-membered heterobicyclyl; and wherein -L¹- is substituted with at least one -L²-Z and wherein -L¹- is optionally further substituted, provided that the hydrogen marked with the asterisk in formula (II) is not replaced by -L²-Z or a substituent.

Preferably -L¹- of formula (II) is substituted with one moiety -L²-Z.

In one embodiment -L¹- of formula (II) is not further substituted.

It is understood that if —R³/—R³ᵃ of formula (II) are joined together with the nitrogen atom to which they are attached to form a 3- to 10-membered heterocycle, only such 3- to 10-membered heterocycles may be formed in which the atoms directly attached to the nitrogen are SP³-hybridized carbon atoms. In other words, such 3- to 10-membered heterocycle formed by —R³/—R³ᵃ together with the nitrogen atom to which they are attached has the following structure:

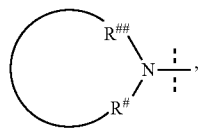

wherein
the dashed line indicates attachment to the rest of -L¹-;
the ring comprises 3 to 10 atoms comprising at least one nitrogen; and
R# and R## represent an SP³-hybridized carbon atom.

It is also understood that the 3- to 10-membered heterocycle may be further substituted.

Exemplary embodiments of suitable 3- to 10-membered heterocycles formed by —R³/—R³ᵃ of formula (II) together with the nitrogen atom to which they are attached are the following:

 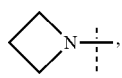

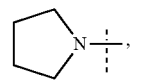

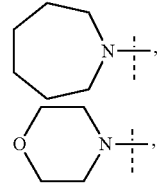

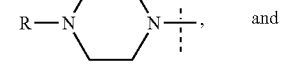

wherein
dashed lines indicate attachment to the rest of the molecule; and
—R is selected from the group consisting of —H and C₁₋₆ alkyl.

-L¹- of formula (II) may optionally be further substituted. In general, any substituent may be used as far as the cleavage principle is not affected, i.e. the hydrogen marked with the asterisk in formula (II) is not replaced and the nitrogen of the moiety $$\begin{array}{c} R^3 \\ \diagdown \\ N\text{---} \\ \diagup \\ R^{3a} \end{array}$$

of formula (II) remains part of a primary, secondary or tertiary amine, i.e. —R³ and —R³ᵃ are independently of each other —H or are connected to —N< through an SP³-hybridized carbon atom.

The nitrogen of -D linked to -L¹- of formula (II) is in certain embodiments the nitrogen of an amine functional group, which may be a primary, secondary or tertiary amine group. In certain embodiments the nitrogen of -D linked to -L¹- of formula (II) is the nitrogen of an amine functional group, which is a primary or secondary amine group. In certain embodiments the nitrogen of -D linked to -L¹- of formula (II) is the nitrogen of a primary amine functional group. In certain embodiments the nitrogen of -D linked to -L¹- of formula (II) is the nitrogen of a primary amine functional group. If -L¹- of formula (II) is conjugated to -D, wherein -D is a protein or peptide drug moiety the amine functional may in certain embodiments be the N-termina amine functional group or the amine functional group of a lysine site chain. If -L¹- of formula (II) is conjugated to -D, wherein -D is a protein or peptide drug moiety, the amine functional may in certain embodiments be the amine functional group of a lysine site chain.

In one embodiment —R¹ or —R¹ᵃ of formula (II) is substituted with -L²-Z or -L²-Z'. In another embodiment —R² or —R²ᵃ of formula (II) is substituted with -L²-Z or -L²-Z'. In another embodiment —R³ or —R³ᵃ of formula (II) is substituted with -L²-Z or -L²-Z'. In another embodiment —R⁴ of formula (II) is substituted with -L²-Z or -L²-Z'. In another embodiment —R⁵ or —R⁵ᵃ of formula (II) is substituted with -L²-Z or -L²-Z'. In another embodiment —R⁶ of formula (II) is substituted with -L²-Z or -L²-Z'. In another embodiment —R⁷ or —R⁷ᵃ of formula (II) is substituted with -L²-Z or -L²-Z'. In another embodiment —R⁸ or —R⁸ᵃ of formula (II) is substituted with -L²-Z or -L²-Z'. In another embodiment —R⁹ or —R⁹ᵃ of formula (II) is substituted with -L²-Z or -L²-Z'.

In certain embodiments -L$^1$- has a structure as disclosed in WO2016/020373A1. Accordingly, in certain embodiments the moiety -L$^1$- is of formula (III):

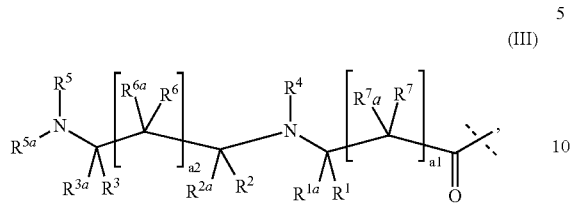

(III)

wherein
the dashed line indicates attachment to a primary or secondary amine or hydroxyl of -D by forming an amide or ester linkage, respectively;
—R$^1$, —R$^{1a}$, —R$^2$, —R$^{2a}$, —R$^3$ and —R$^{3a}$ are independently of each other selected from the group consisting of —H, —C(R$^8$R$^{8a}$R$^{8b}$), —C(=O)R$^8$, —C≡N, —C(=NR$^8$)R$^{8a}$, —CR$^8$(=CR$^{8a}$R$^{8b}$), —C≡CR$^8$ and -T; —R$^4$, —R$^5$ and —R$^{5a}$ are independently of each other selected from the group consisting of —H, —C(R$^9$R$^{9a}$R$^{9b}$) and -T;
a1 and a2 are independently of each other 0 or 1;
each —R$^6$, —R$^{6a}$, —R$^7$, —R$^{7a}$, —R$^8$, —R$^{8a}$, —R$^{8b}$, —R$^9$, —R$^{9b}$ are independently of each other selected from the group consisting of —H, halogen, —CN, —COOR$^{10}$, —OR$^{10}$, —C(O)R$^{10}$, —C(O)N(R$^{10}$R$^{10a}$), —S(O)$_2$N(R$^{10}$R$^{10a}$), —S(O)N(R$^{10}$R$^{10a}$), —S(O)$_2$R$^{10}$, —S(O)R$^{10}$, —N(R$^{10}$)S(O)$_2$N(R$^{10a}$R$^{10b}$), —SR$^{10}$, —N(R$^{10}$R$^{10a}$), —NO$_2$, —OC(O)R$^{10}$, —N(R$^{10}$)C(O)R$^{10a}$, —N(R$^{10}$)S(O)$_2$R$^{10a}$, —N(R$^{10}$)S(O)R$^{10a}$, —N(R$^{10}$)C(O)OR$^{10a}$, —N(R$^{10}$)C(O)N(R$^{10a}$R$^{10b}$), —OC(O)N(R$^{10}$R$^{10a}$), -T, C$_{1-20}$ alkyl, C$_{2-20}$ alkenyl, and C$_{2-20}$ alkynyl; wherein -T, C$_{1-20}$ alkyl, C$_{2-20}$ alkenyl, and C$_{2-20}$ alkynyl are optionally substituted with one or more —R$^{11}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;
each —R$^{10}$, —R$^{10a}$, —R$^{10b}$ is independently selected from the group consisting of —H, -T, C$_{1-20}$ alkyl, C$_{2-20}$ alkenyl, and C$_{2-20}$ alkynyl; wherein -T, C$_{1-20}$ alkyl, C$_{2-20}$ alkenyl, and C$_{2-20}$ alkynyl are optionally substituted with one or more —R$^{11}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;
each T is independently of each other selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T is independently optionally substituted with one or more —R$^{11}$, which are the same or different;

each —R$^{11}$ is independently of each other selected from halogen, —CN, oxo (=O), —COOR$^{13}$, —OR$^{13}$, —C(O)R$^{13}$, —C(O)N(R$^{13}$R$^{13a}$), —S(O)$_2$N(R$^{13}$R$^{13a}$), —S(O)N(R$^{13}$R$^{13a}$), —S(O)$_2$R$^{13}$, —S(O)R$^{13}$, —N(R$^{13}$)S(O)$_2$N(R$^{13a}$R$^{13b}$), —SR$^{13}$, —N(R$^{13}$R$^{13a}$), —NO$_2$, —OC(O)R$^{13}$, —N(R$^{13}$)C(O)R$^{13a}$, —N(R$^{13}$)S(O)$_2$R$^{13a}$, —N(R$^{13}$)S(O)R$^{13a}$, —N(R$^{13}$)C(O)OR$^{13a}$, —N(R$^{13}$)C(O)N(R$^{13a}$R$^{13b}$), —OC(O)N(R$^{13}$R$^{13a}$), and C$_{1-6}$ alkyl; wherein C$_{1-6}$ alkyl is optionally substituted with one or more halogen, which are the same or different;
each —R$^{12}$, —R$^{12a}$, —R$^{13}$, —R$^{13a}$, —R$^{13b}$ is independently selected from the group consisting of —H, and C$_{1-6}$ alkyl; wherein C$_{1-6}$ alkyl is optionally substituted with one or more halogen, which are the same or different;
optionally, one or more of the pairs —R$^1$/—R$^{1a}$, —R$^2$/—R$^{2a}$, —R$^3$/—R$^{3a}$, —R$^6$/—R$^{6a}$, —R$^7$/—R$^{7a}$ are joined together with the atom to which they are attached to form a C$_{3-10}$ cycloalkyl or a 3- to 10-membered heterocyclyl;
optionally, one or more of the pairs —R$^1$/—R$^2$, —R$^1$/—R$^3$, —R$^1$/—R$^4$, —R$^1$/—R$^5$, —R$^1$/—R$^6$, —R$^1$/—R$^7$, —R$^2$/—R$^3$, —R$^2$/—R$^4$, —R$^2$/—R$^5$, —R$^2$/—R$^6$, —R$^2$/—R$^7$, —R$^3$/—R$^4$, —R$^3$/—R$^5$, —R$^3$/—R$^6$, —R$^3$/—R$^7$, —R$^4$/—R$^5$, —R$^4$/—R$^6$, —R$^4$/—R$^7$, —R$^5$/—R$^6$, —R$^5$/—R$^7$, —R$^6$/—R$^7$ are joint together with the atoms to which they are attached to form a ring A;
A is selected from the group consisting of phenyl; naphthyl; indenyl; indanyl; tetralinyl; C$_{3-10}$ cycloalkyl; 3- to 10-membered heterocyclyl; and 8- to 11-membered heterobicyclyl;
wherein -L$^1$- is substituted with at least one -L$^2$-Z and wherein -L$^1$- is optionally further substituted.

The optional further substituents of -L$^1$- of formula (III) are preferably as described above.

Preferably -L$^1$- of formula (III) is substituted with one moiety -L$^2$-Z.

In one embodiment -L$^1$- of formula (III) is not further substituted.

In another embodiment -L$^1$- has a structure as disclosed in EP1536334B1, WO2009/009712A1, WO2008/034122A1, WO2009/143412A2, WO2011/082368A2, and U.S. Pat. No. 8,618,124B2, which are herewith incorporated by reference.

In certain embodiments -L$^1$- has a structure as disclosed in U.S. Pat. No. 8,946,405B2 and U.S. Pat. No. 8,754,190B2. Accordingly, in certain embodiments -L$^1$- is of formula (IV):

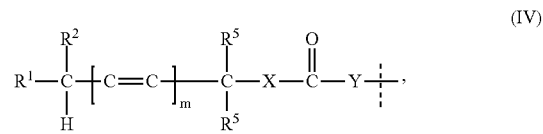

(IV)

wherein
the dashed line indicates attachment to -D through a functional group of -D selected from the group consisting of —OH, —SH and —NH$_2$;
m is 0 or 1;
at least one or both of —R$^1$ and —R$^2$ is/are independently of each other selected from the group consisting of —CN, —NO$_2$, optionally substituted aryl, optionally substituted heteroaryl, optionally substituted alkenyl, optionally substituted alkynyl, —C(O)R³, —S(O)R³, —S(O)₂R³, and —SR⁴, one and only one of —R¹ and —R² is selected from the group consisting of —H, optionally substituted alkyl, optionally substituted arylalkyl, and optionally substituted heteroarylalkyl;

—R³ is selected from the group consisting of —H, optionally substituted alkyl, optionally substituted aryl, optionally substituted arylalkyl, optionally substituted heteroaryl, optionally substituted heteroarylalkyl, —OR⁹ and —N(R⁹)₂;

—R⁴ is selected from the group consisting of optionally substituted alkyl, optionally substituted aryl, optionally substituted arylalkyl, optionally substituted heteroaryl, and optionally substituted heteroarylalkyl;

each —R⁵ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;

—R⁹ is selected from the group consisting of —H and optionally substituted alkyl;

—Y— is absent and —X— is —O— or —S—; or

—Y— is —N(Q)CH₂— and —X— is —O—;

Q is selected from the group consisting of optionally substituted alkyl, optionally substituted aryl, optionally substituted arylalkyl, optionally substituted heteroaryl and optionally substituted heteroarylalkyl;

optionally, —R¹ and —R² may be joined to form a 3 to 8-membered ring; and optionally, both —R⁹ together with the nitrogen to which they are attached form a heterocyclic ring;

wherein -L¹- is substituted with -L²-Z and wherein -L¹- is optionally further substituted.

Only in the context of formula (IV) the terms used have the following meaning:

The term "alkyl" as used herein includes linear, branched or cyclic saturated hydrocarbon groups of 1 to 8 carbons, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, preferably 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, or an additional ring, each optionally further substituted.

Optional substituents on any group, including the above, include halo, nitro, cyano, —OR, —SR, —NR₂, —OCOR, —NRCOR, —COOR, —CONR₂, —SOR, —SO₂R, —SONR₂, —SO₂NR₂, wherein each R is independently alkyl, alkenyl, alkynyl, aryl or heteroaryl, or two R groups taken together with the atoms to which they are attached form a ring.

Preferably -L¹- of formula (IV) is substituted with one moiety -L²-Z.

In certain embodiments -L¹- has a structure as disclosed in WO2013/036857A1. Accordingly, in certain embodiments -L¹- is of formula (V):

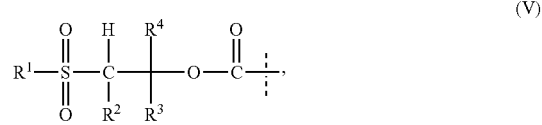

wherein the dashed line indicates attachment to -D through an amine functional group of -D;

—R¹ is selected from the group consisting of optionally substituted C₁-C₆ linear, branched, or cyclic alkyl; optionally substituted aryl; optionally substituted heteroaryl; alkoxy; and —NR⁵2;

—R² is selected from the group consisting of —H; optionally substituted C₁-C₆ alkyl; optionally substituted aryl; and optionally substituted heteroaryl;

—R³ is selected from the group consisting of —H; optionally substituted C₁-C₆ alkyl; optionally substituted aryl; and optionally substituted heteroaryl;

—R⁴ is selected from the group consisting of —H; optionally substituted C₁-C₆ alkyl; optionally substituted aryl; and optionally substituted heteroaryl;

each —R⁵ is independently of each other selected from the group consisting of —H; optionally substituted C₁-C₆ alkyl; optionally substituted aryl; and optionally substituted heteroaryl; or when taken together two —R⁵ can be cycloalkyl or cycloheteroalkyl;

wherein -L¹- is substituted with -L²-Z and wherein -L¹- is optionally further substituted.

Only in the context of formula (V) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, preferably 6-10 carbons, including groups such as phenyl, naphthyl, and anthracene "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiszolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketne; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

In certain embodiments -$L^1$- of formula (V) is substituted with one moiety -$L^2$-Z.

In certain embodiments -$L^1$- has a structure as disclosed in U.S. Pat. No. 7,585,837B2. Accordingly, in certain embodiments -$L^1$- is of formula (VI):

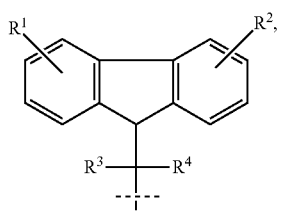

(VI)

wherein the dashed line indicates attachment to -D through an amine functional group of -D;

$R^1$ and $R^2$ are independently selected from the group consisting of hydrogen, alkyl, alkoxy, alkoxyalkyl, aryl, alkaryl, aralkyl, halogen, nitro, —$SO_3H$, —$SO_2NHR^5$, amino, ammonium, carboxyl, $PO_3H_2$, and $OPO_3H_2$;

$R^3$, $R^4$, and $R^5$ are independently selected from the group consisting of hydrogen, alkyl, and aryl;

wherein -$L^1$- is substituted with -$L^2$-Z o and wherein -$L^1$- is optionally further substituted.

Suitable substituents for formulas (VI) are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Only in the context of formula (VI) the terms used have the following meaning:

The terms "alkyl", "alkoxy", "alkoxyalkyl", "aryl", "alkaryl" and "aralkyl" mean alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

In certain embodiments -$L^1$- of formula (VI) is substituted with one moiety -$L^2$-Z.

In certain embodiments -$L^1$- has a structure as disclosed in WO2002/089789A1. Accordingly, in certain embodiments -$L^1$- is of formula (VII):

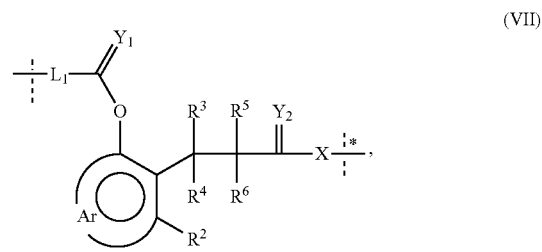

(VII)

wherein the dashed line indicates attachment to -D through an amine functional group of -D;

$Y_1$ and $Y_2$ are independently O, S or $NR^7$;

$R^2$, $R^3$, $R^4$, $R^5$, $R^6$ and $R^7$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula (VII) forms a multisubstituted aromatic hydrocarbon or a multi-substituted heterocyclic group;

X is a chemical bond or a moiety that is actively transported into a target cell, a hydrophobic moiety, or a combination thereof, y is 0 or 1;

wherein -$L^1$- is substituted with -$L^2$-Z and wherein -$L^1$- is optionally further substituted.

Only in the context of formula (VII) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moeities such as methoxy; and phenoxy includes moieties such as 3-nitrophenoxy. Halo-shall be understood to include fluoro, chloro, iodo and bromo.

In certain embodiments -$L^1$- of formula (VII) is substituted with one moiety -$L^2$-Z.

In certain embodiments -L¹- comprises a substructure of formula (VIII)

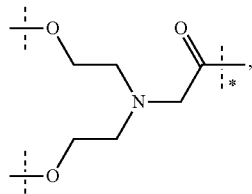

(VIII)

wherein
the dashed line marked with the asterisk indicates attachment to a nitrogen of -D by forming an amide bond;
the unmarked dashed lines indicate attachment to the remainder of -L¹-; and
wherein -L¹- is substituted with -L²-Z and wherein -L¹- is optionally further substituted.

In certain embodiments -L¹- of formula (VIII) is substituted with one moiety -L²-Z.

In certain embodiments -L¹- of formula (VIII) is not further substituted.

In certain embodiments -L¹- comprises a substructure of formula (IX)

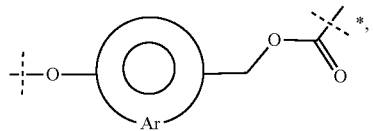

(IX)

wherein
the dashed line marked with the asterisk indicates attachment to a nitrogen of -D by forming a carbamate bond;
the unmarked dashed lines indicate attachment to the remainder of -L¹-; and
wherein -L¹- is substituted with -L²-Z and wherein -L¹- is optionally further substituted.

In certain embodiments -L¹- of formula (IX) is substituted with one moiety -L²-Z.

In certain embodiments -L¹- of formula (IX) is not further substituted.

In certain embodiments -L¹- is of formula (IX-a):

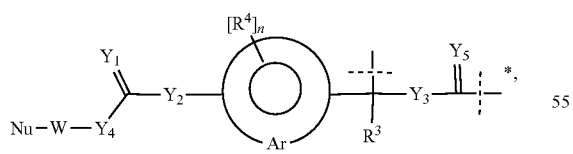

(IX-a)

wherein
the dashed line marked with the asterisk indicates attachment to a nitrogen of -D and the unmarked dashed line indicates attachment to -L²-Z;
n is 0, 1, 2, 3, or 4;
=$Y_1$, is selected from the group consisting of =O and =S;
—$Y_2$— is selected from the group consisting of —O— and —S—;
—$Y_3$— is selected from the group consisting of —O— and —S—;
—$Y_4$— is selected from the group consisting of —O—, —$NR^5$— and —$C(R^6R^{6a})$—;
=$Y_5$ is selected from the group consisting of =O and =S;
—$R^3$, —$R^5$, —$R^6$, —$R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—$R^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, —C(O)N($R^7$)—, —O—, —S— and —N($R^7$)—;
-Nu is a nucleophile selected from the group consisting of —N($R^7R^{7a}$), —N($R^7$OH), —N($R^7$)—N($R^{7a}R^{7b}$), —S($R^7$), —COOH,

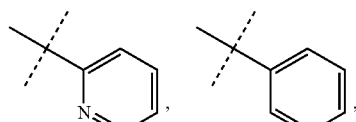

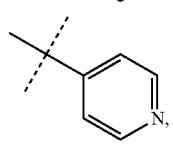

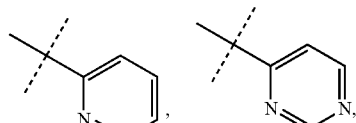

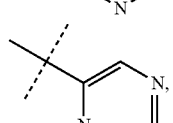

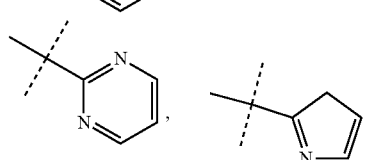

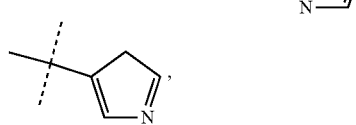

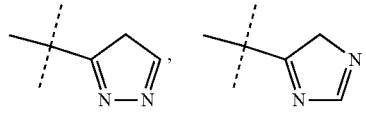

and

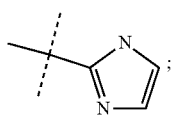

—Ar— is selected from the group consisting of

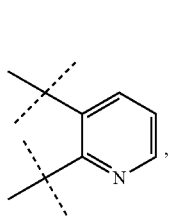
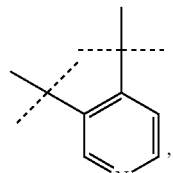
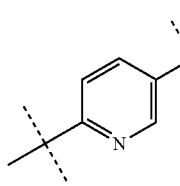
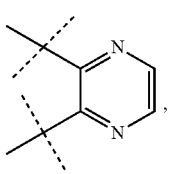
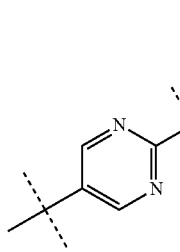
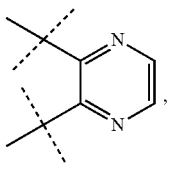
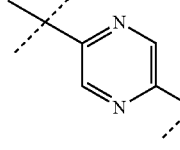
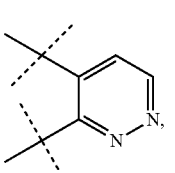
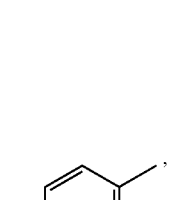
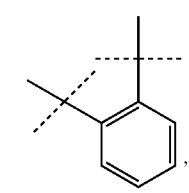
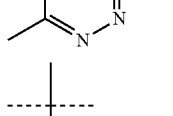
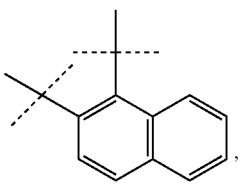

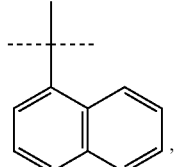
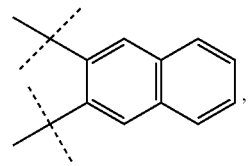
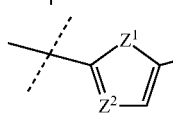
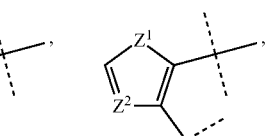
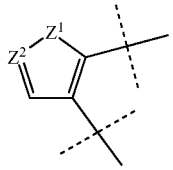

and

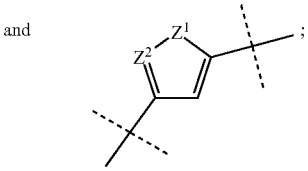

wherein
dashed lines indicate attachment to the remainder of -L$^1$-,
—Z$^1$— is selected from the group consisting of —O—, —S— and —N(R$^7$)—, and
—Z$^2$— is —N(R$^7$)—; and
—R$^7$, —R$^{7a}$, —R$^{7b}$ are independently of each other selected from the group consisting of —H, C$_{1-6}$ alkyl, C$_{2-6}$ alkenyl and C$_{2-6}$ alkynyl;
wherein -L$^1$- is optionally further substituted.

In certain embodiments -L$^1$- is of formula (IX-a), wherein the dashed line marked with the asterisk indicates attachment to a nitrogen of an amine of a lysine side chain or the N-terminus of -D.

In certain embodiments -L$^1$- is of formula (IX-a), wherein the dashed line marked with the asterisk indicates attachment to a nitrogen of an amine of a lysine side chain of -D.

In certain embodiments -L$^1$- is of formula (IX-a), wherein the dashed line marked with the asterisk indicates attachment to the nitrogen of the amine of the N-terminus of -D.

In certain embodiments -L$^1$- of formula (IX-a) is not further substituted.

In certain embodiments -L$^1$- is of formula (IX-b):

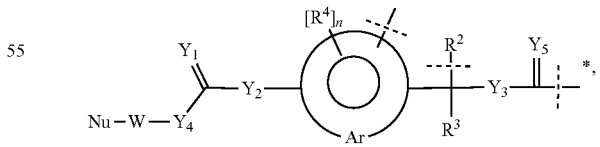

(IX-b)

wherein
the dashed line marked with the asterisk indicates attachment to a nitrogen of -D and the unmarked dashed line indicates attachment to -L$^2$-Z;
n is 0, 1, 2, 3, or 4;
=Y$_1$, is selected from the group consisting of =O and =S;

—Y$_2$— is selected from the group consisting of —O— and —S—;
—Y$_3$— is selected from the group consisting of —O— and —S—;
—Y$_4$— is selected from the group consisting of —O—, —NR$^5$— and —C(R$^6$R$^{6a}$)—;
=Y$_5$ is selected from the group consisting of =O and =S;
—R$^2$, —R$^3$, —R$^5$, —R$^6$, —R$^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—R$^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—W— is selected from the group consisting of C$_{1-20}$ alkyl optionally interrupted by one or more groups selected from the group consisting of C$_{3-10}$ cycloalkyl, 8- to 30-membered carbopolycyclyl, 3- to 10-membered heterocyclyl, —C(O)—, —C(O)N(R$^7$)—, —O—, —S— and —N(R$^7$)—;
-Nu is a nucleophile selected from the group consisting of —N(R$^7$R$^{7a}$), —N(R$^7$OH), —N(R$^7$)—N(R$^{7a}$R$^{7b}$), —S(R$^7$), —COOH,

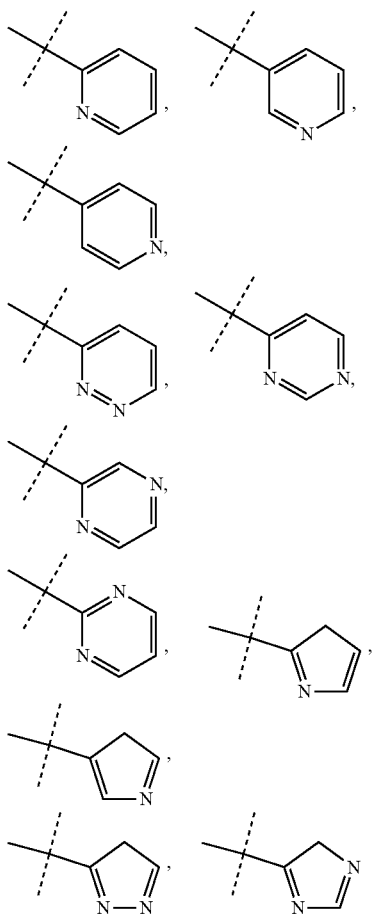

-continued

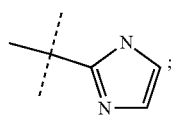

—Ar— is selected from the group consisting of

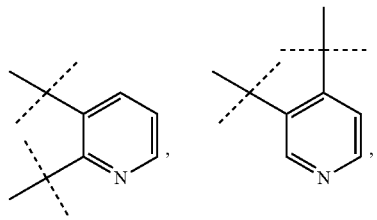

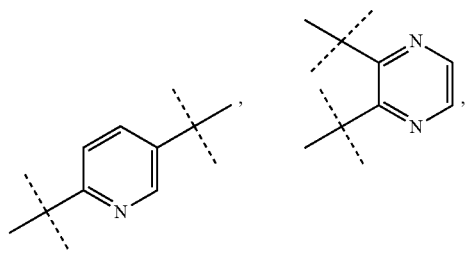

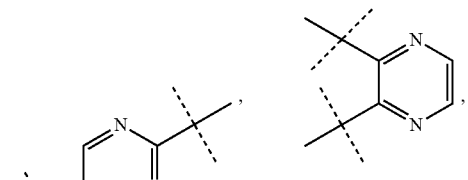

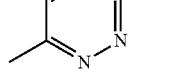

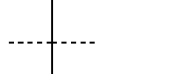

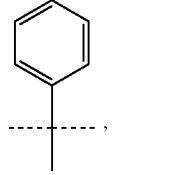

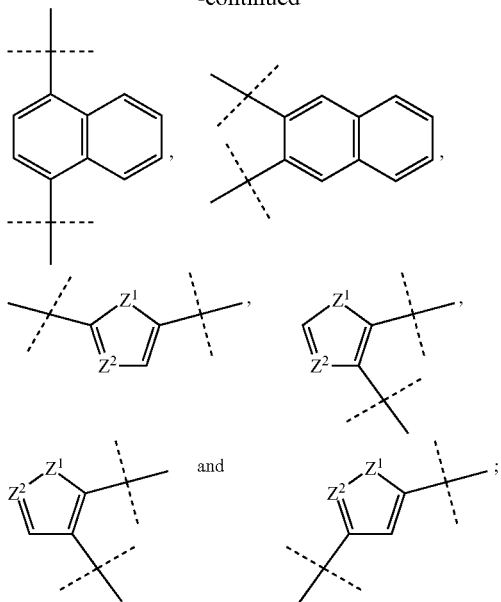

wherein
dashed lines indicate attachment to the remainder of -L¹-,
—Z¹— is selected from the group consisting of —O—, —S— and —N(R⁷)—, and
—Z²— is —N(R⁷)—; and
—R⁷, —R⁷ᵃ, —R⁷ᵇ are independently of each other selected from the group consisting of —H, C$_{1-6}$ alkyl, C$_{2-6}$ alkenyl and C$_{2-6}$ alkynyl;
wherein -L¹- is optionally further substituted.

In certain embodiments -L¹- is of formula (IX-b), wherein the dashed line marked with the asterisk indicates attachment to a nitrogen of an amine of a lysine side chain or the N-terminus of -D.

In certain embodiments -L¹- is of formula (IX-b), wherein the dashed line marked with the asterisk indicates attachment to a nitrogen of an amine of a lysine side chain of -D.

In certain embodiments -L¹- is of formula (IX-b), wherein the dashed line marked with the asterisk indicates attachment to the nitrogen of the amine of the N-terminus of -D.

In certain embodiments -L¹- of formula (IX-b) is not further substituted.

In certain embodiments =Y¹ of formula (IX-a) and (IX-b) is =O.

In certain embodiments —Y²— of formula (IX-a) and (IX-b) is —O—.

In certain embodiments —Y³— of formula (IX-a) and (IX-b) is —O—.

In certain embodiments —Y⁴— of formula (IX-a) and (IX-b) is —NR⁵—.

In certain embodiments =Y⁵ of formula (IX-a) and (IX-b) is =O.

In certain embodiments n of formula (IX-a) and (IX-b) is 0 or 1. In certain embodiments n of formula (IX-a) and (IX-b) is 0. In certain embodiments n of formula (IX-a) and (IX-b) is 1.

In certain embodiments —R² of formula (IX-b) is selected from the group consisting of —H, methyl, ethyl, n-propyl, isopropyl, n-butyl, isobutyl, sec-butyl and tert-butyl. In certain embodiments —R² of formula (IX-b) is selected from the group consisting of —H, methyl, ethyl, n-propyl and isopropyl. In certain embodiments —R² of formula (IX-b) is selected from —H, methyl and ethyl. In certain embodiments —R² of formula (IX-b) is —H.

In certain embodiments —R³ of formula (IX-a) and (IX-b) is selected from the group consisting of —H, methyl, ethyl, n-propyl, isopropyl, n-butyl, isobutyl, sec-butyl and tert-butyl. In certain embodiments —R³ of formula (IX-a) and (IX-b) is selected from the group consisting of —H, methyl, ethyl, n-propyl and isopropyl. In certain embodiments —R³ of formula (IX-a) and (IX-b) is selected from —H, methyl and ethyl. In certain embodiments —R³ of formula (IX-a) and (IX-b) is —H.

In certain embodiments each —R⁴ of formula (IX-a) and (IX-b) is independently selected from methyl, ethyl, n-propyl, isopropyl, n-butyl, isobutyl, sec-butyl and tert-butyl. In certain embodiments —R⁴ of formula (IX-a) and (IX-b) is selected from the group consisting of methyl, ethyl, n-propyl and isopropyl. In certain embodiments —R⁴ of formula (IX-a) and (IX-b) is selected from methyl and ethyl.

In certain embodiments —R⁵ of formula (IX-a) and (IX-b) is selected from the group consisting of —H, methyl, ethyl, n-propyl, isopropyl, n-butyl, isobutyl, sec-butyl and tert-butyl. In certain embodiments —R⁵ of formula (IX-a) and (IX-b) is selected from the group consisting of —H, methyl, ethyl, n-propyl and isopropyl. In certain embodiments —R⁵ of formula (IX-a) and (IX-b) is selected from methyl and ethyl. In certain embodiments —R⁵ of formula (IX-a) and (IX-b) is methyl.

In certain embodiments —R⁶ and —R⁶ᵃ of formula (IX-a) and (IX-b) are independently selected from the group consisting of —H, methyl, ethyl, n-propyl, isopropyl, n-butyl, isobutyl, sec-butyl and tert-butyl. In certain embodiments —R⁶ and —R⁶ᵃ of formula (IX-a) and (IX-b) are independently selected from the group consisting of —H, methyl, ethyl, n-propyl and isopropyl. In certain embodiments —R⁶ and —R⁶ᵃ of formula (IX-a) and (IX-b) are independently selected from —H, methyl and ethyl. In certain embodiments —R⁶ and —R⁶ᵃ of formula (IX-a) and (IX-b) are both —H.

In certain embodiments Ar of formula (IX-a) and (IX-b) is phenyl. In certain embodiments Ar of formula (IX-a) and (IX-b) is

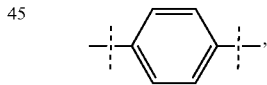

wherein the dashed lines indicate attachment to the remainder of the moiety of formula (IX-a) and (IX-b).

In certain embodiments W of formula (IX-a) and (IX-b) is C$_{1-20}$ alkyl, optionally interrupted with C$_{3-10}$ cycloalkyl, —C(O)—, —C(O)N(R⁷)—, —O—, —S— and —N(R⁷)—. In certain embodiments W of formula (IX-a) and (IX-b) is C$_{1-10}$ alkyl, optionally interrupted with C$_{3-10}$ cycloalkyl, —C(O)—, —C(O)N(R⁷)—, —O—, —S— and —N(R⁷)—. In certain embodiments W of formula (IX-a) and (IX-b) is C$_{1-6}$ alkyl, optionally interrupted with C$_{3-10}$ cycloalkyl, —C(O)—, —C(O)N(R⁷)—, —O—, —S— and —N(R⁷)—. In certain embodiments W of formula (IX-a) and (IX-b) is

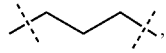

wherein
the dashed lines indicate attachment to the remainder of the moiety of formula (IX-a) or (IX-b), respectively.

In certain embodiments -Nu of formula (IX-a) and (IX-b) is —N(R$^7$R$^{7a}$).

In certain embodiments —R$^7$, —R$^{7a}$ and —R$^{7b}$ of formula (IX-a) and (IX-b) are independently of each other selected from the group consisting of —H, methyl, ethyl, n-propyl, isopropyl, n-butyl, isobutyl, sec-butyl and tert-butyl. In certain embodiments —R$^7$, —R$^{7a}$ and —R$^{7b}$ of formula (IX-a) and (IX-b) are independently of each other selected from —H, methyl, ethyl, n-propyl and isopropyl. In certain embodiments —R$^7$, —R$^{7a}$ and —R$^{7b}$ of formula (IX-a) and (IX-b) are independently of each other selected from methyl or ethyl. In certain embodiments —R$^7$, —R$^{7a}$ and —R$^{7b}$ of formula (IX-a) and (IX-b) are both methyl.

In certain embodiments -L$^1$- is of formula (IX-c)

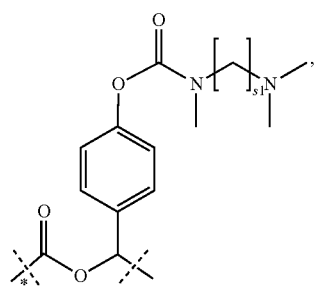

(IX-c)

wherein
the dashed line marked with the asterisk indicates attachment to a nitrogen of -D;
the unmarked dashed line indicates attachment to -L$^2$-Z; and
s1 is an integer selected from the group consisting of 1, 2, 3, 4, 5, 6, 7, 8, 9 and 10.

In certain embodiments -L$^1$- is of formula (IX-c), wherein the dashed line marked with the asterisk indicates attachment to a nitrogen of an amine of a lysine side chain or the N-terminus of -D.

In certain embodiments -L$^1$- is of formula (IX-c), wherein the dashed line marked with the asterisk indicates attachment to a nitrogen of an amine of a lysine side chain of -D.

In certain embodiments -L$^1$- is of formula (IX-c), wherein the dashed line marked with the asterisk indicates attachment to the nitrogen of the amine of the N-terminus of -D.

In certain embodiments s1 of formula (IX-c) is an integer selected from the group consisting of 1, 2, 3, 4 and 5. In certain embodiments s1 of formula (IX-c) is 1. In certain embodiments s1 of formula (IX-c) is 2. In certain embodiments s1 of formula (IX-c) is 3. In certain embodiments s1 of formula (IX-c) is 4. In certain embodiments s1 of formula (IX-c) is 5.

In certain embodiments -L$^1$- is of formula (IX-d)

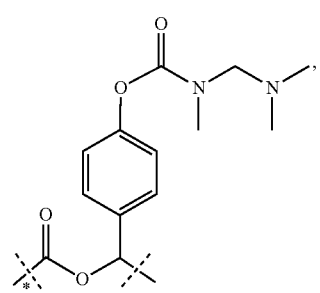

(IX-d)

wherein
the dashed line marked with the asterisk indicates attachment to a nitrogen of -D; and
the unmarked dashed line indicates attachment to -L$^2$-Z.

In certain embodiments -L$^1$- is of formula (IX-d), wherein the dashed line marked with the asterisk indicates attachment to a nitrogen of an amine of a lysine side chain or the N-terminus of -D.

In certain embodiments -L$^1$- is of formula (IX-d), wherein the dashed line marked with the asterisk indicates attachment to a nitrogen of an amine of a lysine side chain of -D.

In certain embodiments -L$^1$- is of formula (IX-d), wherein the dashed line marked with the asterisk indicates attachment to the nitrogen of the amine of the N-terminus of -D.

In certain embodiments -L$^1$- has a structure as disclosed in WO2020/206358 A1. Accordingly, in certain embodiments the moiety -L$^1$- is of formula (X):

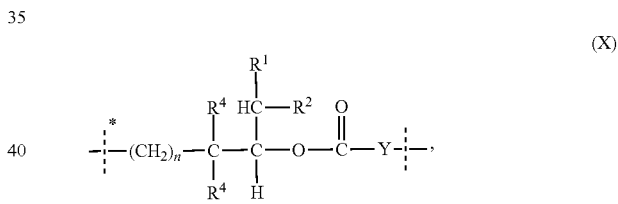

(X)

wherein
the unmarked dashed line indicates attachment to -D;
the dashed line marked with the asterisk indicates attachment to -L$^2$-Z or -L$^2$-Z';
n is an integer selected from the group consisting of 0, 1, 2, 3, 4, 5 and 6;
—R$^1$ and —R$^2$ are independently an electron-withdrawing group, alkyl, or —H, and wherein at least one of —R$^1$ or —R$^2$ is an electron-withdrawing group;
each —R$^4$ is independently C$_1$-C$_3$ alkyl or the two —R$^4$ are taken together with the carbon atom to which they are attached to form a 3- to 6-membered ring; and
—Y— is absent when -D is a drug moiety connected through an amine, or —Y— is —N(R$^6$)CH$_2$— when -D is a drug moiety connected through a phenol, alcohol, thiol, thiophenol, imidazole, or non-basic amine; wherein —R$^6$ is optionally substituted C$_1$-C$_6$ alkyl, optionally substituted aryl, or optionally substituted heteroaryl.

In certain embodiments n of formula (X) is an integer selected from 1, 2, 3, 4, 5 and 6. In certain embodiments n of formula (X) is an integer selected from 1, 2 and 3. In certain embodiments n of formula (X) is an integer from 0, 1, 2 and 3. In certain embodiments n of formula (X) is 1. In certain embodiments n of formula (X) is 2. In certain embodiments n of formula (X) is 3.

In certain embodiments the electron-withdrawing group of —$R^1$ and —$R^2$ of formula (X) is selected from the group consisting of —CN; —$NO_2$; optionally substituted aryl; optionally substituted heteroaryl; optionally substituted alkenyl; optionally substituted alkynyl; —$COR^3$, —$SOR^3$, or —$SO_2R^3$, wherein —$R^3$ is —H, optionally substituted alkyl, optionally substituted aryl, optionally substituted arylalkyl, optionally substituted heteroaryl, optionally substituted heteroarylalkyl, —$OR^8$ or —$NR^8{}_2$, wherein each —$R^8$ is independently —H or optionally substituted alkyl, or both —$R^8$ groups are taken together with the nitrogen to which they are attached to form a heterocyclic ring; or —$SR^9$, wherein —$R^9$ is optionally substituted alkyl, optionally substituted aryl, optionally substituted arylalkyl, optionally substituted heteroaryl, or optionally substituted heteroarylalkyl.

In certain embodiments the electron-withdrawing group of —$R^1$ and —$R^2$ of formula (X) is —CN. In certain embodiments the electron-withdrawing group of —$R^1$ and —$R^2$ of formula (X) is —$NO_2$. In certain embodiments the electron-withdrawing group of —$R^1$ and —$R^2$ of formula (X) is optionally substituted aryl comprising 6 to 10 carbons. In certain embodiments the electron-withdrawing group of —$R^1$ and —$R^2$ of formula (X) is optionally substituted phenyl, naphthyl, or anthracenyl. In certain embodiments the electron-withdrawing group of —$R^1$ and —$R^2$ of formula (X) is optionally substituted heteroaryl comprising 3 to 7 carbons and comprising at least one N, O, or S atom. In certain embodiments the electron-withdrawing group of —$R^1$ and —$R^2$ of formula (X) is optionally substituted pyrrolyl, pyridyl, pyrimidinyl, imidazolyl, oxazolyl, isoxazolyl, thiazolyl, isothiazolyl, quinolyl, indolyl, or indenyl. In certain embodiments the electron-withdrawing group of —$R^1$ and —$R^2$ of formula (X) is optionally substituted alkenyl containing 2 to 20 carbon atoms. In certain embodiments the electron-withdrawing group of —$R^1$ and —$R^2$ of formula (X) is optionally substituted alkynyl comprising 2 to 20 carbon atoms. In certain embodiments the electron-withdrawing group of —$R^1$ and —$R^2$ of formula (X) is —$COR^3$, —$SOR^3$, or —$SO_2R^3$, wherein —$R^3$ is —H, optionally substituted alkyl comprising 1 to 20 carbon atoms, optionally substituted aryl, optionally substituted arylalkyl, optionally substituted heteroaryl, optionally substituted heteroarylalkyl, —$OR^8$ or —$NR^8{}_2$, wherein each —$R^8$ is independently —H or optionally substituted alkyl comprising 1 to 20 carbon atoms, or both —$R^8$ groups are taken together with the nitrogen to which they are attached to form a heterocyclic ring. In certain embodiments the electron-withdrawing group of —$R^1$ and —$R^2$ of formula (X) is —$SR^9$, wherein —$R^9$ is optionally substituted alkyl comprising 1 to 20 carbon atoms, optionally substituted aryl, optionally substituted arylalkyl, optionally substituted heteroaryl, or optionally substituted heteroarylalkyl.

In certain embodiments at least one of —$R^1$ or —$R^2$ of formula (X) is —CN, —$SOR^3$ or —$SO_2R^3$. In certain embodiments at least one of —$R^1$ and —$R^2$ of formula (X) is —CN or —$SO_2R^3$. In certain embodiments at least one of —$R^1$ and —$R^2$ of formula (X) is —CN or —$SO_2R^3$, wherein —$R^3$ is optionally substituted alkyl, optionally substituted aryl, or —$NR^8{}_2$. In certain embodiments at least one of —$R^1$ and —$R^2$ of formula (X) is —CN, —$SO_2N(CH_3)_2$, —$SO_2CH_3$, phenyl substituted with —$SO_2$ and —Cl, —$SO_2N(CH_2CH_2)_2O$, —$SO_2CH(CH_3)_2$, —$SO_2N(CH_3)(CH_2CH_3)$, or —$SO_2N(CH_2CH_2OCH_3)_2$.

In certain embodiments each —$R^4$ of formula (X) is independently $C_1$-$C_3$ alkyl. In certain embodiments both —$R^4$ are methyl.

In certain embodiments —Y— of formula (X) is absent. In certain embodiments —Y— of formula (X) is —$N(R^6)CH_2$—.

In certain embodiments -$L^1$- is of formula (X), wherein n is 1, —$R^1$ is —CN, —$R^2$ is —H, and —$R^4$ is —$CH_3$. In certain embodiments -$L^1$- is of formula (X), wherein n is 1, —$R^1$ is —$SO_2N(CH_3)_2$, —$R^2$ is —H, and —$R^4$ is —$CH_3$. In certain embodiments -$L^1$- is of formula (X), wherein n is 1, —$R^1$ is $SO_2CH_3$, —$R^2$ is —H, and —$R^4$ is —$CH_3$. In certain embodiments -$L^1$- is of formula (X), wherein n is 1, —$R^1$ is —$SO_2N(CH_2CH_2)_2CHCH_3$, —$R^2$ is —H, and —$R^4$ is —$CH_3$. In certain embodiments -$L^1$- is of formula (X), wherein n is 1, —$R^1$ is phenyl substituted with —$SO_2$, —$R^2$ is —H, and —$R^4$ is —$CH_3$. In certain embodiments -$L^1$- is of formula (X), wherein n is 1, —$R^1$ is phenyl substituted with —$SO_2$ and —Cl, —$R^2$ is —H, and —$R^4$ is —$CH_3$. In certain embodiments -$L^1$- is of formula (X), wherein n is 1, —$R^1$ is —$SO_2N(CH_2CH_2)_2O$, —$R^2$ is —H, and —$R^4$ is —$CH_3$. In certain embodiments -$L^1$- is of formula (X), wherein n is 1, —$R^1$ is —$SO_2CH(CH_3)_2$, —$R^2$ is —H, and —$R^4$ is —$CH_3$. In certain embodiments -$L^1$- is of formula (X), wherein n is 1, —$R^1$ is —$SO_2N(CH_3)(CH_2CH_3)$, —$R^2$ is —H, and —$R^4$ is —$CH_3$. In certain embodiments -$L^1$- is of formula (X), wherein n is 1, —$R^1$ is —$SO_2N(CH_2CH_2OCH_3)_2$, —$R^2$ is —H, and —$R^4$ is —$CH_3$. In certain embodiments -$L^1$- is of formula (X), wherein n is 1, —$R^1$ is phenyl substituted with —$SO_2$ and —$CH_3$, —$R^2$ is —H, and —$R^4$ is —$CH_3$.

In certain embodiments -$L^1$- is of formula (X), wherein n is 2, —$R^1$ is —CN, —$R^2$ is —H, and —$R^4$ is —$CH_3$. In certain embodiments -$L^1$- is of formula (X), wherein n is 2, —$R^1$ is —$SO_2N(CH_3)_2$, —$R^2$ is —H, and —$R^4$ is —$CH_3$. In certain embodiments -$L^1$- is of formula (X), wherein n is 2, —$R^1$ is $SO_2CH_3$, —$R^2$ is —H, and —$R^4$ is —$CH_3$. In certain embodiments -$L^1$- is of formula (X), wherein n is 2, —$R^1$ is —$SO_2N(CH_2CH_2)_2CHCH_3$, —$R^2$ is —H, and —$R^4$ is —$CH_3$. In certain embodiments -$L^1$- is of formula (X), wherein n is 2, —$R^1$ is phenyl substituted with —$SO_2$, —$R^2$ is —H, and —$R^4$ is —$CH_3$. In certain embodiments -$L^1$- is of formula (X), wherein n is 2, —$R^1$ is phenyl substituted with —$SO_2$ and —Cl, —$R^2$ is —H, and —$R^4$ is —$CH_3$. In certain embodiments -$L^1$- is of formula (X), wherein n is 2, —$R^1$ is —$SO_2N(CH_2CH_2)_2O$, —$R^2$ is —H, and —$R^4$ is —$CH_3$. In certain embodiments -$L^1$- is of formula (X), wherein n is 2, —$R^1$ is —$SO_2CH(CH_3)_2$, —$R^2$ is —H, and —$R^4$ is —$CH_3$. In certain embodiments -$L^1$- is of formula (X), wherein n is 2, —$R^1$ is —$SO_2N(CH_3)(CH_2CH_3)$, —$R^2$ is —H, and —$R^4$ is —$CH_3$. In certain embodiments -$L^1$- is of formula (X), wherein n is 2, —$R^1$ is —$SO_2N(CH_2CH_2OCH_3)_2$, —$R^2$ is —H, and —$R^4$ is —$CH_3$. In certain embodiments -$L^1$- is of formula (X), wherein n is 2, —$R^1$ is phenyl substituted with —$SO_2$ and —$CH_3$, —$R^2$ is —H, and —$R^4$ is —$CH_3$.

In certain embodiments -$L^1$- is of formula (X), wherein n is 3, —$R^1$ is —CN, —$R^2$ is —H, and —$R^4$ is —$CH_3$. In certain embodiments -$L^1$- is of formula (X), wherein n is 3, —$R^1$ is —$SO_2N(CH_3)_2$, —$R^2$ is —H, and —$R^4$ is —$CH_3$. In certain embodiments -$L^1$- is of formula (X), wherein n is 3, —$R^1$ is $SO_2CH_3$, —$R^2$ is —H, and —$R^4$ is —$CH_3$. In certain embodiments -$L^1$- is of formula (X), wherein n is 3, —$R^1$ is —$SO_2N(CH_2CH_2)_2CHCH_3$, —$R^2$ is —H, and —$R^4$ is —$CH_3$. In certain embodiments -$L^1$- is of formula (X), wherein n is 3, —$R^1$ is phenyl substituted with —$SO_2$, —$R^2$ is —H, and —$R^4$ is —$CH_3$. In certain embodiments -$L^1$- is of formula (X), wherein n is 3, —$R^1$ is phenyl substituted with —$SO_2$ and —Cl, —$R^2$ is —H, and —$R^4$ is —$CH_3$. In certain embodiments -$L^1$- is of formula (X), wherein n is 3, —$R^1$ is —$SO_2N(CH_2CH_2)_2O$, —$R^2$ is —H, and —$R^4$ is —$CH_3$. In certain embodiments -$L^1$- is of formula (X), wherein n is 3, —$R^1$ is —$SO_2CH(CH_3)_2$, —$R^2$ is —H, and —$R^4$ is —$CH_3$. In certain embodiments -$L^1$- is of formula (X), wherein n is 3, —$R^1$ is —$SO_2N(CH_3)(CH_2CH_3)$, —$R^2$ is —H, and —$R^4$ is —$CH_3$. In certain embodiments -$L^1$- is of formula (X), wherein n is 3, —$R^1$ is —$SO_2N(CH_2CH_2OCH_3)_2$, —$R^2$ is —H, and —$R^4$ is —$CH_3$. In certain embodiments -$L^1$- is of formula (X), wherein n is 3, —$R^1$ is phenyl substituted with —$SO_2$ and —$CH_3$, —$R^2$ is —H, and —$R^4$ is —$CH_3$.

Only in the context of formula (X) the terms used have the following meaning:

The term "alkyl" refers to linear, branched, or cyclic saturated hydrocarbon groups of 1 to 20, 1 to 12, 1 to 8, 1 to 6, or 1 to 4 carbon atoms. In certain embodiments an alkyl is linear or branched. Examples of linear or branched alkyl groups include methyl, ethyl, n-propyl, isopropyl, n-butyl, t-butyl, isobutyl, sec-butyl, n-pentyl, n-hexyl, n-heptyl, n-octyl, n-nonyl, and n-decyl. In certain embodiments an alkyl is cyclic. Examples of cyclic alkyl groups include cyclopropyl, cyclobutyl, cyclopentyl, cyclopentadienyl, and cyclohexyl.

The term "alkoxy" refers to alkyl groups bonded to oxygen, including methoxy, ethoxy, isopropoxy, cyclopropoxy, and cyclobutoxy.

The term "alkenyl" refers to non-aromatic unsaturated hydrocarbons with carbon-carbon double bonds and 2 to 20, 2 to 12, 2 to 8, 2 to 6, or 2 to 4 carbon atoms.

The term "alkynyl" refers to non-aromatic unsaturated hydrocarbons with carbon-carbon triple bonds and 2 to 20, 2 to 12, 2 to 8, 2 to 6, or 2 to 4 carbon atoms.

The term "aryl" refers to aromatic hydrocarbon groups of 6 to 18 carbons, preferably 6 to 10 carbons, including groups such as phenyl, naphthyl, and anthracenyl. The term "heteroaryl" refers to aromatic rings comprising 3 to 15 carbons comprising at least one N, O or S atom, preferably 3 to 7 carbons comprising at least one N, O or S atom, including groups such as pyrrolyl, pyridyl, pyrimidinyl, imidazolyl, oxazolyl, isoxazolyl, thiazolyl, isothiazolyl, quinolyl, indolyl, and indenyl.

In certain embodiments alkenyl, alkynyl, aryl or heteroaryl moieties may be coupled to the remainder of the molecule through an alkyl linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" or "halo" refers to bromo, fluoro, chloro and iodo.

The term "heterocyclic ring" or "heterocyclyl" refers to a 3- to 15-membered aromatic or non-aromatic ring comprising at least one N, O, or S atom. Examples include piperidinyl, piperazinyl, tetrahydropyranyl, pyrrolidine, and tetrahydrofuranyl, as well as the exemplary groups provided for the term "heteroaryl" above. In certain embodiments a heterocyclic ring or heterocyclyl is non-aromatic. In certain embodiments a heterocyclic ring or heterocyclyl is aromatic.

The term "optionally substituted" refers to a group may be unsubstituted or substituted by one or more (e.g., 1, 2, 3, 4 or 5) of the substituents which may be the same or different. Examples of substituents include alkyl, alkenyl, alkynyl, halogen, —CN, —$OR^{aa}$, —$SR^{aa}$, —$NR^{aa}R^{bb}$, —$NO_2$, —C=$NH(OR^{aa})$, —$C(O)R^{aa}$, —$OC(O)R^{aa}$, —$C(O)OR^{aa}$, —$C(O)NR^{aa}R^{bb}$, —$OC(O)NR^{aa}R^{bb}$, —$NR^{aa}C(O)R^{bb}$, —$NR^{aa}C(O)OR^{bb}$, —$S(O)R^{aa}$, —$S(O)_2R^{aa}$, —$NR^{aa}S(O)R^{bb}$, —$C(O)NR^{aa}S(O)R^{bb}$, —$NR^{aa}S(O)_2R^{bb}$, —$C(O)NR^{aa}S(O)_2R^{bb}$, —$S(O)NR^{aa}R^{bb}$, —$S(O)_2NR^{aa}R^{bb}$, —$P(O)(OR^{aa})(OR^{bb})$, heterocyclyl, heteroaryl, or aryl, wherein the alkyl, alkenyl, alkynyl, cycloalkyl, heterocyclyl, heteroaryl, and aryl are each independently optionally substituted by —$R^{cc}$, wherein —$R^{aa}$ and —$R^{bb}$ are each independently —H, alkyl, alkenyl, alkynyl, heterocyclyl, heteroaryl, or aryl, or —$R^{aa}$ and —$R^{bb}$ are taken together with the nitrogen atom to which they attach to form a heterocyclyl, which is optionally substituted by alkyl, alkenyl, alkynyl, halogen, hydroxyl, alkoxy, or —CN, and wherein: each —$R^{cc}$ is independently alkyl, alkenyl, alkynyl, halogen, heterocyclyl, heteroaryl, aryl, —CN, or —$NO_2$.

In certain embodiments -$L^2$- is a chemical bond. In certain embodiments -$L^2$- is a spacer moiety.

In certain embodiments -$L^2$- is selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo (=O), —$COOR^{y5}$, —$OR^{y5}$, —$C(O)R^{y5}$, —$C(O)N(R^{y5}R^{y5a})$, —$S(O)_2N(R^{y5}R^{y5a})$, —$S(O)N(R^{y5}R^{y5a})$, —$S(O)_2R^{y5}$, —$S(O)R^{y5}$, —$N(R^{y5})S(O)_2N(R^{y5a}R^{y5b})$, —$SR^{y5}$, —$N(R^{y5}R^{y5a})$, —$NO_2$, —$OC(O)R^{y5}$, —$N(R^{y5})C(O)R^{y5a}$, —$N(R^{y5})S(O)_2R^{y5a}$, —$N(R^{y5})S(O)R^{y5a}$, —$N(R^{y5})C(O)OR^{y5a}$, —$N(R^{y5})C(O)N(R^{y5a}R^{y5b})$, —$OC(O)N(R^{y5}R^{y5a})$, and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently selected from the group consisting of —H, and $C_{1-6}$ alkyl, wherein $C_{1-6}$ alkyl is optionally substituted with one or more halogen, which are the same or different.

In certain embodiments -L$^2$- is selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-20}$ alkyl, C$_{2-20}$ alkenyl, and C$_{2-20}$ alkynyl are optionally substituted with one or more —R$^{y2}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently of each other selected from the group consisting of —H, -T, C$_{1-10}$ alkyl, C$_{2-10}$ alkenyl, and C$_{2-10}$ alkynyl; wherein -T, C$_{1-10}$alkyl, C$_{2-10}$ alkenyl, and C$_{2-10}$ alkynyl are optionally substituted with one or more —R$^{y2}$, which are the same or different, and wherein C$_{1-10}$ alkyl, C$_{2-10}$ alkenyl, and C$_{2-10}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^{y2}$, which are the same or different;

—R$^{y2}$ is selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

In certain embodiments -L$^2$- is selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently selected from the group consisting of —H, -T, C$_{1-10}$ alkyl, C$_{2-10}$ alkenyl, and C$_{2-10}$ alkynyl;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —R$^{y2}$ is independently selected from the group consisting of halogen, and C$_{1-6}$ alkyl; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

In certain embodiments -L$^2$- is a C$_{1-20}$ alkyl chain, which is optionally interrupted by one or more groups independently selected from —O—, -T- and —C(O)N(R$^{y1}$)—; and which C$_{1-20}$ alkyl chain is optionally substituted with one or more groups independently selected from —OH, -T and —C(O)N(R$^{y6}$R$^{y6a}$); wherein —R$^{y1}$, —R$^{y6}$, —R$^{y6a}$ are independently selected from the group consisting of H and C$_{1-4}$ alkyl and wherein T is selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

In certain embodiments -L$^2$- has a molecular weight in the range of from 14 g/mol to 750 g/mol.

In certain embodiments -L$^2$- comprises a moiety selected from the group consisting of

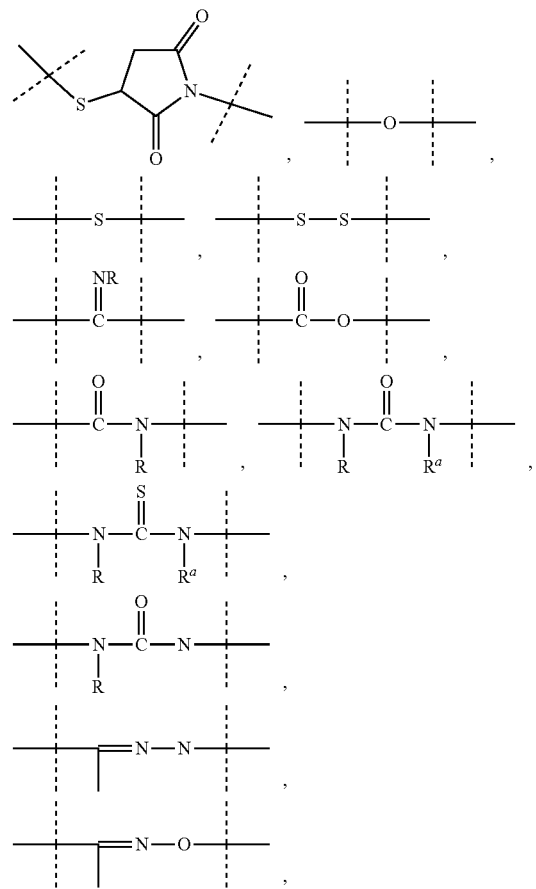

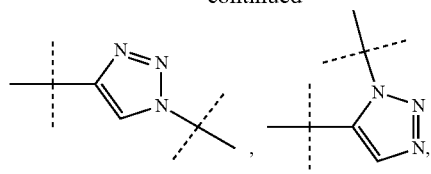
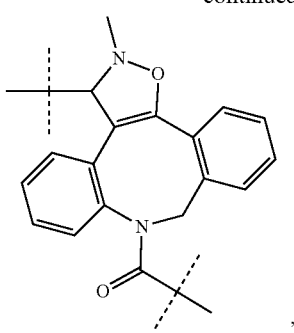
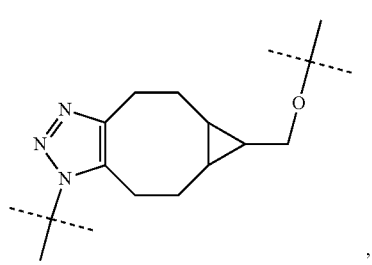
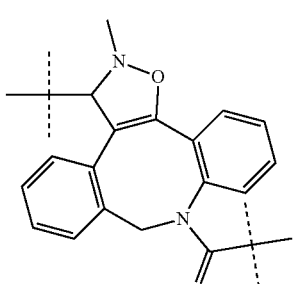
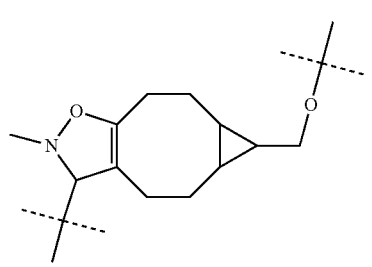
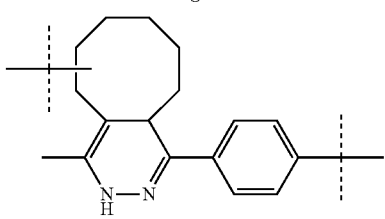
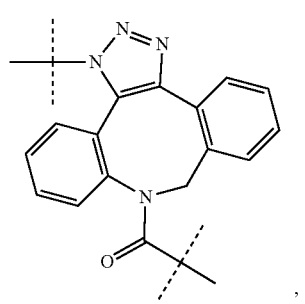
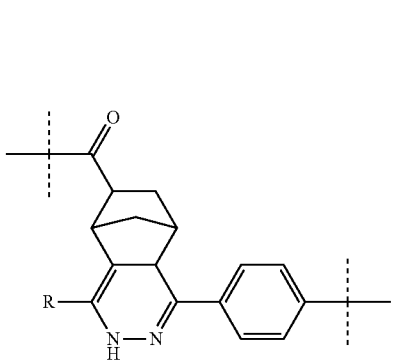
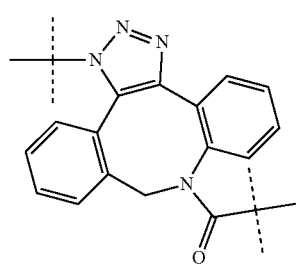
, and
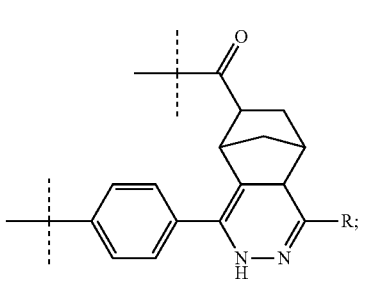
;

wherein dashed lines indicate attachment to -L$^1$-, the remainder of -L$^2$- or to —Z, respectively; and —R and —R$^a$ are independently of each other selected from the group consisting of —H, methyl, ethyl, propyl, butyl, pentyl and hexyl.

In certain embodiments -L$^2$- is of formula (IX-e)

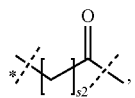

(IX-e)

wherein the dashed line marked with the asterisk indicates attachment to -L$^1$-;

the unmarked dashed line indicates attachment to —Z; and s2 is an integer selected from the group consisting of 0, 1, 2, 3, 4, 5, 6, 7, 8, 9, 10, 11, 12, 13, 14, 15, 16, 17, 18, 19 and 20.

In certain embodiments s2 of formula (IX-e) is an integer selected from the group consisting of 1, 2, 3, 4, 5, 6, 7, 8, 9, 10, 11 and 12. In certain embodiments s2 of formula (IX-e) is an integer selected from the group consisting of 1, 2, 3, 4, 5, 6, 7 and 8. In certain embodiments s2 of formula (IX-e) is 1. In certain embodiments s2 of formula (IX-e) is 2. In certain embodiments s2 of formula (IX-e) is 3. In certain embodiments s2 of formula (IX-e) is 4. In certain embodiments s2 of formula (IX-e) is 5. In certain embodiments s2 of formula (IX-e) is 6. In certain embodiments s2 of formula (IX-e) is 7. In certain embodiments s2 of formula (IX-e) is 8.

In certain embodiments the moiety -L$^1$-L$^2$- is of formula (IX-f)

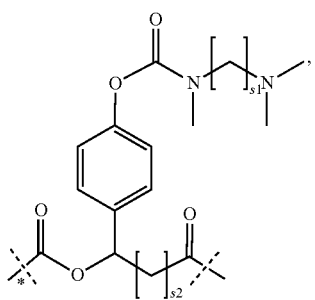

(IX-f)

wherein the dashed line marked with the asterisk indicates attachment to a nitrogen of -D;

the unmarked dashed line indicates attachment to —Z;

s1 is an integer selected from the group consisting of 1, 2, 3, 4, 5, 6, 7, 8, 9 and 10; and s2 is an integer selected from the group consisting of 0, 1, 2, 3, 4, 5, 6, 7, 8, 9, 10, 11, 12, 13, 14, 15, 16, 17, 18, 19 and 20.

In certain embodiments -L$^1$-L$^2$- is of formula (IX-f), wherein the dashed line marked with the asterisk indicates attachment to a nitrogen of an amine of a lysine side chain or the N-terminus of -D.

In certain embodiments -L$^1$-L$^2$- is of formula (IX-f), wherein the dashed line marked with the asterisk indicates attachment to a nitrogen of an amine of a lysine side chain of -D.

In certain embodiments -L$^1$-L$^2$- is of formula (IX-f), wherein the dashed line marked with the asterisk indicates attachment to the nitrogen of the amine of the N-terminus of -D.

Accordingly, the linkage between the moiety -L$^1$- and -D formed in the compound of formula (IX-f) is a carbamate.

In certain embodiments s1 of formula (IX-f) is an integer selected from the group consisting of 1, 2, 3, 4 and 5. In certain embodiments s1 of formula (IX-f) is 1. In certain embodiments s1 of formula (IX-f) is 2. In certain embodiments s1 of formula (IX-f) is 3. In certain embodiments s1 of formula (IX-f) is 4. In certain embodiments s1 of formula (IX-f) is 5.

In certain embodiments s2 of formula (IX-f) is an integer selected from the group consisting of 1, 2, 3, 4, 5, 6, 7, 8, 9, 10, 11 and 12. In certain embodiments s2 of formula (IX-f) is an integer selected from the group consisting of 1, 2, 3, 4, 5, 6, 7 and 8. In certain embodiments s2 of formula (IX-f) is 1. In certain embodiments s2 of formula (IX-f) is 2. In certain embodiments s2 of formula (IX-f) is 3. In certain embodiments s2 of formula (IX-f) is 4. In certain embodiments s2 of formula (IX-f) is 5. In certain embodiments s2 of formula (IX-f) is 6. In certain embodiments s2 of formula (IX-f) is 7. In certain embodiments s2 of formula (IX-f) is 8.

In certain embodiments s1 of formula (IX-f) is 3 and s2 of formula (IX-f) is 3.

In one embodiment the IL-2 conjugate is of formula (Ia). In certain embodiments x is 1. In certain embodiments x is 2. In certain embodiments x is 3. In certain embodiments x is 4.

In certain embodiments the IL-2 conjugate is of formula (Ib). In certain embodiments y is 2. In certain embodiments y is 3. In certain embodiments y is 4.

In certain embodiments the moiety -L$^1$-L$^2$-Z is of formula (XI)

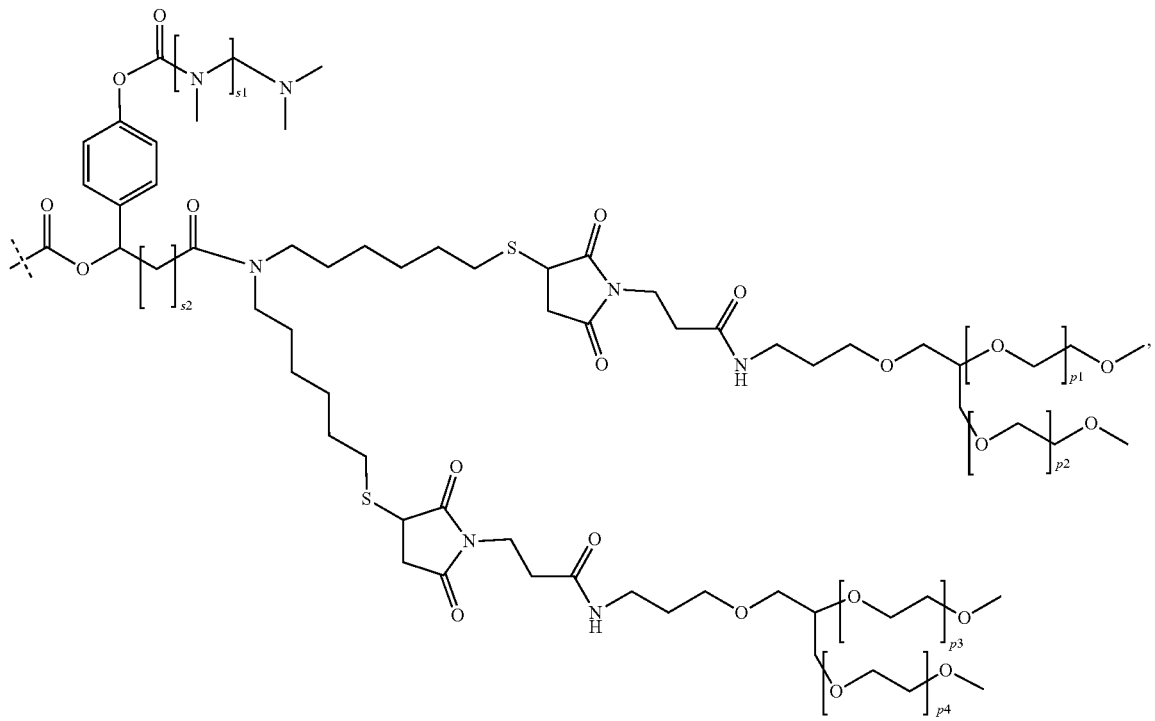

wherein the dashed line indicates attachment to a nitrogen of -D;
s1 is an integer selected from the group consisting of 1, 2, 3, 4, 5, 6, 7, 8, 9 and 10;
s2 is an integer selected from the group consisting of 0, 1, 2, 3, 4, 5, 6, 7, 8, 9, 10, 11, 12, 13, 14, 15, 16, 17, 18, 19 and 20; and
p1, p2, p3, p4 are independently of each other an integer ranging from 70 to 900.

In certain embodiments -L$^1$-L$^2$-Z is of formula (XI), wherein the dashed line indicates attachment to a nitrogen of an amine of a lysine side chain or the N-terminus of -D.

In certain embodiments -L$^1$-L$^2$-Z is of formula (XI), wherein the dashed line indicates attachment to a nitrogen of an amine of a lysine side chain of -D.

In certain embodiments -L$^1$-L$^2$-Z is of formula (XI), wherein the dashed line indicates attachment to the nitrogen of the amine of the N-terminus of -D.

Accordingly, the linkage between the moiety -L$^1$- and -D formed in the compound of formula (XI) is a carbamate.

In certain embodiments s1 of formula (XI) is an integer selected from the group consisting of 1, 2, 3, 4 and 5. In certain embodiments s1 of formula (XI) is 1. In certain embodiments s1 of formula (XI) is 2. In certain embodiments s1 of formula (XI) is 3. In certain embodiments s1 of formula (XI) is 4. In certain embodiments s1 of formula (XI) is 5.

In certain embodiments s2 of formula (XI) is an integer selected from the group consisting of 1, 2, 3, 4, 5, 6, 7, 8, 9, 10, 11 and 12. In certain embodiments s2 of formula (XI) is an integer selected from the group consisting of 1, 2, 3, 4, 5, 6, 7 and 8. In certain embodiments s2 of formula (XI) is 1. In certain embodiments s2 of formula (XI) is 2. In certain embodiments s2 of formula (XI) is 3. In certain embodiments s2 of formula (XI) is 4. In certain embodiments s2 of formula (XI) is 5. In certain embodiments s2 of formula (XI) is 6. In certain embodiments s2 of formula (XI) is 7. In certain embodiments s2 of formula (XI) is 8.

In certain embodiments s1 of formula (XI) is 3 and s2 of formula (XI) is 3.

In certain embodiments p1 of formula (XI) is an integer ranging from 115 to 680. In certain embodiments p1 of formula (XI) is an integer ranging from 115 to 560. In certain embodiments p1 of formula (XI) is an integer ranging from 185 to 450. In certain embodiments p1 of formula (XI) is an integer ranging from 220 to 240. In certain embodiments p1 of formula (XI) is about 115. In certain embodiments p1 of formula (XI) is about 160. In certain embodiments p1 of formula (XI) is about 225. In certain embodiments p1 of formula (XI) is about 270. In certain embodiments p1 of formula (XI) is about 340. In certain embodiments p1 of formula (XI) is about 450. In certain embodiments p1 of formula (XI) is about 560.

In certain embodiments p2 of formula (XI) is an integer ranging from 115 to 680. In certain embodiments p2 of formula (XI) is an integer ranging from 115 to 560. In certain embodiments p2 of formula (XI) is an integer ranging from 185 to 450. In certain embodiments p2 of formula (XI) is an integer ranging from 220 to 240. In certain embodiments p2 of formula (XI) is about 115. In certain embodiments p2 of formula (XI) is about 160. In certain embodiments p2 of formula (XI) is about 225. In certain embodiments p2 of formula (XI) is about 270. In certain embodiments p2 of formula (XI) is about 340. In certain embodiments p2 of formula (XI) is about 450. In certain embodiments p2 of formula (XI) is about 560.

In certain embodiments p3 of formula (XI) is an integer ranging from 115 to 680. In certain embodiments p3 of formula (XI) is an integer ranging from 115 to 560. In certain embodiments p3 of formula (XI) is an integer ranging from 185 to 450. In certain embodiments p3 of formula (XI) is an integer ranging from 220 to 240. In certain embodiments p3 of formula (XI) is about 115. In certain embodiments p3 of formula (XI) is about 160. In certain embodiments p3 of formula (XI) is about 225. In certain embodiments p3 of formula (XI) is about 270. In certain embodiments p3 of formula (XI) is about 340. In certain embodiments p3 of formula (XI) is about 450. In certain embodiments p3 of formula (XI) is about 560.

In certain embodiments p4 of formula (XI) is an integer ranging from 115 to 680. In certain embodiments p4 of formula (XI) is an integer ranging from 115 to 560. In certain embodiments p4 of formula (XI) is an integer ranging from 185 to 450. In certain embodiments p4 of formula (XI) is an integer ranging from 220 to 240. In certain embodiments p4 of formula (XI) is about 115. In certain embodiments p4 of formula (XI) is about 160. In certain embodiments p4 of formula (XI) is about 225. In certain embodiments p4 of formula (XI) is about 270. In certain embodiments p4 of formula (XI) is about 340. In certain embodiments p4 of formula (XI) is about 450. In certain embodiments p4 of formula (XI) is about 560.

In certain embodiments p1, p2, p3 of formula (XI) and p4 are identical. In certain embodiments p1, p2, p3 and p4 range from 220 to 240.

In certain embodiments the moiety -$L^1$-$L^2$-Z is of formula (XI-a)

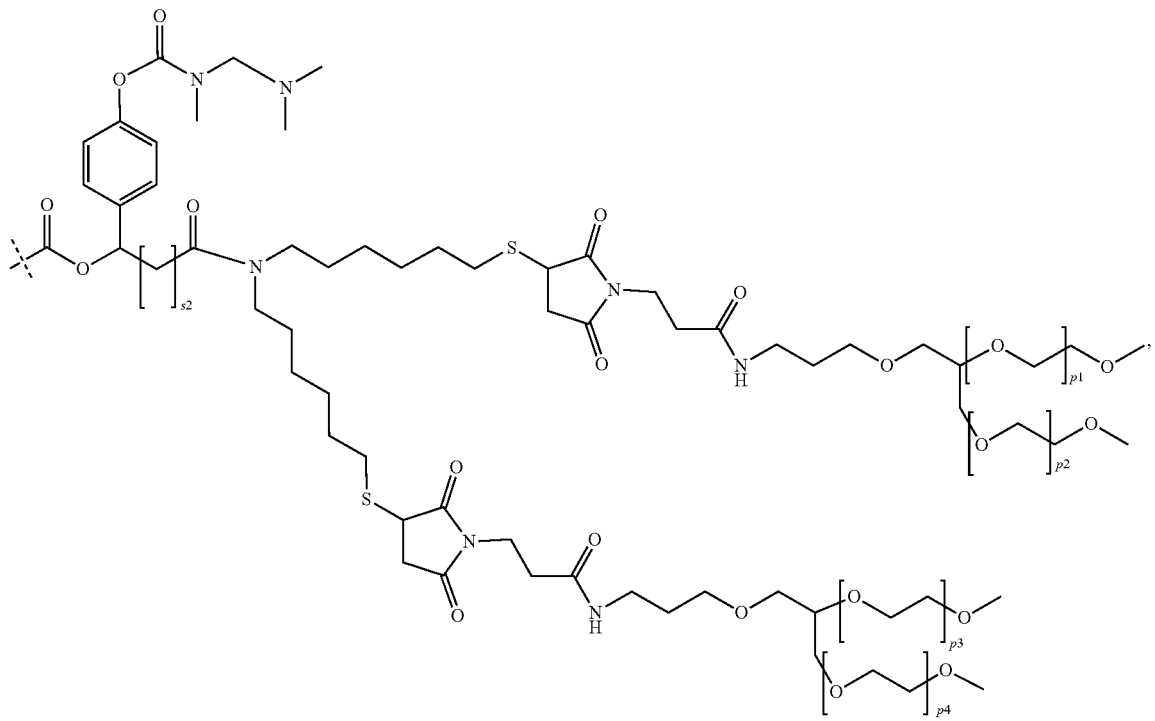

wherein the dashed line indicates attachment to a nitrogen of -D; and p1, p2, p3, p4 are independently of each other an integer ranging from 70 to 900.

In certain embodiments -$L^1$-$L^2$-Z is of formula (XI-a), wherein the dashed line indicates attachment to a nitrogen of an amine of a lysine side chain or the N-terminus of -D.

In certain embodiments -$L^1$-$L^2$-Z is of formula (XI-a), wherein the dashed line indicates attachment to a nitrogen of an amine of a lysine side chain of -D.

In certain embodiments -$L^1$-$L^2$-Z is of formula (XI-a), wherein the dashed line indicates attachment to the nitrogen of the amine of the N-terminus of -D.

Accordingly, the linkage between the moiety -$L^1$- and -D formed in the compound of formula (XI-a) is a carbamate.

In certain embodiments p1 of formula (XI-a) is an integer ranging from 115 to 680. In certain embodiments p1 of formula (XI-a) is an integer ranging from 115 to 560. In certain embodiments p1 of formula (XI-a) is an integer ranging from 185 to 450. In certain embodiments p1 of formula (XI-a) is an integer ranging from 220 to 240. In certain embodiments p1 of formula (XI-a) is about 115. In certain embodiments p1 of formula (XI-a) is about 160. In certain embodiments p1 of formula (XI-a) is about 225. In certain embodiments p1 of formula (XI-a) is about 270. In certain embodiments p1 of formula (XI-a) is about 340. In certain embodiments p1 of formula (XI-a) is about 450. In certain embodiments p1 of formula (XI-a) is about 560.

In certain embodiments p2 of formula (XI-a) is an integer ranging from 115 to 680. In certain embodiments p2 of formula (XI-a) is an integer ranging from 115 to 560. In certain embodiments p2 of formula (XI-a) is an integer ranging from 185 to 450. In certain embodiments p2 of formula (XI-a) is an integer ranging from 220 to 240. In certain embodiments p2 of formula (XI-a) is about 115. In certain embodiments p2 of formula (XI-a) is about 160. In certain embodiments p2 of formula (XI-a) is about 225. In certain embodiments p2 of formula (XI-a) is about 270. In certain embodiments p2 of formula (XI-a) is about 340. In certain embodiments p2 of formula (XI-a) is about 450. In certain embodiments p2 of formula (XI-a) is about 560.

In certain embodiments p3 of formula (XI-a) is an integer ranging from 115 to 680. In certain embodiments p3 of formula (XI-a) is an integer ranging from 115 to 560. In certain embodiments p3 of formula (XI-a) is an integer ranging from 185 to 450. In certain embodiments p3 of formula (XI-a) is an integer ranging from 220 to 240. In certain embodiments p3 of formula (XI-a) is about 115. In certain embodiments p3 of formula (XI-a) is about 160. In certain embodiments p3 of formula (XI-a) is about 225. In certain embodiments p3 of formula (XI-a) is about 270. In certain embodiments p3 of formula (XI-a) is about 340. In certain embodiments p3 of formula (XI-a) is about 450. In certain embodiments p3 of formula (XI-a) is about 560.

In certain embodiments p4 of formula (XI-a) is an integer ranging from 115 to 680. In certain embodiments p4 of formula (XI-a) is an integer ranging from 115 to 560. In certain embodiments p4 of formula (XI-a) is an integer ranging from 185 to 450. In certain embodiments p4 of formula (XI-a) is an integer ranging from 220 to 240. In certain embodiments p4 of formula (XI-a) is about 115. In certain embodiments p4 of formula (XI-a) is about 160. In certain embodiments p4 of formula (XI-a) is about 225. In certain embodiments p4 of formula (XI-a) is about 270. In certain embodiments p4 of formula (XI-a) is about 340. In certain embodiments p4 of formula (XI-a) is about 450. In certain embodiments p4 of formula (XI-a) is about 560.

In certain embodiments p1, p2, p3 of formula (XI-a) and p4 are identical. In certain embodiments p1, p2, p3 and p4 range from 220 to 240.

In certain embodiments the conjugate of the present invention comprises an IL-2 moiety of SEQ ID NO:14, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:14, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:14, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:14, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:14, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:14, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:14, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:14, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:14, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:14, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:13, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:13, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:13, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:13, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:13, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:13, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:13, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and (ii) at least one conjugated comprising an IL-2 moiety of SEQ ID NO:13, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises (i) at least one conjugate comprising an IL-2 moiety of SEQ ID NO:13, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and (ii) at least one conjugated comprising an IL-2 moiety of SEQ ID NO:13, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:22, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:22, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:22, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:22, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:22, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:22, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises (i) at least one conjugate comprising an IL-2 moiety of SEQ ID NO:22, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and (ii) at least one conjugated comprising an IL-2 moiety of SEQ ID NO:22, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:22, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:22, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:23, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:23, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:23, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:23, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:23, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:23, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:23, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:23, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:23, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:23, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:24, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:24, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:24, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:24, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:24, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:24, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:24, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:24, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:24, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and (ii) at least one conjugated comprising an IL-2 moiety of SEQ ID NO:24, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:25, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:25, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:25, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:25, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:25, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:25, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:25, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:25, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:25, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:25, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:26, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:26, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:26, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:26, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:26, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:26, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:26, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:26, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:26, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:26, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:27, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:27, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:27, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:27, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:27, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:27, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:27, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:27, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:27, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:27, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:28, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:28, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:28, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:28, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:28, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:28, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
   (i) at least one conjugate comprising an IL-2 moiety of SEQ ID NO:28, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
   (ii) at least one conjugated comprising an IL-2 moiety of SEQ ID NO:28, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
   (i) at least one conjugate comprising an IL-2 moiety of SEQ ID NO:28, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
   (ii) at least one conjugated comprising an IL-2 moiety of SEQ ID NO:28, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:29, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:29, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:29, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:29, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:29, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:29, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises (i) at least one conjugate comprising an IL-2 moiety of SEQ ID NO:29, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and (ii) at least one conjugated comprising an IL-2 moiety of SEQ ID NO:29, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises (i) at least one conjugate comprising an IL-2 moiety of SEQ ID NO:29, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and (ii) at least one conjugated comprising an IL-2 moiety of SEQ ID NO:29, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:30, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:30, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:30, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:30, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:30, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:30, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:30, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:30, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:30, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:30, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:31, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:31, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:31, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:31, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:31, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:31, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:31, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:31, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:31, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:31, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:32, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:32, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:32, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:32, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:32, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:32, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:32, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:32, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:32, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:32, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:33, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:33, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:33, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:33, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:33, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:33, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:33, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:33, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:33, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:33, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:34, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:34, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:34, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:34, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:34, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:34, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
(i) at least one conjugate comprising an IL-2 moiety of SEQ ID NO:34, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
(ii) at least one conjugated comprising an IL-2 moiety of SEQ ID NO:34, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:34, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:34, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:35, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:35, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:35, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:35, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:35, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:35, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:35, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:35, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:35, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:35, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:36, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:36, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:36, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:36, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:36, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:36, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:36, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:36, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:36, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:36, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:37, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:37, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:37, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:37, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:37, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:37, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:37, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:37, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:37, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:37, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:38, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:38, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:38, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:38, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:38, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:38, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:38, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:38, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:38, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:38, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the conjugate of the present invention comprises an IL-2 moiety of SEQ ID NO:39, to which a moiety $M_{mod}$ of formula (A-1a) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:39, to which a moiety $M_{mod}$ of formula (A-1a) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:39, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:39, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:39, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the conjugate of the present invention comprises an IL-2 moiety of SEQ ID NO:39, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240. In certain embodiments b3 is about 112. In certain embodiments the moiety of formula (XI-a) is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:39, to which a moiety $M_{mod}$ of formula (A-1d) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:39, to which a moiety $M_{mod}$ of formula (A-1e) is conjugated to the sulfur of the cysteine at position 38, wherein b1 is 2, b2 is 2 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

In certain embodiments the IL-2 conjugate is present as a mixture, wherein the mixture comprises
  (i) at least one conjugate comprising an IL-2 moiety of SEQ ID NO:39, to which a moiety $M_{mod}$ of formula (A-1d) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240; and
  (ii) at least one conjugated comprising an IL-2 moiety of SEQ ID NO:39, to which a moiety $M_{mod}$ of formula (A-1e) is conjugated to the sulfur of the cysteine at position 38, wherein b1 is 2, b2 is 3 and b3 is an integer ranging from about 100 to 125, and to which IL-2 moiety a moiety of formula (XI-a) is conjugated to the nitrogen of a primary amine of the N-terminus or a lysine side chain residue of the IL-2 moiety and p1, p2, p3 and p4 range from 220 to 240.

In certain embodiments p1, p2, p3 and p4 in each conjugate of the mixture is about 112. In certain embodiments the moiety of formula (XI-a) of each conjugate of the mixture is conjugated to the nitrogen of a primary amine of a lysine side chain residue of the IL-2 moiety.

Another aspect of the present invention is a pharmaceutical composition comprising at least one IL-2 protein of formula (I) or at least one IL-2 conjugate comprising at least one IL-2 protein of formula (I) as described herein and at least one excipient. In certain embodiments such the pharmaceutical composition has a pH ranging from and including pH 3 to pH 8.

In certain embodiments such pharmaceutical composition is a liquid formulation. In certain embodiments the pharmaceutical composition is a dry formulation.

Such liquid or dry pharmaceutical composition comprises at least one excipient. Excipients used in parenteral formulations may be categorized as, for example, buffering agents, isotonicity modifiers, preservatives, stabilizers, anti-adsorption agents, oxidation protection agents, viscosifiers/viscosity enhancing agents, or other auxiliary agents. However, in some cases, one excipient may have dual or triple functions. In certain embodiments the at least one excipient comprised in the pharmaceutical composition of the present invention is selected from the group consisting of
  (i) Buffering agents: physiologically tolerated buffers to maintain pH in a desired range, such as sodium phosphate, bicarbonate, succinate, histidine, citrate and acetate, sulphate, nitrate, chloride, pyruvate; antacids such as $Mg(OH)_2$ or $ZnCO_3$ may be also used;
  (ii) Isotonicity modifiers: to minimize pain that can result from cell damage due to osmotic pressure differences at the injection depot; glycerin and sodium chloride are examples; effective concentrations can be determined by osmometry using an assumed osmolality of 285-315 mOsmol/kg for serum;

(iii) Preservatives and/or antimicrobials: multidose parenteral formulations require the addition of preservatives at a sufficient concentration to minimize risk of patients becoming infected upon injection and corresponding regulatory requirements have been established; typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride;

(iv) Stabilizers: Stabilisation is achieved by strengthening of the protein-stabilising forces, by destabilisation of the denatured state, or by direct binding of excipients to the protein; stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives; in addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to the inner surface of the formulation's container; e.g., poloxamer (Pluronic F-68), PEG dodecyl ether (Brij 35), polysorbate 20 and 80, dextran, polyethylene glycol, PEG-polyhistidine, BSA and HSA and gelatins; chosen concentration and type of excipient depends on the effect to be avoided but typically a monolayer of surfactant is formed at the interface just above the CMC value;

(vi) Oxidation protection agents: antioxidants such as ascorbic acid, ectoine, methionine, glutathione, monothioglycerol, morin, polyethylenimine (PEI), propyl gallate, and vitamin E; chelating agents such as citric acid, EDTA, hexaphosphate, and thioglycolic acid may also be used;

(vii) Viscosifiers or viscosity enhancers: retard settling of the particles in the vial and syringe and are used in order to facilitate mixing and resuspension of the particles and to make the suspension easier to inject (i.e., low force on the syringe plunger); suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly (glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone; such block copolymers as well as the abovementioned poloxamers may exhibit reverse thermal gelation behavior (fluid state at room temperature to facilitate administration and gel state above sol-gel transition temperature at body temperature after injection);

(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue; a spreading agent such as but not limited to hyaluronidase temporarily decreases the viscosity of the extracellular matrix and promotes diffusion of injected drugs; and (ix) Other auxiliary agents: such as wetting agents, viscosity modifiers, antibiotics, hyaluronidase; acids and bases such as hydrochloric acid and sodium hydroxide are auxiliary agents necessary for pH adjustment during manufacture.

Another aspect relates to the IL-2 protein of formula (I), the IL-2 conjugate comprising at least one IL-2 protein of formula (I) or the pharmaceutical composition comprising at least one IL-2 protein of formula (I) or at least one IL-2 conjugate comprising at least one IL-2 protein of formula (I) for use as a medicament.

Another aspect relates to the IL-2 protein of formula (I), the IL-2 conjugate comprising at least one IL-2 protein of formula (I) or the pharmaceutical composition at least one IL-2 protein of formula (I) or at least one IL-2 conjugate comprising at least one IL-2 protein of formula (I) for use in the treatment of a disease which can be treated with IL-2.

Another aspect relates to the IL-2 protein of formula (I), the IL-2 conjugate comprising at least one IL-2 protein of formula (I) or the pharmaceutical composition at least one IL-2 protein of formula (I) or at least one IL-2 conjugate comprising at least one IL-2 protein of formula (I) for the manufacture of a medicament for treating a disease which can be treated with IL-2.

Another aspect relates to a method of treating, controlling, delaying or preventing in a mammalian patient, preferably a human patient, in need of the treatment of one or more diseases which can be treated with IL-2, comprising the step of administering to said patient in need thereof a therapeutically effective amount of the IL-2 protein of formula (I), the IL-2 conjugate comprising at least one IL-2 protein of formula (I) or the pharmaceutical composition at least one IL-2 protein of formula (I) or at least one IL-2 conjugate comprising at least one IL-2 protein of formula (I).

In certain embodiments the disease which can be treated with IL-2 is cancer. Such cancer may be selected from the group consisting of liquid tumors, solid tumors and lymphomas.

A liquid lymphoma may be a leukemia or myeloid neoplasm, such as chronic lymphocytic leukemia (CLL), chronic myelogenous leukemia (CML), hairy cell leukemia, lymphoblastic leukemia, myeloid leukemia, plasma cell leukemia, acute lymphoblastic leukemia (ALL), acute myeloid leukemia (AML), myelodysplastic syndrome (MDS), myeloproliferative neoplasm (MPN), post-MPN AML, post-MDS AML, del(5q)-associated high risk MDS or AML, blast-phase chronic myelogenous leukemia, multiple myeloma, myelodysplastic syndromes, chronic myeloproliferative disorders, plasma cell neoplasm and Waldenstrom's macroglobulinemia.

A solid tumor or lymphoma may be selected from the group consisting of lip and oral cavity cancer, oral cancer, liver cancer/hepatocellular cancer, primary liver cancer, lung cancer, lymphoma, malignant mesothelioma, malignant thymoma, skin cancer, intraocular melanoma, metastasic squamous neck cancer with occult primary, childhood multiple endocrine neoplasia syndrome, mycosis fungoides, nasal cavity and paranasal sinus cancer, nasopharyngeal cancer, neuroblastoma, oropharyngeal cancer, ovarian cancer, pancreatic cancer, parathyroid cancer, pheochromocytoma, pituitary tumor, adrenocortical carcinoma, AIDS-related malignancies, anal cancer, bile duct cancer, bladder cancer, brain and nervous system cancer, breast cancer, bronchial adenoma/carcinoid, gastrointestinal carcinoid tumor, carcinoma, colorectal cancer, endometrial cancer, esophageal cancer, extracranial germ cell tumor, extragonadal germ cell tumor, extrahepatic bile duct cancer, gallbladder cancer, gastric (stomach) cancer, gestational trophoblastic tumor, head and neck cancer, hypopharyngeal cancer, islet cell carcinoma (endocrine pancreas), kidney cancer/renal cell cancer, laryngeal cancer, pleuropulmonary blastoma, prostate cancer, transitional cell cancer of the renal pelvis and ureter, retinoblastoma, salivary gland cancer, sarcoma, Sezary syndrome, small intestine cancer, genitourinary cancer, malignant thymoma, thyroid cancer, Wilms' tumor, cholangiocarcinoma, and also their related earlier stages of aberrant cell growth such as dysplasias, adenomas, and carcinoma in situs.

In certain embodiments the cancer is a liver cancer/hepatocellular cancer. In certain embodiments the cancer is a lung cancer. In certain embodiments the cancer is a lymphoma. In certain embodiments the cancer is a malignant thymoma. In certain embodiments the cancer is a skin cancer. In certain embodiments the cancer is a is a metastasic squamous neck cancer with occult primary. In certain embodiments the cancer is a neuroblastoma. In certain embodiments the cancer is an ovarian cancer. In certain embodiments the cancer is a pancreatic cancer. In certain embodiments the cancer is a bile duct cancer. In certain embodiments the cancer is a bladder cancer. In certain embodiments the cancer is a brain and nervous system cancer. In certain embodiments the cancer is a breast cancer. In certain embodiments the cancer is a gastrointestinal carcinoid tumor. In certain embodiments the cancer is a carcinoma. In certain embodiments the cancer is a colorectal cancer. In certain embodiments the cancer is an extrahepatic bile duct cancer. In certain embodiments the cancer is a gallbladder cancer. In certain embodiments the cancer is a gastric (stomach) cancer. In certain embodiments the cancer is a head and neck cancer. In certain embodiments the cancer is a kidney cancer/renal cell cancer. In certain embodiments the cancer is a prostate cancer. In certain embodiments the cancer is a sarcoma. In certain embodiments the cancer is a small intestine cancer. In certain embodiments the cancer is a genitourinary cancer.

Examples for lung cancer are non-small cell lung cancer and small cell lung cancer. In certain embodiments the cancer is a non-small cell lung cancer. In certain embodiment the cancer is a small cell lung cancer.

Example for lymphomas are AIDS-related lymphoma, primary central nervous system lymphoma, T-cell lymphoma, cutaneous T-cell lymphoma, Hodgkin's lymphoma, Hodgkin's lymphoma during pregnancy, non-Hodgkin's lymphoma, non-Hodgkin's lymphoma during pregnancy and angioimmunoblastic lymphoma.

Examples for skin cancer are melanoma and Merkel cell carcinoma. In certain embodiments the cancer is a skin cancer. In certain embodiments the cancer is a Merkel cell carcinoma.

An ovarian cancer may for example be an epithelial cancer, a germ cell tumor or a low malignant potential tumor. In certain embodiments the cancer is an epithelial cancer. In certain embodiments the cancer is a germ cell tumor. In certain embodiments the cancer is a low malignant potential tumor.

A pancreatic cancer may for example be an exocrine tumor/adenocarcinoma, pancreatic endocrine tumor (PET) or neuroendocrine tumor (NET). In certain embodiments the cancer is an exocrine tumor/adenocarcinoma. In certain embodiments the tumor is a pancreatic endocrine tumor. In certain embodiments the cancer is a neuroendocrine tumor.

Examples for brain and nervous system cancer are medulloblastoma, such as a childhood medulloblastoma, astrocytoma, ependymoma, neuroectodermal tumors, schwannoma, meningioma, pituitary adenoma and glioma. In certain embodiment the cancer is a medullablastoma. In certain embodiments the cancer is a childhood medullablastoma. In certain embodiments the cancer is an astrocytoma. In certain embodiments the cancer is an ependymoma. In certain embodiments the cancer is a neuroectodermal tumor. In certain embodiments the tumor is a schwannoma. In certain embodiments the cancer is a meningioma. In certain embodiments the cancer is a pituitary adenoma. In certain embodiments the cancer is a glioma.

An astrocytoma may be selected from the group consisting of giant cell glioblastoma, glioblastoma, secondary glioblastoma, primary adult glioblastoma, primary pediatric glioblastoma, oligodendroglial tumor, oligodendroglioma, anaplastic oligodendroglioma, oligoastrocytic tumor, oligoastrocytoma, anaplastic oligodendroglioma, oligoastrocytic tumor, oligoastrocytoma, anaplastic oligoastrocytoma, anaplastic astrocytoma, pilocytic astrocytoma, subependymal giant-cell astrocytoma, diffuse astrocytoma, pleomorphic xanthoastrocytoma and cerebellar astrocytoma.

Examples for a neuroectodermal tumor are a pineal primitive neuroectodermal tumor and a supratentorial primitive neuroectodermal tumor.

An ependymoma may be selected from the group consisting of subependymoma, ependymoma, myxopapillary ependymoma and anaplastic ependymoma.

A meningioma may be an atypical meningioma or an anaplastic meningioma.

A glioma may be selected from the group consisting of glioblastoma multiforme, paraganglioma, suprantentorial primordial neuroectodermal tumor (sPNET), brain stem glioma, childhood brain stem glioma, hypothalamic and visual pathway glioma, childhood hypothalamic and visual pathway glioma and malignant glioma.

Examples for breast cancer are breast cancer during pregnancy, triple negative breast cancer, ductal carcinoma in situ (DCIS), invasive ductal carcinoma (IDC), tubular carcinoma of the breast, medullary carcinoma of the breast, mucinous carcinoma of the breast, papillary carcinoma of the breast, cribriform carcinoma of the breast, invasive lobular carcinoma (ILC), inflammatory breast cancer, lobular carcinoma in situ (LCIS), male breast cancer, Paget's disease of the nipple, phyllodes tumors of the breast and metastasic breast cancer. In certain embodiments the cancer is a breast cancer during pregnancy. In certain embodiments the cancer is a triple negative breast cancer. In certain embodiments the cancer is a ductal carcinoma in situ. In certain embodiments the cancer is an invasive ductal carcinoma. In certain embodiments the cancer is a tubular carcinoma of the breast. In certain embodiments the cancer is a medullary carcinoma of the breast. In certain embodiments the cancer is a mucinous carcinoma of the breast. In certain embodiments the cancer is a papillary carcinoma of the breast. In certain embodiments the cancer is a cribriform carcinoma of the breast. In certain embodiments the cancer is an invasive lobular carcinoma. In certain embodiments the cancer is an inflammatory breast cancer. In certain embodiments the cancer is a lobular carcinoma in situ. In certain embodiments the cancer is a male breast cancer. In certain embodiments the cancer is a Paget's disease of the nipple. In certain embodiments the cancer is a phyllodes tumor of the breast. In certain embodiments the cancer is a metastatic breast cancer.

Examples for a carcinoma are neuroendocrine carcinoma, adrenocortical carcinoma and Islet cell carcinoma. In certain embodiments the cancer is a neuroendocrine carcinoma. In certain embodiments the cancer is an adrenocortical carcinoma. In certain embodiments the cancer is an Islet cell carcinoma.

Examples for a colorectal cancer are colon cancer and rectal cancer. In certain embodiments the cancer is a colon cancer. In certain embodiments the cancer is a rectal cancer.

A sarcoma may be selected from the group consisting of Kaposi's sarcoma, osteosarcoma/malignant fibrous histiocytoma of bone, soft tissue sarcoma, Ewing's family of tumors/sarcomas, rhabdomyosarcoma, clear cell sarcoma of tendon sheaths, central chondrosarcoma, central and periosteal chondroma, fibrosarcoma and uterine sarcoma. In certain embodiments the cancer may be a Kaposi's sarcoma. In certain embodiments the cancer may be an osteosarcoma/malignant fibrous histiocytoma of bone. In certain embodiments the cancer may be a soft tissue sarcoma. In certain embodiments the cancer may be an Ewing's family of tumors/sarcomas. In certain embodiments the cancer may be a rhabdomyosarcoma. In certain embodiments the cancer may be a clear cell sarcoma of tendon sheaths. In certain embodiments the cancer may be a central chondrosarcoma. In certain embodiments the cancer may be a central and periosteal chondroma. In certain embodiments the cancer may be a fibrosarcoma. In certain embodiments the cancer may be a uterine sarcoma.

Examples for a genitourinary cancer are testicular cancer, urethral cancer, vaginal cancer, cervical cancer, penile cancer and vulvar cancer. In certain embodiments the cancer may be a testicular cancer. In certain embodiments the cancer may be a urethral cancer. In certain embodiments the cancer may be a vaginal cancer. In certain embodiments the cancer may be a cervical cancer. In certain embodiments the cancer may be a penile cancer. In certain embodiments the cancer may be a vaginal cancer.

It was surprisingly found that in cynomolgus monkeys the IL-2 of the present invention leads to a robust expansion of γδ T cells over baseline noted at doses with minimal eosinophil expansion which were well tolerated.

In certain embodiments, the IL-2 protein of formula (I), the IL-2 conjugate or the pharmaceutical composition of the present invention resulted in an expansion of γδ T cells of at least 100-fold over baseline. In certain embodiments, the IL-2 protein of formula (I), the IL-2 conjugate or the pharmaceutical composition of the present invention resulted in an expansion of γδ T cells of at least 150-fold over baseline. In certain embodiments, the IL-2 protein of formula (I), the IL-2 conjugate or the pharmaceutical composition of the present invention resulted in an expansion of γδ T cells of at least 200-fold over baseline. In certain embodiments, the IL-2 protein of formula (I), the IL-2 conjugate or the pharmaceutical composition of the present invention resulted in an expansion of γδ T cells of at least 300-fold over baseline. In certain embodiments, the IL-2 protein of formula (I), the IL-2 conjugate or the pharmaceutical composition of the present invention resulted in an expansion of γδ T cells of at least 350-fold over baseline.

In certain embodiments, the IL-2 protein of formula (I), the IL-2 conjugate or the pharmaceutical composition of the present invention resulted in an expansion of γ9δ2 T cells of at least 100-fold over baseline. In certain embodiments, the IL-2 protein of formula (I), the IL-2 conjugate or the pharmaceutical composition of the present invention resulted in an expansion of γ9δ2 T cells of at least 150-fold over baseline. In certain embodiments, the IL-2 protein of formula (I), the IL-2 conjugate or the pharmaceutical composition of the present invention resulted in an expansion of γ9δ2 T cells of at least 200-fold over baseline. In certain embodiments, the IL-2 protein of formula (I), the IL-2 conjugate or the pharmaceutical composition of the present invention resulted in an expansion of γ9δ2 T cells of at least 300-fold over baseline. In certain embodiments, the IL-2 protein of formula (I), the IL-2 conjugate or the pharmaceutical composition of the present invention resulted in an expansion of γ9δ2 T cells of at least 350-fold over baseline.

In certain embodiments the treatment with the IL-2 protein of formula (I), the IL-2 conjugate or the pharmaceutical composition of the present invention may be initiated prior to, concomitant with, or following surgical removal of a tumor or radiation therapy. In addition, such treatment may optionally be combined with at least one other cancer therapeutic, such as systemic immunotherapy or local intra-tumoral immunotherapy or intra-lymph node immunotherapy. Examples for the at least one cancer therapeutic, such as systemic immunotherapy, are as provided elsewhere herein for the one or more additional drug that may in certain embodiments be present in the pharmaceutical composition of the present invention. In certain embodiments the IL-2 protein of formula (I), the IL-2 conjugate or the pharmaceutical composition of the present invention is administered systemically prior to, concomitant with, or following combination with at least one systemic immunotherapy or local intra-tumoral immunotherapy or intra-lymph node immunotherapy, prior to radiation therapy or surgical removal of the injected tumor. In certain embodiments the IL-2 protein of formula (I), the IL-2 conjugate or the pharmaceutical composition of the present invention is administered intratumorally prior to, concomitant with, or following combination with at least one systemic immunotherapy or local intra-tumoral immunotherapy or intra-lymph node immunotherapy, prior to radiation therapy or surgical removal of the injected tumor. In certain embodiments the conjugate, its pharmacologically acceptable salt or the pharmaceutical composition of the present invention is administered intratumorally prior to, concomitant with, or following combination with at least one systemic immunotherapy or local intra-tumoral immunotherapy or intra-lymph node immunotherapy, following radiation therapy or surgical removal of a tumor. In certain embodiments the IL-2 protein of formula (I), the IL-2 conjugate or the pharmaceutical composition of the present invention is administered into tumor draining lymph nodes prior to, concomitant with, or following surgical removal of a tumor or radiation therapy. In certain embodiments the IL-2 protein of formula (I), the IL-2 conjugate or the pharmaceutical composition of the present invention is administered into tumor draining lymph nodes prior to, concomitant with, or following combination with at least one systemic immunotherapy or local intra-tumoral immunotherapy or intra-lymph node immunotherapy, and prior to, concomitant with, or following surgical removal of a tumor or radiation therapy. In certain embodiments the IL-2 protein of formula (I), the IL-2 conjugate or the pharmaceutical composition of the present invention is administered intratumorally into metastatic tumors that may arise prior to or following surgical removal or radiation therapy of primary tumor. In certain embodiments the IL-2 protein of formula (I), the IL-2 conjugate or the pharmaceutical composition of the present invention is administered intratumorally into metastatic tumors that may arise prior to, concomitant with, or following combination with at least one systemic immunotherapy or local intra-tumoral immunotherapy or intra-lymph node immunotherapy, and prior to, concomitant with, or following surgical removal or radiation therapy of primary tumor. In certain embodiments at least one systemic therapy is administered prior to surgical removal of a tumor or radiation therapy, followed by systemic administration or intra-tumoral administration or intra-lymph node administration of the IL-2 protein of formula (I), the IL-2 conjugate or the pharmaceutical composition of the present invention. In certain embodiments intra-tumoral administration of the IL-2 protein of formula (I), the IL-2 conjugate or the pharmaceutical composition of the present invention is administered first, followed by subsequent treatment in combination with at least one systemic therapy or local intra-tumoral immunotherapy or intra-lymph node immunotherapy. In certain embodiments at least one systemic therapy is administered prior to surgical removal of a tumor, followed by administration the IL-2 protein of formula (I), the IL-2 conjugate or the pharmaceutical composition of the present invention systemically or to draining lymph nodes or to the tumor bed following surgery or by intra-tumoral administration in tumor not removed by surgery.

In certain embodiments the IL-2 protein of formula (I), the IL-2 conjugate or the pharmaceutical composition of the present invention elicits epitope spreading. Epitope spreading is advantageous because it may lead to a stronger or more comprehensive immune response. In particular, the generation of epitope spreading and expansion of newly activated T cells to new epitopes with diverse specificities may contribute to important clinical benefits. For example, metastatic lesions may share some epitopes with an index tumor, but still be genetically distinct from the index tumor, and thus epitope spreading may help eradicate distant metastases based on an initial immune response shared between the index tumor and the metastatic tumor which then spreads to unique epitopes in the distant metastases and helps the immune system clear those metastases. Epitope spreading has been associated with increase efficiency if patients with cancer (Clin Cancer Res 2020; 26:4442-7).

In certain embodiments the IL-2 protein of formula (I), the IL-2 conjugate or the pharmaceutical composition of the present invention is administered to the patient prior to, simultaneously with, or after administration of one or more additional drug, which one or more additional drug is in certain embodiments selected from the group consisting of pattern recognition receptor agonists (PRRA), cytotoxic/chemotherapeutic agents, immune checkpoint inhibitors or antagonists, immune checkpoint agonists, immune activating receptor agonists, multi-specific drugs, antibody-drug conjugates (ADC), antibody-adjuvant conjugates (AAC), radionuclides or targeted radionuclide therapeutics, DNA damage repair inhibitors, tumor metabolism inhibitors, pattern recognition receptor agonists, protein kinase inhibitors, chemokine and chemoattractant receptor agonists, chemokine or chemokine receptor antagonists, cytokine receptor agonists, death receptor agonists, CD47 or SIRPα antagonists, oncolytic drugs, signal converter proteins, epigenetic modifiers, tumor peptides or tumor vaccines, heat shock protein (HSP) inhibitors, proteolytic enzymes, ubiquitin and proteasome inhibitors, adhesion molecule antagonists, hormones including hormone peptides and synthetic hormones, and adoptive cellular therapies such as Tumor Infiltrating Lymphocyte (TIL) therapy, Chimeric Antigen Receptor (CAR) therapy, T cell therapy, Natural Killer (NK) cell therapy, CAR-T therapy, CAR-NK therapy, CAR-γδ therapy, CAR-Macrophage therapy, or any other cellular therapy with a genetically modified or genetically unmodified immune cell type.

Such one or more additional drug may either be in its free or unmodified form or may be in the form of a sustained-release compound, i.e. in a form from which the drug is released with a certain half-life, such as with a half-life ranging from 6 hours to six months.

The PRRA may be selected from the group consisting of Toll-like receptor (TLR) agonists, NOD-like receptor agonists (NLRs), RIG-I-like receptor agonists, cytosolic DNA sensor agonists, STING agonists, and aryl hydrocarbon receptor agonists (AhR).

In certain embodiments the PRRA is a Toll-like receptor agonist, such as a Toll-like receptor agonists selected from the group consisting of agonists of TLR1/2, such as peptidoglycans, lipoproteins, Pam3CSK4, Amplivant, SLP-AM-PLIVANT, HESPECTA, ISA101 and ISA201; agonists of TLR2, such as LAM-MS, LPS-PG, LTA-BS, LTA-SA, PGN-BS, PGN-EB, PGN-EK, PGN-SA, CL429, FSL-1, Pam2CSK4, Pam3CSK4, zymosan, CBLB612, SV-283, ISA204, SMP105, heat killed *Listeria monocytogenes*; agonists of TLR3, such as poly(A:U), poly(I:C) (poly-ICLC), rintatolimod, apoxxim, IPH3102, poly-ICR, PRV300, RGCL2, RGIC.1, Riboxxim (RGC100, RGIC100), Riboxxol (RGIC50)), synthetic natural or modified double stranded RNA, synthetic natural or modified nucleic acid oligomers and Riboxxon; agonists of TLR4, such as lipopolysaccharides (LPS), neoceptin-3, glucopyranosyl lipid adjuvant (GLA), GLA-SE, G100, GLA-AF, clinical center reference endotoxin (CCRE), monophosphoryl lipid A, grass MATA MPL, PEPA10, ONT-10 (PET-Lipid A, oncothyreon), G-305, ALD046, CRX527, CRX675 (RC527, RC590), GSK1795091, OM197MPAC, OM294DP, tumor targeted TLR4 agonists, and SAR439794; agonists of TLR2/4, such as lipid A, OM174 and PGN007; agonists of TLR5, such as flagellin, entolimod, mobilan, protectan CBLB501; agonists of TLR6/2, such as diacylated lipoproteins, diacylated lipopeptides, FSL-1, MALP-2 and CBLB613; agonists of TLR7, such as CL264, CL307, imiquimod (R837), TMX- 101, TMX-201, TMX-202, TMX302, gardiquimod, S-27609, 851, UC-IV150, 852A (3M-001, PF-04878691), loxoribine, polyuridylic acid, GSK2245035, GS-9620, RO6864018 (ANA773, RG7795), RO7020531, isatoribine, AN0331, ANA245, ANA971, ANA975, DSP0509, DSP3025 (AZD8848), GS986, MBS2, MBS5, RG7863 (RO6870868), sotirimod, SZU101, synthetic natural or modified single stranded RNA, synthetic nucleic acids, synthetic natural or modified nucleic acid oligomers, tumor targeted TLR7 agonists, and TQA3334; agonists of TLR8, such as ssPolyUridine, ssRNA40, TL8-506, XG-1-236, VTX-2337 (motolimod), VTX-1463, VTX378, VTX763, DN1508052, SBT6050, synthetic natural or modified single stranded RNA, synthetic nucleic acids, synthetic natural or modified nucleic acid oligomers, tumor targeted TLR8 agonists, and GS9688; agonists of TLR7/8, such as TransCon™ TLR7/8 agonist, CL075, CL097, poly(dT), resiquimod (R-848, VML600, S28463), MEDI9197 (3M-052), NKTR262, DV1001, IMO4200, IPH3201, synthetic natural or modified single stranded RNA, synthetic nucleic acids, synthetic nucleic acid oligomers, BDC-1001, other tumor targeted TLR7/8 agonists and VTX1463; agonists of TLR9, such as CpG DNA, CpG ODN, lefitolimod (MGN1703), SD-101, QbG10, CYT003, CYT003-QbG10, DUK-CpG-001, CpG-7909 (PF-3512676), GNKG168, EMD 1201081, IMO-2125, IMO-2055, CpG10104, AZD1419, AST008, IMO2134, MGN1706, IRS 954, 1018 ISS, actilon (CPG10101), ATP00001, AVE0675, AVE7279, CMP001, DIMS0001, DIMS9022, DIMS9054, DIMS9059, DV230, DV281, EnanDIM, heplisav (V270), kappaproct (DIMS0150), NJP834, NPI503, SAR21609, synthetic natural or modified nucleic acid oligomers and tolamba; and agonists of TLR7/9, such as DV1179.

In certain embodiments the one or more additional drug is an agonist of TLR1/2. In certain embodiments the one or more additional drug is an agonist of TLR2. In certain embodiments the one or more additional drug is an agonist of TLR3. In certain embodiments the one or more additional drug is an agonist of TLR4. In certain embodiments the one or more additional drug is an agonist of TLR2/4. In certain embodiments the one or more additional drug is an agonist of TLR5. In certain embodiment the one or more additional drug is an agonist of TLR6/2. In certain embodiments the one or more additional drug is an agonist of TLR7. In certain embodiments the one or more additional drug is an agonist of TLR8. In certain embodiments the one or more additional drug is an agonist of TLR7/8. In certain embodiments the one or more additional drug is an agonist of TLR9.

Examples for CpG ODN are ODN 1585, ODN 2216, ODN 2336, ODN 1668, ODN 1826, ODN 2006, ODN 2007, ODN BW006, ODN D-SL01, ODN 2395, ODN M362 and ODN D-SL03.

In certain embodiments the one or more additional drug is resiquimod. In certain embodiments the one or more additional drug is imiquimod.

In certain embodiments the one or more additional drug is resiquimod in its free form. In certain embodiments the one or more additional drug is a conjugate comprising a polymer, to which one or more moieties of formula (A-i) are conjugated

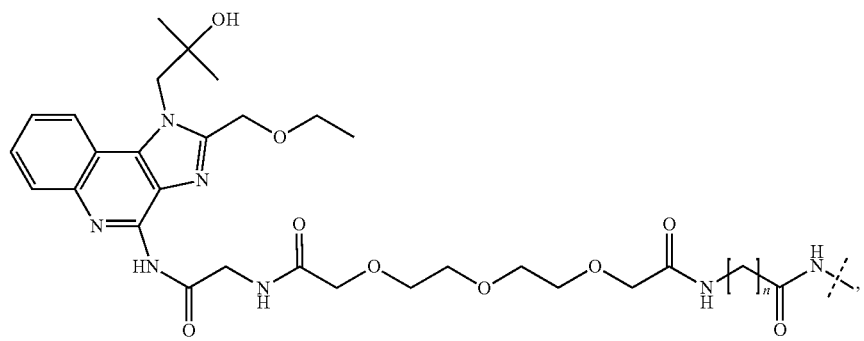

(A-i)

wherein
the dashed line indicates attachment to the polymer; and
n is an integer selected from the group consisting of 1, 2, 3, 4, 5, 6, 7, 8, 9, 10, 11, 12, 13, 14, 15, 16, 17, 18, 19 or 20.

In certain embodiments the polymer to which the one or more moieties of formula (A-i) are conjugated is a water-soluble polymer. In certain embodiments such water-soluble polymer is a PEG-based or hyaluronic acid-based polymer. In certain embodiments the polymer is a PEG-based polymer. In certain embodiments the polymer is a hydrogel, such as a PEG-based or hyaluronic acid-based hydrogel. In certain embodiments the hydrogel is a PEG-based hydrogel. In certain embodiments n of formula (A-i) is 1. In certain embodiments n of formula (A-i) is 2. In certain embodiments n of formula (A-i) is 3. In certain embodiments n of formula (A-i) is 4.

In certain embodiments the one or more additional drugs is a conjugate comprising a PEG-based hydrogel to which a multitude of the moieties of formula (A-i) is conjugated, wherein n in formula (A-i) is 2. In certain embodiments the one or more additional drugs is compound 12 or 14 from WO2020/141221A1 as shown on page 217 and 219, respectively, which are herewith incorporated by reference. In certain embodiments the one or more additional drugs is compound 12 from WO2020/141221A1 as shown on page 217. In certain embodiments the one or more additional drugs is compound 14 from WO2020/141221A1 as shown on page 219. Compounds 12 and 14 can be synthesized as disclosed in WO2020/141221A1.

In certain embodiments the PRRA is a NOD-like receptor agonist. If the one or more additional drug is a NOD-like receptor agonist, such NOD-like receptor agonist may be selected from the group consisting of agonists of NOD1, such as C12-iE-DAP, C14-Tri-LAN-Gly, iE-DAP, iE-Lys, and Tri-DAP; and agonists of NOD2, such as L18-MDP, MDP, M-TriLYS, murabutide and N-glycolyl-MDP. In certain embodiments the one or more additional drug is an agonist of NOD1. In certain embodiments the one or more additional drug is an agonist of NOD2.

In certain embodiments the PRRA is a RIG-I-like receptor agonist. If the one or more additional drug is a RIG-I-like receptor agonist, such RIG-I-like receptor agonist may be selected from the group consisting of 3p-hpRNA, 5'ppp-dsRNA, 5'ppp RNA (M8), 5'OH RNA with kink (CBS-13-BPS), 5'PPP SLR, KIN100, KIN 101, KIN1000, KIN1400, KIN1408, KIN1409, KIN1148, KIN131A, poly(dA:dT), SB9200, RGT100 and hiltonol.

In certain embodiments the PRRA is a cytosolic DNA sensor agonist. If the one or more additional drug is a cytosolic DNA sensor agonist, such cytosolic DNA sensor agonist may be selected from the group consisting of cGAS agonists, dsDNA-EC, G3-YSD, HSV-60, ISD, ODN TTAGGG (A151), poly(dG:dC) and VACV-70.

In certain embodiments the PRRA is a STING agonist. If the one or more additional drug is a STING agonist, such STING agonist may be selected from the group consisting of MK-1454, ADU-S100 (MIW815), 2'3'-cGAMP, 3'3'-cGAMP, c-di-AMP, c-di-GMP, cAIMP (CL592), cAIMP difluor (CL614), cAIM(PS)2 difluor (Rp/Sp) (CL656), 2'2'-cGAMP, 2'3'-cGAM(PS)2 (Rp/Sp), 3'3'-cGAM fluorinated, c-di-AMP fluorinated, 2'3'-c-di-AMP, 2'3'-c-di-AM(PS)2 (Rp,Rp), c-di-GMP fluorinated, 2'3'-c-di-GMP, c-di-IMP, c-di-UMP and DMXAA (vadimezan, ASA404). In certain embodiments the one or more additional drug is MK-1454. In certain embodiments the one or more additional drug is ADU-S100 (MIW815). In certain embodiments the one or more additional drug is 2'3'-cGAMP.

In certain embodiments the PRRA is an aryl hydrocarbon receptor agonist. If the one or more additional drug is an aryl hydrocarbon receptor (AhR) agonist, such AhR agonist may be selected from the group consisting of FICZ, ITE and L-kynurenine.

In certain embodiments the one or more additional drug is a cytotoxic/chemotherapeutic agent. In certain embodiments the one or more additional drug is an immune checkpoint inhibitor or antagonist. In certain embodiments the one or more additional drug is an immune activating receptor agonist. In certain embodiments the one or more additional drug is a multi-specific drug. In certain embodiments the one or more additional drug is an antibody-drug conjugate (ADC). In certain embodiments the one or more additional drug is an antibody-adjuvant conjugate (AAC). In certain embodiments the one or more additional drug is a radionuclide or a targeted radionuclide therapeutic. In certain embodiments the one or more additional drug is DNA damage repair inhibitor. In certain embodiments the one or more additional drug is a tumor metabolism inhibitor. In certain embodiments the one or more additional drug is a pattern recognition receptor agonist. In certain embodiments the one or more additional drug is a protein kinase inhibitor. In certain embodiments the one or more additional drug is a chemokine and chemoattractant receptor agonist. In certain embodiments the one or more additional drug is a chemokine or chemokine receptor antagonist. In certain embodiments the one or more additional drug is a cytokine receptor agonist. In certain embodiments the one or more additional drug is a death receptor agonist. In certain embodiments the one or more additional drug is a CD47 antagonist. In certain embodiments the one or more additional drug is a SIRPα antagonist. In certain embodiments the one or more additional drug is an oncolytic drug. In certain embodiments the one or more additional drug is a signal converter protein. In certain embodiments the one or more additional drug is an epigenetic modifier. In certain embodiments the one or more additional drug is a tumor peptide or tumor vaccine. In certain embodiments the one or more additional drug is a heat shock protein (HSP) inhibitor. In certain embodiments the one or more additional drug is a proteolytic enzyme. In certain embodiments the one or more additional drug is a ubiquitin and proteasome inhibitor. In certain embodiments the one or more additional drug is an adhesion molecule antagonist. In certain embodiments the one or more additional drug is a hormone including hormone peptides and synthetic hormones.

The cytotoxic or chemotherapeutic agent may be selected from the group consisting of alkylating agents, anthracyclines, pyrrolobenzodiazepines, nitrogen mustards, platinum agents, anti-metabolites, anti-microtubule agents, topoisomerase inhibitors, cytotoxic antibiotics, auristatins, enediynes, lexitropsins, duocarmycins, cyclopropylpyrroloindoles, puromycin, dolastatins, maytansine derivatives, alkylsufonates, triazenes and piperazine.

The alkylating agent may be selected from the group consisting of nitrogen mustards, such as mechlorethamine, cyclophosphamide, melphalan, chlorambucil, ifosfamide and busulfan; nitrosoureas, such as N-nitroso-N-methylurea, carmustine, lomustine, semustine, fotemustine and streptozotocin; tetrazines, such as dacarbazine, mitozolomide and temozolomide; ethylenimines, such as altretamine; aziridines, such as thiotepa, mitomycin and diaziquone; cisplatin and derivatives, such as cisplatin, carboplatin, oxaliplatin; and non-classical alkylating agents, such as procarbazine and hexamethylmelamine.

The anti-metabolite may be selected from the group consisting of anti-folates, such as methotrexate and pemetrexed; fluoropyrimidines, such as fluorouracil and capecitabine; deoxynucleoside analogues, such as cytarabine, gemcitabine, decitabine, azacytidine, fludarabine, nelarabine, cladribine, clofarabine and pentostatin; and thiopurines, such as thioguanine and mercaptopurine.

The anti-microtubule agent may be selected from the group consisting of Vinca alkaloids, such as vincristine, vinblastine, vinorelbine, vindesine and vinflunine; taxanes, such as paclitaxel and docetaxel; podophyllotoxins and derivatives, such as podophyllotoxin, etoposide and teniposide; stilbenoid phenol and derivatives, such as zybrestat (CA4P); and BNC105.

The topoisomerase inhibitor may be selected from the group consisting of topoisomerase I inhibitors, such as irinotecan, topotecan and camptothecin; and topoisomerase II inhibitors, such as etoposide, doxorubicin, mitoxantrone, teniposide, novobiocin, merbarone and aclarubicin.

In certain embodiments the one or more additional drug is doxorubicin.

The cytotoxic antibiotic may be selected from the group consisting of anthracyclines, such as doxorubicin, daunorubicin, epirubicin and idarubicin; pirarubicin, aclarubicin, bleomycin, mitomycin C, mitoxantrone, actinomycin, dactinomycin, adriamycin, mithramycin and tirapazamine.

The auristatin may be selected from the group consisting of monomethyl auristatin E (MMAE) and monomethyl auristatin F (MMAF).

The enediyne may be selected from the group consisting of neocarzinostatin, lidamycin (C-1027), calicheamicins, esperamicins, dynemicins and golfomycin A.

The maytansine derivative may be selected from the group consisting of ansamitocin, mertansine (emtansine, DM1) and ravtansine (soravtansine, DM4).

The immune checkpoint inhibitor or antagonist may be selected from the group consisting of inhibitors of CTLA-4 (cytotoxic T-lymphocyte-associated protein 4), such as ipilimumab, tremelimumab, MK-1308, FPT155, PRS010, BMS-986249, BPI-002, CBT509, JS007, ONC392, TE1254, IBI310, BR02001, CG0161, KN044, PBI5D3H5, BCD145, ADU1604, AGEN1884, AGEN1181, CS1002 and CP675206; inhibitors of PD-1 (programmed death 1), such as pembrolizumab, nivolumab, pidilizumab, AMP-224, BMS-936559, cemiplimab and PDR001; inhibitors of PD-L1 (programmed cell death protein 1), such as MDX-1105, MEDI4736, atezolizumab, avelumab, BMS-936559 and durvalumab; inhibitors of PD-L2 (programmed death-ligand 2); inhibitors of KIR (killer-cell immunoglobulin-like receptor), such as lirilumab (IPH2102) and IPH2101; inhibitors of B7-H3, such as MGA271; inhibitors of B7-H4, such as FPA150; inhibitors of BTLA (B- and T-lymphocyte attenuator); inhibitors of LAG3 (lymphocyte-activation gene 3), such as IMP321 (eftilagimod alpha), relatlimab, MK-4280, AVA017, BI754111, ENUM006, GSK2831781, INCAGN2385, LAG3Ig, LAG525, REGN3767, Sym016, Sym022, TSR033, TSR075 and XmAb22841; inhibitors of TIM-3 (T-cell immunoglobulin and mucin-domain containing-3), such as LY3321367, MBG453, and TSR-022; inhibitors of VISTA (V-domain Ig suppressor of T cell activation), such as JNJ-61610588; inhibitors of ILT2/LILRB1 (Ig-like transcript 2/leukocyte Ig-like receptor 1); inhibitor of ILT3/LILRB4 (Ig-like transcript 3/leukocyte Ig-like receptor 4); inhibitors of ILT4/LILRB2 (Ig-like transcript 4/leukocyte Ig-like receptor 2), such as MK-4830; inhibitors of TIGIT (T cell immunoreceptor with Ig and ITIM domains), such as MK-7684, PTZ-201, RG6058 and COM902; inhibitors of NKG2A, such as IPH-2201; and inhibitors of PVRIG, such as COM701.

One example of a an inhibitor of CTLA-4 is an anti-CTLA4 conjugate or a pharmaceutically acceptable salt thereof, wherein said conjugate comprises a plurality of anti-CTLA4 moieties -$D_{CTLA4}$ covalently conjugated via at least one moiety -$L^1$-$L^2$- to a polymeric moiety Z, wherein -$L^1$- is covalently and reversibly conjugated to -$D_{CTLA4}$ and -$L^2$- is covalently conjugated to Z and wherein -$L^1$- is a linker moiety and -$L^2$- is a chemical bond or a spacer moiety, wherein the moieties -$L^1$-, -$L^2$- and Z are as described elsewhere herein for the conjugate of the present invention. In certain embodiments -$D_{CTLA4}$ is selected from the group consisting of wild-type $F_c$ anti-CTLA4 antibodies, Fc enhanced for effector function/FcγR binding anti-CTLA4 antibodies, anti-CTLA4 antibodies conditionally active in tumor microenvironment, anti-CTLA4 small molecules, CTLA4 antagonist fusion proteins, anti-CTLA4 anticalins, anti-CTLA4 nanobodies and anti-CTLA4 multispecific biologics based on antibodies, scFVs or other formats. In certain embodiments -$D_{CTLA4}$ is ipilimumab. In certain embodiments -$D_{CTLA4}$ is tremelimumab. In certain embodiments the anti-CTLA4 conjugate has the following structure:

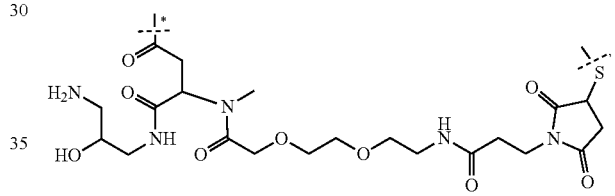

wherein
the dashed line marked with the asterisk indicates attachment to the nitrogen of an amine functional group of -$D_{CTLA4}$, in particular to the nitrogen of an amine functional group of ipilimumab; and
the unmarked dashed line indicates attachment to Z, such as a hydrogel, in particular to a crosslinked hyaluronic acid hydrogel.

It is understood that a multitude of moieties -$D_{CTLA4}$-$L^1$-$L^2$- are connected to Z, if Z is a hydrogel, such as a crosslinked hyaluronic acid hydrogel.

In certain embodiments the nitrogen of an amine functional group of -$D_{CTLA4}$ and in particular of ipilimumab is an amine of a lysine residue. In certain embodiments the nitrogen of an amine functional group of -$D_{CTLA4}$ and in particular of ipilimumab is the N-terminal amine.

In certain embodiments the one or more additional drug is an inhibitor of CTLA4 as described above.

In certain embodiments the one or more additional drug is an inhibitor of PD-1 or PD-L1. In certain embodiments the one or more additional drug is an inhibitor of PD-1. In certain embodiments the one or more additional drug is an inhibitor of PD-L1. In certain embodiments the one or more additional drug is pembrolizumab.

The immune activating receptor agonist may be selected from the group consisting of agonists of CD27, such as recombinant CD70, such as HERA-CD27L, and varlilumab (CDX-1127); agonists of CD28, such as recombinant CD80, recombinant CD86, TGN1412 and FPT155; agonists of CD40, such as recombinant CD40L, CP-870,893, dacetuzumab (SGN-40), Chi Lob 7/4, ADC-1013 and CDX1140; agonists of 4-1BB (CD137), such as recombinant 4-1BBL, urelumab, utomilumab and ATOR-1017; agonists of OX40, such as recombinant OX40L, MEDI0562, GSK3174998, MOXR0916 and PF-04548600; agonists of GITR, such as recombinant GITRL, TRX518, MEDI1873, INCAGN01876, MK-1248, MK-4166, GWN323 and BMS-986156; and agonists of ICOS, such as recombinant ICOSL, JTX-2011 and GSK3359609.

The multi-specific drug may be selected from the group consisting of biologics and small molecule immune checkpoint inhibitors. Examples for biologics are multi-specific immune checkpoint inhibitors, such as CD137/HER2 multispecifics, PD-(L)1/LAG3 antagonists (for example FS118, MGD013), CTLA4/LAG3 antagonists (for example XmAb22841) and CTLA4/PD-(L)1 antagonists (for example XmAb20717, MGD019); multispecific immune activating receptor agonists, immunocytokines and multi-specific immune checkpoint agonists. Such multi-specific immune checkpoint agonists may be selected from the group consisting of Ig superfamily agonists, such as ALPN-202, FPT155, TGN1412, GSK3359609, JTX-2011; TNF superfamily agonists, such as FAP-4-1BBL (RG7826), OX40-41BB (FS120) ATOR-1015, ATOR-1144, ALG.APV-527, lipocalin/PRS-343, PRS344/ONC0055, FAP-CD40 DARPin, MP0310 DARPin, FAP-OX40 DARPin, EGFR-CD40 DARPin, EGFR41BB/CD137 DARPin, EGFR-OX40/DARFPin, HER2-CD40 DARPin, HER2-41BB/CD137 DARPin, HER2-OX40 DARPin, FIBRONECTIN ED-B-CD40 DARPin, FIBRONECTIN ED-B-41BB/CD137 and FIBRONECTIN ED-B-OX40 DARPin; CD3 multispecific agonists, such as blinatumomab, solitomab, MEDI-565, ertumaxomab, anti-HER2/CD3, 1Fab-immunoblobulin G TDB, GBR 1302, MGD009, MGD007, EGFRBi, EGFR-CD Probody, RG7802, PF-06863135, PF-06671008, AMG212/BAY2010112, CD3-5T4, XmAb14045, XmAb13676, XmAb18087, S80880, REGN1979, REGN5458, REGN4018, RG6026, Mosunetuzumab, EM801, ERY974, RG6194, AMG420, AMG330, AMG 212, AMG 596, AMG 160, AMG 427, AMG 562, AMG 673, AMG 701, AMG 757, AFM13, AMF24, AFM26, AFM11. TNB-486, TNB-383B, GEN3013, JNJ-63709178, JNJ-63898081, JNJ-64007957, JNJ-64407564, JNJ-67571244, AMV564, APVO414 (MOR209, ES414), APV0436, HPN424, HPN536, HPN217, HPN 328 and other multispecific CD3 agonists or T cell receptor (TCR) agonists including 76 TCR agonists targeting T cell activity towards a tumor cell antigen or viral antigen or expressing cell; Natural Killer (NK) cell receptor multispecific agonists targeting an activating NK receptor and a target tumor cell antigen, such as NKG2D multispecific agonists, NKp30 multispecific agonists, NKp44 multispecific agonists, NKp46 multispecific agonists, NKp80 multispecific agonists, NKG2C multispecific agonists, 2B4 (CD244) multispecific agonists, CD32a multispecific agonists, CD64 multispecific agonists, multispecific agonists that bind to a tumor antigen as well as activating receptors such as NKG2D or NKp30 or other NK receptors listed above as well as binding to Fc receptors such as TriNKeTs, and CD16 multispecific agonists, such as 1633 BiKE, 161533 TriKE, OXS-3550, OXS-C3550, AFM13 and AFM24; and other therapeutic antibodies capable of binding a target antigen as well as Fc receptors such as CD16, CD32a, CD64.

Other examples of immune activating receptor agonists include Dectin agonists (Imprime PGG), recombinant NKG2D ligands, ligand or modifiers of γδ TCR signaling such as anti-BTN3A1 mAbs or anti-BTN2A1 mAbs or Vγ9/Vδ2 TCR activating ligand such as phospho antigens and pyrophosphate antigens, or agents which increase endogenous Vγ9/Vδ2 ligands such as bisphosphonates like pamidronate and zoledronate.

An example for a small molecule immune checkpoint inhibitor is CA-327 (TIM3/PD-L1 antagonist).

The antibody-drug conjugate may be selected from the group consisting of ADCs targeting hematopoietic cancers, such as gemtuzumab ozogamicin, brentuximab vedotin, inotuzumab ozogamicin, SAR3419, BT062, SGN-CD19A, IMGN529, MDX-1203, polatuzumab vedotin (RG7596), pinatuzumab vedotin (RG7593), RG7598, milatuzumab-doxorubicin and OXS-1550; and ADCs targeting solid tumor antigens, such as trastuzumab emtansine, glembatumomab vedotin, SAR56658, AMG-172, AMG-595, BAY-94-9343, BIIB015, vorsetuzumab mafodotin (SGN-75), ABT-414, ASG-5ME, enfortumab vedotin (ASG-22ME), ASG-16M8F, IMGN853, indusatumab vedotin (MLN-0264), vadortuzumab vedotin (RG7450), sofituzumab vedotin (RG7458), lifastuzumab vedotin (RG7599), RG7600, DEDN6526A (RG7636), PSMA TTC, 1095 from Progenics Pharmaceuticals, lorvotuzumab mertansine, lorvotuzumab emtansine, IMMU-130, sacituzumab govitecan (IMMU-132), PF-06263507 and MEDI0641.

The antibody-adjuvant conjugate may be a boltbody, such as the boltbodies described in WO2018112108A1 and WO2018009916A1. In certain embodiments the boltbody is selected from the group consisting of BDC-1001 and BDC-2034. In certain embodiments the boltbody is BDC-1001. In certain embodiments the boltbody is BDC-2034.

In certain embodiments the boltbody has the structure of formula (BT-I)

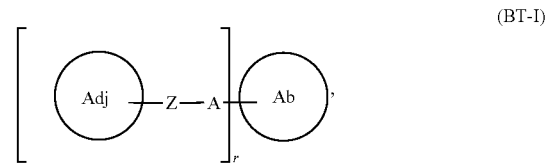

(BT-I)

wherein Ab is an antibody moiety;
A is an unmodified amino acid sidechain in the antibody moiety or a modified amino acid sidechain in the antibody moiety;
Z is a linking moiety;
Adj is an adjuvant moiety; and
r is an integer selected from 1 to 10.

It is understood that r amino acid side chains of a moiety Ab of formula (BT-I) are connected to a moiety Adj-Z.

In certain embodiments A of formula (BT-I) comprises an amino acid sidechain in the antibody moiety comprising an amine functional group.

In certain embodiments the boltbody has the structure of formula (BT-II)

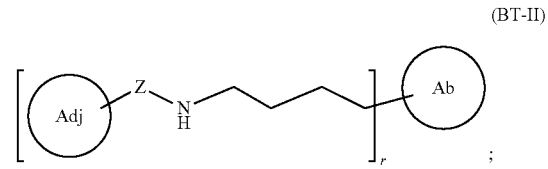

(BT-II)

;

wherein
Ab is an antibody moiety;

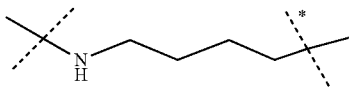

represents a sidechain of a lysine residue of Ab, wherein the unmarked dashed line indicates attachment to Z and the dashed line marked with the asterisk indicates attachment to the alpha carbon of the lysine residue;
Adj is an adjuvant moiety;
r is an integer selected from 1 to 10;
and Z is a divalent linking moiety having an ethylene glycol group or a glycine residue.
It is understood that the moiety

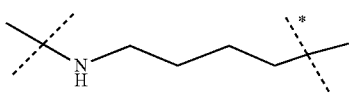

of formula (BT-II) corresponds to A of formula (BT-I). Likewise, it is understood that r lysine side chain moieties of moiety Ab of formula (BT-II) are connected to a moiety Adj-Z.

In certain embodiments Z of formulas (BT-I) and (BT-II) is bonded to Adj via an amide bond, a C—N single bond, a C—O single bond, or a C—C single bond, and to Ab via an amide bond or a C—N single bond.

In certain embodiments Z of formulas (BT-I) and (BT-II) is bonded to a nitrogen group of Adj and a nitrogen group of Ab. In such embodiments Z of formulas (BT-I) and (BT-II) is bonded to adjacent nitrogen groups via amide bonds, C—N single bonds, or a combination thereof.

In some embodiments Z of formulas (BT-I) and (BT-II) comprises a PEG moiety.

In certain embodiments Z of formulas (BT-I) and (BT-II) comprises at least 2 ethylene glycol groups, such as at least 3 ethylene glycol groups, at least 4 ethylene glycol groups, at least 5 ethylene glycol groups, at least 6 ethylene glycol groups, at least 7 ethylene glycol groups, at least 8 ethylene glycol groups, at least 9 ethylene glycol groups, at least 10 ethylene glycol groups, at least 11 ethylene glycol groups, at least 12 ethylene glycol groups, at least 13 ethylene glycol groups, at least 14 ethylene glycol groups, at least 15 ethylene glycol groups, at least 16 ethylene glycol groups, at least 17 ethylene glycol groups, at least 18 ethylene glycol groups, at least 19 ethylene glycol groups, at least 20 ethylene glycol groups, at least 21 ethylene glycol groups, at least 22 ethylene glycol groups, at least 23 ethylene glycol groups, at least 24 ethylene glycol groups, or at least 25 ethylene glycol groups.

In certain embodiments Z of formulas (BT-I) and (BT-II) comprises 2 ethylene glycol groups, 3 ethylene glycol groups, 4 ethylene glycol groups, 5 ethylene glycol groups, 6 ethylene glycol groups, 8 ethylene glycol groups, 12 ethylene glycol groups, 24 ethylene glycol groups, or 25 ethylene glycol groups.

In certain embodiments Z of formulas (BT-I) and (BT-II) comprises a glycine residue.

In certain embodiments Z of formulas (BT-I) and (BT-II) comprises at least 2 glycine residues, such as at least 3 glycine residues, at least 4 glycine residues, at least 5 glycine residues, at least 6 glycine residues, at least 7 glycine residues, at least 8 glycine residues, at least 9 glycine residues, at least 10 glycine residues, at least 11 glycine residues, at least 12 glycine residues, at least 13 glycine residues, at least 14 glycine residues, at least 15 glycine residues, at least 16 glycine residues, at least 17 glycine residues, at least 18 glycine residues, at least 19 glycine residues, at least 20 glycine residues, at least 21 glycine residues, at least 22 glycine residues, at least 23 glycine residues, at least 24 glycine residues, or at least 25 glycine residues.

In certain embodiments Z of formulas (BT-I) and (BT-II) comprises 2 glycine residues, 3 glycine residues, 4 glycine residues, 5 glycine residues, 6 glycine residues, 8 glycine residues, 12 glycine residues, 24 glycine residues, or 25 glycine residues.

In certain embodiments Z of formulas (BT-I) and (BT-II) further comprises a divalent cyclohexylene group In certain embodiments Ab of formulas (BT-I) and (BT-II) comprises an antibody binding domain that binds to an antigen selected from the group consisting of CDH1, CD19, CD20, CD29, CD30, CD38, CD40, CD47, CEA, EpCAM, MUC1, MUC16, EGFR, VEGF, HER2, SLAMF7, PDG-FRa, gp75, CTLA4, PD-1, PD-L1, PD-L2, LAG-3, B7-H4, KIR, TNFRSF4, OX40L, IDO-1, IDO-2, CEACAM1, BTLA, TIM3, A2Ar, VISTA, CLEC4C (BDCA-2, DLEC, CD303, CLECSF7), CLEC4D (MCL, CLECSF8), CLEC4E (Mincle), CLEC6A (Dectin-2), CLEC5A (MDL-1, CLECSF5), CLEC1B (CLEC-2), CLEC9A (DNGR-1), and CLEC7A (Dectin-1).

In certain embodiments Ab of formulas (BT-I) and (BT-II) comprises an antibody binding domain that binds to HER2. In certain embodiments Ab of formulas (BT-I) and (BT-II) comprises an antibody binding domain that binds to EGFR. In certain embodiments Ab of formulas (BT-I) and (BT-II) comprises an antibody binding domain that binds to CCR8. In certain embodiments Ab of formulas (BT-I) and (BT-II) comprises an antibody binding domain that binds to PD-L1. In certain embodiments Ab of formulas (BT-I) and (BT-II) comprises an antibody binding domain that binds to CEA.

In certain embodiments Ab of formulas (BT-I) and (BT-II) comprises an antibody selected from the group consisting of pembrolizumab, nivolumab, atezolizumab, avelumab, ipilimumab, obinutuzumab, trastuzumab, cetuximab, rituximab, pertuzumab, bevacizumab, daratumumab, etanercept, olaratumab, elotuzumab, margetuximab, and a biosimilar thereof.

In certain embodiments Ab of formulas (BT-I) and (BT-II) comprises trastuzumab. In certain embodiments Ab of formulas (BT-I) and (BT-II) comprises pembrolizumab. In certain embodiments Ab of formulas (BT-I) and (BT-II) comprises nivolumab.

In certain embodiments Adj of formulas (BT-I) and (BT-II) comprises a PRRA.

In certain embodiments Adj of formulas (BT-I) and (BT-II) is a PRRA selected from the group consisting of toll-like receptors (TLR) agonists, c-type lectin receptors (CLR) agonists, NOD-like receptors (NLR) agonists, Rig-I-like receptors (RLR) agonists, stimulator of interferon genes (STING) agonists and combination thereof.

In certain embodiments Adj of formulas (BT-I) and (BT-II) is a TLR agonist, such as a TLR agonist selected from the group consisting of TLR1 agonists, TLR2 agonists, TLR3 agonists, TLR4 agonists, TLR5 agonists, TLR6 agonists, TLR7 agonists, TLR7/8 agonists, TLR8 agonists, TLR9 agonists, TLR10 agonists, TLR11 agonists and combination thereof.

In certain embodiments Adj of formulas (BT-I) and (BT-II) is a TLR agonist selected from the group consisting of CL264, CL401, CL413, CL419, CL553, CL572, Pam$_3$CSK$_4$, and Pam$_2$CSK$_4$.

In certain embodiments, Adj of formulas (BT-I) and (BT-II) is selected from the group consisting of

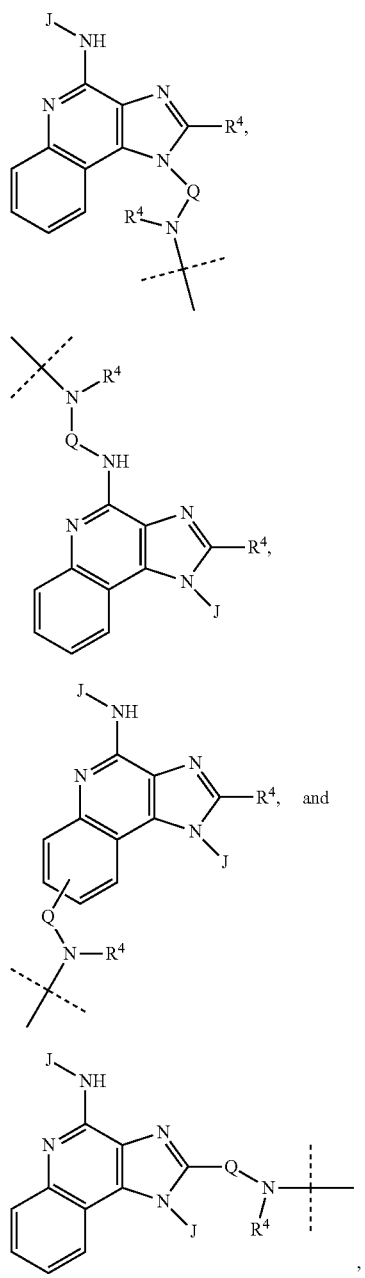

(BT-IIIa)

(BT-IIIb)

(BT-IIIc)

(BT-IIId)

wherein
each -J is independently selected from the group consisting of —H, —OR$^4$, and —R$^4$;
each —R$^4$ is independently selected from the group consisting of —H, an alkyl, heteroalkyl, cycloalkyl, heterocycloalkyl, aryl, heteroaryl, arylalkyl, and heteroarylalkyl group comprising from 1, 2, 3, 4, 5, 6, 7, or 8 carbon units;
-Q- is absent or is selected from the group consisting of alkyl, heteroalkyl, cycloalkyl, heterocycloalkyl, aryl, heteroaryl, arylalkyl, and heteroarylalkyl comprising from 1, 2, 3, 4, 5, 6, 7, or 8 carbon units; and
the dashed line indicates attachment to Z.

In certain embodiments Adj of formulas (BT-I) and (BT-II) is of formula

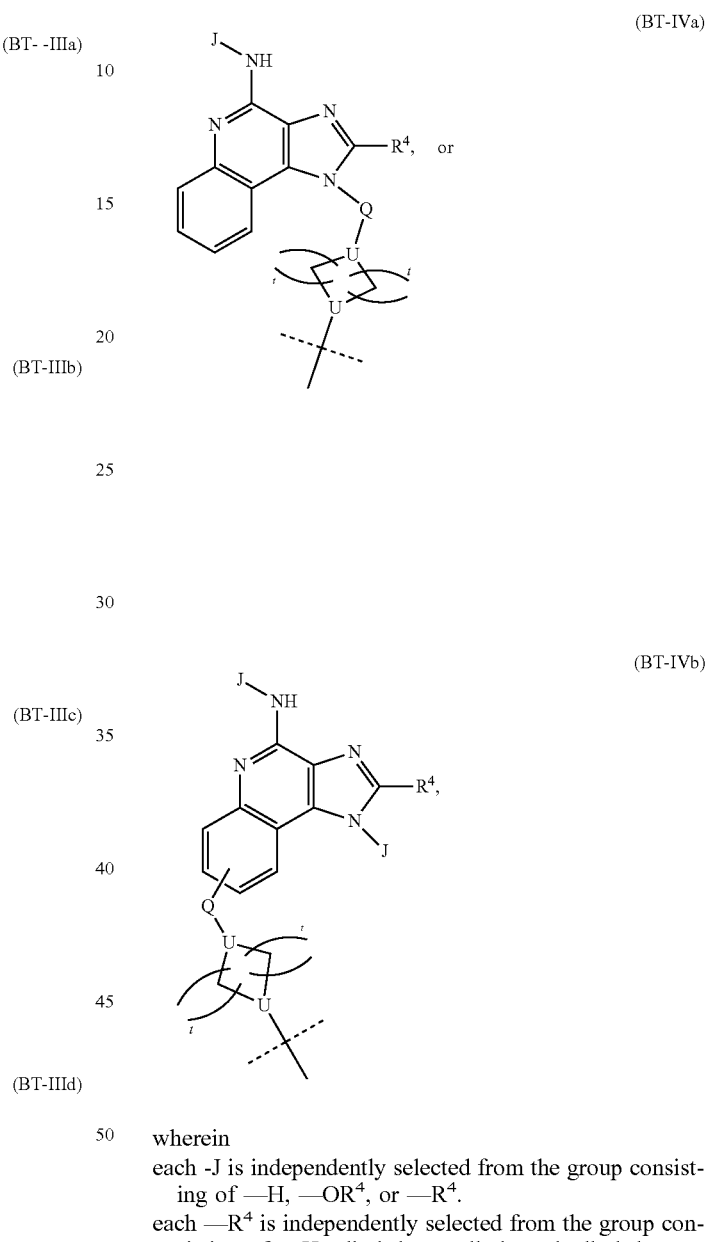

(BT-IVa)

(BT-IVb)

wherein
each -J is independently selected from the group consisting of —H, —OR$^4$, or —R$^4$.
each —R$^4$ is independently selected from the group consisting of —H, alkyl, heteroalkyl, cycloalkyl, heterocycloalkyl, aryl, heteroaryl, arylalkyl, and heteroarylalkyl comprising from 1, 2, 3, 4, 5, 6, 7, or 8 carbon units;
each —U— is independently —CH— or —N—, wherein at least one —U— is —N—;
each t is independently an integer selected from 1, 2 and 3;
-Q- is absent or is selected from the group consisting of alkyl, heteroalkyl, cycloalkyl, heterocycloalkyl, aryl, heteroaryl, arylalkyl, and heteroarylalkyl comprising from 1, 2, 3, 4, 5, 6, 7, or 8 carbon units, and
the dashed line indicates attachment to Z.

In certain embodiments, Adj of formulas (BT-I) and (BT-II) is selected from the group consisting of formulas (BT-Va)

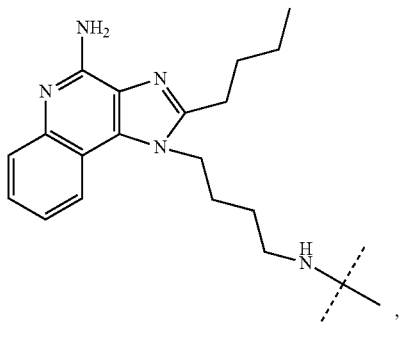

, (BT-Vb)

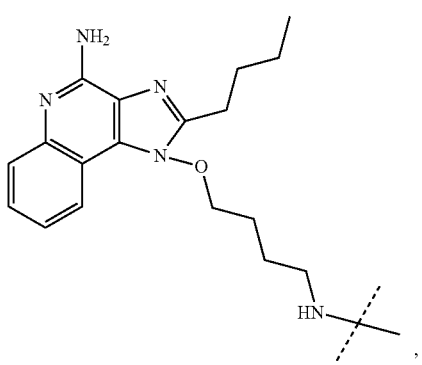

, (BT-Vc)

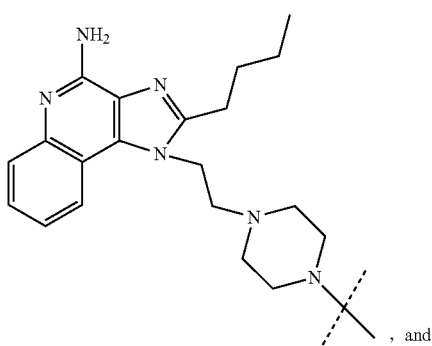

, and (BT-Vd)

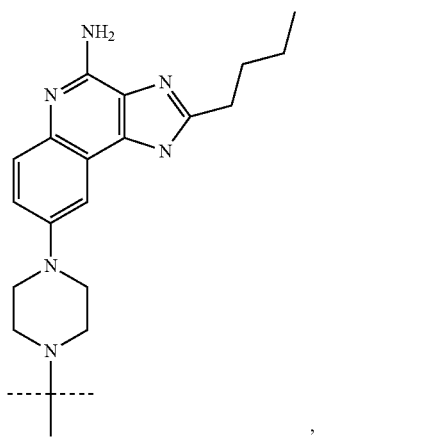

, wherein the dashed line indicates attachment to Z.

In certain embodiments Adj of formulas (BT-I) and (BT-II) is selected from the adjuvant moieties disclosed in paragraphs [118] to [136] of WO2018112108A1.

In certain embodiments the boltbody comprises more than one distinct adjuvant moiety.

In certain embodiments the boltbody has the structure of formula (BT-VI)

(BT-VI)

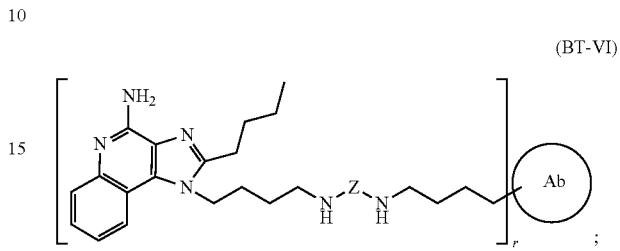

wherein
Ab is an antibody moiety;

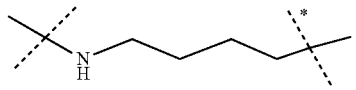

represents a sidechain of a lysine residue of Ab, wherein the unmarked dashed line indicates attachment to Z and the dashed line marked with the asterisk indicates attachment to the alpha carbon of the lysine residue;

r is an integer selected from 1 to 10; and

Z is a divalent linking moiety comprising at least one ethylene glycol group or at least one glycine residue.

In certain embodiments Z of formula (BT-VI) is used as defined for formulas (BT-I) and (BT-II).

In certain embodiments the boltbody has the structure of formula (BT-VII)

(BT-VII)

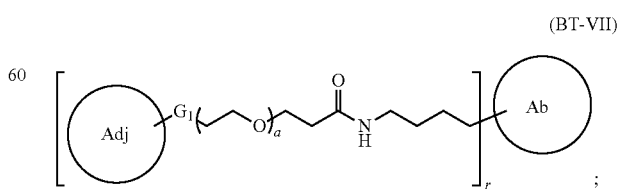

;

wherein

Ab is an antibody moiety comprising (i) an antigen binding domain and (ii) an Fc domain;

Adj is an adjuvant moiety of formula (BT-IVb)

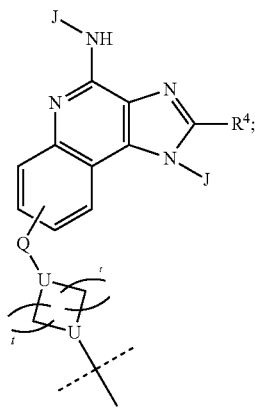

(BT-IVb)

wherein

—$R^4$ is selected from the group consisting of alkyl, heteroalkyl, cycloalkyl, heterocycloalkyl, aryl, heteroaryl, arylalkyl, and heteroarylalkyl comprising from 1 to 8 carbons;

each -J is —H;

each —U— is —N—;

each t is 2;

-Q- is absent;

the dashed line indicates attachment to $G^1$;

-$G_1$- is a bond;

a is an integer selected from 1 to 40; and r is an integer selected from 1 to 10.

In certain embodiments the boltbody has the structure of formula (BT-VII)

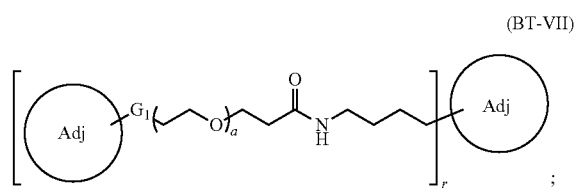

(BT-VII)

wherein

Ab is trastuzumab;

Adj is an adjuvant moiety of formula (BT-IVb)

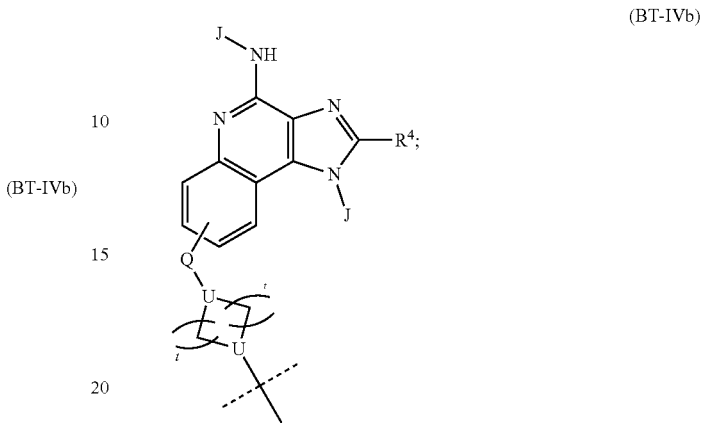

(BT-IVb)

wherein

—$R^4$ is butyl;

each -J is —H;

each —U— is —N—;

each t is 2;

-Q- is absent;

the dashed line indicates attachment to -$G_1$-;

$G_1$- is a bond;

a is an integer selected from 1 to 40; and r is an integer selected from 1 to 4.

In certain embodiments the boltbody has the structure of formula (BT-VIII)

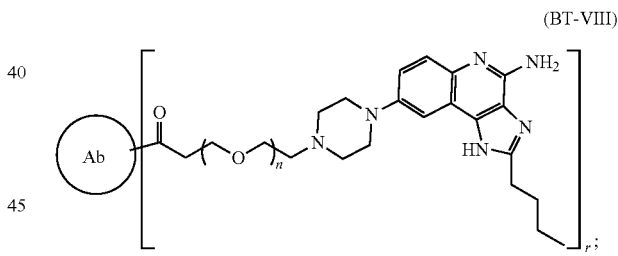

(BT-VIII)

wherein r is an integer selected from 1 to 10;

n is an integer selected from about 2 to about 25; and

Ab is an antibody moiety.

In certain embodiments r of formula (BT-VIII) is 1. In certain embodiments r of formula (BT-VIII) is 2. In certain embodiments r of formula (BT-VIII) is 3. In certain embodiments r of formula (BT-VIII) is 4.

In certain embodiments n of formula (BT-VIII) is an integer selected from 6, 7, 8, 9, 10, 11 and 12. In certain embodiments n of formula (BT-VIII) is an integer selected from 8, 9, 10, 11 and 12. In certain embodiments n of formula (BT-VIII) is 10.

In certain embodiments Ab of formula (BT-VIII) comprises an antigen binding domain that binds HER2, EGFR, PD-L1 or CEA. In certain embodiments the antibody moiety of formula (BT-VIII) comprises an antigen binding domain that binds HER2. In certain embodiments Ab of formula (BT-VIII) comprises an antigen binding domain that binds EGFR. In certain embodiments Ab of formula (BT-VIII) comprises an antigen binding domain that binds PD-L1.

In certain embodiments Ab of formula (BT-VIII) comprises an antigen binding domain that binds CEA.

Only in the context of formulas (BT-IIIa), (BT-IIIb), (BT-IIIc), (BT-IIId), (BT-IVa), and (BT-IVb) the terms used have the following meaning: The term "alkyl" refers to a straight or branched, saturated, aliphatic radical having the number of carbon atoms indicated. Alkyl may include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl comprises methyl, ethyl, propyl, isopropyl, butyl, isobutyl, sec-butyl, tert-butyl, pentyl, isopentyl, hexyl. Alkyl may also comprise alkyl groups having up to 30 carbons atoms, such as heptyl, octyl, nonyl, decyl. Alkyl groups may be substituted or unsubstituted. "Substituted alkyl" groups may be substituted with one or more groups selected from halo, hydroxy, amino, oxo (=O), alkylamino, amido, acyl, nitro, cyano, and alkoxy.

The term "aryl" refers to an aromatic ring system having any suitable number of ring atoms and any suitable number of rings. Aryl groups may comprise any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups may be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl.

The term "carbocycle" refers to a saturated or partially unsaturated, monocyclic, fused bicyclic, or bridged poly cyclic ring assembly containing from 3 to 12 ring atoms, or the number of atoms indicated. Carbocycles may include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic carbocyclic rings include, for example, cyclopropyl, cyclobutyl, cyclopentyl, cyclohexyl, and cyclooctyl. Saturated bicyclic and polycyclic carbocyclic rings include, for example, norbornane, [2.2.2] bicyclooctane, decahydronaphthalene and adamantane. Carbocyclic groups may also be partially unsaturated, having one or more double or triple bonds in the ring. Representative carbocyclic groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene.

The term "heteroalkyl" refers to an alkyl group, wherein one or more carbon atoms are optionally and independently replaced with heteroatom selected from N, O, and S.

The term "heterocycle" refers to heterocycloalkyl groups and heteroaryl groups. "Heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms may also be useful, such as B, Al, Si and P. The heteroatoms may be oxidized to form moieties such as, such as —S(O)— and —S(O)$_2$—. Heteroaryl groups may include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms may be include in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. The heteroaryl group may include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups may also be fused to aromatic ring systems, such as a phenyl ring, to form members, such as benzopyrroles, such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups may be substituted or unsubstituted. "Substituted heteroaryl" groups may be substituted with one or more groups selected from halo, hydroxy, amino, oxo (=O), alkylamino, amido, acyl, nitro, cyano, and alkoxy. Heteroaryl groups may be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole, such as 1-, 2- and 3-indole, isoindole, such as 1- and 2-isoindole, quinoline, such as 2-, 3- and 4-quinoline, isoquinoline, such as 1-, 3- and 4-isoquinoline, quinazoline, such as 2- and 4-quinoazoline, cinnoline, such as 3- and 4-cinnoline, benzothiophene, such as 2- and 3-benzothiophene, and benzofuran, such as 2- and 3-benzofuran.

The term "heterocycloalkyl," by itself or as part of another substituent, refers to a saturated ring system having from 3 to 12 ring members and from 1 to 4 heteroatoms of N, O and S. Additional heteroatoms may also be useful, such as B, Al, Si and P. The heteroatoms may be oxidized to form moieties, such as —S(O)— and —S(O)$_2$—. Heterocycloalkyl groups may include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms may be included in the heterocycloalkyl groups, such as 1, 2, 3, or 4, or 1 to 2, 1 to 3, 1 to 4, 2 to 3, 2 to 4, or 3 to 4. The heterocycloalkyl group may include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups may also be fused to aromatic or non-aromatic ring systems to form members, such as indoline. Heterocycloalkyl groups may be unsubstituted or substituted. "Substituted heterocycloalkyl" groups may be substituted with one or more groups selected from halo, hydroxy, amino, oxo (=O), alkylamino, amido, acyl, nitro, cyano, and alkoxy. Heterocycloalkyl groups may be linked via any position on the ring. For example, aziridine may be 1- or 2-aziridine, azetidine may be 1- or 2-azetidine, pyrrolidine may be 1-, 2- or 3-pyrrolidine, piperidine may be 1-, 2-, 3- or 4-piperidine, pyrazolidine may be 1-, 2-, 3-, or 4-pyrazolidine, imidazolidine may be 1-, 2-, 3- or 4-imidazolidine, piperazine may be 1-, 2-, 3- or 4-piperazine, tetrahydrofuran may be 1- or 2-tetrahydrofuran, oxazolidine may be 2-, 3-, 4- or 5-oxazolidine, isoxazolidine may be 2-, 3-, 4- or 5-isoxazolidine, thiazolidine may be 2-, 3-, 4- or 5-thiazolidine, isothiazolidine may be 2-, 3-, 4- or 5-isothiazolidine, and morpholine may be 2-, 3- or 4-morpholine.

The term "arylalkyl" refers to any aryl derivative of an alkyl group. In certain embodiments one or more aryl moieties may be coupled to the remainder of the molecule through an alkyl linkage. Under those circumstances, the substituent will be referred to as an arylalkyl, indicating that an alkylene moiety is between the aryl moiety and the molecule to which the aryl is coupled. Representative arylalkyl groups include phenylmethyl, phenylethyl, phenylpropyl, phenylisopropyl, phenylbutyl, phenyl-isobutyl, phenyl-sec-butyl, phenyl-tert-butyl, phenylpentyl, phenylisopentyl, phenylhexyl, naphthylmethyl, naphthylethyl, naphthylpropyl, naphthylisopropyl, naphthylbutyl, naphthyl-isobutyl, naphthyl-sec-butyl, naphthyl-tert-butyl, naphthylpentyl, naphthyl-isopentyl, naphthylhexyl, biphenylmethyl, biphenylethyl, biphenylpropyl, biphenylisopropyl, biphenylbutyl, biphenyl-isobutyl, biphenyl-sec-butyl, biphenyl-tert-butyl, biphenylpentyl, biphenyl-isopentyl, and biphenylhexyl, The term "heteroarylalkyl" refers to an arylalkyl group wherein one or more carbon atoms are optionally and independently replaced with heteroatom selected from N, O, and S.

In certain embodiments the one or more additional drug is a radionuclide which may be selected from the group consisting of β-emitters, such as $^{177}$Lutetium, $^{166}$Holmium, $^{186}$Rhenium, $^{188}$Rhenium, $^{67}$Copper, $^{149}$Promethium, $^{199}$Gold, $^{77}$Bromine, $^{153}$Samarium, $^{105}$Rhodium, $^{89}$Strontium, $^{90}$Yttrium, $^{131}$Iodine; α-emitters, such as $^{213}$Bismuth, $^{223}$Radium, $^{225}$Actinium, $^{211}$Astatine; and Auger electron-emitters, such as $^{77}$Bromine, $^{111}$Indium, $^{123}$Iodine and $^{125}$Iodine.

The targeted radionuclide therapeutics may be selected from the group consisting of zevalin ($^{90}$Y-ibritumomab tiuxetan), bexxar ($^{131}$I-tositumomab), oncolym ($^{131}$I-Lym 1), lymphocide ($^{90}$Y-epratuzumab), cotara ($^{131}$I-chTNT-1/B), labetuzumab ($^{90}$Y or $^{131}$I-CEA), theragyn ($^{90}$Y-pemtumomab), licartin ($^{131}$I-metuximab), radretumab ($^{131}$I-L19) PAM4 ($^{90}$Y-clivatuzumab tetraxetan), xofigo ($^{223}$Ra dichloride), lutathera ($^{177}$Lu-DOTA-Tyr$^3$-Octreotate) and $^{131}$I-MIBG.

The DNA damage repair inhibitor may be selected from the group consisting of poly (ADP-ribose) polymerase (PARP) inhibitors, such as olaparib, rucaparib, niraparib, veliparib, CEP 9722 and E7016; CHK1/CHK2 dual inhibitors, such as AZD7762, V158411, CBP501 and XL844; CHK1 selective inhibitors, such as PF477736, MK8776/SCH900776, CCT244747, CCT245737, LY2603618, LY2606368/prexasertib, AB-IsoG, ARRY575, AZD7762, CBP93872, ESP01, GDC0425, SAR020106, SRA737, V158411 and VER250840; CHK2 inhibitors, such as CCT241533 and PV1019; ATM inhibitors, such as AZD0156, AZD1390, KU55933, M3541 and SX-RDS1; ATR inhibitors, such as AZD6738, BAY1895344, M4344 and M6620 (VX-970); and DNA-PK inhibitors, such as M3814.

The tumor metabolism inhibitor may be selected from the group consisting of inhibitors of the adenosine pathway, inhibitors of the tryptophan metabolism and inhibitors of the arginine pathway.

Examples for an inhibitor of the adenosine pathway are inhibitors of A2AR (adenosine A2A receptor), such as ATL-444, istradefylline (KW-6002), MSX-3, preladenant (SCH-420,814), SCH-58261, SCH412,348, SCH-442,416, ST-1535, caffeine, VER-6623, VER-6947, VER-7835, vipadenant (BIIB-014), ZM-241,385, PBF-509 and V81444; inhibitors of CD73, such as IPH53 and SRF373; and inhibitors of CD39, such as IPH52.

Examples for an inhibitor of the tryptophane metabolism are inhibitors of IDO, such as indoximod (NLG8189), epacadostat, navoximod, BMS-986205 and MK-7162; inhibitors of TDO, such as 680C91; and IDO/TDO dual inhibitors.

Examples for inhibitors of the arginine pathway are inhibitors of arginase, such as INCB001158.

The protein kinase inhibitor may be selected from the group consisting of receptor tyrosine kinase inhibitors, intracellular kinase inhibitors, cyclin dependent kinase inhibitors, phosphoinositide-3-kinase inhibitors, mitogen-activated protein kinase inhibitors, inhibitors of nuclear factor kappa-β kinase (IKK), and Wee-1 inhibitors.

Examples for receptor tyrosine kinase inhibitors are EGF receptor inhibitors, such as afatinib, cetuximab, erlotinib, gefitinib, pertuzumab and margetuximab; VEGF receptor inhibitors, such as axitinib, lenvatinib, pegaptanib and linifanib (ABT-869); C-KIT Receptor inhibitors, such as CDX0158 (KTN0158); ERBB2 (HER2) inhibitors, such as herceptin (trastuzumab); ERBB3 receptor inhibitors, such as CDX3379 (MEDI3379, KTN3379) and AZD8931 (sapitinib); FGF receptor inhibitors, such as erdafitinib; AXL receptor inhibitors, such as BGB324 (BGB 324, R 428, R428, bemcentinib) and SLC391; and MET receptor inhibitors, such as CGEN241.

Examples for intracellular kinase inhibitors are Bruton's tyrosine kinase (BTK) inhibitors, such as ibrutinib, acalabrutinib, GS-4059, spebrutinib, BGB-3111, HM71224, zanubrutinib, ARQ531, BI-BTK1 and vecabrutinib; spleen tyrosine kinase inhibitors, such as fostamatinib; Bcr-Abl tyrosine kinase inhibitors, such as imatinib and nilotinib; Janus kinase inhibitors, such as ruxolitinib, tofacitinib and fedratinib; and multi-specific tyrosine kinase inhibitors, such as bosutinib, crizotinib, cabozantinib, dasatinib, entrectinib, lapatinib, mubritinib, pazopanib, sorafenib, sunitinib, SU6656 and vandetanib.

One example of a tyrosine kinase inhibitor is a tyrosine kinase inhibitor ("TKI") conjugate or a pharmaceutically acceptable salt thereof, wherein said conjugate comprises a plurality of TKI moieties -D$_{TKI}$ covalently conjugated via at least one moiety -L$^1$-L$^2$- to a polymeric moiety Z, wherein -L$^1$- is covalently and reversibly conjugated to -D$_{TKI}$ and -L$^2$- is covalently conjugated to Z and wherein -L$^1$- is a linker moiety and -L$^2$- is a chemical bond or a spacer moiety, wherein the moieties -L$^1$-, -L$^2$- and Z are as described elsewhere herein for the conjugate of the present invention. In certain embodiments -D$_{TKI}$ is selected from the group consisting of receptor tyrosine kinase inhibitors, intracellular kinase inhibitors, cyclin dependent kinase inhibitors, phosphoinositide-3-kinase (PI3K) inhibitors, mitogen-activated protein kinase inhibitors, inhibitors of nuclear factor kappa-β kinase (IKK), and Wee-1 inhibitors. In certain embodiments -D$_{TKI}$ is axitinib. In certain embodiments -D$_{TKI}$ is lenvatinib. In certain embodiments -D$_{TKI}$ is pegaptanib. In certain embodiments -D$_{TKI}$ is linifanib.

Examples for cyclin dependent kinase inhibitors are ribociclib, palbociclib, abemaciclib, trilaciclib, purvalanol A, olomucine II and MK-7965.

Examples for phosphoinositide-3-kinase inhibitors are IPI549, GDc-0326, pictilisib, serabelisib, IC-87114, AMG319, seletalisib, idealisib and CUDC907.

Examples for mitogen-activated protein kinase inhibitors are Ras/farnesyl transferase inhibitors, such as tipirafinib and LB42708; Raf inhibitors, such as regorafenib, encorafenib, vemurafenib, dabrafenib, sorafenib, PLX-4720, GDC-0879, AZ628, lifirafenib, PLX7904 and RO5126766; MEK inhibitors, such as cobimetinib, trametinib, binimetinib, selumetinib, pimasertib, refametinib and PD0325901; ERK inhibitors, such as MK-8353, GDC-0994, ulixertinib and SCH772984.

Examples for inhibitors of nuclear factor kappa-β kinase (IKK) are BPI-003 and AS602868.

An example of a Wee-1 inhibitor is adavosertib.

The chemokine receptor and chemoattractant receptor agonist may be selected from the group consisting of CXC chemokine receptors, CC chemokine receptors, C chemokine receptors, CX3C chemokine receptors and chemoattractant receptors.

The CXC chemokine receptor may be selected from the group consisting of CXCR1 agonists, such as recombinant CXCL8 and recombinant CXCL6; CXCR2 agonists, such as recombinant CXCL8, recombinant CXCL1, recombinant CXCL2, recombinant CXCL3, recombinant CXCL5, recombinant CXCL6, MGTA 145 and SB251353; CXCR3 agonists, such as recombinant CXCL9, recombinant CXCL10, recombinant CXCL11 and recombinant CXCL4; CXCR4 agonists, such as recombinant CXCL12, ATI2341, CTCE0214, CTCE0324 and NNZ4921; CXCR5 agonists, such as recombinant CXCL13; CXCR6 agonists, such as recombinant CXCL16; and CXCL7 agonists, such as recombinant CXCL11.

The CC chemokine receptor may be selected from the group consisting of CCR1 agonists, such as recombinant CCL3, ECI301, recombinant CCL4, recombinant CCL5, recombinant CCL6, recombinant CCL8, recombinant CCL9/10, recombinant CCL14, recombinant CCL15, recombinant CCL16, recombinant CCL23, PB103, PB105 and MPIF1; CCR2 agonists, such as recombinant CCL2, recombinant CCL8, recombinant CCL16, PB103 and PB105; CCR3 agonists, such as recombinant CCL11, recombinant CCL26, recombinant CCL7, recombinant CCL13, recombinant CCL15, recombinant CCL24, recombinant CCL5, recombinant CCL28 and recombinant CCL18; CCR4 agonists, such as recombinant CCL3, ECI301, recombinant CCL5, recombinant CCL17 and recombinant CCL22; CCR5 agonists, such as recombinant CCL3, ECI301, recombinant CCL5, recombinant CCL8, recombinant CCL11, recombinant CCL13, recombinant CCL14, recombinant CCL16, PB103 and PB105; CCR6 agonists, such as recombinant CCL20; CCR7 agonists, such as recombinant CCL19 and recombinant CCL21; CCR8 agonists, such as recombinant CCL1, recombinant CCL16, PB103 and PB105; CCR9 agonists, such as recombinant CCL25; CCR10 agonists, such as recombinant CCL27 and recombinant CCL28; and CCR11 agonists, such as recombinant CCL19, recombinant CCL21 and recombinant CCL25.

The C chemokine receptors may be a XCR1 agonist, such as recombinant XCL1 or recombinant XCL2.

The CX3C chemokine receptors may be a CX3CR1 agonist, such as recombinant CX3CL1.

The chemoattractant receptors may be selected from the group consisting of formyl peptide receptor agonists, such as N-formyl peptides, N-formylmethionine-leucyl-phenylalanine, enfuvirtide, T21/DP107, annexin A1, Ac2-26 and Ac9-25; C5a receptor agonists; and chemokine-like receptor 1 agonists, such as chemerin.

The chemokine antagonists may be selected from the group consisting of inhibitors of CXCL chemokines, such as UNBS5162; inhibitors of CXCL8, such as BMS986253 and PA620; inhibitors of CXCL10, such as TM110, eldelumab and NI0801; inhibitors of CXCL12, such as NOX-A12 and JVS100; inhibitors of CXCL13, such as VX5; inhibitors of CCL2, such as PA508, ABN912, AF2838, BN83250, BN83470, C243, CGEN54, CNTO888, NOXE36, VT224 and SSR150106; inhibitors of CCL5, such as HGS1025 and NI0701; inhibitors of CCL2/CCL5, such as BKTP46; inhibitors of CCL5/FMLP receptor, such as RAP160; inhibitors of CCL11, such as bertilimumab and RAP701; inhibitors of CCL5/CXCL4, such as CT2008 and CT2009; inhibitors of CCL20, such as GSK3050002; and inhibitors of CX3CL1, such as quetmolimab.

The chemokine receptor antagonists may be selected from the group consisting of inhibitors of CXCR1, such as repertaxin, CCX832, FX68 and KB03; inhibitors of CXCR2, such as AZD5069, AZD5122, AZD8309, GSK1325756, GSK1325756H, PS291822, SB332235 and SB656933; inhibitors of CXCR1/CXCR2, such as DF1970, DF2156A, DF2162, DF2755A, reparixin, SX576, SX682, PACG31P, AZD4721 and PA401; inhibitors of CXCR3; inhibitors of CXCR4, such as BL8040; inhibitors of CXCR4/E-selectin, such as GMI1359; inhibitors of CXCR6, such as CCX5224; inhibitors of CCR1, such as AZD4818, BAY865047, BMS817399, CCX354, CCX634, CCX9588, CP481715, MLN3701, MLN3897, PS031291, PS375179 and PS386113; inhibitors of CCR2, such as AZD2423, BL2030, BMS741672, CCX140, CCX598, CCX872, CCX915, CNTX6970, INCB3284, INCB3344, INCB8696, JNJ17166864, JNJ27141491, MK0812, OPLCCL2LPM, PF4136309, serocion, STIB0201, STIB0211, STIB0221, STIB0232, STIB0234, TAK202, TPI526; inhibitors of CCR2/CCR5, such as PF04634817, RAP103 and TBR652; inhibitors of CCR2/CCR5/CCR8, such as RAP310; inhibitors of CCR3, such as ASM8, AXP1275, BMS639623, CM101, DPC168, GW766994, GW824575, MT0814, OPLCCL11LPM and QAP642; inhibitors of CCR4, such as AT008, AZD2098, CCX6239, FLX193, FLX475, GBV3019, GSK2239633, IC487892 and poteligeo; inhibitors of CCR5, such as 5P12-RANTES, AZD5672, AZD8566, CMPD167, ESN196, GSK706769, GW873140, HGS004, INCB15050, INCB9471, L872, microbicide, PF232798, PRO140, RAP101, SAR113244, SCH350634, SCH351125, SCH417690, selzentry, TAK779, TBR220, TD0232 and VX286; inhibitors of CCR5/CXCR4, such as AMD887, ND401 and SP01A; inhibitors of CCR6, such as CCX507, CCX9664 and STIB100X; inhibitors of CCR6, such as CCX025, CCX507, CCX807, eut22, MLN3126, POL7085, traficet-EN; inhibitors of CXCR3, such as AMG487, AT010, STIA120X; inhibitors of CXCR4, such as AD114, AD214, ALX0651, ALX40-4C, AMD070, AT007, AT009, BKT170, BMS936564, celixafor, CTCE9908, GBV4086, GSK812397, KRH2731, KRH3140, LY2510924, LY2624587, mozobil, OPLCXCL12LPM, PF06747143, POL6326, Q122, revixil, TG0054, USL311, X4P001 and X4P002; and inhibitors of CXCR7, such as CCX650 and CCX662.

The cytokine receptor agonist may be selected from the group consisting of mRNAs, DNAs or plasmids encoding the genes for IL-2, IL-15, IL-7, IL-10, IL-12, IL-21, IFNα IL-17, IFNβ, IFNγ, IL-18, IL-27, TNFα, GM-CSF, FLT3L, LTα, LTβ and TRAIL and recombinant proteins, such as agonists of IL-2/IL-15 β/γ receptors, agonists of IL-10 receptor, agonists of IL-12 receptor, agonists of IL-18 receptor, agonists of IL-21 receptor, agonists of IL-7 receptor, agonists of IFNα/β receptor, agonists of IFN γ receptor, agonists of FLT3 receptor, agonists of GM-CSF receptor, agonists of LTα receptor, agonists of LTβ receptor, and agonists of TNFα receptor.

Examples for agonists of IL-10 receptor are AG011, dekavil, EG10, IL10 Nanocap, Ilodecakin, AM0010, tenovil and VT310 VIRON.

Examples for agonists of IL-12 receptor are recombinant IL-12 p70, recombinant IL-12 p35, AM0012, AS1409, dodekin, HemaMax, LipoVIL12, MSB0010360N, Ad-RTS-hIL-12, tavokinogene telseplasmid, exoIL-12 and NHS-IL12.

An example for an agonist of IL-18 receptor is SB485232.

An example for an agonist of IL-21 receptor is BMS982470 (denenicokin).

Examples for agonists of IL-7 receptor are CYT107, CYT99007 and GX-17.

An example for an agonist of FLT3R is CDX-301.

Examples for agonist of TNFα receptor are L19-TNFα, aurimune, beromun, BreMel/TNFα, fibromun, refnot and TNFPEG20.

The death receptor agonists may be selected from the group consisting of TRAILR1/DR4 agonists, such as AMG951 (dulanermin), APG350, APG880, HGSETR1 (mapatumumab) and SL231; and TRAILR2/DR5 agonists, such as AMG655, DS8273, HGSETR2 (lexatumumab), HGSTR2J, IDD004/GEN1029, INBRX109, LBY135, MEDI3039, PRO95780, RG7386 and TAS266.

The CD47 antagonists may be selected from the group consisting of ALX148, CC-90002, Hu5F9G4, SRF231, TI061, TTI-621, TTI-622, AO176, IBI188, IMC002, recombinant SIRPα and LYN00301.

An example for a SIRPα antagonist is FSI89 or recombinant CD47.

Examples for oncolytic drugs are CAVATAK, BCG, mobilan, TG4010, Pexa-Vec (JX-594), JX-900, JX-929 and JX-970.

Examples for signal converter proteins are Fn14-TRAIL (KAHR101), CD80-Fc (FTP155), CTLA4-FasL (KAHR102), PD1-41BBL (DSP 105), PD-L1-41BB (PRS-344, NM21-1480, FS222), PD1-CD70 (DSP 106) and SIRPα-41BBL (DSP 107).

The epigenetic modifiers may be selected from the group consisting of DNA methyltransferase inhibitors, lysine-specific demethylase 1 inhibitors, Zeste homolog 2 inhibitors, bromodomain and extra-terminal motif (BET) protein inhibitors such as GSK525762, and histone deacetylase (HDAC) inhibitors such as beleodaq, SNDX275 and CKD-M808.

Examples for tumor peptides/vaccines are NY-ESO, WT1, MART-1, 10102 and PF-06753512 and personalized cancer vaccines using patient derived tumor sequences or neoantigens.

Examples for heat shock protein (HSP) inhibitors are inhibitors of HSP90, such as PF-04929113 (SNX-5422).

Examples of proteolytic enzymes are recombinant hyaluronidase, such as rHuPH20 and PEGPH20.

The ubiquitin and proteasome inhibitors may be selected from the group consisting of ubiquitin-specific protease (USP) inhibitors, such as P005091; 20S proteasome inhibitors, such as bortezimib, carfilzomib, ixazomib, oprozomib, delanzomib and celastrol; and immunoproteasome inhibitors, such as ONX-0914.

The adhesion molecule antagonists may be selected from the group consisting of β2-integrin antagonists and selectin antagonists.

The hormones may be selected from the group consisting of hormone receptor agonists and hormone receptor antagonists.

An example for a hormone receptor agonist are somatostatin receptor agonists, such as somatostatin, lanreotide, octreotide, FX125L, FX141L and FX87L.

Example for hormone receptor antagonists are anti-androgens, anti-estrogens and anti-progestogens. Examples for anti-androgens are steroidal antiandrogens, such as cyproterone acetate, megestrol acetate, chlormadinone acetate, spironolactone, oxendolone and osaterone acetate; non-steroidal anti-androgens, such as flutamide, bicalutamide, nilutamide, topilutamide, enzalutamide and apalutamide; androgen synthesis inhibitors, such as ketoconazole, abiraterone acetate, seviteronel, aminoglutethimide, finasteride, dutasteride, episteride and alfatradiol. Examples for anti-estrogens are selective estrogen receptor modulators (SERMs), such as tamoxifen, clomifene, Fareston and raloxifene; ER silent antagonists and selective estrogen receptor degrader (SERD), such as fulvestrant; aromatase inhibitors, such as anastrozole, letrozole, exemestane, vorozole, formestane and fadrozole; and anti-gonadotropins, such as testosterone, progestogens and GnRH analogues. Examples for anti-progestogens are mifepristone, lilopristone and onapristone.

Examples of cellular therapy include CAR therapies such as CAR-T therapies such as tisagenlecleucel, axicabtagene ciloleucel, bb21217, LCAR-B38M, JCARH125, MCARH171, JNJ-4528, idecabtagene vicleucel (bb2121), SCRI-CAR19x22; CAR therapies targeting tumor antigens such as CAR therapies targeting CD19 expressing cells, CAR therapies targeting CD22 expressing cells, CAR therapies targeting BCMA expressing cells, CAR therapies targeting HER2 expressing cells, CAR therapies targeting CD138 expressing cells, CAR therapies targeting CD133 expressing cells, CAR therapies targeting BCMA expressing cells, CAR therapies targeting CEA expressing cells, CAR therapies targeting Claudin 18.2 expressing cells, CAR therapies targeting EGFR expressing cells, CAR therapies targeting EGFRvIII expressing cells, CAR therapies targeting Eph2A expressing cells, CAR therapies targeting EpCAM expressing cells, CAR therapies targeting GD2 expressing cells, CAR therapies targeting GPC3 expressing cells, CAR therapies targeting MSLN expressing cells, CAR therapies targeting 5T4 expressing cells, CAR therapies targeting LMP1 expressing cells, CAR therapies targeting PD-L1 expressing cells, CAR therapies targeting PSMA expressing cells, CAR therapies targeting FRα expressing cells, and CAR therapies targeting MUC1 expressing cells. Examples of cellular therapy include TIL therapy, NK therapy, Cytokine induced memory NK cell therapy, NK cell therapy with ex vivo expanded cells. Examples of cellular therapy include therapy with αβ or γδ T cells which may be engineered to express a tumor antigen or tumor neoantigen specific T Cell Receptor or which may have been expanded in the context of tumor antigen or tumor neoantigens.

In certain embodiments the IL-2 protein of formula (I), the IL-2 conjugate or the pharmaceutical composition of the present invention, together with one or more additional drug elicits epitope spreading. Epitope spreading has the advantages described elsewhere herein. In certain embodiments one such additional drug is the conjugate comprising a polymer, to which one or more moieties of formula (A-i), as described elsewhere herein.

In certain embodiments the patient is a mammalian patient, such as a human patient.

Administration of the IL-2 protein of formula (I), the IL-2 conjugate or the pharmaceutical composition as described herein may be done by external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection and infusion, direct delivery to the brain via implanted device allowing delivery of the invention or the like to brain tissue or brain fluids (e.g., Ommaya Reservoir), direct intracerebroventricular injection or infusion, injection or infusion into brain or brain associated regions, injection into the subchoroidal space, retro-orbital injection and ocular instillation, preferably via subcutaneous injection. In certain embodiments administration is via subcutaneous injection.

In certain embodiments the IL-2 conjugate of the present invention comprises the IL-2 protein of formula (I) expressed in a mammalian system.

In certain embodiments the IL-2 conjugate of the present invention comprising an IL-2 protein of formula (I) expressed in a mammalian expression system may after administration to cynomolgus macaques exhibit an at least 1.1-fold longer, such as an at least 1.2-fold, 1.3-fold, 1.4-fold, 1.5-fold or 2-fold, pharmacokinetic half-life in vivo of the released IL-2 protein than the corresponding IL-2 conjugate comprising an IL-2 protein having the sequence of the IL-2 protein of formula (I) without the N-terminal alanine, wherein the IL-2 protein without the N-terminal alanine was expressed in an *E. coli* expression system.

In certain embodiments the IL-2 conjugate of the present invention comprising an IL-2 protein of formula (I) expressed in a mammalian expression system may after administration to cynomolgus macaques exhibit an at least 1.1-fold longer, such as an at least 1.2-fold, 1.3-fold, 1.4-fold, 1.5-fold or 2-fold, circulation half-life in vivo of the IL-2 conjugate than the corresponding IL-2 conjugate comprising an IL-2 protein having the sequence of the IL-2 protein of formula (I) without the N-terminal alanine, wherein the IL-2 protein without the N-terminal alanine was expressed in an *E. coli* expression system.

In certain embodiments the IL-2 conjugate of the present invention comprising an IL-2 protein of formula (I) expressed in a mammalian expression system exhibits after administration to cynomolgus macaques an at least 1.1-fold higher, such as an at least 1.2-fold, 1.3-fold, 1.4-fold, 1.5-fold or 2-fold, peak or area under the curve (AUC) value for at least one cell type selected from the group consisting of for CD8+ T cells, memory (CD28+ CD95+) CD8+ T cells, NK cells, γδ T cells, the percentage of Ki67+ cells within CD8+ T cells, the percentage of Ki67+ cells within memory (CD28+ CD95+) CD8+ T cells, the percentage of Ki67+ cells within NK cells and the percentage of Ki67+ cells within γδ T cells compared to administration of the corresponding IL-2 conjugate comprising an IL-2 protein having the sequence of the IL-2 protein of formula (I) without the N-terminal alanine, wherein the IL-2 protein without the N-terminal alanine was expressed in an *E. coli* expression system.

In another aspect the present invention relates to an IL-2 protein sequence of formula (I-i)

SEQ A-Cys*-SEQ B (I-i), wherein

SEQ A has at least 94% sequence identity to SEQ ID NO:1;

SEQ B has at least 94% sequence identity to SEQ ID NO:2;

Cys* is a cysteine residue.

Specific embodiments for SEQ A and SEQ B are as disclosed for the IL-2 protein of formula (I).

In certain embodiments the IL-2 protein of formula (I-i) has the sequence of SEQ ID NO:21.

In another aspect the present invention relates to an oligonucleotide sequence encoding the IL-2 protein of formula (I-i). Specific embodiments for such oligonucleotides are as described elsewhere herein for the oligonucleotides encoding the IL-2 protein of formula (I).

In another aspect the present invention relates to a conjugate comprising one or more of the IL-2 proteins of formula (I-i). Specific embodiments for this conjugate comprising one or more of the IL-2 proteins of formula (I-i) are as described elsewhere herein for the conjugates comprising one or more of the IL-2 proteins of formula (I).

In another aspect the present invention relates to a pharmaceutical composition comprising at least one IL-2 protein of formula (I-i) or at least one IL-2 conjugate comprising one or more such IL-2 proteins of formula (I-i) and at least one excipient. Specific embodiments for such pharmaceutical composition are as described elsewhere herein for the pharmaceutical compositions comprising at least one IL-2 proteins of formula (I) or at least one IL-2 conjugate comprising one or more of the IL-2 proteins of formula (I).

Another aspect relates to the IL-2 protein of formula (I-i), the IL-2 conjugate comprising at least one IL-2 protein of formula (I-i) or the pharmaceutical composition comprising such IL-2 protein or IL-2 conjugate for use as a medicament.

Another aspect relates to the IL-2 protein of formula (I-i), the IL-2 conjugate comprising at least one IL-2 protein of formula (I-i) or the pharmaceutical composition comprising such IL-2 protein or IL-2 conjugate for use in the treatment of a disease which can be treated with IL-2. Specific embodiments for the disease which can be treated with IL-2 are as described elsewhere herein.

Another aspect relates to the IL-2 protein of formula (I-i), the IL-2 conjugate comprising at least one IL-2 protein of formula (I-i) or the pharmaceutical composition comprising such IL-2 protein or IL-2 conjugate for the manufacture of a medicament for treating a disease which can be treated with IL-2. Specific embodiments for the disease which can be treated with IL-2 are as described elsewhere herein.

Another aspect relates to a method of treating, controlling, delaying or preventing in a mammalian patient, preferably a human patient, in need of the treatment of one or more diseases which can be treated with IL-2, comprising the step of administering to said patient in need thereof a therapeutically effective amount of the IL-2 protein of formula (I-i), the IL-2 conjugate comprising at least one IL-2 protein of formula (I-i) or the pharmaceutical composition comprising such IL-2 protein or IL-2 conjugate. Specific embodiments for the disease which can be treated with IL-2 are as described elsewhere herein.

In certain embodiments the IL-2 protein of formula (I-i), the IL-2 conjugate comprising at least one IL-2 protein of formula (I-i) or the pharmaceutical composition comprising such IL-2 protein or IL-2 conjugate is administered to the patient prior to, simultaneously with, or after administration of one or more additional drug. Specific embodiments for such one or more additional drug are as described elsewhere herein. In certain embodiments the IL-2 has the sequence of SEQ ID NO:21 and the one additional drug to be administered to a patient is a conjugate comprising a polymer, to which one or more moieties of formula (A-i) are conjugated as described elsewhere herein.

In another aspect the present invention relates to an IL-2 protein sequence of formula (I-ii)

X-SEQ A-Cys*-SEQ B     (I-ii), wherein
SEQ A has at least 94% sequence identity to SEQ ID NO:1;
SEQ B has at least 94% sequence identity to SEQ ID NO:2;
X is an amino acid residue selected from the group consisting of arginine, asparagine, aspartic acid, cysteine, glutamine, glutamic acid, glycine, histidine, isoleucine, leucine, lysine, methionine, phenylalanine, serine, threonine, tryptophan, tyrosine and valine; and
Cys* is a cysteine residue.

Specific embodiments for SEQ A and SEQ B are as disclosed for the IL-2 protein of formula (I).

In certain embodiments X of formula (I-ii) is an arginine residue. In certain embodiments X of formula (I-ii) is an asparagine residue. In certain embodiments X of formula (I-ii) is an aspartic acid residue. In certain embodiments X of formula (I-ii) is a cysteine residue. In certain embodiments X of formula (I-ii) is a glutamine residue. In certain embodiments X of formula (I-ii) is a glutamic acid residue. In certain embodiments X of formula (I-ii) is a glycine residue. In certain embodiments X of formula (I-ii) is a histidine residue. In certain embodiments X of formula (I-ii) is an isoleucine residue. In certain embodiments X of formula (I-ii) is a leucine residue. In certain embodiments X of formula (I-ii) is a lysine residue. In certain embodiments X of formula (I-ii) is a methionine residue. In certain embodiments X of formula (I-ii) is a phenylalanine residue. In certain embodiments X of formula (I-ii) is a serine residue. In certain embodiments X of formula (I-ii) is a threonine residue. In certain embodiments X of formula (I-ii) is a tryptophan residue. In certain embodiments X of formula (I-ii) is a tyrosine residue. In certain embodiments X of formula (I-ii) is a valine residue.

In another aspect the present invention relates to an oligonucleotide sequence encoding the IL-2 protein of formula (I-ii). Specific embodiments for such oligonucleotides are as described elsewhere herein for the oligonucleotides encoding the IL-2 protein of formula (I), with the exception that the IL-2 protein of formula (I) is replaced with the IL-2 protein of formula (I-ii).

In another aspect the present invention relates to a conjugate comprising one or more of the IL-2 proteins of formula (I-ii). Specific embodiments for this conjugate comprising one or more of the IL-2 proteins of formula (I-ii) are as described elsewhere herein for the conjugates comprising one or more of the IL-2 proteins of formula (I), with the exception that the IL-2 protein of formula (I) is replaced with the IL-2 protein of formula (I-ii).

In another aspect the present invention relates to a pharmaceutical composition comprising at least one IL-2 protein of formula (I-ii) or at least one IL-2 conjugate comprising one or more such IL-2 proteins of formula (I-ii) and at least one excipient. Specific embodiments for such pharmaceutical composition are as described elsewhere herein for the pharmaceutical compositions comprising at least one IL-2 proteins of formula (I) or at least one IL-2 conjugate comprising one or more of the IL-2 proteins of formula (I), with the exception that the IL-2 protein of formula (I) is replaced with the IL-2 protein of formula (I-ii).

Another aspect relates to the IL-2 protein of formula (I-ii), the IL-2 conjugate comprising at least one IL-2 protein of formula (I-ii) or the pharmaceutical composition comprising such IL-2 protein or IL-2 conjugate for use as a medicament.

Another aspect relates to the IL-2 protein of formula (I-ii), the IL-2 conjugate comprising at least one IL-2 protein of formula (I-ii) or the pharmaceutical composition comprising such IL-2 protein or IL-2 conjugate for use in the treatment of a disease which can be treated with IL-2. Specific embodiments for the disease which can be treated with IL-2 are as described elsewhere herein.

Another aspect relates to the IL-2 protein of formula (I-ii), the IL-2 conjugate comprising at least one IL-2 protein of formula (I-ii) or the pharmaceutical composition comprising such IL-2 protein or IL-2 conjugate for the manufacture of a medicament for treating a disease which can be treated with IL-2. Specific embodiments for the disease which can be treated with IL-2 are as described elsewhere herein.

Another aspect relates to a method of treating, controlling, delaying or preventing in a mammalian patient, preferably a human patient, in need of the treatment of one or more diseases which can be treated with IL-2, comprising the step of administering to said patient in need thereof a therapeutically effective amount of the IL-2 protein of formula (I-ii), the IL-2 conjugate comprising at least one IL-2 protein of formula (I-ii) or the pharmaceutical composition comprising such IL-2 protein or IL-2 conjugate. Specific embodiments for the disease which can be treated with IL-2 are as described elsewhere herein.

In certain embodiments the IL-2 protein of formula (I-ii), the IL-2 conjugate comprising at least one IL-2 protein of formula (I-ii) or the pharmaceutical composition comprising such IL-2 protein or IL-2 conjugate is administered to the patient prior to, simultaneously with, or after administration of one or more additional drug. Specific embodiments for such one or more additional drug are as described elsewhere herein.

Materials and Methods

Materials
All materials were commercially available except where stated otherwise.

Concentration determinations of protein solutions were performed on a Tecan Infinite M200 using UV-cuvette micro (neoLAB) and the following conditions: path length 1 cm; absorbance wavelength 280 nm; absorbance wavelength bandwidth 5 nm; reference wavelength 338 nm; reference wavelength bandwidth 25 nm; number of flashes 25. Calculation of the concentration was based on calculated molecular weight of the protein without taking glycosylation or PEGylation into account and calculated extinction coefficient based on sequence.

5 kDa PEG maleimide was purchased from NOF Europe (Sunbright ME-050MA, CAS 883993-35-9, NOF Europe N.V., Grobbendonk, Belgium) and has the structure

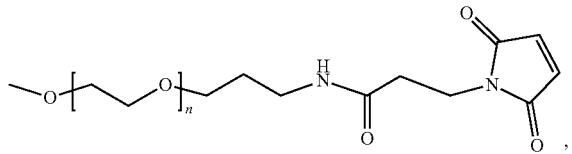

wherein n is an integer in the range of 100 to 125, and an average molecular weight of 5 kDa.

5 kDa PEG maleimide was purchased from Jenkem Technology (M-Mal-5000, Jenkem Technology Co., Beijing, China) and has the structure

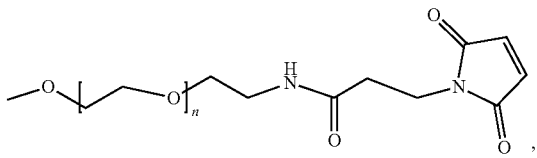

wherein n is an integer in the range of 100 to 125, and an average molecular weight of 5 kDa.

10 kDa PEG maleimide was purchased from NOF Europe (Sunbright ME-100MA, CAS 883993-35-9, NOF Europe N.V., Grobbendonk, Belgium) and has the structure

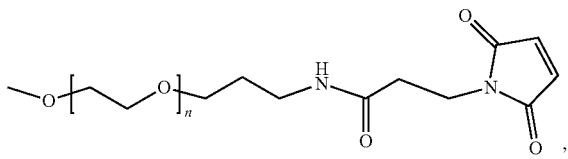

wherein n is an integer in the range of 200 to 250, and an average molecular weight of 10 kDa.

30 kDa PEG maleimide was purchased from NOF Europe (Sunbright ME-300MA, CAS 883993-35-9, NOF Europe N.V., Grobbendonk, Belgium) and has the structure

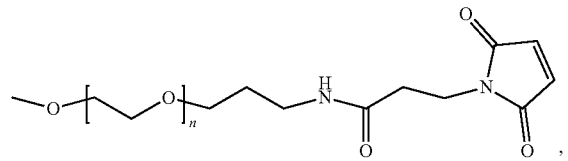

wherein n is an integer in the range of 650 to 700, and an average molecular weight of 30 kDa.

EXAMPLES

Example 1: Expression of IL-2 Muteins M1 and Ala-M1 in *Pichia pastoris*

The DNA sequences encoding IL-2 mutein M1 (SEQ ID NO:16) and IL-2 mutein Ala-M1 (SEQ ID NO:17) were obtained by reverse translation of the amino acid sequences (M1=reference material without the N-terminal alanine, SEQ ID NO:18; and Ala-M1, SEQ ID NO:14). The DNA sequences were generated based on the back-translated amino acid sequences and subsequently codon-optimized for expression in *Pichia pastoris* (Komagataella phaffii). DNA encoding M1 and Ala-M1 was custom synthesized and cloned. In these cloning vectors, the DNA sequences encoding M1 and Ala-M1 are flanked by BspQ1 restriction sites.

The expression vector contained the G1-3 promoter (Glucose inducible), AOX1 TT integration site (single copy), alpha mating factor signal sequence (αMF), lacZ fragment for cloning purposes only, and Zeocin™ resistance. For expression of M1 in *Pichia pastoris*, the plasmid pCSP1007 (SEQ ID NO:19) was constructed by ligation of the linear approximately 4440 bp BspQI fragment of the expression vector containing the leader sequence αMF, with the linear 399 bp BspQI digested fragment from the cloning vector. For expression of Ala-M1 in *Pichia pastoris*, plasmid pCKP1036 (SEQ ID NO:20) was similarly constructed by ligation of the approximately 4440 bp BspQI fragment of the expression vector with the linear 402 bp BspQI digested fragment from the cloning vector. Subsequently, chemically competent DH10B cells were transformed with the ligation mix. After plasmid purification and restriction digest analysis, the gene of interest in the newly generated plasmids was confirmed by sequencing and the strain LP2 (CBS7435) was transformed with the linearized plasmids pCSP1007 or pCKP1036 for subsequent multi copy screening.

After linearization of the plasmids pCSP1007 and pCKP1036 with AscI, the LP2 strain was transformed with the linearized plasmids and plated out onto agar plates containing different concentrations of Zeocin™ (Invitrogen) (500 and 1000 µg/mL). After incubation at 30° C. for 48 h, 11-12 clones per host/plasmid integration were picked and streaked out onto master plates (containing 100 µg/mL Zeocin™) for subsequent expression screening in 24 well plates. Expression experiments were done in 24 well plates (GE Healthcare Life sciences) containing complex media. The main cultures (2 mL) were inoculated to a start OD600 of 4 with overnight cultures grown at 30° C. in YPG (Yeast Peptone Glycerol). Subsequently, the cultures were incubated at 25° C. and 260 rpm shaking and induced by glucose limitation for 48 hrs.

Detection of product in the culture supernatant was performed by SDS PAGE with coomassie stain. The SDS-PAGE was run under reducing conditions. Pre-casted Criterion 12% Bis-Tris SDS gels (Bio-Rad) were used with MES buffer (Bio-Rad). Samples were mixed with NuPAGE 4×LDS loading buffer (Invitrogen) and incubated for 5 min at 95° C. Per lane, 20 µL sample (30 µL culture supernatant, plus 10 µL 4×LDS loading buffer) was loaded. As a molecular weight standard, Mark12 (Invitrogen) was loaded. As reference, 2 µg recombinant IL-2 purchased from Abcam was loaded. Electrophoresis was done for approximately 80 min at 200 V. The separated proteins were visualized by staining with GelCode Blue Stain Reagent (Thermo Scientific) for 1-2 h and destained with water overnight.

Detection of product was also performed by Western blot. For this purpose, the SDS-PAGE was run under reducing conditions. Pre-casted Criterion 12% Bis-Tris SDS gels (Bio-Rad) were used with MES buffer (Bio-Rad). Samples were mixed with NuPAGE 4×LDS loading buffer, reducing conditions (Invitrogen) and incubated for 5 min at 95° C. Per lane, 20 µL sample (30 µL culture supernatant, plus 10 µL 4×LDS loading buffer) was loaded. As a molecular weight standard, SuperSignal Enhanced Molecular Weight Protein Ladder (Thermo Scientific) was loaded. As reference, 0.5 µg recombinant IL-2 purchased from Abcam was loaded. Electrophoresis was done for approx. 60 min at 200 V. The separated proteins were transferred onto a Nitrocellulose membrane (Bio-Rad) using Turboblot (Bio-Rad) for 7 minutes at 25 V. Subsequently, the blots were incubated for 1 h in blocking buffer (TBS+5% milk powder (Merck)). Subsequently, the membrane was incubated for 1 hr in primary antibody solution (TBST+1.5% milk powder+0.1-0.2 ug/mL rabbit Anti-IL-2 antibody (AbCam)). After washing for 3× 5 min in MQ water, the membrane was incubated for 60 min in secondary antibody solution (TBST+1.5% milk powder+1:1000 anti-rabbit-IgG-HRP (AbCam)). After washing (4× 5 min in TBST), the blot was then subjected to Lumi-Light substrate solution (Roche LumiLight Kit) and analyzed with the GeneGnome imaging system.

Results: Among the tested M1 clones, no or very low amounts of secreted M1 product in the culture supernatant could be identified with SDS-PAGE/Coomassie stain. Selected samples were analyzed via Western blot using antibodies against IL-2, confirming the presence of the M1 product in the culture supernatant. However, only a very weak band could be detected at the expected molecular weight, whereas significant product aggregation was seen, in addition to weak degradation bands.

Unlike for M1, the western blot for Ala-M1 containing samples showed a band at the expected size, confirming the expression and secretion of Ala-M1. A weak band indicating dimer formation was also detected.

Example 2: Expression of IL-2 Mutein M1 and IL-2 Mutein Ala-M1 in CHO

The CHO K1 host cell was cultured in CD CHO media (Invitrogen) containing 4 mM Glutamine (J. T Baker) and 1% HT Supplement (Invitrogen) to PDL 30-100 before transient transfection with the product. The CHO Ki host cell was cultured in WAVE bag (36.5° C., pH 6.9-7.2, DO 40-100%).

The amino acid sequences of M1 (SEQ ID NO:18) and Ala-M1 (SEQ ID NO:14) were backtranslated and codon optimized for expression in CHO cells, each in combination with two different N-terminal secretion signal sequences, S1 (SEQ ID NO:47) and S2 (SEQ ID NO:48). The resulting DNA sequences encoding S1-M1, S2-M1, S1-Ala-M1 and S2-Ala-M1 were custom synthesized and cloned into an expression vector downstream of the Human cytomegalovirus (CMV) promoter. In addition to the CMV promoter, the expression vector contained the Thymidine kinase polyadenylation signal (TK pA), the pUC origin of replication, and the Ampicillin(bla) resistance gene. The resulting plasmids (P1 for S1-M1, P2 for S2-M1, P3 for S1-Ala-M1 and P4 for S2-Ala-M1) were maxi-prepared from Top10 *E. coli* cells using NucleoBond Xtra Maxi Kit (Macherey Nagel) for transient expression in CHO K1 cells.

The transient transfection was performed in shake flasks by mixing CHO K1 host cells with polyethylenimine and plasmid DNA. 6 mg DNA was transfected into each 1 L cells with ~16×10$^6$ cells/ml and the mass ratio between DNA and PEI was 1:3. CHO K1 host cells were cultured by perfusion with CD CHO medium in WAVE bags 96 hours before transfection. Cell density was counted using Vi-CELL (Beckman Coulter). A fixed volume of host cell culture was diluted by BM003H medium (WuXi Biologics) in 1:1 ratio. The cell density was adjusted to approximately 18×10$^6$ cells/ml by pre-warmed fresh BM017H medium prior to transfection. The diluted host cells were incubated in a shaker (36.5° C., 85% humidity, 6% $CO_2$, 120 rpm) before use.

The transfected cell cultures were incubated in Kuhner shakers at 36.5° C., 85% humidity, 6% $CO_2$, 120 rpm for 4 hours. Supplements were added and the transfected cultures were then incubated in Kuhner shaker at 31° C., 85% humidity, 6% $CO_2$, 120 rpm for 14 days. Supplements were fed on day 4, day 7 and day 11 after transfection depending on the cell viability and VCD. Glucose was added into the cultures to maintain the glucose level >2 g/L. Cultures were harvested on day 14 or when cell viability was below 60%.

Detection of product was performed by Western blot. Cultivations were harvested on day 14 after transfection. 0.5 ml cell culture was centrifuged at 12000 g for 30 min and supernatants were kept for western blot analysis. The cell pellets were collected and re-suspended into 0.5 mL PBS, and then disrupted by sonication at 4° C. Sonication solution was centrifuged at 12,000 g for 30 min. Total sonication solution and supernatant separated by centrifugation were collected for Western blot analysis.

1 µl sample from cell culture medium supernatants (CMS), cell ultrasonic lysis supernatants (CLS) and cell ultrasonic lysis total (CLT) was added into 10 µl 2× reduced LDS Sample buffer (Invitrogen). The reduced mixtures were heated at 95° C. for 5 min. All reduced samples were loaded on pre-casted NuPAGE 4-12% Bis-Tris Gels (Invitrogen). SDS-PAGE was run at a constant voltage of 180 V for 40 min. Samples were transferred from SDS-PAGE to PVDF membrane. The transfer process was executed at 25 V and 1.3 A for 7 min. The PVDF membrane was incubated with Blocker buffer (Bio-Rad) for 30 min. After block treatment, the PVDF membrane was incubated with primary antibody (anti-IL-2 antibody produced in chicken, Sigma) for 2 h at room temperature. The PVDF membrane was washed with TBST for 3× 5 min. Afterwards, the PVDF membrane was incubated with secondary antibody (goat anti-Chicken IgY (H+L) Secondary Antibody, HRP, Invitrogen) for 2 h at room temperature. The PVDF membrane was washed with TBST for 3× 5 min. ECL substrate solution A and B (Bio-Rad) were mixed and added to the PVDF membrane for 2 min incubation. The PVDF membrane was analyzed with the Chemi DOC MP Imaging System (Bio-Rad).

Western blot analysis of reduced samples of culture supernatants from cells transfected with S1-M1 P1 and S2-M1 P2 showed nearly undetectable levels of IL-2 product of the expected size, whereas clear product bands of the expected size was detected in the supernatants from cells transfected with S1-Ala-M1 P3 and S2-Ala-M1 P4. For all samples a double IL-2 product band was observed, as expected for non-glycosylated and O-glycosylated product. The concentrations of secreted product in the supernatants were quantified to approximately 6 mg/L for S1-M1 P1 and S2-M1 P2, 76 mg/L for S1-Ala-M1 P3 and 148 mg/L for S2-Ala-M1 P4.

Western blot analysis of reduced samples from lysed cells showed a clear band of the expected size for all samples. The product concentrations in the cell lysis samples were quantified to 153 mg/L for S1-M1 P1, 161 mg/L for S1-Ala-M1 P3 and 209 mg/L for S2-Ala-M1 P4. The fraction of secreted product of total product (secreted product/[secreted product+intracellular product]) was therefore approximately 4% for S1-M1 P1, 32% for S1-Ala-M1 P3 and 41% for S2-Ala-M1 P4).

Example 3: Purification of Culture Supernatants

Cultivations were harvested on day 14 by centrifugation at 8000 g for 40 min. Filtered supernatants were purified for further characterization of IL-2 mutein Ala-M1. The supernatant was concentrated and loaded onto a Superdex 75 prep grade column (GE Healthcare Life Sciences, now Cytiva) equilibrated in 25 mM Tris, 200 mM NaCl pH 8.0. Fractions were analyzed by SDS-PAGE and fractions containing target protein were pooled. Further purification was done by cation exchange chromatography on an SP Sepharose HP column (GE Healthcare Life Sciences, now Cytiva) equilibrated in 25 mM Na-acetate pH 5.5. Before loading, the protein pool was pH adjusted to 5.5 and diluted with water. Elution was done by linear salt gradient elution. Fractions were analyzed by SDS-PAGE and those containing target protein were pooled to give purified IL-2 mutein Ala-M1 1 (SEQ ID NO:14 with an additional cysteine or glutathione connected to the thiol group of the cysteine at position 38 via a disulfide bridge).

Example 4: Preparation of an IL-2 Mutein Ala-M1 Polymer Prodrug 5

45 mL of purified IL-2 mutein Ala-M1 1 (SEQ ID NO:14) formulated at 0.2 mg/mL in 25 mM sodium acetate, 200 mM NaCl, pH 5.5, were mixed with 13.5 mL 0.5 M sodium phosphate, pH 7.4 and concentrated in Amicon Ultra-15, Ultracel 3 K centrifugation filters (Merck Millipore) to 3.1 mL with 1 at 2.5 mg/mL. 9.1 mg of TCEP were dissolved in 635 µL PBS pH 7.4 to give a 50 mM solution. No adjustment of the pH was performed. 37 µL of the TCEP solution were added to the concentrated protein solution. The sample was incubated at ambient temperature for 30 min. Subsequently, 507 µL of 5 mM 5 kDa PEG maleimide (Sunbright ME-050MA, CAS 883993-35-9, NOF Europe N.V., Grobbendonk, Belgium) in PBS, pH 7.4 (5 mol. eq.) were added to the reaction solution. After incubation at ambient temperature for 30 min, the formation of conjugates was confirmed by analytical size exclusion chromatography. The buffer of the conjugation mixture was exchanged to 100 mM borate, pH 9.0 using an Aekta system equipped with a HiPrep Desalting 26/10 column. The sample was incubated at 25° C. overnight to give unpurified IL-2 mutein conjugate Ala-M1-5 kDa PEG 3. The reaction mixture was then concentrated to 5.2 mg/mL using Amicon Ultra-15, Ultracel 3 K centrifugation filters (Merck Millipore). 0.109 g of 40 kDa mPEG-linker reagent (synthesis can be performed as described for the compound 17ca in the patent WO2009/133137 example 7 using compound 16c and 1A from the same patent) were dissolved in 1.26 mL cold water to give a stock solution of 2.1*10-3 mol/L. The solution was stored on ice. 1.34 mL of the protein solution were diluted to 4 mg/mL by addition of 100 mM borate, pH 9.0, then 873 µL of the cooled 40 kDa mPEG-linker reagent stock solution were added (corresponding to 4 mol. eq. with respect to the protein).

The conjugation mixture was placed in a water bath at 14° C. for 2 h. The pH was shifted to pH 4 by addition of 872 µL of water and 3.488 mL of 200 mM sodium acetate, pH 3.6. After incubation at 25° C. overnight, the conjugate with one single 40 kDa mPEG linker attached (monoconjugate) was isolated from the reaction mixture using a HiScreen Capto MMC ImpRes column (column dimension: 0.77×10 cm) connected to an Aekta system. A flow rate of 1.2 mL/min and a linear gradient from 10 mM succinic acid, pH 5.5 to 80% of 10 mM succinic acid, 1 M NaCl, pH 5.5 in 12 column volumes was applied. The peak containing mainly monoconjugate eluting during the gradient was identified by analytical size exclusion chromatography. The salt content of this fraction was adjusted to 150 mM NaCl by addition of 10 mM succinic acid, 1 M NaCl, pH 5.5, then the fraction was concentrated to 2.48 mL in Amicon Ultra-15, Ultracel 10 K filters (Merck Millipore). The concentrated solution (2.48 mL) was diluted with 130 µL of 10 mM succinic acid, 150 mM NaCl, 1% Tween20, pH 5.5 and 165 µL of 10 mM succinic acid, 150 mM NaCl, 0.05% Tween20, pH 5.5 to a final concentration of 1 mg/mL 1 equivalents (based on molecular weight of the protein without taking the glycosylation into account) to create compound 5, which has the following structure

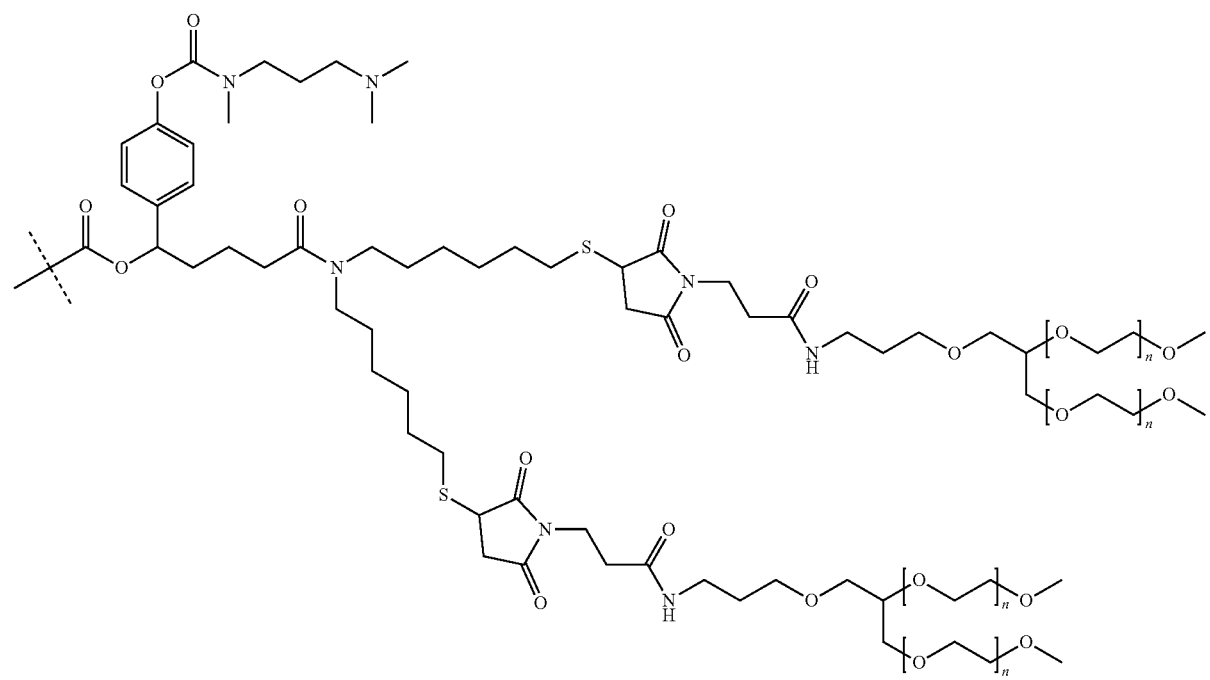

5 wherein the dashed line indicates attachment to a nitrogen of a primary amine of the N-terminus or a lysine side chain of 3 and each n is an integer from 200 to 250.

Example 5: Preparation of an IL-2 Mutein Ala-M1 Polymer Prodrug 6

12 mL of purified IL-2 mutein Ala-M1 1 (SEQ ID NO:14) formulated at 2.5 mg/mL in 20 mM sodium phosphate, 140 mM NaCl, pH 7.4 were used as starting protein solution. 15.3 mg of TCEP. HCl were dissolved in 1068 μL PBS pH 7.4 to give a 50 mM solution. No adjustment of the pH was performed. 93.3 μL of the TCEP solution were added to the concentrated protein solution. The sample was incubated at ambient temperature for 30 min. Subsequently, 1123 μL of 5 mM 5 kDa PEG maleimide (M-Mal-5000, Jenkem Technology Co., Beijing, China) in PBS, pH 7.4 (3 mol. eq.) were added to the reaction solution. After incubation at ambient temperature for 30 min, the formation of conjugates was confirmed by analytical size exclusion chromatography. The buffer of the conjugation mixture was exchanged to 100 mM borate, pH 9.0 using an Aekta system equipped with a HiPrep Desalting 26/10 column. The sample was incubated at 25° C. overnight to give unpurified IL-2 mutein conjugate Ala-M1-5 kDa PEG 4. The reaction mixture was then concentrated to 4.4 mg/mL using Amicon Ultra-15, Ultracel 3 K centrifugation filters (Merck Millipore). 0.307 g of 40 kDa mPEG-linker reagent (synthesis can be performed as described for the compound 17ca in the patent WO2009/133137 example 7 using compound 16c and 1A from the same patent) were dissolved in 3.55 mL cold water to give a stock solution of $2.1*10^{-3}$ mol/L. The solution was stored on ice. 5.8 mL of the protein solution were diluted to 4 mg/mL by addition of 100 mM borate, pH 9.0, then 3.21 mL of the cooled 40 kDa mPEG-linker reagent stock solution were added (corresponding to 4 mol. eq. with respect to the protein).

The conjugation mixture was placed in a water bath at 14° C. for 2 h. The pH was shifted to pH 4 by addition of 3.21 mL of water and 12.83 mL of 200 mM sodium acetate, pH 3.6. After incubation at 25° C. overnight, the conjugate with one single 40 kDa mPEG linker attached (monoconjugate) was isolated from the reaction mixture using a HiScreen Capto MMC ImpRes column (column dimension: 0.77×10 cm) connected to an Aekta system. A flow rate of 1.2 mL/min and a linear gradient from 10 mM succinic acid, pH 5.0 to 80% of 10 mM succinic acid, 1 M NaCl, pH 5.0 in 12 column volumes was applied. The peak containing mainly monoconjugate eluting during the gradient was identified by analytical size exclusion chromatography. The salt content of this fraction was adjusted to 150 mM NaCl by addition of 10 mM succinic acid, 1 M NaCl, pH 5.0, then the fraction was concentrated to 3.64 mL in Amicon Ultra-15, Ultracel 10 K filters (Merck Millipore). The concentrated solution (3.64 mL) was diluted with 192 μL of 10 mM succinic acid, 150 mM NaCl, 1% Tween20, pH 5.0 and 3.59 mL of 10 mM succinic acid, 150 mM NaCl, 0.05% Tween20, pH 5.0 to a final concentration of 1 mg/mL 1 equivalents (based on molecular weight of the protein without taking the glycosylation into account) to create compound 6, which has the following structure

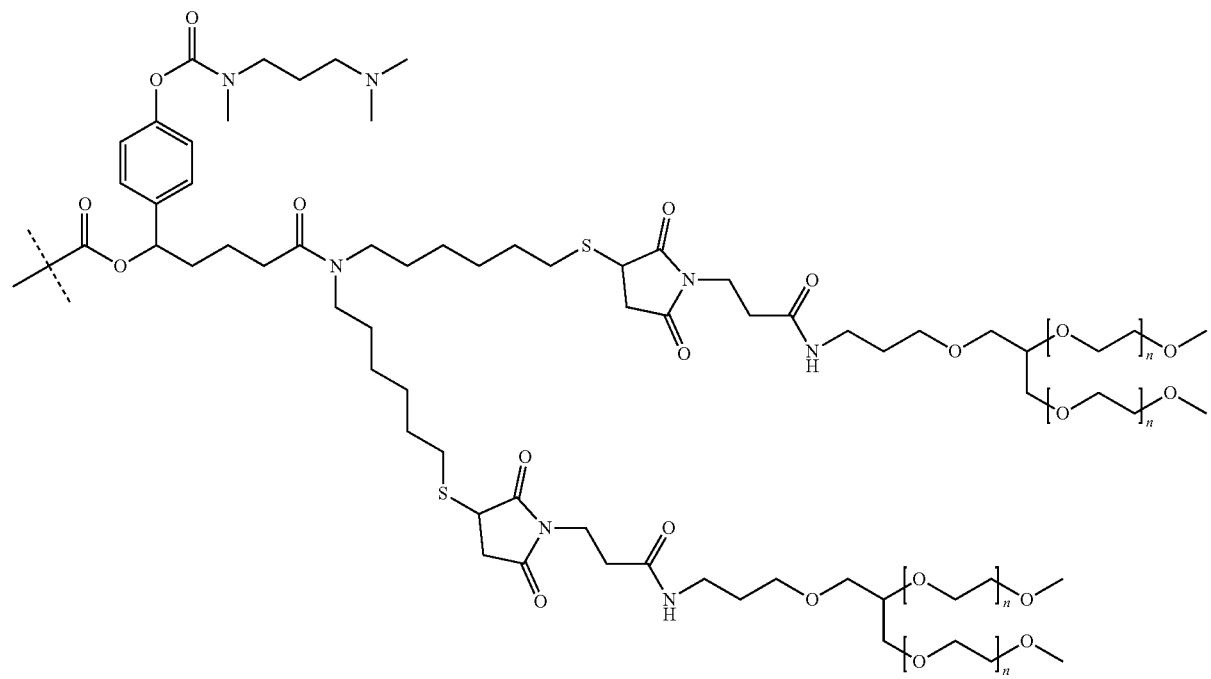

6 wherein the dashed line indicates attachment to a nitrogen of a primary amine of the N-terminus or a lysine side chain of 4 and each n is an integer from 200 to 250.

Example 6: Preparation of IL-2 Mutein Conjugate Ala-M1-5 kDa PEG 3

Compound 3 was generated from the purification process of IL-2 mutein Ala-M1 polymer prodrug 5. During separation of compound 5 on a Capto MMC ImpRes resin the later eluting peak which contains 3 was collected. The collected fraction was diluted with 10 mM succinic acid, pH 5.0 to lower the conductivity to approx. 14 mS/cm and further purified on a Äkta system equipped with a HiScreen Capto Blue column using buffer A (20 mM sodium phosphate, pH 7.5), buffer B (20 mM sodium phosphate, 1 M NaCl, pH 7.5) and a gradient from 0 to 50% buffer B in 6 column volumes. The main peak was collected and concentrated using Amicon Ultra centrifugal device (3 kDa MWCO). The concentrated solution was buffer exchanged to 10 mM Hepes, 150 mM NaCl, 3 mM EDTA, 0.05% polysorbate 20, pH 7.4 by using an Äkta system and a HiPrep 26/10 column and the concentration was adjusted to 0.25 mg/mL to give compound 3.

Example 7: Preparation of IL-2 Mutein Conjugate Ala-M1-5 kDa PEG 3

Compound 3 was purified following conjugation with the 5 kDa PEG maleimide and overnight incubation at pH 9.0 as described in the purification process of IL-2 mutein Ala-M1 polymer prodrug 5 in example 4. The reaction solution after overnight incubation at 25° C. and pH 9.0 was loaded onto an AIEX Poros GoPure XQ 5 mL column using the buffers A (20 mM Tris, pH 8.5) and buffer B (20 mM Tris, 1 M NaCl, pH 8.5) and applying a linear gradient from 0 to 30% buffer B in 11 column volumes. Fractions containing 3 were collected and buffer exchanged into 10 mM Hepes, 150 mM NaCl, 3 mM EDTA, 0.05% polysorbate 20, pH 7.4 by using a HiPrep 26/10 column on a Äkta system. The buffer exchanged protein was concentration adjusted to 0.25 mg/mL and sterile filtered to give compound 3.

Example 8: Preparation of IL-2 Mutein Ala-M1 Polymer Prodrug Release Mixture 7

250 µL of 5 were pH shifted to pH 9.0 by dilution with 205 µL 50 mM borate pH 10.0. The sample was incubated at 37° C. in an incubator for 24 hours. After incubation the percentage of released Ala-M1-5 kDa PEG 3 was determined by RP-HPLC using a Acquity UPLC Peptide BEH C18 column (Waters, 300 Å, 2.1×50 mm, 1.7 µm) on a 1260 Infinity II system (Agilent Technologies). The column temperature was maintained at 30° C. and the flow was set to 0.25 mL/min. UV detection was performed at 215 nm. The content of released 3 was determined against a calibration curve of purified 3 in five different injection volumes in the range of 0.25-2 µg IL2 on column using the same RP-HPLC conditions. IL-2 mutein Ala-M1 polymer prodrug release mixture 7 was used without purification and therefore mainly contains Ala-M1-5 kDa PEG 3 and cleaved 40 kDa mPEG-linker as well as minor amounts of residual 5.

Example 9: Preparation of IL-2 Mutein Conjugate Ala-M1-10 kDa PEG 14

2.0 mL of 1 at 2.3 mg/mL formulated in 20 mM sodium phosphate, 140 mM NaCl, pH 7.4 were first deprotected with TCEP hydrochloride (Sigma-Aldrich, CAS 51805-45-9, catalogue number: 75259-10G, stock: 50 mM in PBS, pH 7.4) at a final concentration of 0.4 mM TCEP at rt for 30 min. Subsequent conjugation was carried out by addition of 10 kDa mPEG-Mal (NOF, Sunbright ME-100MA, stock: 5 mM in PBS, pH 7.4) in a threefold molar excess with respect to protein and incubation at rt for 10 min. Following buffer exchange to 0.1 M borate, pH 9 using an Äkta system equipped with three HiTrap desalting columns (GE Healthcare, each 5 mL) connected in series, the collected protein fraction was incubated at 25° C. for approximately 18 h to achieve the hydrolysis of the thiosuccinimide ring yielding 14. Upon a sixfold dilution with deionized water, 14 was purified by AIEX using an Äkta system equipped with a Poros XQ column (Thermo Scientific, 5 mL) and a salt gradient ranging from 20 mM TRIS, pH 8.5 to 20 mM TRIS, 300 mM NaCl, pH 8.5 in 11 CV at a flow rate of 1.67 mL/min and at an approximate protein load of 0.5 mg per mL resin. Collected fraction of 14 was then buffer exchanged to 10 mM HEPES, 150 mM NaCl, 3 mM EDTA, 0.05% Tween 20, pH 7.4 using an Äkta system equipped with a HiPrep 26/10 desalting column (GE Healthcare, 53 mL), afterwards concentrated to 0.26 mg/mL 1 equivalents (based on the molecular weight of the protein without taking glycosylation into account) using centrifugal filters (Amicon Ultra-15, Merck, Ultracel-3k) and upon sterile filtration (0.22 µm, PVDF) stored at −80° C.

Example 10: Preparation of IL-2 Mutein Conjugate Ala-M1-30 kDa PEG 15

2.2 mL of 1 at 2.3 mg/mL formulated in 20 mM sodium phosphate, 140 mM NaCl, pH 7.4 were first deprotected with TCEP hydrochloride (Sigma-Aldrich, order: 75259-10G, stock: 50 mM in PBS, pH 7.4) at a final concentration of 0.4 mM TCEP at rt for 30 min. Subsequent conjugation was carried out by addition of 30 kDa mPEG-Mal (NOF, Sunbright ME-300MA, stock: 5 mM in PBS, pH 7.4) at a threefold molar excess with respect to protein and incubation at rt for 10 min. Following buffer exchange to 0.1 M borate, pH 9 using an Äkta system equipped with three HiTrap desalting columns (GE Healthcare, each 5 mL) connected in series, the collected protein fraction was incubated at 25° C. for 20 h to achieve the hydrolysis of the thiosuccinimide ring yielding 15. Upon a sixfold dilution with deionized water, 15 was purified by AIEX using an Äkta system equipped with a Poros XQ column (Thermo Scientific, 5 mL) and a salt gradient ranging from 20 mM TRIS, pH 8.5 to 20 mM TRIS, 300 mM NaCl, pH 8.5 in 11 CV at a flow rate of 1.67 mL/min and at an approximate protein load of 0.5 mg per mL resin. Collected fraction of 15 was then buffer exchanged to 10 mM HEPES, 150 mM NaCl, 3 mM EDTA, 0.05% Tween 20, pH 7.4 using an Äkta system equipped with a HiPrep 26/10 desalting column (GE Healthcare, 53 mL), afterwards concentrated to 0.26 mg/mL 1 equivalents (based on the molecular weight of the protein without taking glycosylation into account) using centrifugal filters (Amicon Ultra-15, Merck, Ultracel-10k) and upon sterile filtration (0.22 µm, PVDF) stored at −80° C.

Example 11: Preparation of Aldesleukin 11 for Receptor Binding Studies 1 mL of recombinant human Interleukin-2 11 (Aldesleukin, Akron Biotechnology, AK9993-CSTM, lot number 15104181285) (SEQ ID NO:15) at 2 mg/mL was allowed to stand at ambient temperature until total disappearance of the white precipitate. 4 mL of methanol were added followed by a slight manual shake. Afterwards, 1 mL of chloroform were added to the solution which was then vortexed until only one phase was visible. Finally, 3 mL of water were added, and the sample was vortexed thoroughly. Upon centrifugation (6 min, 9384 ref), the upper organic phase was removed without disturbing the interphase. 3 mL of methanol were added, the sample was vortexed, and centrifuged (3 min, 9384 rcf). The supernatant was then carefully removed, and the protein pellet was slightly dried with nitrogen. 500 μL of 50 mM acetic acid, pH 3.0 were added yielding a 3 mg/mL protein solution, as determined via photometric measurement at 280 nm using an extinction coefficient of 0.614 mL·mg$^{-1}$·cm$^{-1}$. 453 μL of aforementioned solution were then diluted with 50 mM acetic acid, pH 3 to 2 mg/mL. After mixing with 140 mM HEPES, 300 mM sodium chloride, 6 mM EDTA-Na$_2$, 0.1% Tween-20, pH 8.2 in a 1:1 gravimetric ratio and subsequent sterile filtration (0.22 μm, PVDF), 11 was obtained and further used in receptor binding studies.

Example 12: Preparation of Resiquimod Loaded Hydrogel 8

Compound 8 was prepared as described in WO2020/141221 (Example 5, cf. compound 12c) and was obtained as a suspension in PTP buffer with a resiquimod content of 2673 μg eq./mL.

Example 13: Preparation of IL-2 Mutein M1 Polymer Prodrug 10

45.2 mL of IL-2 mutein M1 (SEQ ID NO:18) 2 formulated at 1.84 mg/mL in 10 mM sodium phosphate, 145 mM NaCl, 10% glycerol, pH 7.4, were mixed with 13.6 mL 0.5 M sodium phosphate, pH 7.4. 23.2 mg of TCEP were dissolved in 1619 μL PBS pH 7.4 to give a 50 mM solution. No adjustment of the pH was performed. 710 μL of the TCEP solution were added to the concentrated protein solution. The sample was incubated at ambient temperature for 30 min. Subsequently, 5527 μL of 5 mM 5 kDa PEG maleimide (Sunbright ME-050MA, CAS 883993-35-9, NOF Europe N.V., Grobbendonk, Belgium) in PBS, pH 7.4 (5 mol. eq.) were added to the reaction solution. After incubation at ambient temperature for approx. 20 min, the formation of conjugates was confirmed by analytical size exclusion chromatography. The buffer of the conjugation mixture was exchanged to 100 mM borate, pH 9.0 using an Aekta system equipped with a HiPrep Desalting 26/10 column. The sample was incubated at 25° C. overnight to give unpurified IL-2 mutein conjugate M1-5 kDa PEG 9. The reaction mixture was then concentrated to 5.3 mg/mL using Amicon Ultra-15, Ultracel 3 K centrifugation filters (Merck Millipore). 0.847 g of 40 kDa mPEG-linker reagent (synthesis can be performed as described for the compound 17ca in the patent WO2009/133137 example 7 using compound 16c and 1A from the same patent) were dissolved in 9.746 mL cold water to give a stock solution of 2.1*10$^{-3}$ mol/L. The solution was stored on ice. 12.87 mL of the protein solution were diluted to 4 mg/mL by addition of 100 mM borate, pH 9.0, then 8477 μL of the cooled 40 kDa mPEG-linker reagent stock solution were added (corresponding to 4 mol. eq. with respect to the protein). The conjugation mixture was placed in a water bath at 14° C. for 2 h. The pH was shifted to pH 4 by addition of 8.4 mL of water and 33.5 mL of 200 mM sodium acetate, pH 3.6. After incubation at 25° C. overnight, the conjugate with one single 40 kDa mPEG linker attached (monoconjugate) was isolated from the reaction mixture using a HiScreen Capto MMC ImpRes (column dimension: 0.77×10 cm) connected to an Aekta system. A flow rate of 1.2 mL/min and a linear gradient from 10 mM succinic acid, pH 5.5 to 80% of 10 mM succinic acid, 1 M NaCl, pH 5.5 in 12 column volumes was applied. Three purification runs were performed. The peak containing mainly monoconjugate eluting during the gradient was identified by analytical size exclusion chromatography. The salt content of this fraction was adjusted to 150 mM NaCl by addition of 10 mM succinic acid, 1 M NaCl, pH 5.5, then the fraction was concentrated to 8.1 mL in Amicon Ultra-15, Ultracel 10 K filters (Merck Millipore). The concentrated solution was diluted with 425 μL of 10 mM succinic acid, 150 mM NaCl, 1% Tween20, pH 5.5 and 14.36 mL of 10 mM succinic acid, 150 mM NaCl, 0.05% Tween20, pH 5.5 to a final concentration of 1 mg/mL IL-2 mutein M1 2 equivalents (based on molecular weight of the protein) to create compound 10, which has the following structure

10

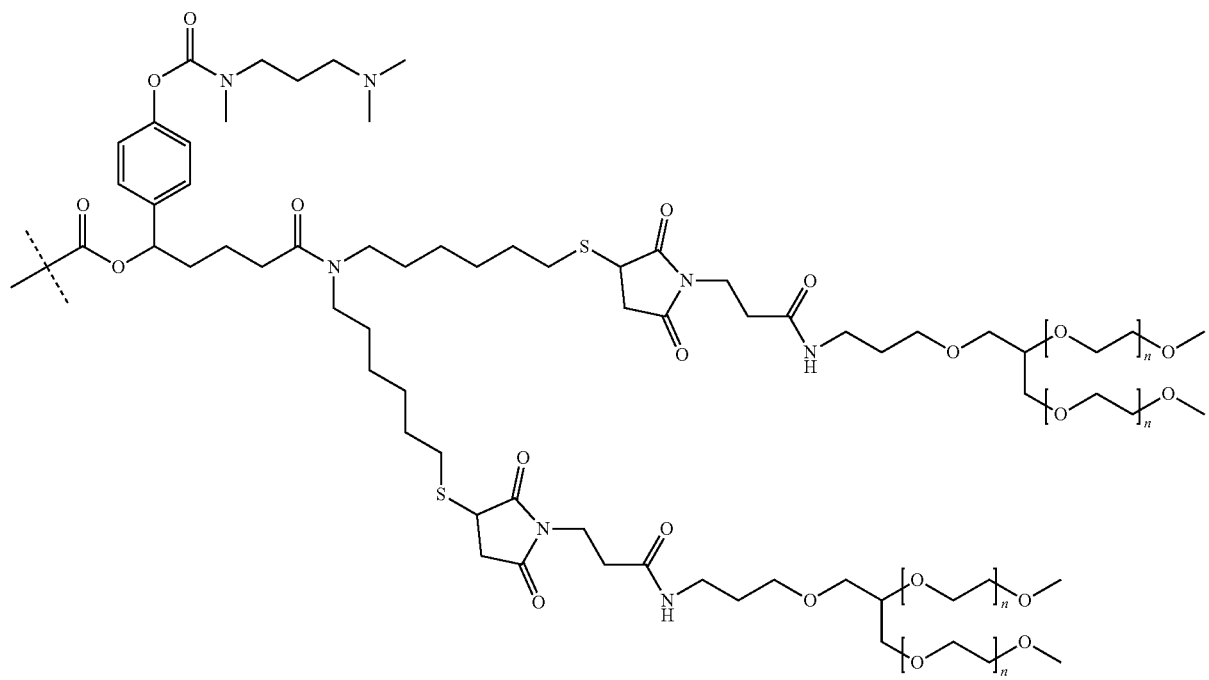

Example 14: Pharmacodynamic Effects of IL-2 Mutein Ala-M1 Polymer Prodrug 5 or 6 in Cynomolgus (Cyno) Macaques (Monkeys)

Two studies were conducted to measure the pharmacodynamic effects of either Aldesleukin (Prometheus, National Drug Code 65483011607) (SEQ ID NO:15) 11 or 5 in Cynos. In the first study, four Cynos ranging in weight from 7.77-10.6 kg (average 9.2 kg) were treated intravenously with five sequential daily 0.4 mg doses of 11 on days 1-5 (average mg/kg: 0.044). In the second study, four Cynos ranging in weight from 2.46-3.69 kg (average 3.13 kg) were treated with a single intravenous dose of either 0.1 mg/kg (n=2) or 0.3 mg/kg (n=2) of 5. All animals were chair trained prior to the study. For both studies, peripheral blood samples were taken before and after treatment at various timepoints as indicated and analyzed for lymphocyte counts, eosinophil counts and cytokines. For animals treated with 5, additional flow cytometry experiments were performed. For measurements of (absolute) lymphocyte counts and eosinophil counts, whole blood was processed on hematology analyzers. For IL-5 and IL-6 cytokine measurements, serum was processed from whole blood and analyzed by ELISA or MSD. For flow cytometry measurements (Immunophenotyping, IPT, FACS), Cynomolgus monkey whole blood was collected in EDTA anticoagulant and kept at room temperature until processed for flow cytometry. Blood was lysed and samples were stained for extracellular surface markers and intracellular phenotypic and lineage markers by standard methods. Cell populations were analyzed using the following phenotypes and gated for percentage of cells which were positive for proliferation marker Ki67.

TABLE 1

Phenotypes of cells analyzed by flow cytometry:

| Phenotypes | Markers |
| --- | --- |
| Lymphocytes | CD14−, Side Scatter Low, CD45+ |
| Populations within Lymphocytes: | |
| Total T Cells | CD45+CD3+ |
| CD4 T Cells | CD45+CD3+CD4+ |
| CD8 T Cells | CD45+CD3+CD8+ |
| T Regulatory Cells | CD3+CD4+CD25+FOXP3+ |
| Natural Killer Cells | CD45+CD3−CD159a+ |
| γδ T cells | CD45+CD3+CD4−CD8− γδ TCR+ |

The following reagents were used for flow cytometry profiling (see Table 2):

TABLE 2

Summary of antibodies used for flow cytometry:

| Reagent and Color | Clone | Staining method |
| --- | --- | --- |
| CD3 BV605 | SP34-2 | Extracellular |
| CD4 BV711 | L200 | Extracellular |
| CD8 AF700 | SK1 | Extracellular |
| CD14 BUV737 | M5E2 | Extracellular |
| CD25 BUV395 | 2 A3 | Extracellular |
| CD28 PE-Cy5 | CD28.2 | Extracellular |
| CD45 BV786 | D058-1283 | Extracellular |
| CD95 BV421 | DX2 | Extracellular |
| CD159a PC7 | Z199 | Extracellular |
| FOXP3 PE | 259D/C7 | Intracellular |
| Granzyme B Alexa Fluor® 647 | GB11 | Intracellular |
| Ki-67 Alexa Fluor® 488 | B56 | Intracellular |
| TCR γδ APC/Fire™ 750 | B1 | Extracellular |

Populations listed in Table 1 were analyzed for the percentage of Ki67+ cells within each population. Populations listed in Table 1 were analyzed for cell counts by multiplying the lymphocyte count at each timepoint by the flow cytometry analyzed frequency of that cell type within the flow cytometry analyzed lymphocyte gate. Fold change measurements were made by measuring the ratio of cell counts at a given timepoint to the pre-dosing baseline timepoint on Day −4. CD8/Treg ratios, NK/Treg ratios, and γδ T cell/Treg ratios were calculated by using the frequencies of each cell type within the flow cytometry analyzed lymphocyte gate on a given timepoint.

Lymphocyte and eosinophil counts: Monkeys treated with compound 11 demonstrated average 2.77 fold and 2.79 fold increases in lymphocyte counts on Days 8 and 10 respectively, while demonstrating average 6.92 fold and 5.94 fold increases in eosinophil counts on Days 8 and 10, respectively (Table 3).

Monkeys treated with 0.1 mg/kg 5 demonstrated average 3.62 fold and 2.53 fold increases in lymphocyte counts on Days 8 and 10 respectively, while demonstrating average 1.13 fold and 1.39 fold increases in eosinophil counts on Days 8 and 10 respectively (Table 4).

Monkeys treated with 0.3 mg/kg 5 demonstrated substantially larger increases in lymphocyte counts, with average 27.4 fold and 10.82 fold increases in lymphocyte counts on Days 8 and 10 respectively, while demonstrating no substantial increases in eosinophils. An average 1.32 fold increase in eosinophil counts was seen on Day 10 and on Day 8 no eosinophils were detected in hematology analysis of peripheral blood samples from 0.3 mg/kg treated animals (Table 4).

TABLE 3

Peripheral blood lymphocyte and eosinophil counts from 11 treated Cynos:

| | Lymphocyte Counts/µL | | | | Eosinophil Counts/µL | | | |
| --- | --- | --- | --- | --- | --- | --- | --- | --- |
| Study Day | Animal 1 ~0.044 mg/kg | Animal 2 ~0.044 mg/kg | Animal 3 ~0.044 mg/kg | Animal 4 ~0.044 mg/kg | Animal 1 ~0.044 mg/kg | Animal 2 ~0.044 mg/kg | Animal 3 ~0.044 mg/kg | Animal 4 ~0.044 mg/kg |
| −5 (Baseline) | 4074 | 3530.6 | 4719 | 4376.3 | 0 | 292.1 | 195 | 535 |
| −4 (Baseline) | 4032 | 4514.4 | 4189.5 | 3564 | 168 | 422.4 | 117.6 | 396 |
| 1 | 4995 | 4670.6 | 4845 | 4617.6 | 0 | 411.4 | 255 | 691.2 |

TABLE 3-continued

Peripheral blood lymphocyte and eosinophil counts from 11 treated Cynos:

| | Lymphocyte Counts/μL | | | | Eosinophil Counts/μL | | | |
|---|---|---|---|---|---|---|---|---|
| Study Day | Animal 1 ~0.044 mg/kg | Animal 2 ~0.044 mg/kg | Animal 3 ~0.044 mg/kg | Animal 4 ~0.044 mg/kg | Animal 1 ~0.044 mg/kg | Animal 2 ~0.044 mg/kg | Animal 3 ~0.044 mg/kg | Animal 4 ~0.044 mg/kg |
| 2 | 4246 | 2473.5 | 2551.5 | 2086.5 | 965 | 523.8 | 451.5 | 567.1 |
| 3 | 4898 | 2040 | 2692.8 | 2387 | 632 | 397.8 | 198 | 539 |
| 4 | 3739.1 | 2646 | 2703.2 | 3034 | 1042.5 | 392 | 228.9 | 738 |
| 5 | 4144.5 | 3990 | 3784 | 3990 | 985.5 | 114 | 0 | 570 |
| 8 | 11186 | 11088 | 8086 | 14958 | 476 | 756 | 2177 | 2770 |
| 9 | 10260 | 10045 | 9548 | 13878 | 228 | 735 | 5852 | 3598 |
| 10 | 8316 | 10664 | 12079 | 14885 | 945 | 3224 | 4112 | 2061 |
| 11 | 7304 | 9640 | 8736 | 7720 | 332 | 3615 | 5824 | 2123 |
| 12 | 5652 | 9520 | 8325 | 7518 | 785 | 2856 | 4070 | 1432 |
| 15 | 6720 | 9700 | 5468.3 | 6198.4 | 210 | 1746 | 2324.4 | 1311.2 |
| 19 | 2385.6 | 3965.5 | 2067 | 3139.5 | 142 | 607.7 | 74.2 | 161 |

TABLE 4

Peripheral blood lymphocyte and eosinophil counts from 5 treated Cynos:

| | Lymphocyte Counts/μL | | | | Eosinophil Counts/μL | | | |
|---|---|---|---|---|---|---|---|---|
| Study Day | Animal 1 0.1 mg/kg | Animal 2 0.1 mg/kg | Animal 3 0.3 mg/kg | Animal 4 0.3 mg/kg | Animal 1 0.1 mg/kg | Animal 2 0.1 mg/kg | Animal 3 0.3 mg/kg | Animal 4 0.3 mg/kg |
| −4 | 7580 | 8610 | 3140 | 7910 | 310 | 370 | 200 | 490 |
| 2 | 2370 | 4780 | 1650 | 2120 | 210 | 170 | 50 | 350 |
| 8 | 36480 | 20830 | 133950 | 96000 | 540 | 190 | 0 | 0 |
| 10 | 20490 | 20210 | 43040 | 62760 | 600 | 310 | 300 | 560 |
| 15 | 11180 | 10550 | 7040 | 20740 | 310 | 400 | 220 | 890 |

Cytokine Results: Monkeys treated with 11 demonstrated clear and substantial increases in IL-5 in all animals with average serum peak IL-5 levels of 117.78 pg/ml (Table 5). In contrast, monkeys treated with 0.1 or 0.3 mg/kg 5 demonstrated minimal increases in IL-5. In three out of four animals tested, no serum IL-5 was detectable in the analyzed timepoints while in the $4^{th}$ animal, a value of 6.41 pg/ml was seen at Study Day 5 (Table 6). Monkeys treated with 11 demonstrated clear and substantial increases in IL-6 in all animals with average serum peak IL-6 levels of 58.66 pg/ml (Table 5). In contrast, monkeys treated with 0.1 or 0.3 mg/kg 5 demonstrated minimal increases in IL-6. In two out of four animals tested, no serum IL-6 was detectable at the analyzed timepoints while in two out of four animals, values of 5.26 and 3.44 pg/ml were seen at a single timepoint, 6 h post dosing (Table 6).

TABLE 5

IL-5 and IL-6 cytokine levels in peripheral blood from 11 treated Cynos

| | IL-5 pg/ml | | | | IL-6 pg/ml | | | |
|---|---|---|---|---|---|---|---|---|
| Study Day | Animal 1 ~0.044 mg/kg | Animal 2 ~0.044 mg/kg | Animal 3 ~0.044 mg/kg | Animal 4 ~0.044 mg/kg | Animal 1 ~0.044 mg/kg | Animal 2 ~0.044 mg/kg | Animal 3 ~0.044 mg/kg | Animal 4 ~0.044 mg/kg |
| −3 | 0.28 | 0.1895 | 0.2445 | 0.233 | 0.40 | 0.21 | 0.10 | 0.29 |
| 1 | 0.35 | 0.223 | 0.231 | 0.578 | 0.27 | 0.10 | 0.12 | 0.30 |
| 1.25 | 6.40 | 36.65 | 10.75 | 26.55 | 7.83 | 23.6 | 64.35 | 26.7 |
| 2 | 9.62 | 78.6 | 15.15 | 45.2 | 5.67 | 1.95 | 1.00 | 4.80 |
| 2.25 | 17.1 | 237.5 | 58.55 | 65.9 | 6.79 | 9.02 | 7.69 | 9.95 |
| 2.29 | 18.7 | 186 | 47.2 | 55.6 | 120 | 12.1 | 8.85 | 15.7 |
| 3 | 6.2 | 74.95 | 14.15 | 13.7 | 3.80 | 0.79 | 1.93 | 0.91 |
| 3.25 | 15.8 | 179 | 57.55 | 57.1 | 4.77 | 6.11 | 2.58 | 5.45 |

TABLE 5-continued

IL-5 and IL-6 cytokine levels in peripheral blood from 11 treated Cynos

| | IL-5 pg/ml | | | | IL-6 pg/ml | | | |
|---|---|---|---|---|---|---|---|---|
| Study Day | Animal 1 ~0.044 mg/kg | Animal 2 ~0.044 mg/kg | Animal 3 ~0.044 mg/kg | Animal 4 ~0.044 mg/kg | Animal 1 ~0.044 mg/kg | Animal 2 ~0.044 mg/kg | Animal 3 ~0.044 mg/kg | Animal 4 ~0.044 mg/kg |
| 4 | 5.855 | 39.95 | 12.2 | 8.46 | 1.54 | 0.36 | 0.34 | 0.63 |
| 4.25 | 25.8 | 268 | 71.55 | 69.95 | 4.02 | 3.2 | 1.46 | 2.46 |
| 5 | 4.92 | 44.85 | 16.35 | 8.06 | 0.75 | 0.81 | 0.46 | 0.48 |
| 5.25 | 38.85 | 288 | 74.3 | 50.6 | 3.67 | 3.59 | 2.42 | 4.21 |
| 6 | 4.96 | 44.75 | 9.99 | 3.695 | 0.83 | 2.46 | 0.23 | 0.57 |
| 8 | <LLOQ | 0.542 | 0.07745 | 0.0219 | 0.25 | 0.20 | 0.08 | 0.27 |
| 10 | 0.0331 | <LLOQ | <LLOQ | <LLOQ | 0.74 | 0.12 | 0.07 | 0.21 |
| 12 | 0.0811 | 0.048 | <LLOQ | <LLOQ | 0.29 | 0.51 | 0.19 | 0.18 |
| 15 | <LLOQ | <LLOQ | 0.00682 | <LLOQ | 0.11 | 0.21 | 0.05 | 0.12 |

LLOQ (IL-15) = 0.260 pg/ml);
LLOQ (IL-6) = 0.178 pg/ml

TABLE 6

IL-5 and IL-6 cytokine levels in peripheral blood from 5 treated Cynos

| | IL-5 pg/ml | | | | IL-6 pg/ml | | | |
|---|---|---|---|---|---|---|---|---|
| Study Day | Animal 1 0.1 mg/kg | Animal 2 0.1 mg/kg | Animal 3 0.3 mg/kg | Animal 4 0.3 mg/kg | Animal 1 0.1 mg/kg | Animal 2 0.1 mg/kg | Animal 3 0.3 mg/kg | Animal 4 0.3 mg/kg |
| 1 | <LLOQ | <LLOQ | <LLOQ | <LLOQ | <LLOQ | <LLOQ | <LLOQ | <LLOQ |
| 1.25 | <LLOQ | <LLOQ | <LLOQ | <LLOQ | 5.26 | <LLOQ | 3.44 | <LLOQ |
| 2 | <LLOQ | <LLOQ | <LLOQ | 2.48 | <LLOQ | <LLOQ | <LLOQ | <LLOQ |
| 5 | <LLOQ | <LLOQ | <LLOQ | 6.41 | <LLOQ | <LLOQ | <LLOQ | <LLOQ |
| 8 | <LLOQ | <LLOQ | <LLOQ | <LLOQ | <LLOQ | <LLOQ | <LLOQ | <LLOQ |
| 15 | <LLOQ | <LLOQ | <LLOQ | 2.95 | <LLOQ | <LLOQ | <LLOQ | <LLOQ |

LLOQ (IL-5) = 2.44 pg/ml;
LLOQ (IL-6) = 2.44 pg/ml

Flow Cytometry Results:

The data described herein is from an internal gating analysis of flow cytometry raw data collected by at an external CRO and represent a preliminary analysis prior to receiving final data from the CRO. Monkeys treated with 0.1 mg/kg 5 demonstrated very robust increases in the percentage of proliferating Ki67+ cells within NK cells with averages of 96.8% and 91.4% observed on Day 6 and Day 10, respectively (Table 7). Similarly, monkeys treated with 0.1 mg/kg 5 demonstrated robust increases in the percentage of proliferating Ki67+ cells within CD8 T cells with averages of 68.3% and 49.2% observed on Day 6 and Day 10, respectively (Table 7). Additionally, monkeys treated with 0.1 mg/kg 5 demonstrated robust increases in the percentage of proliferating Ki67+ cells within γδ T cells with averages of 95.5% and 89.5% observed on Day 6 and Day 10, respectively (Table 7).

Monkeys treated with 0.3 mg/kg 5 demonstrated very robust increases in the percentage of proliferating Ki67+ cells within NK cells with averages of 98.7% and 90.7% observed on Day 6 and Day 10, respectively (Table 7). Similarly, monkeys treated with 0.3 mg/kg 5 demonstrated very robust increases in the percentage of proliferating Ki67+ cells within CD8 T cells with averages of 91.1% and 71.3% observed on Day 6 and Day 10, respectively (Table 7). Additionally, monkeys treated with 0.3 mg/kg 5 demonstrated very robust increases in the percentage of proliferating Ki67+ cells within γδ T cells with averages of 99.5% and 95.3% observed on Day 6 and Day 10, respectively (Table 7).

TABLE 7

Percentage of peripheral blood Ki67+ NK cells, CD8 T cells and γδ T cells from 5 treated Cynos

| | % Ki67+ of NK cells | | | | % Ki67+ of CD8 T cells | |
|---|---|---|---|---|---|---|
| Study Day | Animal 1 0.1 mg/kg | Animal 2 0.1 mg/kg | Animal 3 0.3 mg/kg | Animal 4 0.3 mg/kg | Animal 1 0.1 mg/kg | Animal 2 0.1 mg/kg |
| -4 | 38.3 | 31.6 | 20.4 | 28.5 | 21.7 | 10.8 |
| 1 | 34.5 | 23.7 | 22.8 | 28.3 | 24.8 | 9.87 |
| 5 | 99 | 92 | 97.6 | 99 | 70.6 | 44.6 |
| 6 | 99.4 | 94.2 | 98 | 99.3 | 77.5 | 59.1 |

TABLE 7-continued

Percentage of peripheral blood Ki67+ NK cells, CD8 T cells and γδ T cells from 5 treated Cynos

| | | | | | | |
|---|---|---|---|---|---|---|
| 8 | 97.6 | 94.1 | 95.2 | 98.2 | 72.9 | 46.8 |
| 10 | 93.5 | 89.2 | 86.9 | 94.5 | 58.3 | 40 |
| 15 | 24.5 | 27.8 | 19.7 | 34.3 | 19.2 | 14.7 |

| | % Ki67+ of CD8 T cells | | % Ki67+ of γδ T cells | | | |
|---|---|---|---|---|---|---|
| Study Day | Animal 3 0.3 mg/kg | Animal 4 0.3 mg/kg | Animal 1 0.1 mg/kg | Animal 2 0.1 mg/kg | Animal 3 0.3 mg/kg | Animal 4 0.3 mg/kg |
| −4 | 7.67 | 15.4 | 25.3 | 18.1 | 8.7 | 19.5 |
| 1 | 9.78 | 11.3 | 26.6 | 18.9 | 16.3 | 18.2 |
| 5 | 78 | 78 | 90.8 | 88.5 | 98.0 | 94.5 |
| 6 | 90.1 | 92.1 | 94.9 | 96.1 | 99.6 | 99.3 |
| 8 | 81.4 | 89.4 | 95.1 | 95.5 | 98.3 | 99.20 |
| 10 | 65.5 | 77.1 | 85.2 | 93.8 | 93.4 | 97.2 |
| 15 | 14.5 | 25.8 | 18.0 | 15.3 | 12.9 | 15.4 |

Monkeys treated with 0.1 mg/kg 5 demonstrated robust increases in fold changes from baseline of NK cells with averages fold change values of 7.28 and 4.42 observed on Day 8 and Day 10, respectively (Table 8). Similarly, monkeys treated with 0.1 mg/kg 5 demonstrated robust increases in fold changes from baseline of CD8 T cells with average fold change values of 3.78 and 2.26 observed on Day 8 and Day 10, respectively (Table 8). Additionally, monkeys treated with 0.1 mg/kg 5 demonstrated even more robust increases in fold changes from baseline of γδ T cells with average fold change values of 26.47 and 24.94 observed on Day 8 and Day 10, respectively (Table 8).

Monkeys treated with 0.3 mg/kg 5 demonstrated robust increases in fold changes from baseline of NK cells with averages fold change values of 24.69 and 12.56 observed on Day 8 and Day 10, respectively (Table 8). Similarly, monkeys treated with 0.3 mg/kg 5 demonstrated robust increases in fold changes from baseline of CD8 T cells with average fold change values of 17.34 and 7.57 observed on Day 8 and Day 10, respectively (Table 8). Additionally, monkeys treated with 0.1 mg/kg 5 demonstrated even more substantial increases in fold changes from baseline of γδ T cells with average fold change values of 607.34 and 213.27 observed on Day 8 and Day 10, respectively (Table 8).

TABLE 8

Fold Change from Baseline of peripheral blood NK cell, CD8 T cell and γδ T cell counts from prodrug 5 treated Cynos

| | Fold Change of NK cell counts | | | | Fold Change of CD8 T cell counts | |
|---|---|---|---|---|---|---|
| Study Day | Animal 1 0.1 mg/kg | Animal 2 0.1 mg/kg | Animal 3 0.3 mg/kg | Animal 4 0.3 mg/kg | Animal 1 0.1 mg/kg | Animal 2 0.1 mg/kg |
| −4 | 1.0 | 1.0 | 1.0 | 1.0 | 1.0 | 1.0 |
| 2 | 0.01 | 0.03 | 0.01 | 0.01 | 0.29 | 0.60 |
| 8 | 8.75 | 5.81 | 31.37 | 18.00 | 4.89 | 2.67 |
| 10 | 4.23 | 4.61 | 12.05 | 13.06 | 2.35 | 2.17 |
| 15 | 1.85 | 1.83 | 2.17 | 3.21 | 1.52 | 1.27 |

| | Fold Change of CD8 T cell counts | | Fold Change of γδ T cell counts | | | |
|---|---|---|---|---|---|---|
| Study Day | Animal 3 0.3 mg/kg | Animal 4 0.3 mg/kg | Animal 1 0.1 mg/kg | Animal 2 0.1 mg/kg | Animal 3 0.3 mg/kg | Animal 4 0.3 mg/kg |
| −4 | 1.0 | 1.0 | 1.0 | 1.0 | 1.0 | 1.0 |
| 2 | 0.48 | 0.18 | 0.14 | 0.27 | 0.22 | 0.11 |
| 8 | 21.16 | 13.51 | 28.32 | 24.61 | 1005.54 | 209.14 |
| 10 | 7.97 | 7.17 | 16.49 | 33.38 | 294.19 | 132.34 |
| 15 | 3.31 | 3.47 | 4.70 | 8.78 | 19.45 | 28.93 |

Monkeys treated with 0.1 mg/kg 5 demonstrated clear increases in the ratio of NK cells to Tregs with average NK/Treg ratios at pre-dose baseline (Day −4) of 7.10 and at Day 8 of 31.97 (Table 9). Similarly, monkeys treated with 0.1 mg/kg 5 demonstrated clear increases in the ratio of CD8 T cells to Tregs with average CD8/Treg ratios at pre-dose baseline of 12.61 and at Day 8 of 29.23 (Table 9). Additionally, monkeys treated with 0.1 mg/kg 5 demonstrated clear increases in the ratio of γδ T cells to Tregs with average γδ/Treg ratios at pre-dose baseline of 2.24 and at Day 8 of 35.23 (Table 9).

Monkeys treated with 0.3 mg/kg 5 demonstrated clear increases in the ratio of NK cells to Tregs with average NK/Treg ratios at pre-dose baseline of 4.19 and at Day 8 of 28.06 (Table 9). Similarly, monkeys treated with 0.3 mg/kg 5 demonstrated clear increases in the ratio of CD8 T cells to Tregs with average CD8/Treg ratios at pre-dose baseline of 7.63 and at Day 8 of 36.35 (Table 9). Additionally, monkeys treated with 0.3 mg/kg 5 demonstrated clear increases in the ratio of γδ T cells to Tregs with average γδ/Treg ratios at pre-dose baseline of 1.90 and at Day 8 of 287.33 (Table 9).

TABLE 9

CD8/Treg, NK/Treg and γδ/Treg ratios in peripheral blood from 5 treated Cynos

| | NK/Treg Ratios | | | | CD8 T/Treg Ratios | |
|---|---|---|---|---|---|---|
| Study Day | Animal 1 0.1 mg/kg | Animal 2 0.1 mg/kg | Animal 3 0.3 mg/kg | Animal 4 0.3 mg/kg | Animal 1 0.1 mg/kg | Animal 2 0.1 mg/kg |
| −4 | 9.4 | 4.8 | 3.64 | 4.73 | 14.7 | 10.52 |
| 1 | 7.92 | 10.29 | 3.43 | 4.17 | 15.56 | 18.33 |
| 5 | 18.13 | 12.54 | 9.84 | 4.04 | 32.6 | 20.77 |
| 6 | 33.71 | 18.5 | 28.21 | 14.16 | 41.29 | 24.77 |
| 8 | 44.9 | 19.04 | 27.44 | 28.67 | 39.22 | 19.23 |
| 10 | 33.39 | 17.42 | 19.44 | 26.92 | 28.98 | 17.96 |
| 15 | 19.75 | 11.28 | 6.34 | 15.62 | 25.38 | 17.16 |

| | CD8 T/Treg Ratios | | γδ/Treg Ratios | | | |
|---|---|---|---|---|---|---|
| Study Day | Animal 3 0.3 mg/kg | Animal 4 0.3 mg/kg | Animal 1 0.1 mg/kg | Animal 2 0.1 mg/kg | Animal 3 0.3 mg/kg | Animal 4 0.3 mg/kg |
| −4 | 6.07 | 9.19 | 3.46 | 1.01 | 1.79 | 2.01 |
| 1 | 8.6 | 10.63 | 3.31 | 1.73 | 1.74 | 1.79 |
| 5 | 14.95 | 11.83 | 11.15 | 4.23 | 38.74 | 5.89 |
| 6 | 46.32 | 30.39 | 20.86 | 10.56 | 331.58 | 44.42 |
| 8 | 30.88 | 41.82 | 53.53 | 16.92 | 433.13 | 141.52 |
| 10 | 21.44 | 28.72 | 47.97 | 26.45 | 233.70 | 115.90 |
| 15 | 16.15 | 32.8 | 18.50 | 11.38 | 28.02 | 59.80 |

Overall, compound 5 induced several expected pharmacological effects for an IL-2 therapy with reduced IL-2Rα binding in cynomolgus monkeys based on public data including CD8+ T cell and NK cell expansion with minimal eosinophil expansion or IL-5 induction (Joseph et al. 2019, Rafei 2020). This is noteworthy as IL-5 induced eosinophil expansion and activation is hypothesized to be a major mechanism by which IL-2 induces effects such as VLS (Rand 1991, Van Haelst et al. 1991, Van Gool et al. 2014, Abo et al. 2019). Treatment with compound 5 induced a prominent window between lymphocyte and eosinophil responses (i.e. 27.4 fold increase in lymphocytes and 1.32 fold increase in eosinophils at 0.3 mg/kg) compared to historical comparators. Treatment with compound 5 also induced potent (>200 fold expansion) γδ T cell proliferation responses.

In additional studies, six cynos were treated with a single intravenous dose of either 0.7 mg/kg (n=3 males) or 0.6 mg/kg (n=3 females) of 6 and peripheral blood samples were taken before and after treatment at various timepoints and analyzed by flow cytometry using similar methods as described above. In these experiments, the effects of 6 on γδ T cells subsets such as the potently anti-tumor γ9δ2 T cell subset were measured using γ9 specific antibodies (Biolegend, Clone B3). Compound 6 demonstrated similar effects on γ9δ2 T cells as compared to total γδ T cells (i.e. average fold expansion in all animals on Day 8 of 399.87 vs 438.56, respectively) demonstrating that compound 6 robustly expands γ9δ2 T cells (Table 10).

TABLE 10

Compound 6 induced Fold Changes at Day 8 for γ9δ2 T cells or total γδ T cells.

| Sex | Dose(mg/kg) | Day 8 Fold Change γ9δ2 T cells | Day 8 Fold Change Total γδ T cells |
|---|---|---|---|
| Male | 0.7 | 529.87 | 434.70 |
| Male | 0.7 | 263.38 | 226.49 |
| Male | 0.7 | 714.29 | 827.17 |

TABLE 10-continued

Compound 6 induced Fold Changes at Day 8 for γ9δ2 T cells or total γδ T cells.

| Sex | Dose(mg/kg) | Day 8 Fold Change γ9δ2 T cells | Day 8 Fold Change Total γδ T cells |
|---|---|---|---|
| Female | 0.6 | 334.06 | 399.91 |
| Female | 0.6 | 210.29 | 363.13 |
| Female | 0.6 | 347.33 | 379.93 |
| Average | all | 399.87 | 438.56 |

Example 15: Anti-Tumor Activity of IL-2 Mutein M1 Polymer Prodrug 10 in Combination with Resiquimod Loaded Hydrogel 8

The study was conducted in female BALB/C mice with an age of 9-11 weeks at the day of tumor inoculation. Mice were implanted with $5 \times 10^5$ CT26 tumor cells into the right rear flank. When tumors were grown to a mean tumor volume of approx. 85 mm$^3$, mice were randomized into treatment cohorts (day 0) and treated with either one intravenous dose on Day 0 and one intravenous dose on Day 6 and one intravenous dose on Day 16 of 200 μL of Buffer Control, a single 50 μL intratumoral injection of 8 on Day 0, or the combination of one intravenous dose on Day 0 and one intravenous dose on Day 6 and one intravenous dose on Day 16 of 200 μL of 60 μg of 10 and a single 50 μL intratumoral injection of 134 μg of 8 on Day 0.

To test immune memory to the challenged tumor, mice that had completely cleared colon derived CT26 tumors or mice with tumor sizes smaller than initial tumor volumes (complete responders, CRs) were re-challenged by inoculation with $5 \times 10^5$ CT26 tumor cells in the opposite flank from the original CT26 tumors 73 days after the initial start of dosing. As a control, naïve BALB/c mice were also inoculated with $5 \times 10^5$ CT26 tumor cells. To test the ability of treatments to protect against distinct tumors, mice who were able to reject the re-challenged colon derived CT26 tumors were challenged by inoculation at a third distinct site with $5 \times 10^5$ mammary derived EMT6 tumor cells. As a control, naïve BALB/c mice were also inoculated with $5 \times 10^5$ EMT6 tumor cells. Following treatment initiation, anti-tumor efficacy was assessed by determination of tumor volumes at various time points from tumor size measurements with a caliper. Tumor volumes were calculated according to the formula: Tumor volume=(L×W$^2$)×0.5 where L is the length of the tumor and W the width (both in mm). Mice were removed from the study once tumors were greater than 3000 mm$^3$.

At day 14 after initiation of treatment of the original CT26 tumors, while the average tumor volume in control treated mice was 1643.66 mm$^3$, mice treated with 8 had a statistically lower average volume (455.58 mm$^3$, T test p-value <0.001) compared to the control mice (Table 11). Similarly, mice treated with the combination of 10 and 8 also had a statistically lower average volume (373.46 mm$^3$, T test p-value <0.001) compared to the control mice (Table 11).

At day 23, mice treated with the combination of 10 and 8 also had a statistically lower average volume (653.10 mm$^3$, T-test p-value 0.01) compared to mice treated with 8 alone (2156.90 mm$^3$, Table 12), demonstrating that treatment with 10 can enhance the treatment effects of other immunotherapies such as treatment with 8. Similarly, by Day 100, 6/8 mice treated with the combination of 10 and 8 demonstrated complete responses with no detectable tumors compared to only 2/8 mice treated with 8 alone (Table 12).

TABLE 11

Tumor sizes of original CT26 tumors Day 14 after treatment initiation

| Treatment | N | Day 14 Average tumor size mm$^3$ | SD | T test p-Value vs Control group |
|---|---|---|---|---|
| Control | 8 | 1643.66 | 693.04 | 1.00 |
| 8 | 8 | 455.58 | 182.84 | <0.001 |
| 8 + 10 | 8 | 373.46 | 207.71 | <0.001 |

TABLE 12

Tumor sizes of original CT26 tumors Day 23 after treatment initiation and number of Complete Responders (CRs) 100 days after treatment initiation

| Treatment | N | Day 23 Average tumor size mm$^3$ | SD | T test p-Value vs TLR alone | Day 100 # CRs |
|---|---|---|---|---|---|
| 8 | 8 | 2156.90 | 1236.93 | 1.00 | 2 of 8 |
| 8 + 10 | 8 | 653.10 | 719.81 | 0.010 | 6 of 8 |

WT naïve untreated mice or mice demonstrating complete responses or having tumors less than the 80 mm$^3$ initial randomization tumor sizes were re-challenged with CT26 by inoculation in the opposite flank 73 days after the initial treatment initiation. At Day 21 after re-challenge, naïve mice demonstrated clear tumor growth with an average tumor size of 1320.28 mm$^3$ while mice previously treated with 8 or the combination of 8 and 10 all rejected the re-challenged CT26 colon derived tumor cells, demonstrating immune memory (Table 13).

TABLE 13

Tumor sizes of re-challenged CT26 tumors Day 21 after treatment initiation and number of Complete Responders (CRs) 21 days after treatment initiation

| Animals | N | Day 21 post CT26 re-challenge Average tumor size mm$^3$ | SD | T test p-Value vs Naïve mice | Number of CRs to new CT26 challenge |
|---|---|---|---|---|---|
| Naïve | 8 | 1320.28 | 340.65 | 1.00 | 0 of 8 |
| CRs from 8 treatment | 2 | 0 | 0 | <0.001 | 2 of 2 |
| CRs from 8 + 10 treatment | 6 | 0 | 0 | <0.001 | 6 of 6 |

WT naïve untreated mice or mice demonstrating complete responses to re-challenge with CT26 were challenged with mammary derived EMT6 tumor cells by inoculation in a third distinct site 28 days after CT26 re-challenge. At Day 18 after EMT6 challenge, naïve, untreated mice demonstrated clear tumor growth with an average tumor size of 2224.38 mm$^3$ while mice previously treated with 8 demonstrated an average tumor size of 529.24 mm$^3$ and no complete responses to EMT6 tumor challenge (Table 14). In contrast, mice previously treated with the combination on 8 and 10 demonstrated a significantly lower average tumor size of 12.21 mm³ (T-test p-value <0.001) and with 4/6 mice showing complete responses to EMT6 challenge (Table 14).

TABLE 14

Tumor sizes of re-challenged EMT6 tumors Day 18 after treatment initiation and number of Complete Responders (CRs) 18 days after treatment initiation

| Animals | N | Day 18 post EMT6 Challenge | | | |
|---|---|---|---|---|---|
| | | Average tumor size mm³ | SD | T test p-Value vs Naïve mice | Number of CRs to EMT6 challenge |
| Naïve | 8 | 2224.38 | 1048.32 | 1.00 | 0 of 8 |
| CRs from 8 treatment & CT26 re-challenge | 2 | 529.24 | 281.00 | 0.061 | 0 of 2 |
| CRs from 8 + 10 treatment & CT26 re-challenge | 6 | 12.21 | 18.94 | <0.001 | 4 of 6 |

Example 16: Pharmacodynamic Effects of IL-2 Mutein Ala-M1 Polymer Prodrug 5 in CD1 Outbred Mice Studies were conducted to measure the pharmacodynamic effects of 5 in healthy mice. 5 was administered intravenously into CD-1 mice as part of a 22-day repeat dosing study with weekly (three doses in total) dosing. The study included four dose groups (0, 1.8, 3.6 and 6.0 mg/kg/week) receiving 5 IV by slow bolus once weekly and included assessment of lymphocyte cell subtypes via flow cytometry immunophenotyping (see Table 15). 5 induced robust expansion and activation of CD8⁺ T cells and NK cells in healthy CD-1 mice including increased ratios of CD8⁺ T cells to CD4⁺ T cells and CD8⁺ T cells to Tregs as compared to untreated mice.

TABLE 15

Lymphocyte Subsets Evaluated via Flow Cytometry Immunophenotyping in the 22-Day Repeat Dose Toxicity Study in Mice

| Lymphocyte Subset | Phenotype |
|---|---|
| Total T cells | CD45⁺CD3⁺ |
| Helper T cells (CD4⁺ T cells): | CD45⁺CD3⁺CD4⁺ |
| Cytotoxic T cells (CD8⁺ T cells): | CD45⁺CD3⁺CD8⁺ |
| T Regulatory cells: | CD45⁺CD3⁺CD4⁺ CD25⁺ FOXP3⁺ |
| Natural Killer cells: | CD45⁺CD3⁻CD8⁺ CD335⁺ (NKp46⁺) CD11b⁺/⁻ |
| Granzyme B⁺ NK cells: | CD45⁺CD3⁻CD8⁺ CD335⁺ (NKp46⁺) CD11b⁺/⁻ Granzyme B⁺ |
| γδ T cells: | CD45⁺CD3⁺γδ⁺CD4⁻CD8⁻ |
| CD44⁺ Helper T cells: | CD45⁺CD3⁺CD4⁺CD44⁺ |
| CD44⁺ Cytotoxic T cells: | CD45⁺CD3⁺CD8⁺CD44⁺ |
| Granzyme B⁺ Cytotoxic T cells | CD45⁺CD3⁺CD8⁺ Granzyme B⁺ |

Blood samples for immunophenotyping analyses were collected after the first dose on Day 1 and the third dose at Day 15 at 48, 96 and 168 hours postdose and after the second dose on Day 8 at 96 and 168 hours postdose. Robust expansion and activation of CD8⁺ T cells was observed following treatment of mice with 5. CD8⁺ T cell frequencies within T cells increased in a dose-dependent manner with 5 treatment (data not shown) as did the ratios of CD8⁺ T cells to CD4⁺ T cells (Table 16) and these ratios increased further upon the second and third dosing cycles resulting in cumulative effects.

TABLE 16

Average CD8/CD4 ratios per dosing group and gender in 5 treated CD1 mice:

| Sex | Study Day | 0 mg/kg | 1.8 mg/kg | 3.6 mg/kg | 6.0 mg/kg |
|---|---|---|---|---|---|
| F | 3 | 0.35 | 0.41 | 0.30 | 0.22 |
| F | 5 | 0.32 | 0.55 | 0.56 | 0.91 |
| F | 8 | 0.32 | 0.59 | 0.60 | 1.39 |
| F | 12 | 0.40 | 0.91 | 1.41 | 3.52 |
| F | 15 | 0.32 | 1.77 | 1.06 | 2.14 |
| F | 17 | 0.40 | 0.96 | 0.97 | 1.27 |
| F | 19 | 0.52 | 0.77 | 2.25 | 5.53 |
| F | 22 | 0.44 | 3.43 | 4.77 | 26.51 |
| M | 3 | 0.43 | 0.39 | 0.40 | 0.23 |
| M | 5 | 0.47 | 0.59 | 0.76 | 1.31 |
| M | 8 | 0.45 | 0.75 | 1.32 | 1.89 |
| M | 12 | 0.42 | 0.93 | 1.93 | n.d. |
| M | 15 | 0.40 | 0.94 | 3.66 | n.d. |
| M | 17 | 0.37 | 1.55 | 3.39 | n.d. |
| M | 19 | 0.38 | 0.96 | 2.54 | n.d. |
| M | 22 | 0.43 | 2.46 | 5.33 | n.d. | n.d. not determined

Furthermore, the ratio of CD8⁺ T cells to Tregs also increased with 5 treatment in a cumulative manner with additional dosing cycles (Table 17).

TABLE 17

Average CD8/Treg ratios per dosing group and gender in 5 treated CD1 mice:

| Sex | Study Day | 0 mg/kg | 1.8 mg/kg | 3.6 mg/kg | 6.0 mg/kg |
|---|---|---|---|---|---|
| F | 3 | 5.83 | 4.91 | 2.76 | 2.52 |
| F | 5 | 5.87 | 3.47 | 1.48 | 1.45 |
| F | 8 | 8.01 | 9.17 | 6.85 | 4.37 |
| F | 12 | 8.34 | 6.05 | 5.49 | 4.63 |
| F | 15 | 5.80 | 13.43 | 5.66 | 10.08 |
| F | 17 | 5.07 | 8.18 | 9.25 | 6.80 |
| F | 19 | 10.19 | 5.89 | 7.50 | n.d. |
| F | 22 | 10.47 | 30.27 | 33.44 | 44.63 |
| M | 3 | 10.87 | 3.71 | 3.64 | 3.84 |
| M | 5 | 7.97 | 4.50 | 3.83 | 2.33 |
| M | 8 | 12.64 | 9.64 | 12.19 | 5.04 |
| M | 12 | 8.26 | 5.58 | 4.56 | n.d. |
| M | 15 | 14.39 | 11.24 | 19.78 | n.d. |
| M | 17 | 6.66 | 15.27 | 10.25 | n.d. |
| M | 19 | 8.63 | 5.85 | 7.50 | n.d. |
| M | 22 | 8.58 | 41.05 | 33.30 | n.d. | n.d. not determined

Finally, CD8⁺ T cells displayed an increased effector/memory phenotype after 5 treatment with dose- and time-dependent increases observed in the percent of CD44⁺ cells within the CD8⁺ T cell population (Table 18). Of note, control mice did not demonstrate changes in these features. For all of these measures of CD8⁺ T cell activation, a stronger effect was often seen in males vs. females, particularly at 3.6 mg/kg/week.

TABLE 18

Percent CD44+ CD8 T cells per dosing group
and gender in 5 treated CD1 mice:

| Sex | Study Day | 0 mg/kg | 1.8 mg/kg | 3.6 mg/kg | 6.0 mg/kg |
|---|---|---|---|---|---|
| F | 3 | 53.23 | 64.97 | 48.87 | 55.43 |
| F | 5 | 48.70 | 51.77 | 70.20 | 82.80 |
| F | 8 | 53.93 | 69.87 | 79.13 | 80.77 |
| F | 12 | 32.47 | 82.07 | 83.87 | 95.67 |
| F | 15 | 53.03 | 75.80 | 81.03 | 93.87 |
| F | 17 | 43.47 | 73.33 | 82.53 | 87.90 |
| F | 19 | 38.53 | 71.97 | 90.33 | 95.97 |
| F | 22 | 30.67 | 90.60 | 91.73 | 98.93 |
| M | 3 | 58.63 | 49.03 | 63.73 | 62.53 |
| M | 5 | 48.93 | 58.97 | 76.17 | 96.10 |
| M | 8 | 47.93 | 70.13 | 82.47 | 90.05 |
| M | 12 | 45.63 | 81.67 | 95.43 | n.d. |
| M | 15 | 44.37 | 70.53 | 89.83 | n.d. |
| M | 17 | 48.87 | 85.50 | 90.80 | n.d. |
| M | 19 | 68.30 | 75.27 | 85.63 | n.d. |
| M | 22 | 44.77 | 83.90 | 89.67 | n.d. | n.d. not determined

In addition to effects on T cells, robust increases in NIK cell counts/µL of blood were noted in a dose-dependent manner after 5 treatment (Table 19).

TABLE 19

NK cell counts/µL blood per dosing group
and gender in 5 treated CD1 mice:

| Sex | Study Day | 0 mg/kg | 1.8 mg/kg | 3.6 mg/kg | 6.0 mg/kg |
|---|---|---|---|---|---|
| F | 3 | 156 | 339 | 168 | 110 |
| F | 5 | 181 | 1659 | 6257 | 5760 |
| F | 8 | 71 | 477 | 2412 | 8488 |
| F | 12 | 229 | 3702 | 13228 | 12354 |
| F | 15 | 189 | 984 | 5131 | 25376 |
| F | 17 | 182 | 433 | 1101 | 17301 |
| F | 19 | 172 | 1263 | 9955 | 18148 |
| F | 22 | 153 | 1588 | 3709 | 91167 |
| M | 3 | 61 | 149 | 118 | 53 |
| M | 5 | 304 | 4628 | 7920 | 12466 |
| M | 8 | 135 | 2545 | 6463 | 22322 |
| M | 12 | 99 | 14263 | 12822 | n.d. |
| M | 15 | 105 | 296 | 17025 | n.d. |
| M | 17 | 107 | 2906 | 5038 | n.d. |
| M | 19 | 222 | 5462 | 8726 | n.d. |
| M | 22 | 93 | 1129 | 41788 | n.d. | n.d. not determined

Furthermore, 5 treatment induced an activated NK cell phenotype as measured by the percent of Granzyme B+ NK cells (Table 20). Of note, control mice did not demonstrate changes in these features.

TABLE 20

Percent of NK cells displaying an activated Granzyme B+
phenotype per dosing group and gender in 5 treated CD1 mice:

| Sex | Study Day | 0 mg/kg | 1.8 mg/kg | 3.6 mg/kg | 6.0 mg/kg |
|---|---|---|---|---|---|
| F | 3 | 1.7 | 30.9 | 62.3 | 87.5 |
| F | 5 | 8.3 | 23.6 | 61.4 | 94.8 |
| F | 8 | 12.3 | 17.9 | 50.5 | 82.3 |
| F | 12 | 7.6 | 56.3 | 84.2 | 73.7 |
| F | 15 | 7.3 | 38.5 | 76.1 | 97.4 |
| F | 17 | 3.2 | 62.3 | 81.6 | 93.6 |
| F | 19 | 5.4 | 41.2 | 81.3 | 87.7 |
| F | 22 | 8.7 | 33.9 | 68.7 | 62.8 |
| M | 3 | 1.7 | 42.9 | 71.2 | 88.1 |
| M | 5 | 1.6 | 13.1 | 25.7 | 98.0 |
| M | 8 | 12.7 | 29.0 | 56.3 | 93.7 |
| M | 12 | 6.6 | 72.4 | 87.9 | n.d. |

TABLE 20-continued

Percent of NK cells displaying an activated Granzyme B+
phenotype per dosing group and gender in 5 treated CD1 mice:

| Sex | Study Day | 0 mg/kg | 1.8 mg/kg | 3.6 mg/kg | 6.0 mg/kg |
|---|---|---|---|---|---|
| M | 15 | 9.4 | 25.1 | 70.5 | n.d. |
| M | 17 | .3 | 94.2 | 97.3 | n.d. |
| M | 19 | 3 | 63.9 | 77.2 | n.d. |
| M | 22 | 6.6 | 31.1 | 81.6 | n.d. | n.d. not determined

Overall, dose and time dependent pharmacological changes were observed in 5 treated mice which showed robust increases in the number of NK cells and a selective increase in $CD8^+$ T cells vs $CD4^+$ T cells along with induction of memory/effector cell phenotype ($CD44^+$) within the $CD8^+$ T cells.

Example 17: Toxicokinetics of 5 and 3 in Cynomolgus Monkeys

The toxicokinetics of 5 and 3 released from 5 was determined after 5 was administered on Days 1 and 15 to monkeys via intravenous (IV) slow bolus administration according to the dosing scheme shown in Table 21.

TABLE 21

Dose levels and number of animals for each dosage group

| Group | No. of animals | | Dose level |
| | Male | Female | (mg/kg/occasion)* |
|---|---|---|---|
| 1 (low) | 1 | 1 | 0.1 |
| 2 (intermediate) | 1 | 1 | 0.3 |
| 3 (high) | 1 | 1 | Day 1: 0.9 |
| | | | Day 15: 0.75 |

*Dose in mg 1 equivalents

Blood samples were collected from all animals on Day 1 predose and at approximately 2, 6, 24, 48, 96, 144, 216, and 336 hours (before $2^{nd}$ dose) postdose. Additionally, blood samples were collected on from all animals on Day 15 at approximately 2, 6, 24, 48, 96, 144, 216, and 336 hours postdose. Blood samples were processed to plasma and analyzed for 5 and 3. 5 was quantified in cynomolgus monkey Lithium-Heparin (Li-Hep) plasma using a sandwich ELISA method. A 96-well plate was coated with a rat monoclonal immunoglobulin G (IgG) anti-IL-2 antibody. After blocking of the plate, samples containing 5 were pipetted into the wells, followed by addition of a biotinylated rabbit monoclonal IgG anti-PEG antibody to bind to immobilized 5. The complex was detected by streptavidin-labelled peroxidase. After a wash to remove unbound reagents, the enzyme was revealed by its action on the substrate TMB. After stopping the reaction with a strong acid, the intensity of the color (read at 450 nm; correction wavelength of 620 nm) was directly proportional to the amount of 5 present in the sample.

Released 3 was separated from 5 in the monkey Li-Hep plasma samples using agarose beads coated with a mouse monoclonal immunoglobulin M (IgM) anti-PEG antibody. The separation step was followed by sandwich ELISA for quantification of 3. A 96-well plate was coated with a rat monoclonal IgG anti-IL-2 capture antibody. After blocking of the plate, samples containing 3 were pipetted into the wells, followed by addition of a biotinylated rabbit polyclonal IgG anti-IL-2 detection antibody to bind to immobilized 3. The biotinylated detection antibody is recognized by a streptavidin-horseradish peroxidase conjugate. The binding of this conjugate to the antibody-3 complex was assayed with the conversion of 3,3',5,5'-Tetramethylbenzidin (TMB). The reaction was stopped via acidification and UV absorption at 450 nm was recorded.

A summary of the individual and mean toxicokinetic parameters for 5 and released 3 in monkey plasma are shown below in Table 22 and Table 23, respectively.

Sex differences in 5 and 3 mean $C_{max}$ and $AUC_{0-336}$ values were less than 2-fold. Exposure, as assessed by 5 and 3 mean $C_{max}$ and $AUC_{0-336}$ values, increased with the increase in dose levels of 5 from 0.1 to 0.9 mg/kg/occasion on Day 1 and from 0.1 to 0.75 mg/kg/occasion on Day 15. The increases in mean $C_{max}$ and $AUC_{0-336}$ values were generally dose proportional. No accumulation of 5 or 3 was observed after multiple doses of 5 in monkeys at the 0.1 and 0.3 mg/kg/occasion dose levels (no conclusion for the high dose level due to different doses on Day 1 and Day 15).

TABLE 22

Summary of the Individual and Mean Toxicokinetic Parameters of 5 in Monkey Plasma

| Interval (Day) | Dose group | Dose Level of 5 (mg/kg/occasion) | Sex | Animal | $C_{max}$ (ng/mL) | $t_{max}$ (h) | $AUC_{0-336}$ (h*ng/mL) | $t_{1/2}$ (h) |
|---|---|---|---|---|---|---|---|---|
| 1 | 1 | 0.1 | M | P0001 | 2,490 | 2.00 | 116,000 | 38.7 |
|   |   |     | F | P0301 | 2,370 | 2.00 | 126,000 | 48.5 |
|   |   |     |   | mean  | 2,430 | 2.00 | 121,000 | 43.6 |
|   | 2 | 0.3 | M | P0101 | 7,500 | 2.00 | 310,000 | 47.0 |
|   |   |     | F | P0401 | 7,530 | 2.00 | 334,000 | 54.8 |
|   |   |     |   | mean  | 7,520 | 2.00 | 322,000 | 50.9 |
|   | 3 | 0.9 | M | P0201 | 18,600 | 6.00 | 881,000 | 51.0 |
|   |   |     | F | P0501 | 18,500 | 6.00 | 862,000 | 44.1 |
|   |   |     |   | mean  | 18,600 | 6.00 | 872,000 | 47.5 |
| 15 | 1 | 0.1 | M | P0001 | 3,180 | 24.0 | 149,000 | 30.3 |
|   |   |     | F | P0301 | 2,540 | 2.00 | 118,000 | 55.9 |
|   |   |     |   | mean  | 2,860 | 13.0 | 133,000 | 43.1 |
|   | 2 | 0.3 | M | P0101 | 6,540 | 2.00 | 215,000 | 50.5 |
|   |   |     | F | P0401 | 5,440 | 2.00 | 255,000 | 57.8 |
|   |   |     |   | mean  | 5,990 | 2.00 | 235,000 | 54.1 |
|   | 3 | 0.75 | M | P0201 | 15,900 | 2.00 | 548,000 | 51.0 |
|   |   |     | F | P0501 | 15,700 | 2.00 | 610,000 | 48.4 |
|   |   |     |   | mean  | 15,800 | 2.00 | 579,000 | 49.7 |

Notes:
Median values are presented for $t_{max}$.
Doses were administered on Days 1 and 15

TABLE 23

Summary of the Individual and Mean Toxicokinetic Parameters of 3 released from 5 in Monkey Plasma

| Interval (Day) | Dose group | Dose Level of 5 (mg/kg/occasion) | Sex | Animal | $C_{max}$ (ng/mL) | $t_{max}$ (h) | $AUC_{0-336}$ (h*ng/mL) | $t_{1/2}$ (h) |
|---|---|---|---|---|---|---|---|---|
| 1 | 1 | 0.1 | M | P0001 | 28.0 | 2.00 | 1,020 | 35.4 |
|   |   |     | F | P0301 | 36.0 | 2.00 | 1,350 | 34.5 |
|   |   |     |   | mean  | 32.0 | 2.00 | 1,190 | 35.0 |
|   | 2 | 0.3 | M | P0101 | 88.0 | 2.00 | 3,730 | 29.6 |
|   |   |     | F | P0401 | 110  | 2.00 | 4,540 | 41.1 |
|   |   |     |   | mean  | 99.0 | 2.00 | 4,130 | 35.4 |
|   | 3 | 0.9 | M | P0201 | 290  | 2.00 | 12,600 | 43.0 |
|   |   |     | F | P0501 | 270  | 2.00 | 10,700 | 39.3 |
|   |   |     |   | mean  | 280  | 2.00 | 11,600 | 41.2 |
| 15 | 1 | 0.1 | M | P0001 | 43.0 | 24.0 | 1,690 | 39.4 |
|   |   |     | F | P0301 | 33.0 | 2.00 | 1,390 | 40.6 |
|   |   |     |   | mean  | 38.0 | 13.0 | 1,540 | 40.0 |
|   | 2 | 0.3 | M | P0101 | 120  | 2.00 | 2,920 | 34.7 |
|   |   |     | F | P0401 | 100  | 2.00 | 4,340 | 45.0 |
|   |   |     |   | mean  | 110  | 2.00 | 3,630 | 39.8 |
|   | 3 | 0.75 | M | P0201 | 250  | 2.00 | 9,380 | 63.0 |
|   |   |     | F | P0501 | 220  | 2.00 | 6,760 | 44.7 |
|   |   |     |   | mean  | 235  | 2.00 | 8,070 | 53.8 |

Notes:
Median values are presented for $t_{max}$.
Doses were administered on Days 1 and 15

Example 18: Receptor Binding of IL-2 Mutein Conjugate Ala-M1-5 kDa PEG 3 and 4 as Well as IL-2 Mutein Ala-M1 Polymer Prodrug Release Mixture 7 in IL-2Rα and IL-2RβBinding Experiments and Calculation of Bias The mode of action of prodrugs 5 and 6 was demonstrated by testing its active component 3 and 4, respectively, for its IL-2R subunit specific binding. The active component was either the purified variant 3 or 4 or the main component in the IL-2 mutein Ala-M1 polymer prodrug release mixture 7. Binding studies using Biacore were performed by injecting 3, 4, 7 and unbiased control recombinant human IL-2, compound 12 (SEQ ID NO:45), onto human IL-2Rα—Fc or human IL-2Rβ—Fc coated sensor chips. The results are summarized in Table 24. 3, 4 and 7 are biased IL-2 molecules because all of them demonstrated no binding to IL-2Rα up to a concentration of 2 µM in contrast to 12, but all showed binding to IL-2Rβ. 3, 4, and 7 showed highly comparable dissociation constants to IL-2Rβ ($K_D$s of approx. 2 µM) which is slightly reduced (3-5-fold) compared to 12 (approx. 0.5 µM).

TABLE 24

Biacore binding results for binding to human IL-2Rα or IL-2Rβ

| Compound | $K_D$ for IL-2Rα [nM] | $K_D$ for IL-2Rβ [µM] |
| --- | --- | --- |
| 12 | 9.57 | 0.45 |
| 3 | NA | 1.84 |
| 7 | NA | 2.23 |
| 4 | NA | 1.79 |

NA = not applicable, i.e. no value calculable due to lack of binding.

In an independent measurement receptor binding of Aldesleukin 11 was measured against unbiased control recombinant human IL-2, compound 12 (SEQ ID NO:45). Aldesleukin 11 was prepared according to example 11. Both compounds 12 and 11 were found to have highly comparable $K_D$ values for both IL-2Rα and IL-2Rβ and thus have comparable binding affinities to both receptors.

The bias of IL-2 is defined based on the $K_D$ ratios of modified IL-2 to Aldesleukin with respect to their IL-2Rα and IL-2Rβ binding, respectively, as described by the following formula.

$$\text{bias} = \frac{Ratio_{biased\ IL-2}}{Ratio_{aldesleukin}} > 1$$

wherein $$Ratio_{biased\ IL-2} = \frac{K_D \text{ biased } IL-2 \text{ to } IL-2R\alpha}{K_D \text{ biased } IL-2 \text{ to } IL-2R\beta}$$

$$Ratio_{aldesleukin} = \frac{K_D \text{ aldesleukin to } IL-2R\alpha}{K_D \text{ aldesleukin to } IL-2R\beta}$$

with

"$K_D$ biased IL-2 to IL-2Rα" being the $K_D$ of biased IL-2 to IL-2Rα,
"$K_D$ biased IL-2 to IL-2Rβ" being the $K_D$ of biased IL-2 to IL-2Rβ,
"$K_D$ aldesleukin to IL-2Rα" being the $K_D$ of aldesleukin to IL-2Rα, and
"$K_D$ aldesleukin to IL-2Rβ" being the $K_D$ of aldesleukin to IL-2Rβ.

With $K_D$ 11=$K_D$ 12 for both IL-2Rα and IL-2Rβ binding and by using the above-mentioned formula, the following ratios were calculated and are summarized in Table 25.

TABLE 25

Ratio biased IL-2 to Ratio aldesleukin for different IL-2 mutein conjugates.

| Compound | Bias = $Ratio_{biased\ IL-2}$/$Ratio_{aldesleukin}$ * |
| --- | --- |
| 3 | >51 |
| 7 | >42 |
| 4 | >53 |

* due to no binding to IL-2Rα the highest concentration tested (2 µM) was used for calculations Example 19: Bioactivity of 3 and 7 in HH, an IL-2Rβγ Expressing Cell Line To confirm bioactivity of 3 and 7, experiments were performed with the HH cell line, a mature T cell line derived from peripheral blood of a patient with aggressive cutaneous T cell leukemia/lymphoma (ATCC® CRL-2105™) which been demonstrated to only express the IL-2Rβ/γ. One of the earliest events in cytokine mediated activation of lymphocytes such as CD8$^+$ T cells and NK cells is Janus Associated Kinase mediated phosphorylation and activation of Signal transducer and activator of transcription (pSTAT5). Thus, pSTAT5 was used to measure biological activity of 3 and 7 alongside 12. 3 demonstrated clear bioactivity in IL-2Rβ/γ expressing HH cells ($EC_{50}$: 773 ng/ml) that was approximately 3.5 fold lower than 12 ($EC_{50}$: 233 ng/ml). Additionally, 7 induced bioactivity ($EC_{50}$: 756 ng/ml) very similar to 3, demonstrating that 7 retains bioactivity after being released from prodrug 5 even after accelerated (stress) conditions.

Example 20: Bioactivity of 3 and 7 in Primary Human, Cyno, and Mouse Blood Lymphocytes Amino acid sequence identities of IL-2 and its receptor subunits between humans and mice or humans and cynomolgus monkeys are shown in Table 26.

TABLE 26

Percent Amino Acid Sequence Identity Between Humans, Mice and Cynomolgus Monkeys IL-2 and IL-2 Receptor Subunits

| Protein | Human vs mouse sequence identity | Human vs cynomolgus monkey sequence identity |
| --- | --- | --- |
| IL-2 | 63% | 96% |
| IL-2Rα | 61% | 92% |
| IL-2Rβ | 58% | 94% |
| IL-2Rγ | 71% | 97% |

Although the IL-2 and IL-2 receptor sequence identities between human and mouse are only between 58-71%, mouse models have been extensively used to test the pharmacological and anti-tumor effects of IL-2 and IL-2 variants. In contrast, the cynomolgus monkey has much higher IL-2 and IL-2R sequence identities with human (92-97%, Table 26). To qualify experimentally that cynomolgus monkeys and mice are relevant species for studying 5, PD experiments using 3 as well as his-tagged mammalian expressed control human IL-2, compound 13 (SEQ ID NO:46), were performed testing for bioactivity using human, cynomolgus monkey, or mouse blood samples.

To evaluate the cell type specific immunostimulatory effects of 3 in primary human or monkey cells, whole human or cynomolgus monkey blood from two donors each was incubated with various concentrations of 3 or 13 for 30 minutes and analyzed by flow cytometry for intracellular levels of phosphorylated STAT5 (pSTAT5) in unique cell subsets such as Tregs which predominately express IL-2Rα/β/γ as well as CD8+ T cells (CD8) and NK cells which predominately express IL-2Rβ/γ. Additionally, CD8+ T cells were further analyzed for CD8+ CD45RA+ Naïve (CD8 N) as well as CD8+ CD45RA- Memory (CD8 M) subsets. Similar experiments were performed with mouse blood using a different panel of mouse specific antibodies. All subsets were analyzed for median fluorescence intensities of pSTAT5 and $EC_{50}$ values were calculated for each compound across all cell types.

In both human and cynomolgus monkeys, compared to 13, 3 demonstrated substantially reduced potency in Tregs while maintaining similar and slightly reduced potency to CD8+ T cells and NK cells. For example, in human blood 13 demonstrated an $EC_{50}$ value for pSTAT5 in Tregs of 0.09 ng/ml while 3 showed a considerably higher $EC_{50}$ value of 34.5 ng/ml in this population. In contrast, 13 demonstrated an $EC_{50}$ value for pSTAT5 in human NK cells of 6.01 ng/ml while 3 showed a comparable and slightly less potent $EC_{50}$ value of 11.84 ng/ml in this population (Table 27)

TABLE 27

Summary of pSTAT5 Potency Values in Human, Cynomolgus Monkey, and Mouse Blood

| $EC_{50}$ (ng/mL) | Treg | CD8 | NK |
|---|---|---|---|
| Human | | | |
| 13 | 0.09 | 25.69 | 6.01 |
| 3 | 34.50 | 62.15 | 11.84 |
| Cynomolgus Monkey | | | |
| 13 | 0.09 | 45.10 | 10.52 |
| 3 | 52.16 | 86.4 | 16.26 |
| Mouse | | | |
| 13 | 0.37 | 24,040.56 | 9,694.74 |
| 3 | 92.24 | 10,297.50 | 3,614.68 |

In mice, compared to 13, 3 demonstrated substantially reduced potency in mouse Tregs while maintaining similar and slightly increased potency to CD8+ T cells and NK cells (Table 27). For example, in mouse blood 13 demonstrated an $EC_{50}$ value for pSTAT5 in Tregs of 0.37 ng/ml while 3 showed a considerably higher $EC_{50}$ value of 92.24 ng/ml in this population. In contrast, 13 demonstrated an $EC_{50}$ value for pSTAT5 in mouse NK cells of 9,694.74 ng/ml while 3 showed a comparable $EC_{50}$ value of 3,614.68 this population (Table 27).

While cynomolgus monkey lymphocyte subsets demonstrated similar potencies to 3 vs their human counterparts (1.37-1.51 fold lower potencies, Table 28), the same was not true in mice. Notably, while mouse Tregs displayed similar overall 3 potency compared to human Tregs (i.e. 2.67 fold lower potency, Table 28), mouse IL-2Rβ/γ+ CD8+ T cells and NK cells displayed markedly reduced sensitivity to 3 compared to humans (165.69 fold lower potency in CD8+ T cells and 305.29 fold lower potency in NK cells, Table 28). In other words, mouse CD8+ T cells and NK cells appear to require much higher doses of 3 for activity vs their human counterparts (Table 28) or compared to mouse Tregs (Table 27). Of note, the same general trends were apparent for 13.

TABLE 28

Fold Potency Loss of Cynomolgus Monkey or Mouse Lymphocyte Subsets Compared to their corresponding Human Subsets

| Fold Potency Loss vs Human | Treg | CD8 | NK |
|---|---|---|---|
| Cynomolgus Monkey | | | |
| 13 | 1 | 1.76 | 1.75 |
| 3 | 1.51 | 1.39 | 1.37 |
| Mouse | | | |
| 13 | 4.11 | 935.79 | 1613.10 |
| 3 | 2.67 | 165.69 | 305.29 |

In additional experiments with human blood, IL-2 mutein Ala-M1 polymer prodrug release mixture 7 showed near identical bioactivity to 3 (Table 29), demonstrating that 7 maintains full bioactivity after release from 5.

TABLE 29

Summary of pSTAT5 Potency Values in Additional Human Blood Experiments

| $EC_{50}$ (ng/mL) | Treg | CD8 | NK |
|---|---|---|---|
| Human | | | |
| 13 | 0.047 | 4.94 | 17.59 |
| 3 | 22.02 | 9.34 | 51.22 |
| 7 | 15.01 | 9.79 | 48.18 |

Overall, these experiments demonstrate that human, cynomolgus monkey and mouse primary cells can be activated by 3, and that for all three species 3 demonstrates substantially reduced Treg potency compared to 13, consistent with the loss of IL-2Rα binding seen in vitro and the desired mechanism of action. It was noted that unlike cynomologus monkeys or humans, mice require higher concentrations of 3 (and likely higher doses of 5) for CD8+ T cell and NK cell activation relative to activation of IL-2Rα expressing cells.

Example 21: Bioactivity of 3, 14, 15 in Human Peripheral Blood Mononuclear Cell Lymphocyte Subsets To further understand the impact of the PEG size at the cysteine38 attachment point in compound 1, additional experiments were undertaken to compare the bioassay potency in cryopreserved human PBMCs of Ala-M1 with either 5 kDa (3), 10 kDa (14) or 30 kDa (15) PEG attachments at cysteine38. Similar methods as described in e.g. example 20 were used to investigate pSTAT5 induction in distinct lymphocyte subsets using flow cytometry after 30 minutes of stimulation with the indicated compounds. The data is summarized in Tables 30 and 31 and demonstrate that increasing the PEG size at the IL-2Rα binding interface particularly past 10 kDa reduces potency not just in Tregs but in IL2Rβγ expressing cells such as CD8+ T cells and NK cells. For example, 15 showed a $EC_{50}$ potency value in CD8+ T cells which was 5.4 times lower than 3 (802.17 vs 148.31, respectively, Table 30) and 16.46 fold lower potency than control IL-2, compound 13 (Table 31). Similarly, 15 showed a $EC_{50}$ potency value in NK cells which was 6.77 times lower than 3 (192.25 vs 28.41, respectively, Table 30) and 14.73 fold lower potency than control IL-2, compound 13 (Table 31). Overall these data show that increasing the IL-2Rα blocking PEG size past 10 kDa inhibits potency on IL2Rβγ expressing cell types while smaller 5 kDa PEG sizes achieve IL-2Rα blocking while maintaining better potency on IL2Rβγ expressing cells.

TABLE 30

Summary of pSTAT5 Potency Values for 3, 14, and 15 in Cryopreserved Human PBMCs.

| $EC_{50}$ (ng/mL) | Treg | CD8 | NK |
|---|---|---|---|
| 3 | 105.48 | 148.31 | 28.41 |
| 14 | 162.87 | 242.50 | 49.41 |
| 15 | 432.88 | 802.17 | 192.25 |

TABLE 31

Fold Potency loss compared to control IL-2 13 for 3, 14, and 15 in cryopreserved Human PBMCs

| $EC_{50}$ (ng/mL) | CD4− CD8− T cells | CD8 | NK |
|---|---|---|---|
| 3 | 3.24 | 3.04 | 2.18 |
| 14 | 4.92 | 4.97 | 3.78 |
| 15 | 16.24 | 16.46 | 14.73 |

Example 22: Bioactivity of 3 and 4 in Human Peripheral Blood Mononuclear Cell Lymphocyte Subsets Experiments were undertaken to compare the bioassay potency of 1 with 5 kDa PEG variants represented by compounds 3 or 4. Similar methods as described in e.g. example 20 were used to investigate pSTAT5 induction in distinct lymphocyte subsets using flow cytometry after 30 minutes of stimulation with the indicated compounds. The data is summarized in Table 32 and demonstrate that compounds 3 and 4 demonstrate very similar potency

TABLE 32

Summary of pSTAT5 Potency Values for compounds 3 and 4 in Cryopreserved Human PBMCs.

| $EC_{50}$ (ng/mL) | Treg | CD4 | CD8 | CD4−CD8− T cells | NK |
|---|---|---|---|---|---|
| 3 | 86.36 | 485.76 | 126.59 | 142.31 | 22.05 |
| 4 | 90.93 | 485.83 | 133.77 | 155.85 | 24.02 |

For example, compounds 3 and 4 in this experiment showed very similar $EC_{50}$ potency values in CD8+ T cells of 126.59 and 133.77, respectively. Similarly, compounds 3 and 4 in this experiment showed very similar $EC_{50}$ potency values in NK cells of 22.05 and 24.02, respectively. Overall, these data show that no substantial differences in the potency of compounds 3 and 4 across IL-2Rα/β/γ+ cell types such as Tregs as well as IL-2Rβ/γ+ cell types such as CD8+ T cells and NK cells.

Example 23: Anti-Tumor Activity of IL-2 Mutein M1 Polymer Prodrug 10 in Combination with Anti-PD1 or Anti-CTLA4 Immunotherapy The study was conducted in female BALB/C mice with an age of 9-11 weeks at the day of tumor inoculation. Mice were implanted with $5 \times 10^5$ CT26 tumor cells into the right rear flank. When tumors were grown to a mean tumor volume of approx. 85 mm³, mice were randomized into treatment cohorts (day 0) to receive with either intravenous doses on Day 0, Day 6, and Day 16 of 200 μL of Buffer Control, 10 mg/kg of anti-mCTLA4 (9D9) dosed intraperitoneally twice a week for two weeks on days 0, 3, 7 and 10, 10 mg/kg anti-mPD1 (RMP1-14) dosed intraperitoneally twice a week for two weeks on days 0, 3, 7 and 10, one intravenous dose on Day 0 and one intravenous dose on Day 6 and one intravenous dose on Day 16 of 200 μL of 60 μg of 10, or combinations of one intravenous dose on Day 0 and one intravenous dose on Day 6 and one intravenous dose on Day 16 of 200 μL of 60 μg of 10 and either the anti-CTLA4 or anti-PD1 treatments as described above.

Tumor volumes were calculated according to the formula: Tumor volume=$(L \times W^2) \times 0.5$ where L is the length of the tumor and W the width (both in mm). Mice were removed from the study once tumors were greater than 3000 mm3 and the study was run according to local animal welfare guidelines. To compare relative tumor volumes of different groups at a pre-specified day, Bartlett's test was used to check the assumption of homogeneity of variance across all groups. When the p-value of Bartlett's test was ≥0.05, one-way ANOVA was performed to test overall equality of means across all groups. If the p-value of the one-way ANOVA was <0.05, post hoc was further performed testing by running Tukey's HSD (honest significant difference) tests for all pairwise comparisons, and Dunnett's tests for comparing each treatment group with the vehicle group. When the p-value of Bartlett's test was <0.05, Kruskal-Wallis tests were performed to test overall equality of medians among all groups. If the p-value of the Kruskal-Wallis test was <0.05, post hoc testing was performed by running Conover's non-parametric test for all pairwise comparisons or for comparing each treatment group with the vehicle group, both with single-step p-value adjustment. Tumor growth inhibition (TGI) was used as an indicator of antitumor activities and was calculated from the relative tumor volumes of the control and treatment groups due to the variance of tumor volumes among groups at Day 0. TGI (%)=$(1-T/C) \times 100\%$; T/C=$MTV_T/MTV_C$, $MTV_T$: mean tumor volume in treatment group at Day t, $MTV_C$: mean tumor volume in control group at Day t. Moreover, the statistical analysis was performed on the data collected on the day when all or most of the mice in the control groups were alive.

The TGI values for Day 14 in each group are summarized in Table 33: When compared to Buffer treated animals, Tumor Growth Inhibition (TGI) values of 32.53%, 51.79%, and 60.65% were observed with treatment of 10, anti-CTLA4 monotherapy, or the combination of 10 and anti-CTLA4, respectively. Additionally, the combination 10 and anti-CTLA4 demonstrated lower average tumor volumes and lower p-values vs buffer treated animals than treatment with 10 or anti-CTLA4 alone (Table 33). Similarly, when compared to buffer treated animals, TGI values of 47.21% and 57.82% were observed for groups treated with anti-PD1 or the combination of anti-PD1+10. In summary, at day 14 the data show a increased tumor growth inhibition, lower average tumor volumes and lower (more significant) p-values compared to buffer treated animals in groups receiving CTLA4 or PD1 in combination with 10 compared to groups receiving CTLA4 or PD1 alone (Table 33).

TABLE 33

Antitumor Activity of 10 alone or in Combination with anti-mCTLA4 (9D9), or Anti-mPD1 (RMP1-14) in CT26 tumor bearing mice

| Group | Treatment Description | Mean Tumor Volume (mm³)[a] on day 14 | T/C (%)[b] | TGI (%) | P value[c] |
|---|---|---|---|---|---|
| 1 | Buffer Control | 1643.66 ± 245.03 (8) | 100.0 | 0.0 | 1.00 |
| 2 | 10 | 1109.03 ± 146.30 (8) | 67.47 | 32.53 | 0.748 |
| 3 | Anti-mCTLA4 (9D9) | 792.33 ± 183.49 (8) | 48.21 | 51.79 | 0.0082 |
| 4 | Anti-mCTLA4 (9D9) 10 | 646.73 ± 162.41 (7) | 39.35 | 60.65 | 0.0006 |
| 5 | Anti-mPD1 (RMP1-14) | 867.66 ± 134.52 (8) | 52.79 | 47.21 | 0.0709 |
| 6 | Anti-mPD1 (RMP1-14) 10 | 693.22 ± 85.35 (7) | 42.18 | 57.82 | 0.0066 |

Notes:
[a]Mean ± SEM (N), N is the remaining animal number in each group.
[b]T/C = MTV$_t$/MTV$_c$, MTVt: mean tumor volume in the treatment groups, MTV mean tumor volume in Group 1 Buffer Control group.
[c]TGI in treated groups vs. Group 1 Buffer Control group.

Example 24: In Vitro Release Kinetic of IL-2 Mutein Ala-M1 Polymer Prodrug 5

In vitro release kinetics of IL-2 mutein Ala-M1 polymer prodrug 5 was determined at pH 7.4 and 37° C. to mimic physiological pH and temperature conditions. For this purpose, the IL-2 mutein Ala-M1 polymer prodrug 5 was buffer exchanged into 25 mM HEPES, 135 mM NaCl, 1 mM EDTA, 10 mM L-Methionine, 2 mg/mL Pluronic F-68, pH 7.4 using an Äkta system and two connected HiTrap desalting columns (Cytiva) using a flow rate of 2 mL/min and UV detection at 280 nm. The buffer exchanged samples were incubated at 37° C. under temperature-controlled conditions in a water bath for up to two weeks (333.5 h). Determination of linker cleavage and release of 3 was performed after acidification of the samples by reversed-phase high pressure liquid chromatography on an Acquity UPLC I-Class Plus System (Waters) equipped with an Acquity UPLC Peptide BEH C18 column (300 Å, 1.7 µm, 2.1 mm×50 mm). The release was quantified at eight different time points by integration of the peak of IL-2 mutein Ala-M1 polymer prodrug 5 and release-related species (3 and cleaved 40 kDa mPEG-linker species) in the respective RP-HPLC chromatogram at 215 nm. The percentage of liberated species was plotted against the incubation time and curve fitting software was used to apply a nonlinear one-phase association fit to determine the half time of the linker cleavage kinetics. The in vitro linker half-life has been determined with 54 hours (95% confidence interval=50-58 hours) at pH 7.4 and 37° C.

Example 25: O-Glycosylation Pattern for IL-2 Mutein Ala-M1 1 (SEQ ID NO:14)

To search for O-glycosylation sites in IL-2 mutein Ala-M1 1 (SEQ ID NO:14), a peptide map was performed. For this purpose, two batches of IL-2 mutein Ala-M1 1 (SEQ ID NO:14) were digested with a mixture of Trypsin and Endoproteinase Lys-C for 18 hours at pH 8 and 37° C. (enzyme to substrate ratio=1:10). After digestion, the samples were diluted with the same volume of water and analyzed by reversed-phase high pressure liquid chromatography using a Halo C18 column (Advanced Materials Technology, 90 Å, 2.1×100 mm, 2.7 µm). The mobile phase consisted of 0.075% TFA in water (A) and 0.060% TFA in acetonitrile (B). The gradient program followed a starting composition of 0.5% B that was held for 1 min, increased to 25.7% B in 8.2 min, increased to 33% B in 1.3 min, increased to 61% B in 15.5 min followed by an increase to 99.9% B in 0.2 min (flow rate=0.5 mL/min, column temperature=20.9° C.). Identification of the peptide fragments was performed by high resolution mass spectrometry using a quadrupole time-of-flight mass spectrometer. The most intense glycosylated species were determined by comparison of the peak intensities at 215 nm.

The digested peptide fragment 1-8 (APTSSSTK) was found to be O-glycosylated (no non-glycosylated APTSSSTK fragment was found). The possible O-glycosylations were identified by comparison of the found masses for the peptide fragment and theoretical masses from a database (GlycoMod Tool, ExPASy, Swiss Institute of Bioinformatics). The qualitative results are summarized in Table 34 (only biological relevant glycoforms were considered for matches).

TABLE 34

Proposed glycoforms of peptide fragment APTSSSTK in two batches of IL-2 mutein Ala-M1 1 (SEQ ID NO: 14)

| Found mass(es) [M + H]⁺ | Theoretical mass [M + H]⁺ | Deviation [ppm] | Proposed structure |
|---|---|---|---|
| 1434.6346 1434.6308 | 1434.622 | 5.9-8.6 | (Hex)1 (HexNAc)1 (NeuAc)1 |
| 1450.6256 | 1450.617 | 5.9 | (Hex)1 (HexNAc)1 (NeuGc)1 |
| 1451.6288 | 1451.637 | −5.7 | (Hex)2 (HexNAc)1 (Deoxyhexose)1 |
| 1637.7126 1637.7108 | 1637.701 | 5.3-5.8 | (Hex)1 (HexNAc)2 (NeuAc)1 |
| 1725.7322 1725.7284 | 1725.717 | 6.4-8.7 | (Hex)1 (HexNAc)1 (NeuAc)2 or (Hex)1 (HexNAc)3 (HexA)1 |
| 1741.7200 1741.7216 | 1741.712 | 4.4-5.4 | (Hex)1 (HexNAc)1 (NeuAc)1 (NeuGc)1 |
| 1799.7680 1799.7646 | 1799.754 | 5.7-8.8 | (Hex)1 (HexNAc)2 (Deoxyhexose)1 (NeuGc)1 or (Hex)2 (HexNAc)2 (NeuAc)1 |

The most intense glycoforms in both batches were (Hex)1 (HexNAc)1 (NeuAc)2 and (Hex)1 (HexNAc)1 (NeuAc)1.

Example 26: Expression of IL-2 Muteins in *E. coli*

For expression of IL-2 variants with mutations at K35, DNA sequences encoding Ala-M1 [SEQ ID NO:40], Ala-M1 K35E [SEQ ID NO:41], Ala-M1 K35D [SEQ ID NO:42], Ala-M1 K35Q [SEQ ID NO:43] and Ala-M1 K35S [SEQ ID NO:44] were obtained from the amino acid sequences (Ala-M1 [SEQ ID NO:14], Ala-M1 K35E [SEQ ID NO:35], Ala-M1 K35D [SEQ ID NO:39], Ala-M1 K35Q [SEQ ID NO:33] and Ala-M1 K35S [SEQ ID NO:29]) by reverse translation and codon optimization for expression in *Escherichia coli* (*E. coli*). An ATG codon was added to the 5' end of each of the DNA sequences to enable cytosolic expression in *E. coli*. The DNA sequences were synthesized (GeneArt) and cloned into expression vectors under the control of the IPTG-inducible Tac promoter. The expression vectors, additionally containing a kanamycin resistance gene for selection, were transformed into the *E. coli* host strain BL21 and the resulting strains were used for expression of Ala-M1 K35 mutants. Strains were grown overnight in LB-Kan medium (37° C., 250 rpm), and the overnight cultures were used to inoculate 50 mL TB-Mg-Kan medium in 250 mL shake flasks (37° C., 250 rpm). When OD600 of the cultures reached 1, expression was induced by adding 0.1 mM IPTG and the cultures were left with shaking for 5 hours before harvest.

For analysis of the product yield in the soluble and insoluble cell fraction, soluble proteins were extracted from 2×1 mL culture from each shake flask using 300 µL Bug-Buster reagent. The remaining cell pellet was dissolved in 300 µL sample buffer containing DTT, representing the insoluble fraction, and both fractions were analyzed by SDS-PAGE after loading. The results showed that the product was present only in the insoluble fraction for all tested IL-2 variants.

For refolding experiments, IL-2 inclusion bodies were solubilized in solubilization buffer (6 M guanidine HCl, 8 mM DTT, 50 mM Tris, pH 8.5) and were then refolded by 50-fold dilution in refolding buffer (1.2 M urea, 500 mM arginine HCl, 20% glycerol, 0.0010% Tween 80, 12 mM L-cysteine, 0.15 mM cystamine 2HCl, 35 mM Tris, pH 8.5). The mixture was incubated for 55 h with stirring at room temperature. Refolding was followed by taking out samples for RP-HPLC analysis over the time course of refolding. The RP-HPLC method (Waters X-bridge BEH C18 column, 300 Å, 3.5 µm, 2.1×100 mm. Temperature: 40° C. Eluent A: 0.05% TFA in UPW and Eluent B: 0.05% TFA in ACN. Linear gradient from 25% to 75% B over 36 min. Flow rate 0.4 mL/min, 50 µL injection volume and UV detection at 220 nm) allowed for separation of the fully reduced IL-2 starting material and the refolded monomeric IL-2 variants with cysteine capping at R38C.

The results show an increasing concentration of correctly folded monomeric product over time for all tested variants. A higher initial rate of formation and higher final concentration of refolded monomeric product was observed for Ala-M1 K35D and Ala-M1 K35E compared to Ala-M1. The Ala-M1 K35Q and Ala-M1 K35S mutants did not show refolding improvement, but rather had very similar rates of formation and final concentration of refolded monomeric product compared to Ala-M1. The highest final concentration of correctly refolded monomer was obtained with the Ala-M1 K35D variant (approximately 1.8-fold higher than Ala-M1), whereas the Ala-M1 K35E variant had a final concentration of refolded monomer that was approximately 1.5-fold higher than for Ala-M1. The fold improvement of final concentration was here estimated by comparing the refolded product peak areas of the K35 variants to the Ala-M1 refolded product peak area after 47 hours of refolding.

In an attempt to achieve soluble, periplasmic expression of Ala-M1 [SEQ ID NO:14] and M1[SEQ ID NO:18] in *E. coli*, Ala-M1 and M1 were N-terminally fused to a range of bacterial signal peptides (dsbA, glll, mal, OmpA, OpmC, OmpT, pelB, phoA, torA, torT, EOX, STLL, SfmC, lamb, MglB, MmAp and tolB). Amino acid sequences of the IL-2 muteins alone and fused with the signal peptides were backtranslated and the resulting DNA sequences were codon optimized for expression in *E. coli*. The resulting DNA sequences were synthesized and cloned into an expression vector containing a kanamycin resistance gene for selection, under the control of the rhamnose-inducible rham promoter (Atum). Plasmid constructed in this way were transformed into the *E. coli* host strain BL21 and the resulting strains were used for small-scale expression tests. Strains were grown at 37° C. overnight in TB-Kan medium and the overnight cultures were used to inoculate 0.5 mL TB-Mg-Kan to a starting OD600 of 0.2. When OD600 of the cultures reached 0.8, expression was induced by adding 4 mM rhamnose and the cultures were incubated with shaking for 4 hours before harvest by centrifugation. The outer membrane of the periplasmic space was disrupted and periplasmic protein was extracted from the cells, before preparing a total cell lysate from the remaining cell material. The total cell lysate was separated in soluble and non-soluble fractions. Samples from the total, soluble and periplasmic protein fractions were then denatured and run on SDS-PAGE at reducing conditions. Expression levels were estimated by densitometry of full-length protein bands relative to an IL-2 standard on coomassie-stained gels. The samples were also analyzed by Western blot analysis using an IL-2 antibody. Positive (cells expressing a protein present in all analyzed fractions) and negative (cells with empty expression plasmid) controls were included in the analyses for reference. The SDS-PAGE analysis detected no IL-2 product in either the soluble or periplasmic samples from either M1 or Ala-M1 with any of the tested signal peptides. For M1 and Ala-M1 expressed without a signal sequence, protein bands of the expected size were observed in the total cell lysate fraction on the SDS-PAGE gels and the identity of the product was verified by Western blot. For M1 and Ala-M1 expressed with signal sequences, protein bands of slightly increased sizes were observed in the total cell lysate samples on SDS-PAGE, and the identity of the bands were verified by Western blot. The slight increase in product size was consistent with the signal peptide not being cleaved off. For some of the signal sequences, no product could be detected in any of the fractions, including in the total cell lysate. For M1, this was the case for 7 of the 17 tested signal peptides (dsbA, torT, tolB, EOX, STLL, SfmC and MmAp), while for Ala-M1, it was only the case for 3 of signal peptides (dsbA, torT and tolB).

Abbreviations

AIEX anion exchange chromatography
bp Base pair
CHO Chinese hamster ovary
CV column volume
DNA Deoxyribonucleic acid
DO Dissolved oxygen
EDTA Ethylenediaminetetraacetic acid, 2,2',2'',2'''-(Ethane-1,2-diyldinitrilo)tetraacetic acid
eq equivalents
HEPES 2-[4-(2-hydroxyethyl)piperazin-1-yl]ethanesulfonic acid
Hex Hexose
HexNAc N-Acetylhexose
IL-2 Interleukin-2
MES 4-Morpholineethanesulfonic acid
mPEG methoxypolyethylene glycol
NeuAc N-acetyl neuraminic acid
NeuGc N-glycolyl neuraminic acid
PBS Phosphate buffered saline
*P. pastoris* Pichia pastoris
PTP 5 mM phosphate, 90 g/L trehalose dihydrate, 0.2% Pluronic F-68, pH 7.4
PVDF Polyvinylidene fluoride, Poly(1,1-difluoroethylene)
rcf relative centrifugal force
RP reversed phase
RP-HPLC Reversed-phase high-performance liquid chromatography
rt room temperature
SDS-PAGE Sodium dodecyl sulfate polyacrylamide gel electrophoresis
SEC Size exclusion chromatography
TBS Tris-buffered saline
TCEP (Tris(2-carboxyethyl)phosphine hydrochloride)
TMB 3,3',5,5'-Tetramethylbenzidin
TRIS tris(hydroxymethyl)aminomethane, 2-Amino-2-(hydroxymethyl)propane-1,3-diol
UPLC Ultra performance liquid chromatography
VCD Viable cell density

The invention claimed is:

1. A method of treating, controlling, or delaying a cancer, which can be treated with IL-2 in a mammalian patient in need thereof, comprising the step of administering to the patient in need thereof a therapeutically effective amount of a conjugate or a pharmaceutically acceptable salt thereof of formula (Ia) or (Ib)

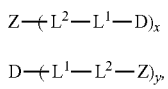

wherein
-D comprises an IL-2 protein of formula (I)
Ala-SEQ A-Cys*-SEQ B (I),
wherein
SEQ A has at least 94% sequence identity to SEQ ID NO:1;
SEQ B has at least 94% sequence identity to SEQ ID NO:2;
Ala is an alanine residue; and
Cys* is a cysteine residue;
-$L^1$- is a linker moiety covalently and reversibly attached to -D;
-$L^2$- is a chemical bond or is a spacer moiety;
Z is a polymeric moiety or a substituted fatty acid moiety;
x is an integer selected from the group consisting of 1, 2, 3, 4, 5, 6, 7, 8, 9, 10, 11, 12, 13, 14, 15 or 16; and
y is an integer selected from the group consisting of 2, 3, 4 and 5.

2. The method of claim 1, wherein SEQ A is selected from the group consisting of SEQ ID NO:1, SEQ ID NO:3, SEQ ID NO:4, SEQ ID NO:5, SEQ ID NO:6, SEQ ID NO: 7, SEQ ID NO:8, SEQ ID NO:9, SEQ ID NO: 10 and SEQ ID NO:11.

3. The method of claim 1, wherein SEQ A has the sequence of SEQ ID NO:1.

4. The method of claim 1, wherein SEQ B has the sequence of SEQ ID NO:2.

5. The method of claim 1, wherein SEQ B has the sequence of SEQ ID NO:12.

6. The method of claim 1, wherein the IL-2 protein has the sequence of SEQ ID NO: 14.

7. The method of claim 1, wherein the IL-2 protein comprises a moiety $M_{mod}$ conjugated to the cysteine marked with the asterisk in the IL-2 protein of formula (I).

8. The method of claim 7, wherein $M_{mod}$ is a polymeric moiety.

9. The method of claim 7, wherein $M_{mod}$ is of formula (A-1)

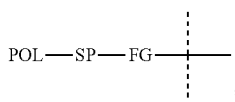

wherein
-FG- is a linkage;
-SP- is a spacer moiety; and
-POL is a polymer.

10. The method of claim 7, wherein $M_{mod}$ has a molecular weight ranging from 0.5 kDa to 120 kDa.

11. The method of claim 7, wherein $M_{mod}$ is a PEG-based polymer.

12. The method of claim 7, wherein attachment of $M_{mod}$ to the IL-2 protein is via a stable linkage.

13. The method of claim 7, wherein $M_{mod}$ is of formula (A-1a)

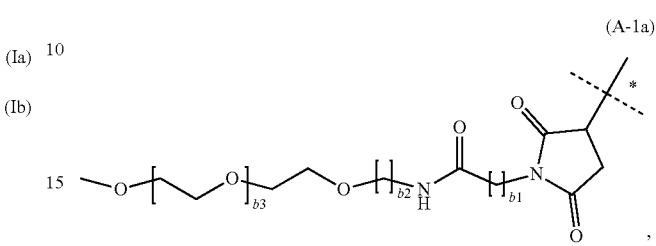

wherein
the dashed line marked with the asterisk indicates attachment to the sulfur of the cysteine marked with the asterisk in formula (I);
b1 is an integer selected from the group consisting of 1, 2, 3, 4, 5, 6, 7, 8, 9, 10, 11, 12, 13, 14, 15, 16, 17, 18, 19 and 20;
b2 is an integer selected from the group consisting of 1, 2, 3, 4, 5, 6, 7, 8, 9, 10, 11, 12, 13, 14, 15, 16, 17, 18, 19 and 20; and
b3 is an integer ranging from 12 to 22700.

14. The method of claim 7, wherein $M_{mod}$ is of formula (A-1d)

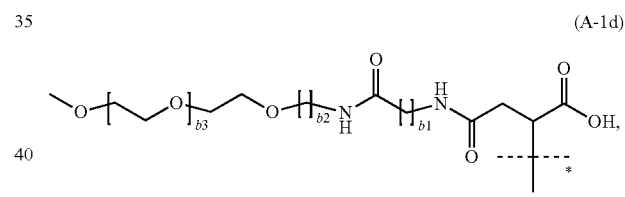

wherein
the dashed line marked with the asterisk indicates attachment to the sulfur of the cysteine marked with the asterisk in formula (I);
b1 is an integer selected from the group consisting of 1, 2, 3, 4, 5, 6, 7, 8, 9, 10, 11, 12, 13, 14, 15, 16, 17, 18, 19 and 20;
b2 is an integer selected from the group consisting of 1, 2, 3, 4, 5, 6, 7, 8, 9, 10, 11, 12, 13, 14, 15, 16, 17, 18, 19 and 20; and
b3 is an integer ranging from 12 to 22700.

15. The method of claim 7, wherein $M_{mod}$ is of formula (A-1e)

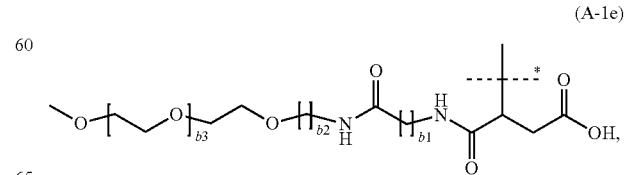

wherein
the dashed line marked with the asterisk indicates attachment to the sulfur of the cysteine marked with the asterisk in formula (I);
b1 is an integer selected from the group consisting of 1, 2, 3, 4, 5, 6, 7, 8, 9, 10, 11, 12, 13, 14, 15, 16, 17, 18, 19 and 20;
b2 is an integer selected from the group consisting of 1, 2, 3, 4, 5, 6, 7, 8, 9, 10, 11, 12, 13, 14, 15, 16, 17, 18, 19 and 20; and
b3 is an integer ranging from 12 to 22700.

16. The method of claim 7, wherein in a plurality of conjugates $M_{mod}$ comprises a mixture of formula (A-1d) and formula (A-1e).

17. The method of claim 1, wherein the conjugate is a biased IL-2.

18. The method of claim 1, wherein —Z is a PEG-based polymeric moiety.

19. The method of claim 1, wherein —Z comprises a moiety of formula (A)

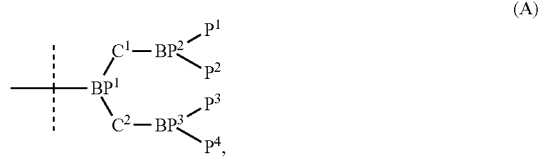

(A)

wherein
—BP1<, —BP2<, —BP3< are independently of each other selected from the group consisting of —N< and —C($R^8$)<;
$R^8$ is selected from the group consisting of H, $C_{1-6}$ alkyl, $C_{2-6}$ alkenyl and $C_{2-6}$ alkynyl;
—P1, —P2, —P3, —P4 are independently of each other a PEG-based chain comprising at least 40% PEG and having a molecular weight ranging from 3 to 40 kDa;
—$C^1$—, —$C^2$— are independently of each other selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $R^9$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{10}$)—, —S(O)$_2$N($R^{10}$)—, —S(O)N($R^{10}$)—, —S(O)$_2$—, —S(O)—, —N($R^{10}$)S(O)$_2$N($R^{10a}$)—, —S—, —N($R^{10}$)—, —OC(O$R^{10}$)($R^{10a}$)—, —N($R^{10}$)C(O)N($R^{10a}$)—, and —OC(O)N($R^{10}$)—;
each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^9$, which are the same or different;
each $R^9$ is independently selected from the group consisting of halogen, —CN, oxo (=O), —COO$R^{11}$, —O$R^{11}$, —C(O) $R^{11}$, —C(O)N($R^{11}R^{11a}$), —S(O)$_2$N($R^{11}R^{11a}$), —S(O)N($R^{11}R^{11a}$), —S(O)$_2R^{11}$, —S(O)$R^{11}$, —N($R^{11}$)S(O)$_2$N($R^{11a}R^{11b}$), —S$R^{11}$, —N($R^{11}R^{11a}$), —NO$_2$, —OC(O)$R^{11}$, —N($R^{11}$)C(O)$R^{11a}$, —N($R^{11}$)S(O)$_2R^{11a}$, —N($R^{11}$)S(O)$R^{11a}$, —N($R^{11}$)C(O)O$R^{11a}$, —N($R^{11}$)C(O)N($R^{11a}R^{11b}$), —OC(O)N($R^{11}R^{11a}$), and $C_{1-6}$ alkyl; wherein $C_{1-6}$ alkyl is optionally substituted with one or more halogen, which are the same or different; and
each $R^{10}$, $R^{10a}$, $R^{11}$, $R^{11a}$ and $R^{11b}$ is independently selected from the group consisting of —H, and $C_{1-6}$ alkyl, wherein $C_{1-6}$ alkyl is optionally substituted with one or more halogen, which are the same or different.

20. The method of claim 19, wherein $C^1$ and $C^2$ are of formula (A-a)

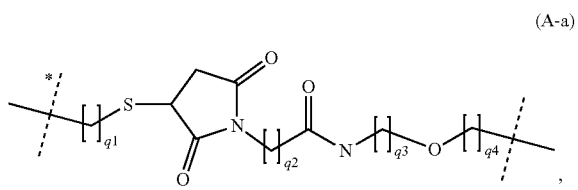

(A-a)

wherein
the dashed line marked with the asterisk indicates attachment to $BP^1$;
the unmarked dashed line indicates attachment to $BP^2$ or $BP^3$, respectively;
q1 is selected from the group consisting of 1, 2, 3, 4, 5, 6, 7 and 8;
q2 is selected from the group consisting of 1, 2, 3, 4, and 5;
q3 is selected from the group consisting of 1, 2, 3, 4, 5, 6, 7 and 8; and
q4 is selected from the group consisting of 1, 2 and 3.

21. The method of claim 19, wherein $P^1$, $P^2$, $P^3$ and $P^4$ are independently of each other of formula (A-b)

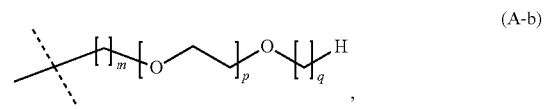

(A-b)

wherein
the dashed line indicates attachment to the remainder of —Z;
m is 0 or 1;
p is an integer ranging from 70 to 900; and
q is selected from the group consisting of 1, 2, 3, 4, 5, and 6.

22. The method of claim 1, wherein -$L^1$- is of formula (IX-a):

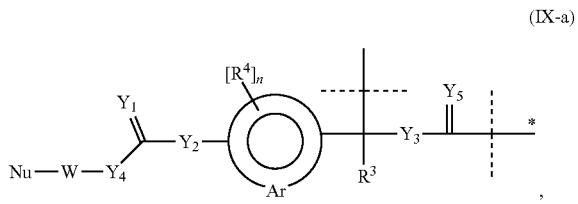

(IX-a)

wherein
the dashed line marked with the asterisk indicates attachment to a nitrogen of -D and the unmarked dashed line indicates attachment to -$L^2$-Z;
n is 0, 1, 2, 3, or 4;

=Y, is selected from the group consisting of =O and =S;
—Y$_2$— is selected from the group consisting of —O— and —S—;
—Y$_3$— is selected from the group consisting of —O— and —S—;
—Y$_4$— is selected from the group consisting of —O—, —NR$^5$— and —C(R$^6$R$^{6a}$)—;
=Y$_5$ is selected from the group consisting of =O and =S;
—R$^3$, —R$^5$, —R$^6$, —R$^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—R$^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—W— is selected from the group consisting of C$_{1-20}$ alkyl optionally interrupted by one or more groups selected from the group consisting of C$_{3-10}$ cycloalkyl, 8- to 30-membered carbopolycyclyl, 3- to 10-membered heterocyclyl, —C(O)—, —C(O)N(R$^7$)—, —O—, —S— and —N(R$^7$)—;
—Nu is a nucleophile selected from the group consisting of —N(R$^7$R$^{7a}$), —N(R$^7$OH), —N(R$^7$)—N(R$^{7a}$R$^{7b}$), —S(R$^7$), —COOH,

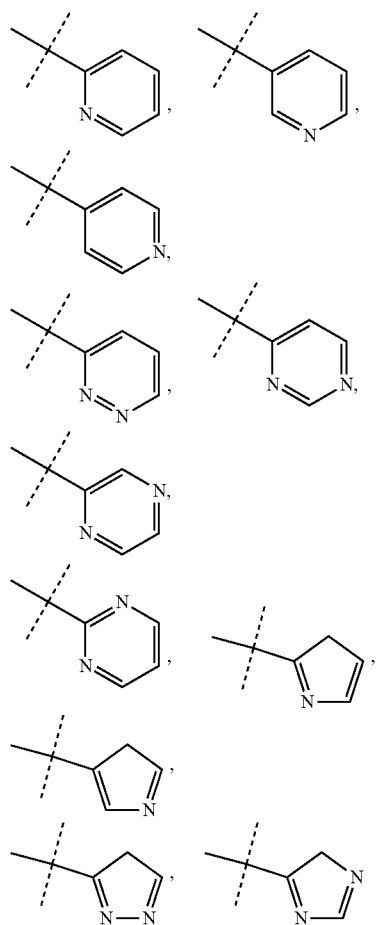

and

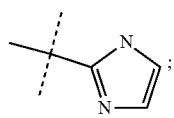

—Ar— is selected from the group consisting of

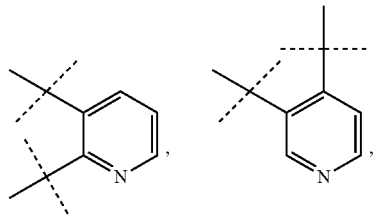

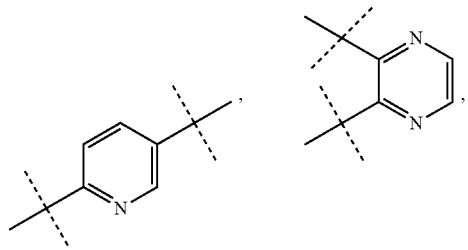

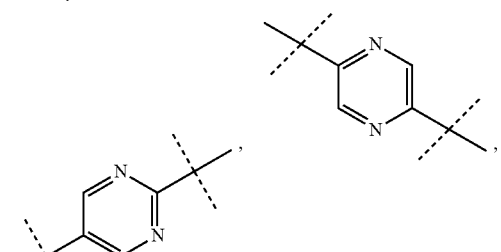

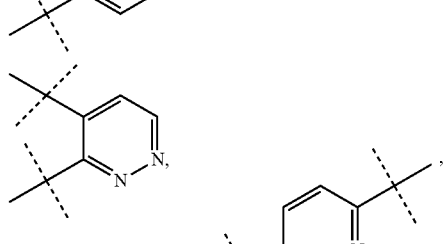

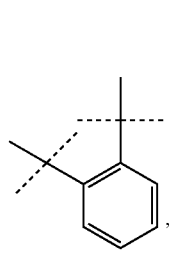

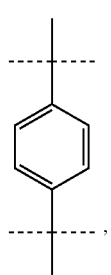

-continued

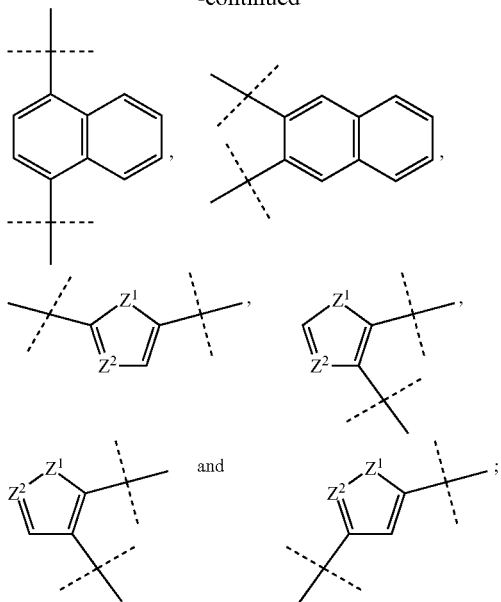

wherein
dashed lines indicate attachment to the remainder of -L¹-,
—Z¹— is selected from the group consisting of —O—, —S— and —N(R⁷)—, and
—Z²— is —N(R⁷)—; and
—R⁷, —R⁷ᵃ, —R⁷ᵇ are independently of each other selected from the group consisting of —H, C₁₋₆ alkyl, C₂₋₆ alkenyl and C₂₋₆ alkynyl;
wherein -L¹- is optionally further substituted.

23. The method of claim 1, wherein -L¹- is of formula (IX-c)

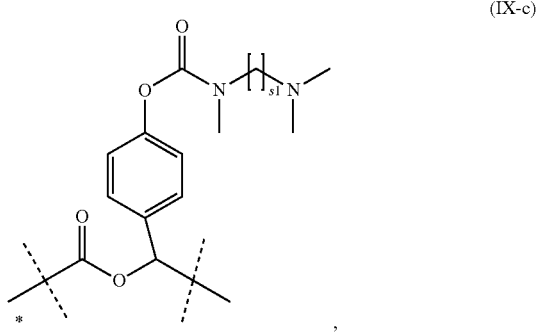

(IX-c)

wherein
the dashed line marked with the asterisk indicates attachment to a nitrogen of -D;
the unmarked dashed line indicates attachment to -L²-Z; and
s1 is an integer selected from the group consisting of 1, 2, 3, 4, 5, 6, 7, 8, 9 and 10.

24. The method of claim 1, wherein -L²— is selected from the group consisting of -T-, —C(O)O—, —O—, —C(O)—, —C(O)N(R^{y1})—, —S(O)₂N(R^{y1})—, —S(O)N(R^{y1})—, —S(O)₂—, —S(O)—, —N(R^{y1})S(O)₂N(R^{y1a})—, —S—, —N(R^{y1})—, —OC(OR^{y1})(R^{y1a})—, —N(R^{y1})C(O)N(R^{y1a})—, —OC(O)N(R^{y1})—, C₁₋₅₀ alkyl, C₂₋₅₀ alkenyl, and C₂₋₅₀ alkynyl; wherein -T-, C₁₋₅₀ alkyl, C₂₋₅₀ alkenyl, and C₂₋₅₀ alkynyl are optionally substituted with one or more —R^{y2}, which are the same or different and wherein C₁₋₅₀ alkyl, C₂₋₅₀ alkenyl, and C₂₋₅₀ alkynyl are optionally interrupted by one or more groups selected from the group consisting of -T-, —C(O)O—, —O—, —C(O)—, —C(O)N(R^{y3})—, —S(O)₂N(R^{y3})—, —S(O)N(R^{y3})—, —S(O)₂—, —S(O)—, —N(R^{y3})S(O)₂N(R^{y3}a)-, —S—, —N(R^{y3})—, —OC(OR^{y3})(R^{y3a})—, —N(R^{y3})C(O)N(R^{y3a})—, and —OC(O)N(R^{y3})—;

—R^{y1} and —R^{y1a} are independently of each other selected from the group consisting of —H, -T, C₁₋₅₀ alkyl, C₂₋₅₀ alkenyl, and C₂₋₅₀ alkynyl; wherein -T, C₁₋₅₀ alkyl, C₂₋₅₀ alkenyl, and C₂₋₅₀ alkynyl are optionally substituted with one or more —R^{y2}, which are the same or different, and wherein C₁₋₅₀ alkyl, C₂₋₅₀ alkenyl, and C₂₋₅₀ alkynyl are optionally interrupted by one or more groups selected from the group consisting of -T-, —C(O)O—, —O—, —C(O)—, —C(O)N(R^{y4})—, —S(O)₂N(R^{y4})—, —S(O)N(R^{y4})—, —S(O)₂—, —S(O)—, —N(R^{y4})S(O)₂N(R^{y4a})—, —S—, —N(R^{y4})—, —OC(OR^{y4})(R^{y4a})—, —N(R^{y4})C(O)N(R^{y4a})—, and —OC(O)N(R^{y4})—;

each T is independently selected from the group consisting of phenyl, naphthyl, indenyl, indanyl, tetralinyl, C₃₋₁₀ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more -R^{y2}, which are the same or different;

each —R^{y2} is independently selected from the group consisting of halogen, —CN, oxo (=O), —COOR^{y5}, —OR^{y5}, —C(O)R^{y5}, —C(O)N(R^{y5}R^{y5a}), —S(O)₂N(R^{y5}R^{y5a}), —S(O)N(R^{y5}R^{y5a}), —S(O)₂R^{y5}, —S(O)R^{y5}, —N(R^{y5})S(O)₂N(R^{y5a}R^{y5b}), —SR^{y5}, —N(R^{y5}R^{y5a}), —NO₂, —OC(O)R^{y5}, —N(R^{y5})C(O)R^{y5a}, —N(R^{y5})S(O)₂R^{y5a}, —N(R^{y5}) S(O) R^{y5a}, —N(R^{y5})C(O)OR^{y5a}, —N(R^{y5})C(O)N(R^{y5a}R^{y5b}), —OC(O)N(R^{y5}R^{y5a}), and C₁₋₆ alkyl; wherein C₁₋₆ alkyl is optionally substituted with one or more halogen, which are the same or different; and each —R^{y3}, —R^{y3a}, —R^{y4}, —R^{y4a}, —R^{y5}, —R^{y5a} and —R^{y5b} is independently selected from the group consisting of —H, and C₁₋₆ alkyl, wherein C₁₋₆ alkyl is optionally substituted with one or more halogen, which are the same or different.

25. The method of claim 1, wherein -L²- is of formula (IX-e)

(IX-e)

wherein
the dashed line marked with the asterisk indicates attachment to -L¹-;
the unmarked dashed line indicates attachment to —Z; and
s2 is an integer selected from the group consisting of 0, 1, 2, 3, 4, 5, 6, 7, 8, 9, 10, 11, 12, 13, 14, 15, 16, 17, 18, 19 and 20.

26. The method of claim 1, wherein the mammalian patient is human.

* * * * *